(12) United States Patent
Jessiman et al.

(10) Patent No.: US 10,934,282 B2
(45) Date of Patent: *Mar. 2, 2021

(54) HETEROAROMATIC MODULATORS OF THE RETINOID-RELATED ORPHAN RECEPTOR GAMMA

(71) Applicant: LEO PHARMA A/S, Ballerup (DK)

(72) Inventors: Alan Stuart Jessiman, Ballerup (DK); Patrick Stephen Johnson, Ballerup (DK); Kristoffer Maansson, Ballerup (DK); Morten Dahl Sørensen, Ballerup (DK)

(73) Assignee: LEO Pharma A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/874,961

(22) Filed: May 15, 2020

(65) Prior Publication Data

US 2020/0291010 A1    Sep. 17, 2020

Related U.S. Application Data

(63) Continuation of application No. 16/317,655, filed as application No. PCT/EP2017/067390 on Jul. 11, 2017, now Pat. No. 10,662,181.

(30) Foreign Application Priority Data

Jul. 13, 2016 (EP) .................................... 16020268

(51) Int. Cl.
| C07D 413/14 | (2006.01) |
| C07D 413/12 | (2006.01) |
| C07D 417/14 | (2006.01) |
| C07D 241/04 | (2006.01) |

(52) U.S. Cl.
CPC ......... *C07D 413/12* (2013.01); *C07D 241/04* (2013.01); *C07D 413/14* (2013.01); *C07D 417/14* (2013.01)

(58) Field of Classification Search
CPC .. C07D 413/14; C07D 241/04; C07D 413/12; C07D 417/14; A61K 31/496
See application file for complete search history.

(56) References Cited

U.S. PATENT DOCUMENTS 10,662,181 B2 *  5/2020  Jessiman ................. A61P 29/00

FOREIGN PATENT DOCUMENTS

| EA | 023638 B1 | 6/2016 |
| EP | 0129207 | 3/1988 |
| RU | 2445308 C2 | 3/2012 |
| SU | 1542415 A3 | 2/1990 |

| WO | WO 2006/1064037 A2 | 10/2006 |
| WO | WO 2012/140020 A1 | 10/2012 |
| WO | WO 2014/086894 A1 | 6/2014 |

(Continued)

OTHER PUBLICATIONS

Bettelli, Estelle et al., "$T_H$-17 cells in the circle of immunity and autoimmunity," Nature Immunology, vol. 8, No. 4, pp. 345-350 (2007).
Fouser, Lynette A et al., Th17 cytokines and their emerging roles in inflammation and autoimmunity, Immunological Reviews, vol. 226, pp. 87-102 (2008).
Ivanov, Ivaylo I. et al., "The Orphan Nuclear Receptor RORγt Directs the Differentiation Program of Proinflammatory IL-17+ T Helper Cells," Cell 126, pp. 1121-1133 (2006).
Kojetin, Douglas J. et al., "REV-ERB and ROR nuclear receptors as drug targets," Nature Rev. Drug Discovery, vol. 13, pp. 197-216 (2014).
Jetten, Anton M. et al., "Retinoid-related orphan receptors (RORs): Roles in cellular differentiation and developments," Advances in Developmental Biology, vol. 16, pp. 313-355 (2006).
Yang et al., "Targeting Th 17 cells in autoimmune diseases," Trends in Pharmacological Sciences, vol. 35, No. 10, pp. 493-500 (2014).
Zhang et al., "ROR nuclear receptors: structures, related diseases, and drug discovery," Acta Pharmacologica Sinica, 36, pp. 71-87 (2015).
International Search Report for International Application No. PCT/EP2017/067390, dated Oct. 25, 2017. (4 pages).

(Continued)

*Primary Examiner* — Deepak R Rao
(74) *Attorney, Agent, or Firm* — Finnegan, Henderson, Farabow, Garrett & Dunner, LLP

(57) ABSTRACT

The present invention relates to a compound according to general formula (I) wherein X represents N or CH; $R_1$ is —CN, $(C_1-C_6)$alkyl, $(C_3-C_7)$cycloalkyl, (3-7 membered) heterocycloalkyl, (5-6 membered)heteroaryl, $(C_3-C_7)$cycloalkyl$(C_1-C_4)$alkyl, (3-7 membered)heterocycloalkyl-$(C_1-C_4)$alkyl or (5-6 membered)heteroaryl-$(C_1-C_4)$alkyl; $R_2$ is halogen, cyano, $(C_1-C_4)$alkyl or $(C_3-C_7)$cycloalkyl; $R_3$ is halogen, cyano, $(C_1-C_4)$alkyl, $(C_1-C_4)$haloalkyl or $(C_3-C_7)$cycloalkyl; $R_4$ is $(C_1-C_4)$alkyl or $(C_1-C_4)$haloalkyl; $R_5$ is $(C_1-C_6)$alkyl, $(C_3-C_7)$cycloalkyl, $(C_1-C_6)$alkyl-$(C_3-C_7)$cycloalkyl, $(C_3-C_7)$cycloalkyl-$(C_1-C_6)$alkyl, (3-7 membered) heterocycloalkyl, phenyl, (5-6 membered)heteroaryl or —$OR_a$. The invention further relates to said compounds for use in therapy, to pharmaceutical compositions comprising said compounds and to intermediates for preparation of said compounds.

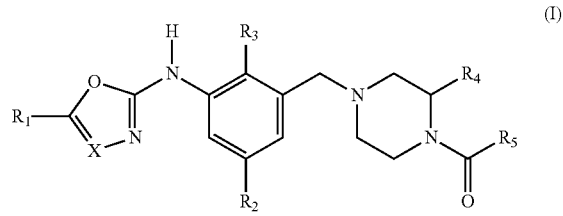

(I)

5 Claims, No Drawings
Specification includes a Sequence Listing.

(56) References Cited

FOREIGN PATENT DOCUMENTS

WO     WO 2015/180612 A1    12/2015
WO     WO 2015/180613 A1    12/2015
WO     WO 2015/180614 A1    12/2015

OTHER PUBLICATIONS

Written Opinion of the International Searching Authority for International Application No. PCT/EP2017/067390. (5 pages) (2017).
Translation of Search Report for Russian Application No. 2019103883 filed Jul. 11, 2017. (2 pages).

* cited by examiner

SEQUENCE LISTING

```
<160> NUMBER OF SEQ ID NOS: 1

<210> SEQ ID NO 1
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala His His His His His Gly Ser Asp Tyr Lys Asp Asp Asp
1               5                   10                  15

Asp Lys Gly Ser Ser Gly Ala Ser Leu Thr Glu Ile Glu His Leu Val
                20                  25                  30

Gln Ser Val Cys Lys Ser Tyr Arg Glu Thr Cys Gln Leu Arg Leu Glu
            35                  40                  45

Asp Leu Leu Arg Gln Arg Ser Asn Ile Phe Ser Arg Glu Val Thr
        50                  55                  60

Gly Tyr Gln Arg Lys Ser Met Trp Glu Met Trp Glu Arg Cys Ala His
65                  70                  75                  80
```

```
His Leu Thr Glu Ala Ile Gln Tyr Val Val Glu Phe Ala Lys Arg Leu
            85              90              95

Ser Gly Phe Met Glu Leu Cys Gln Asn Asp Gln Ile Val Leu Leu Lys
            100             105             110

Ala Gly Ala Met Glu Val Val Leu Val Arg Met Cys Arg Ala Tyr Asn
            115             120             125

Ala Asp Asn Arg Thr Val Phe Phe Glu Gly Lys Tyr Gly Gly Met Glu
130             135             140

Leu Phe Arg Ala Leu Gly Cys Ser Glu Leu Ile Ser Ser Ile Phe Asp
145             150             155             160

Phe Ser His Ser Leu Ser Ala Leu His Phe Ser Glu Asp Glu Ile Ala
            165             170             175

Leu Tyr Thr Ala Leu Val Leu Ile Asn Ala His Arg Pro Gly Leu Gln
            180             185             190

Glu Lys Arg Lys Val Glu Gln Leu Gln Tyr Asn Leu Glu Leu Ala Phe
            195             200             205

His His His Leu Cys Lys Thr His Arg Gln Ser Ile Leu Ala Lys Leu
            210             215             220

Pro Pro Lys Gly Lys Leu Arg Ser Leu Cys Ser Gln His Val Glu Arg
225             230             235             240

Leu Gln Ile Phe Gln His Leu His Pro Ile Val Val Gln Ala Ala Phe
            245             250             255

Pro Pro Leu Tyr Lys Glu Leu Phe Ser Thr Glu Thr Glu Ser Pro Val
            260             265             270

Gly Leu Ser Lys
            275
```

HETEROAROMATIC MODULATORS OF THE RETINOID-RELATED ORPHAN RECEPTOR GAMMA

This application is a continuation of U.S. patent application Ser. No. 16/317,655 filed Jan. 14, 2019, now U.S. Pat. No. 10,662,181, which is a national stage filing under 35 U.S.C. § 371 of International Application No. PCT/EP2017/067390, filed on Jul. 11, 2017, which claims priority of European Patent Application No. 16020268.5, filed on Jul. 13, 2016. The contents of these applications are each incorporated herein by reference.

The instant application contains a Sequence Listing which has been submitted electronically in ASCII format and is hereby incorporated by reference in its entirety. Said ASCII copy, created on Jan. 16, 2020, is named 14894_0025-00000_SL.txt and is 2,864 bytes in size.

FIELD OF THE INVENTION

This invention relates to compounds which are ROR-gamma (RORγ) modulators, to intermediates for the preparation thereof, to said compounds for use in therapy and to pharmaceutical compositions comprising said compounds and to methods of treating diseases with said compounds.

BACKGROUND OF THE INVENTION

The Retinoic acid-related orphan receptor (ROR) gene family is part of the nuclear hormone receptor super-family and consists of three members ROR alpha, ROR beta and ROR gamma (RORα, RORβ and RORγ). Each ROR gene is expressed in different isoforms; the isoforms differ in their pattern of tissue-specific expression and can regulate distinct physiological processes and target genes. More specifically two isoforms of RORγ have been identified; RORγ1 and RORγ2 (known as RORγt). RORγ1 is expressed in multiple tissues, such as heart, brain, kidney, lung, liver and muscle; whereas RORγt is restricted to the cells of the immune system and is expressed in lymphoid organs, such as the thymus (Jetten, A. M.; Adv. Dev. Biol. (2006), 16, 313-355).

RORγt has been shown to be crucial for the development of T helper 17 cells ($T_H17$ cells) (Ivanov et. al., Cell (2006), 126, 1121-1133). $T_H17$ cells, which produce IL-17, IL-21 and IL-22, have an essential role in the development of many autoimmune and inflammatory disorders, such as multiple sclerosis, psoriasis and rheumatoid arthritis. (Betelli, E. et al., Nature Immunol. (2007), 8, 345-350; Fouser, L. et al. Immunol. Rev. (2008), 226, 87-102); suggesting that development of RORγ modulators may be beneficial for treatment of autoimmune and inflammatory diseases (Kojetin, D. et al.; Nature Rev Drug Discovery (2014) 13, 197-215).

Recently, Proof-of-Concept was shown with an oral RORγt inhibitor (VTP 43742) in a Phase 2a clinical trial in psoriatic patients.

Several other compounds modulating RORγt have been reported, for example; WO2014/086894 discloses 'Modulators of the retinoid-related orphan receptor gamma (ROR-gamma) for use in the treatment of autoimmune and inflammatory diseases.' WO2015/180612, WO2015/180613 and WO2015/180614 disclose novel retinoid-related orphan receptor gamma (ROR-gamma) modulators and their use in the treatment of autoimmune and inflammatory diseases.

Thus it is desirable to provide compounds that modulate the activity of RORγ for use in the treatment of autoimmune and inflammatory disorders.

SUMMARY OF THE INVENTION

The inventors have surprisingly found that novel compounds of the present invention exhibit modulating effect on ROR-gamma and may be useful as therapeutic agents for diseases mediated by ROR-gamma, including autoimmune or inflammatory diseases such as psoriasis, psoriatic arthritis, multiple sclerosis, rheumatoid arthritis, Crohns disease, ulcerative colitis, alopecia areata, contact dermatitis, including irritative contact dermatitis and allergic contact dermatitis, spondyloarthritis; and cancers, including prostate cancer and non-small cell lung cancer.

Compounds of the present invention may have favourable pharmacokinetic and pharmacodynamic properties such as favourable oral bioavailability, solubility, absorption and metabolic stability or a favourable toxicity profile.

Compounds of the present invention may have low clearance in human liver microsomes thus making them suitable for oral use; or compounds of the present invention may have high clearance in human liver microsomes thus making them suitable for topical use as they may have reduced systemic side-effects while retaining the topical anti-inflammatory efficacy.

Accordingly, the present invention relates to a compound according to general formula (I)

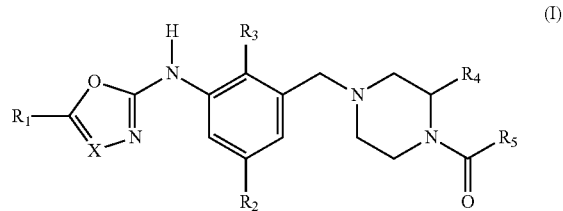

(I)

wherein X represents N or CH;

$R_1$ is selected from the group consisting of —CN, ($C_1$-$C_6$)alkyl, ($C_3$-$C_7$)cycloalkyl, (3-7 membered)heterocycloalkyl, (5-6 membered)heteroaryl, ($C_3$-$C_7$)cycloalkyl($C_1$-$C_4$)alkyl, (3-7 membered)heterocycloalkyl-($C_1$-$C_4$)alkyl and (5-6 membered)heteroaryl-($C_1$-$C_4$)alkyl, wherein said ($C_1$-$C_6$)alkyl, ($C_3$-$C_7$)cycloalkyl, (3-7 membered)heterocycloalkyl, (5-6-membered)heteroaryl, ($C_3$-$C_7$)cycloalkyl($C_1$-$C_4$) alkyl, (3-7 membered)heterocycloalkyl-($C_1$-$C_4$)alkyl and (5-6 membered)heteroaryl-($C_1$-$C_4$)alkyl is optionally substituted with one or more substituents independently selected from $R_6$;

$R_2$ is selected from the group consisting of halogen, cyano, ($C_1$-$C_4$)alkyl and ($C_3$-$C_7$)cycloalkyl, wherein said ($C_1$-$C_4$)alkyl and ($C_3$-$C_7$)cycloalkyl is optionally substituted with one or more substituents independently selected from —OH and halogen;

$R_3$ is selected from the group consisting of halogen, cyano, ($C_1$-$C_4$)alkyl, ($C_1$-$C_4$)haloalkyl and ($C_3$-$C_7$)cycloalkyl;

$R_4$ is selected from the group consisting of ($C_1$-$C_4$)alkyl and ($C_1$-$C_4$)haloalkyl; $R_5$ is selected from the group consisting of ($C_1$-$C_6$)alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl, (3-7 membered)heterocycloalkyl, phenyl, (5-6 membered)heteroaryl and —$OR_a$; wherein said ($C_1$-$C_6$)alkyl, ($C_3$-$C_7$) cycloalkyl, ($C_1$-$C_6$)alkyl-($C_3$-$C_7$)cycloalkyl, ($C_3$-$C_7$)cycloalkyl-($C_1$-$C_6$)alkyl, (3-7 membered)heterocycloalkyl, phenyl, (5-6 membered)heteroaryl and —OR$_a$ is optionally substituted with one or more substituents independently selected from R$_7$;

R$_6$ represents the group consisting of —OH, —CN, halogen, =O, —S(O)$_2$R$_b$, —NR$_c$R$_d$, —NR$_c$C(O)R$_d$, —C(O)NR$_c$R$_d$, —S(O)$_2$NR$_c$R$_d$, —NR$_c$S(O)$_2$R$_b$, —OR$_b$ —C(O)R$_b$, (C$_1$-C$_4$)alkyl, hydroxy(C$_1$-C$_4$)alkyl, halo(C$_1$-C$_4$)alkyl, (C$_3$-C$_7$)cycloalkyl, (3-7 membered)heterocycloalkyl and (5-6 membered)heteroaryl;

R$_7$ represents the group consisting of —OH, —CN, halogen, (C$_1$-C$_4$)alkyl, (C$_3$-C$_7$)cycloalkyl and (C$_1$-C$_6$)alkyl-(C$_3$-C$_7$)cycloalkyl-;

R$_a$ represents (C$_1$-C$_6$)alkyl, (C$_3$-C$_7$)cycloalkyl, (C$_1$-C$_6$)alkyl-(C$_3$-C$_7$)cycloalkyl- or (C$_3$-C$_7$)-cycloalkyl(C$_1$-C$_6$)alkyl;

R$_b$ represents (C$_1$-C$_6$)alkyl or (C$_3$-C$_7$)cycloalkyl;

R$_c$ and R$_d$ each independently represents H, (C$_1$-C$_6$)alkyl or (C$_3$-C$_7$)cycloalkyl;

or pharmaceutically acceptable salts, hydrates or solvates thereof.

In another aspect, the invention relates to a compound of general formula (I) for use as a medicament.

In yet another aspect, the invention relates to a compound of general formula (I) for use in treatment of autoimmune or inflammatory diseases.

In yet another aspect, the invention relates to a pharmaceutical composition comprising a compound according to general formula (I) together with a pharmaceutically acceptable vehicle or excipient or pharmaceutically acceptable carrier(s).

In yet another aspect, the invention relates to a method of preventing, treating or ameliorating psoriasis, the method comprising administering to a person suffering from psoriasis an effective amount of one or more compounds according to general formula (I), optionally together with a pharmaceutically acceptable carrier or one or more excipients, optionally in combination with other therapeutically active compounds.

In another aspect the invention relates to a compound according to general formula (II), which is useful as intermediate for the preparation of a compound of general formula (I),

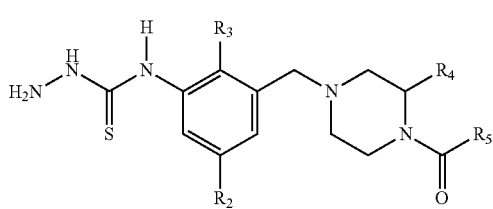

(II)

wherein

R$_2$ is selected from the group consisting of halogen, cyano, (C$_1$-C$_4$)alkyl and (C$_3$-C$_7$)cycloalkyl, wherein said (C$_1$-C$_4$)alkyl and (C$_3$-C$_7$)cycloalkyl is optionally substituted with one or more substituents independently selected from —OH and halogen;

R$_3$ is selected from the group consisting of halogen, cyano, (C$_1$-C$_4$)alkyl, (C$_1$-C$_4$)haloalkyl and (C$_3$-C$_7$)cycloalkyl;

R$_4$ is selected from the group consisting of (C$_1$-C$_4$)alkyl and (C$_1$-C$_4$)haloalkyl;

R$_5$ is selected from the group consisting of (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl, (3-7 membered)heterocycloalkyl, phenyl, (5-6 membered)heteroaryl and —OR$_a$; wherein said (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl, (3-7 membered) heterocycloalkyl, phenyl, (5-6 membered)heteroaryl and —OR$_a$ is optionally substituted with one or more substituents independently selected from R$_7$;

R$_7$ represents the group consisting of —OH, —CN, halogen, (C$_1$-C$_4$)alkyl, (C$_3$-C$_7$)cycloalkyl and (C$_1$-C$_6$)alkyl-(C$_3$-C$_7$)cycloalkyl-.

In yet another aspect the invention relates to a compound according to general formula (IX), which is useful as intermediate for the preparation of a compound of general formula (I),

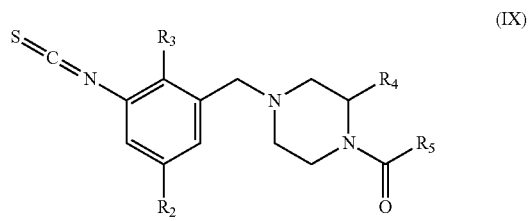

(IX)

wherein

R$_2$ is selected from the group consisting of halogen, cyano, (C$_1$-C$_4$)alkyl and (C$_3$-C$_7$)cycloalkyl, wherein said (C$_1$-C$_4$)alkyl and (C$_3$-C$_7$)cycloalkyl is optionally substituted with one or more substituents independently selected from —OH and halogen;

R$_3$ is selected from the group consisting of halogen, cyano, (C$_1$-C$_4$)alkyl, (C$_1$-C$_4$)haloalkyl and (C$_3$-C$_7$)cycloalkyl;

R$_4$ is selected from the group consisting of (C$_1$-C$_4$)alkyl and (C$_1$-C$_4$)haloalkyl;

R$_5$ is selected from the group consisting of (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl, (3-7 membered)heterocycloalkyl, phenyl, (5-6 membered)heteroaryl and —OR$_a$; wherein said (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl, (3-7 membered) heterocycloalkyl, phenyl, (5-6 membered)heteroaryl and —OR$_a$ is optionally substituted with one or more substituents independently selected from R$_7$;

R$_7$ represents the group consisting of —OH, —CN, halogen, (C$_1$-C$_4$)alkyl, (C$_3$-C$_7$)cycloalkyl and (C$_1$-C$_6$)alkyl-(C$_3$-C$_7$)cycloalkyl-.

DETAILED DESCRIPTION OF THE INVENTION

Definitions

The term "alkyl" is intended to indicate a radical obtained when one hydrogen atom is removed from a branched or linear hydrocarbon. Said alkyl comprises 1-6, preferably 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

The term "alkylcycloalkyl" is intended to indicate an alkyl radical appended to the parent molecular moiety through a cycloalkyl group, as defined herein.

The term "($C_1$-$C_6$)alkyl-($C_3$-$C_7$)cycloalkyl" is intended to indicate an "($C_1$-$C_6$)alkyl radical appended to the parent molecular moiety through a ($C_3$-$C_7$)cycloalkyl group, as defined herein.

The term "alkylheteroaryl" is intended to indicate an alkyl radical appended to the parent molecular moiety through a heteroaryl group, as defined herein.

The term "alkylheterocycloalkyl" is intended to indicate an alkyl radical appended to the parent molecular moiety through a heterocycloalkyl group, as defined herein.

The terms "alkyloxy" and "alkoxy" are intended to indicate a radical of the formula —OR, wherein R is alkyl as indicated herein, wherein the alkyl group is appended to the parent molecular moiety through an oxygen atom, e.g. methoxy (—$OCH_3$), ethoxy (—$OCH_2CH_3$), n-propoxy, iso-propoxy, butoxy, tert-butoxy, and the like.

The term "aryl" is intended to indicate a radical of aromatic carbocyclic rings comprising 6-13 carbon atoms, such as 6-9 carbon atoms, such as 6 carbon atoms, in particular 5- or 6-membered rings, including fused carbocyclic rings with at least one aromatic ring. If the aryl group is a fused carbocyclic ring, the point of attachment of the aryl group to the parent molecular moiety may be through an aromatic or through an aliphatic carbon atom within the aryl group. Representative examples of aryl include, but are not limited to phenyl, naphthyl, indenyl, indanyl, dihydronaphthyl, tetrahydronaphthyl and fluorenyl.

The term "cyano" is intended to indicate a —CN group attached to the parent molecular moiety through the carbon atom.

The term "cycloalkyl" is intended to indicate a saturated cycloalkane hydrocarbon radical, including polycyclic radicals such as bicyclic radicals, comprising 3-7 carbon atoms, preferably 3-6 carbon atoms, such as 3-5 carbon atoms or such as 3-4 carbon atoms, e.g. cyclopropyl, cyclobutyl, cyclopentyl, cyclohexyl, or cycloheptyl.

The term "cycloalkylalkyl" is intended to indicate a cycloalkyl radical appended to the parent molecular moiety through an alkyl group, as defined herein.

The term "($C_3$-$C_7$)cycloalkyl($C_1$-$C_4$)alkyl" is intended to indicate a ($C_3$-$C_7$)cycloalkyl radical appended to the parent molecular moiety through an ($C_1$-$C_4$)alkyl group, as defined herein.

The term "($C_3$-$C_7$)cycloalkyl($C_1$-$C_6$)alkyl" is intended to indicate a ($C_3$-$C_7$)cycloalkyl radical appended to the parent molecular moiety through an ($C_1$-$C_6$)alkyl group, as defined herein.

The term "haloalkyl" is intended to indicate an alkyl group as defined herein substituted with one or more halogen atoms as defined herein, e.g. fluoro or chloro, such as difluoromethyl or trifluoromethyl.

"($C_1$-$C_4$)haloalkyl" is intended to indicate a ($C_1$-$C_4$)alkyl group as defined herein substituted with one or more halogen atoms as defined herein, e.g. fluoro or chloro, such as difluoromethyl or trifluoromethyl.

The term "halogen" is intended to indicate a substituent from the $7^{th}$ main group of the periodic table, such as fluoro, chloro and bromo.

The term "heteroaryl" is intended to indicate radicals of monocyclic heteroaromatic rings.

The term "(5-6 membered)heteroaryl" is intended to indicate radicals of monocyclic heteroaromatic rings, comprising 5- or 6-membered rings, i.e. having a ring size of 5 or 6 atoms, which contain from 1-5 carbon atoms and from 1-5 heteroatoms selected from oxygen, sulphur and nitrogen, such as 1 heteroatom, such as 1-2 heteroatoms, such as 1-3 heteroatoms, such as 1-4 heteroatoms selected from oxygen, sulphur and nitrogen. The heteroaryl radical may be connected to the parent molecular moiety through a carbon atom or a nitrogen atom contained anywhere within the heteroaryl group. Representative examples of (5-6 membered)heteroaryl groups include, but are not limited to furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, tetrazolyl, thiadiazolyl, thiazolyl, thienyl, triazolyl.

The term "(5-membered)heteroaryl" is intended to indicate radicals of monocyclic heteroaromatic rings, comprising 5-membered rings, i.e. having a ring size of 5 atoms, which contain from 1-4 carbon atoms and from 1-4 heteroatoms selected from oxygen, sulphur and nitrogen, such as 1 heteroatom, such as 1-2 heteroatoms, such as 1-3 heteroatoms, such as 1-4 heteroatoms selected from oxygen, sulphur and nitrogen. The heteroaryl radical may be connected to the parent molecular moiety through a carbon atom or a nitrogen atom contained anywhere within the heteroaryl group. Representative examples of (5-membered)heteroaryl groups include, but are not limited to furanyl, imidazolyl, isothiazolyl, isoxazolyl, oxadiazolyl, oxazolyl, pyrazolyl, pyrrolyl, tetrazolyl, thiadiazolyl, thiazolyl, thienyl, triazolyl.

The term "heteroarylalkyl" is intended to indicate a heteroaryl radical appended to the parent molecular moiety through an alkyl group, as defined herein.

The term "(5-6 membered)heteroaryl-($C_1$-$C_4$)alkyl" is intended to indicate a "(5-6 membered)heteroaryl radical appended to the parent molecular moiety through an ($C_1$-$C_4$)alkyl group, as defined herein.

The term "heterocycloalkyl" is intended to indicate a cycloalkane radical as described herein, wherein one or more carbon atoms are replaced by heteroatoms.

The term "(3-7 membered)heterocycloalkyl" is intended to indicate a cycloalkane radical as described herein, wherein one or more carbon atoms are replaced by heteroatoms, having a ring size of 3-7 atoms, comprising 1-6 carbon atoms, e.g. 2-5 or 2-4 carbon atoms, further comprising 1-6 heteroatoms, preferably 1, 2, or 3 heteroatoms, selected from O, N, or S, such as 1 heteroatom or such as 1-2 heteroatoms selected from O, N, or S; such as 4-membered heterocycloalkyl comprising 3 carbon atoms and 1 heteroatom selected from oxygen, nitrogen and sulphur; such as (5-6 membered)heterocycloalkyl comprising 3-5 carbon atoms and 1-2 heteroatoms selected from oxygen, nitrogen and sulphur, such as (5-membered)heterocycloalkyl comprising 4 carbon atoms and 1 heteroatom selected from oxygen, nitrogen and sulphur, such as (6-membered)heterocycloalkyl comprising 4-5 carbon atoms and 1-2 heteroatoms selected from oxygen, nitrogen and sulphur. The heterocycloalkyl radical may be connected to the parent molecular moiety through a carbon atom or a nitrogen atom contained anywhere within the heterocycloalkyl group. Representative examples of (3-7 membered)heterocycloalkyl groups include, but are not limited to azepanyl, azetidinyl, aziridinyl, dioxolanyl, dioxolyl, imidazolidinyl, morpholinyl, oxetanyl, piperazinyl, piperidinyl, pyrrolidinyl tetrahydrofuranyl, tetrahydropyranyl, tetrahydrothiophenyl, tetrahydrothiopyranyl, thietanyl.

The term "heterocycloalkylalkyl" is intended to indicate a heterocycloalkyl radical appended to the parent molecular moiety through an alkyl group, as defined herein.

The term "(3-7 membered)heterocycloalkyl-($C_1$-$C_4$)alkyl" is intended to indicate a "(3-7 membered)heterocycloalkyl appended to the parent molecular moiety through an ($C_1$-$C_4$)alkyl group, as defined herein.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-10 carbon atoms, and preferably comprises 1-8, e.g. 1-6, e.g. 1-4, e.g. 1-3, e.g. 1-2 carbon atoms. The term includes alkyl, alkenyl, cycloalkyl, cycloalkenyl, alkynyl and aryl, as indicated herein.

The number of carbon atoms in a hydrocarbon radical (e.g. alkyl and cycloalkyl, as indicated below) is indicated by the prefix "$(C_a\text{-}C_b)$", wherein a is the minimum number and b is the maximum number of carbons in the hydrocarbon radical. Thus, for example $(C_1\text{-}C_4)$alkyl is intended to indicate an alkyl radical comprising from 1 to 4 carbon atoms, $(C_1\text{-}C_6)$alkyl is intended to indicate an alkyl radical comprising from 1 to 6 carbon atoms and $(C_3\text{-}C_7)$cycloalkyl is intended to indicate a cycloalkyl radical comprising from 3 to 7 carbon ring atoms.

The term "hydroxyalkyl" is intended to indicate an alkyl group as defined above substituted with one or more hydroxy, e.g. hydroxymethyl, hydroxyethyl, hydroxypropyl.

The term "oxo" is intended to indicate an oxygen atom which is connected to the parent molecular moiety via a double bond (=O).

When two or more of the above defined terms are used in combination, such as arylalkyl, heteroarylalkyl, cycloalkylalkyl and the like, it is to be understood that the first mentioned radical is a substituent on the latter mentioned radical, where the point of attachment to the parent molecular moiety is on the latter radical.

The group C(O) is intended to represent a carbonyl group (C=O)

If substituents are described as being independently selected from a group, each substituent is selected independent of the other. Each substituent may therefore be identical or different from the other substituent(s).

The term "optionally substituted" means "unsubstituted or substituted", and therefore the general formulas described herein encompasses compounds containing the specified optional substituent(s) as well as compounds that do not contain the optional substituent(s).

The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroacetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic, fumaric and ethylenediaminetetraacetic acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, hydroxy-lower alkylamines, cycloalkylamines, or benzylamines, or L-arginine or L-lysine. Further examples of pharmaceutical acceptable salts are listed in Berge, S. M.; J. Pharm. Sci.; (1977), 66(1), 1-19, which is incorporated herein by reference.

The terms "ROR gamma" and "RORγ" are used to describe RORγ1 and/or RORγt

The term "solvate" is intended to indicate a species formed by interaction between a compound, e.g. a compound of formula I, and a solvent, e.g. alcohol, glycerol or water, wherein said species are in an amorphous or in a crystalline form. When water is the solvent, said species is referred to as a hydrate.

The term "protic solvent" is intended to indicate a solvent which has an acidic hydrogen, such as water, or such as alcohols, e.g. methanol, ethanol or isopropanol.

The term "aprotic solvent" is intended to indicate a solvent which does not have an acidic hydrogen, such as for example dichloromethane, acetonitrile, dimethylformamide, dimethyl sulfoxide or acetone.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

Unless otherwise indicated, all exact values provided herein are representative of corresponding approximate values, e.g. exact exemplary values provided with respect to a particular measurement can be considered to also provide a corresponding approximate measurement, modified by "about" where appropriate.

All references, including publications, patent applications and patents, cited herein are hereby incorporated by reference in their entirety and to the same extent as if each reference were individually and specifically indicated to be incorporated by reference, regardless of any separately provided incorporation of particular documents made elsewhere herein.

EMBODIMENTS OF THE INVENTION

In one or more embodiments of the invention X represents N.

In one or more embodiments of the invention X represents CH.

In one or more embodiments of the invention $R_1$ represents —CN, methyl, ethyl, propyl, cyclopropyl, cyclobutyl, oxetanyl, tetrahydrofuranyl, tetrahydropyranyl, azetidinyl, pyrrolidinyl, oxazolidinyl, morpholinyl, piperidinyl, triazolyl, pyrrazolyl, isoxazolyl, thiadiazolyl or oxadiazolyl.

In one or more embodiments of the invention $R_2$ represents chloro, methyl or difluoromethyl.

In one or more embodiments of the invention $R_3$ represents methyl.

In one or more embodiments of the invention $R_4$ represents methyl.

In one or more embodiments of the invention $R_5$ represents phenyl, propyl, butyl, ethoxy, iso-propyloxy, tert-butyloxy, cyclopropyl, cyclobutyl, cyclopentyl, methylcyclopropyl or cyclobutylmethyl.

In one or more embodiments of the invention $R_6$ represents —OH, —CN, fluoro, —NH2, =O, —S(O)$_2$CH$_3$, methyl, methoxy or hydroxymethyl.

In one or more embodiments of the invention $R_7$ represents fluoro or —OH.

In one or more embodiments of the invention the compound of general formula (I) is selected from the list consisting of 5-[3-[[(3S)-4-benzoyl-3-methyl-piperazin-1-yl]methyl]-5-chloro-2-methyl-anilino]-1,3,4-oxadiazole-2-carbonitrile,

[(2S)-4-[[5-chloro-3-[[5-(methoxymethyl)-1,3,4-oxadiazol-2-yl]amino]-2-methyl-phenyl]methyl]-2-methyl-piperazin-1-yl]-phenyl-methanone,

[(2S)-4-[[5-chloro-2-methyl-3-[(5-tetrahydrofuran-3-yl-1,3,4-oxadiazol-2-yl)amino]phenyl]methyl]-2-methyl-piperazin-1-yl]-phenyl-methanone,

[(2S)-4-[[5-chloro-2-methyl-3-[(5-tetrahydrofuran-2-yl-1,3,4-oxadiazol-2-yl)amino]phenyl]methyl]-2-methyl-piperazin-1-yl]-phenyl-methanone

[(2S)-4-[[5-chloro-3-[(5-cyclopropyl-1,3,4-oxadiazol-2-yl)amino]-2-methyl-phenyl]methyl]-2-methyl-piperazin-1-yl]-phenyl-methanone,

[(2S)-4-[[5-chloro-3-[[5-(1-hydroxycyclopropyl)-1,3,4-oxadiazol-2-yl]amino]-2-methyl-phenyl]methyl]-2-methyl-piperazin-1-yl]-phenyl-methanone, 3-[5-[3-[[(3S)-4-benzoyl-3-methyl-piperazin-1-yl]methyl]-5-chloro-2-methyl-anilino]-1,3,4-oxadiazol-2-yl]propanenitrile, 3-[5-[3-[[(3S)-4-benzoyl-3-methyl-piperazin-1-yl]methyl]-5-chloro-2-methyl-anilino]-1,3,4-oxadiazol-2-yl]propanenitrile, 1-[(2S)-4-[[5-chloro-3-[[5-(methoxymethyl)-1,3,4-oxadiazol-2-yl]amino]-2-methyl-phenyl]methyl]-2-methyl-piperazin-1-yl]-2,2-difluoro-butan-1-one,

[(2S)-4-[[5-chloro-3-[[5-(methoxymethyl)-1,3,4-oxadiazol-2-yl]amino]-2-methyl-phenyl]methyl]-2-methyl-piperazin-1-yl]-(2-fluorophenyl)methanone,

[(2S)-4-[[5-chloro-3-[[5-(methoxymethyl)-1,3,4-oxadiazol-2-yl]amino]-2-methyl-phenyl]methyl]-2-methyl-piperazin-1-yl]-(3,3-difluorocyclopentyl)methanone, (2S)-1-[(2S)-4-[[5-chloro-3-[[5-(methoxymethyl)-1,3,4-oxadiazol-2-yl]amino]-2-methyl-phenyl]methyl]-2-methyl-piperazin-1-yl]-2-methyl-butan-1-one,

[(2S)-4-[[5-chloro-3-[[5-(methoxymethyl)-1,3,4-oxadiazol-2-yl]amino]-2-methyl-phenyl]methyl]-2-methyl-piperazin-1-yl]-cyclobutyl-methanone,

[(2S)-4-[[5-chloro-3-[[5-(methoxymethyl)-1,3,4-oxadiazol-2-yl]amino]-2-methyl-phenyl]methyl]-2-methyl-piperazin-1-yl]-cyclopentyl-methanone, cyclobutyl-[(2S)-4-[[2,5-dimethyl-3-[(5-methyl-1,3,4-oxadiazol-2-yl)amino]phenyl]methyl]-2-methyl-piperazin-1-yl]methanone, 2-[5-[3-[[(3S)-4-(cyclobutanecarbonyl)-3-methyl-piperazin-1-yl]methyl]-2,5-dimethyl-anilino]-1,3,4-oxadiazol-2-yl]acetonitrile, 2-[5-[3-[[(3S)-4-(cyclopropanecarbonyl)-3-methyl-piperazin-1-yl]methyl]-2,5-dimethyl-anilino]-1,3,4-oxadiazol-2-yl]acetonitrile, 2-[5-[3-[[(3S)-4-(3,3-difluorocyclopentanecarbonyl)-3-methyl-piperazin-1-yl]methyl]-2,5-dimethyl-anilino]-1,3,4-oxadiazol-2-yl]acetonitrile, 2-[5-[5-chloro-3-[[4-(cyclopentanecarbonyl)-3-methyl-piperazin-1-yl]methyl]-2-methyl-anilino]-1,3,4-oxadiazol-2-yl]acetonitrile, cyclobutyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone, cyclobutyl-[(2S)-4-[[3-[[5-[(1S)-1-hydroxyethyl]-1,3,4-oxadiazol-2-yl]amino]-2,5-dimethyl-phenyl]methyl]-2-methyl-piperazin-1-yl]methanone, 2,2-difluoro-1-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]butan-1-one, cyclopropyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone,

[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]-(2-methylcyclopropyl)methanone, cyclopentyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone, (3,3-difluorocyclopentyl)-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone, 2-cyclobutyl-1-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]ethanone, cyclobutyl-[(2S)-4-[[5-(difluoromethyl)-3-[[5-[(1S)-1-hydroxyethyl]-1,3,4-oxadiazol-2-yl]amino]-2-methyl-phenyl]methyl]-2-methyl-piperazin-1-yl]methanone, tert-butyl (2S)-4-[[3-[[5-[(1S)-1-hydroxyethyl]-1,3,4-oxadiazol-2-yl]amino]-2,5-dimethyl-phenyl]methyl]-2-methyl-piperazine-1-carboxylate, tert-butyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate, tert-butyl (2S)-4-[[2,5-dimethyl-3-[[5-(3-methyltriazol-4-yl)-1,3,4-oxadiazol-2-yl]amino]phenyl]methyl]-2-methyl-piperazine-1-carboxylate, tert-butyl (2S)-4-[[2,5-dimethyl-3-[[5-(2-methylpyrazol-3-yl)-1,3,4-oxadiazol-2-yl]amino]phenyl]methyl]-2-methyl-piperazine-1-carboxylate, tert-butyl (2S)-4-[[3-[(5-isoxazol-5-yl-1,3,4-oxadiazol-2-yl)amino]-2,5-dimethyl-phenyl]methyl]-2-methyl-piperazine-1-carboxylate, tert-butyl (2S)-4-[[2,5-dimethyl-3-[[5-(1,2,5-thiadiazol-3-yl)-1,3,4-oxadiazol-2-yl]amino]phenyl]methyl]-2-methyl-piperazine-1-carboxylate, tert-butyl (2S)-4-[[2,5-dimethyl-3-[[5-(4-methyl-1,2,5-oxadiazol-3-yl)-1,3,4-oxadiazol-2-yl]amino]phenyl]methyl]-2-methyl-piperazine-1-carboxylate, isopropyl (2S)-4-[[2,5-dimethyl-3-[(5-methyl-1,3,4-oxadiazol-2-yl)amino]phenyl]methyl]-2-methyl-piperazine-1-carboxylate, isopropyl (2S)-4-[[3-[[5-[(1S)-1-amino-2-hydroxy-ethyl]-1,3,4-oxadiazol-2-yl]amino]-2,5-dimethyl-phenyl]methyl]-2-methyl-piperazine-1-carboxylate, isopropyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate, isopropyl (2S)-4-[[3-[[5-[(1S)-1-aminopropyl]-1,3,4-oxadiazol-2-yl]amino]-5-chloro-2-methyl-phenyl]methyl]-2-methyl-piperazine-1-carboxylate, isopropyl (2S)-4-[[5-chloro-3-[[5-[(1R)-1-hydroxyethyl]-1,3,4-oxadiazol-2-yl]amino]-2-methyl-phenyl]methyl]-2-methyl-piperazine-1-carboxylate, isopropyl (2S)-4-[[5-chloro-2-methyl-3-[[5-(oxetan-3-yl)-1,3,4-oxadiazol-2-yl]amino]phenyl]methyl]-2-methyl-piperazine-1-carboxylate, isopropyl (2S)-4-[[3-[[5-[(1S,2R)-1-amino-2-hydroxy-propyl]-1,3,4-oxadiazol-2-yl]amino]-2,5-dimethyl-phenyl]methyl]-2-methyl-piperazine-1-carboxylate, isopropyl (2S)-4-[[3-[[5-(cyanomethyl)-1,3,4-oxadiazol-2-yl]amino]-2,5-dimethyl-phenyl]methyl]-2-methyl-piperazine-1-carboxylate, isopropyl (2S)-4-[[5-(difluoromethyl)-3-[[5-[(1S)-1-hydroxyethyl]-1,3,4-oxadiazol-2-yl]amino]-2-methyl-phenyl]methyl]-2-methyl-piperazine-1-carboxylate, isopropyl (2S)-4-[[5-chloro-2-methyl-3-[(5-tetrahydropyran-3-yl-1,3,4-oxadiazol-2-yl)amino]phenyl]methyl]-2-methyl-piperazine-1-carboxylate, isopropyl (2S)-4-[[5-chloro-3-[[5-(1-hydroxycyclopropyl)-1,3,4-oxadiazol-2-yl]amino]-2-methyl-phenyl]methyl]-2-methyl-piperazine-1-carboxylate, isopropyl (2S)-4-[[5-chloro-3-[[5-[1-(hydroxymethyl)cyclopropyl]-1,3,4-oxadiazol-2-yl]amino]-2-methyl-phenyl]methyl]-2-methyl-piperazine-1-carboxylate, isopropyl (2S)-4-[[5-chloro-2-methyl-3-[[5-(2,2,2-trifluoro-1-hydroxy-ethyl)-1,3,4-oxadiazol-2-yl]amino]phenyl]methyl]-2-methyl-piperazine-1-carboxylate, isopropyl (2S)-4-[[5-chloro-2-methyl-3-[[5-(2-oxopyrrolidin-3-yl)-1,3,4-oxadiazol-2-yl]amino]phenyl]methyl]-2-methyl-piperazine-1-carboxylate, isopropyl (2S)-4-[[3-[[5-[(1S)-1-aminoethyl]-1,3,4-oxadiazol-2-yl]amino]-2,5-dimethyl-phenyl]methyl]-2-methyl-piperazine-1-carboxylate, isopropyl (2S)-4-[[5-(difluoromethyl)-3-[[5-[(1R)-1-hydroxyethyl]-1,3,4-oxadiazol-2-yl]amino]-2-methyl-phenyl]methyl]-2-methyl-piperazine-1-carboxylate, isopropyl (2S)-4-[[2,5-dimethyl-3-[[5-(5-oxopyrrolidin-3-yl)-1,3,4-oxadiazol-2-yl]amino]phenyl]methyl]-2-methyl-piperazine-1-carboxylate, isopropyl (2S)-4-[[2,5-dimethyl-3-[[5-[(5S)-2-oxooxazolidin-5-yl]-1,3,4-oxadiazol-2-yl]amino]phenyl]methyl]-2-methyl-piperazine-1-carboxylate, isopropyl (2S)-4-[[5-chloro-2-methyl-3-[[5-[(2S)-4-oxoazetidin-2-yl]-1,3,4-oxadiazol-2-yl]amino]phenyl]methyl]-2-methyl-piperazine-1-carboxylate, isopropyl (2S)-4-[[2,5-dimethyl-3-[[5-(4-methyl-1,2,5-oxadiazol-3-yl)-1,3,4-oxadiazol-2-yl]amino]phenyl]methyl]-2-methyl-piperazine-1-carboxylate, isopropyl (2S)-4-[[2,5-dimethyl-3-[[5-[(3S)-morpholin-3-yl]-1,3,4-oxadiazol-2-yl]amino]phenyl]methyl]-2-methyl-piperazine-1-carboxylate dihydrochloride, isopropyl (2S)-4-[[3-[[5-[(1R)-1-hydroxyethyl]-1,3,4-oxadiazol-2-yl]amino]-2,5-dimethyl-phenyl]methyl]-2-methyl-piperazine-1-carboxylate, isopropyl (2S)-4-[[2,5-dimethyl-3-[[5-[(2R)-3,3,3-trifluoro-2-hydroxy-propyl]-1,3,4-oxadiazol-2-yl]amino]phenyl]methyl]-2-methyl-piperazine-1-carboxylate, isopropyl (2S)-4-[[2,5-dimethyl-3-[[5-(2-oxo-4-piperidyl)-1,3,4-oxadiazol-2-yl]amino]phenyl]methyl]-2-methyl-piperazine-1-carboxylate, isopropyl (2S)-4-[[2,5-dimethyl-3-[[5-(2-methylpyrazol-3-yl)-1,3,4-oxadiazol-2-yl]amino]phenyl]methyl]-2-methyl-piperazine-1-carboxylate, isopropyl (2S)-4-[[3-[[5-[(2S)-2-hydroxypropyl]-1,3,4-oxadiazol-2-yl]amino]-2,5-dimethyl-phenyl]methyl]-2-methyl-piperazine-1-carboxylate, isopropyl (2S)-4-[[3-[[5-[(2R)-2-hydroxypropyl]-1,3,4-oxadiazol-2-yl]amino]-2,5-dimethyl-phenyl]methyl]-2-methyl-piperazine-1-carboxylate, isopropyl (2S)-4-[[3-[[5-[(1S)-1-hydroxypropyl]-1,3,4-oxadiazol-2-yl]amino]-2,5-dimethyl-phenyl]methyl]-2-methyl-piperazine-1-carboxylate, isopropyl (2S)-4-[[5-chloro-3-[[5-[(1S)-1-hydroxyethyl]-1,3,4-oxadiazol-2-yl]amino]-2-methyl-phenyl]methyl]-2-methyl-piperazine-1-carboxylate, isopropyl (2S)-4-[[5-chloro-3-[[5-(3-hydroxycyclobutyl)-1,3,4-oxadiazol-2-yl]amino]-2-methyl-phenyl]methyl]-2-methyl-piperazine-1-carboxylate, isopropyl (2S)-4-[[2,5-dimethyl-3-[[5-[(2S)-1-methylsulfonylpyrrolidin-2-yl]-1,3,4-oxadiazol-2-yl]amino]phenyl]methyl]-2-methyl-piperazine-1-carboxylate, isopropyl (2S)-4-[[3-[[5-[(1S)-1-hydroxyethyl]-1,3,4-oxadiazol-2-yl]amino]-2,5-dimethyl-phenyl]methyl]-2-methyl-piperazine-1-carboxylate, isopropyl (2S)-4-[[5-chloro-2-methyl-3-[[5-(5-oxopyrrolidin-3-yl)-1,3,4-oxadiazol-2-yl]amino]phenyl]methyl]-2-methyl-piperazine-1-carboxylate, isopropyl (2S)-4-[[3-[[5-[(1R)-1-aminoethyl]-1,3,4-oxadiazol-2-yl]amino]-2,5-dimethyl-phenyl]methyl]-2-methyl-piperazine-1-carboxylate 2,2,2-trifluoroethyl (2S)-4-[[5-chloro-3-[[5-(cyanomethyl)-1,3,4-oxadiazol-2-yl]amino]-2-methyl-phenyl]methyl]-2-methyl-piperazine-1-carboxylate, 2,2,2-trifluoroethyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate, ethyl (2S)-4-[[3-[[5-[(1R)-1-hydroxyethyl]-1,3,4-oxadiazol-2-yl]amino]-2,5-dimethyl-phenyl]methyl]-2-methyl-piperazine-1-carboxylate, isopropyl (2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate, isopropyl (2S)-4-[[5-chloro-2-methyl-3-[(5-morpholin-3-yl-1,3,4-oxadiazol-2-yl)amino]phenyl]methyl]-2-methyl-piperazine-1-carboxylate and tert-butyl (2S)-4-[[5-chloro-3-[[5-(hydroxymethyl)oxazol-2-yl]amino]-2-methyl-phenyl]methyl]-2-methyl-piperazine-1-carboxylate or pharmaceutically acceptable salts, hydrates or solvates thereof.

Any combination of two or more embodiments described herein is considered within the scope of the present invention.

The present invention includes all embodiments wherein $R_1$, $R_2$, $R_3$, $R_4$, $R_5$, $R_6$ and $R_7$ are combined in any combination as anywhere described herein.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

If nothing else is indicated the term 'solid' in the description of the examples means that the compound of the invention was prepared as a non-crystalline compound.

Compounds of formula I comprise asymmetrically substituted (chiral) carbon atoms which give rise to the existence of isomeric forms, e.g. enantiomers and possibly diastereomers. The present invention relates to all such isomers, either in optically pure form or as mixtures thereof (e.g. racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases.

Pure stereoisomeric forms may also be derived from the corresponding pure stereoisomeric forms of the appropriate starting materials, provided that the reaction occur stereoselectively or stereospecifically. Preferably, if a specific stereoisomer is desired, said compound will be synthesized by stereoselective or stereospecific methods of preparation. These methods will advantageously employ chiral pure starting materials.

In the compounds of general Formula I, the atoms may exhibit their natural isotopic abundances, or one or more of the atoms may be artificially enriched in a particular isotope having the same atomic number, but an atomic mass or mass number different from the atomic mass or mass number found in nature. The present invention is meant to include all suitable isotopic variations of the compounds of general Formula I. For example, different isotopic forms of hydrogen include $^1H$, $^2H$ and $^3H$ and different isotopic forms of carbon include $^{12}C$, $^{13}C$ and $^{14}C$. Enriching for deuterium ($^2H$) may for example increase in-vivo half-life or reduce dosage regiments, or may provide a compound useful as a standard for characterization of biological samples. Isotopically enriched compounds within general formula I can be prepared by conventional techniques well known to a person skilled in the art or by processes analogous to those described in the general procedures and examples herein using appropriate isotopically enriched reagents and/or intermediates.

In one or more embodiments of the present invention, the compounds of general formula (I) as defined above are useful in therapy and in particular for use in the treatment of psoriasis.

In one or more embodiments of the present invention, the compounds of general formula (I) as defined above are useful in treatment of a disease, disorder or condition, which disease, disorder or condition is responsive of modulation of ROR-gamma.

In one or more embodiments of present invention provides a pharmaceutical composition comprising a compound according to general formula (I) together with one or more other therapeutically active compound(s) together with a pharmaceutically acceptable vehicle or excipient or pharmaceutically acceptable carrier(s).

In one or more embodiments of the present invention, the compounds of general formula (I) are useful in the manufacture of a medicament for the prophylaxis, treatment or amelioration of autoimmune or inflammatory diseases.

In one or more embodiments of the present invention, the compounds of general formula (I) are useful in the manufacture of a medicament for the prophylaxis, treatment or amelioration of psoriasis.

In one or more embodiments of the present invention, the compounds of general formula (I) are useful in a method of preventing, treating or ameliorating autoimmune or inflammatory diseases or conditions, the method comprising administering to a person suffering from at least one of said diseases an effective amount of one or more compounds according to according to general formula (I), optionally together with a pharmaceutically acceptable carrier or one or more excipients, optionally in combination with other therapeutically active compounds.

Besides being useful for human treatment, the compounds of the present invention may also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition.

The invention therefore relates to a pharmaceutical composition comprising a compound of formula I, optionally together with one or more other therapeutically active compound(s), together with a pharmaceutically acceptable excipient, vehicle or carrier(s). The excipient must be "acceptable" in the sense of being compatible with the other ingredients of the composition and not deleterious to the recipient thereof.

Conveniently, the active ingredient comprises from 0.0001-50% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.001 mg and 1000 mg, preferably between 0.01 mg and 250 mg, such as 50-200 mg of a compound of formula I.

A suitable dosage of the compound of the invention will depend, inter alia, on the age and condition of the patient, the severity of the disease to be treated and other factors well known to the practising physician. The compound may be administered either orally, parenterally, topically, transdermally or interdermally+other routes according to different dosing schedules, e.g. daily, weekly or with monthly intervals. In general a single dose will be in the range from 0.001 to 400 mg/kg body weight. The compound may be administered as a bolus (i.e. the entire daily dose is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid, semisolid or liquid pharmaceutical diluents or carriers.

The term "usage unit" in connection with topical use means a unitary, i.e. a single dose, capable of being administered topically to a patient in an application per square centimetre of the treatment area of from 0.001 microgram to 1 mg and preferably from 0.05 microgram to 0.5 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult Goodman & Gilman's *The Pharmacological Basis of Therapeutics,* $12^{th}$ Ed., L. L. Brunton (Ed.), McGraw-Hill 2010, for useful dosages of said compounds.

The administration of a compound of the present invention with one or more other active compounds may be either concomitantly or sequentially.

The formulations include e.g. those in a form suitable for oral, rectal, parenteral (including subcutaneous, intraperitoneal, intramuscular, intraarticular and intravenous), transdermal, intradermal, ophthalmic, topical, nasal, sublingual or buccal administration.

The formulations may conveniently be presented in dosage unit form and may be prepared by but not restricted to any of the methods well known in the art of pharmacy, e.g. as disclosed in Remington, *The Science and Practice of Pharmacy,* 22nd ed., 2013. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid, such as ethanol or glycerol; or in the form of a gel, a nano- or microemulsion, an oil-in-water emulsion, a water-in-oil emulsion or other dispensing systems. The oils may be edible oils, such as but not restricted to e.g. cottonseed oil, sesame oil, coconut oil or peanut oil. Suitable dispersing or suspending agents for aqueous suspensions include synthetic or natural surfactants and viscosifying agents such as but not restricted to tragacanth, alginate, acacia, dextran, sodium carboxymethylcellulose, gelatin, methylcellulose, hydroxypropylmethylcellulose, hydroxypropylcellulose, carbomers, polyvinylpyrrolidone, polysorbates, sorbitan fatty acid esters. The active ingredients may also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler, such as e.g. lactose, glucose, mannitol starch, gelatine, acacia gum, tragacanth gum, sodium alginate, calcium phosphates, microcrystalline cellulose, carboxymethylcellulose, methylcellulose, hydroxypropylcellulose, hydroxypropylmethylcellulose, ethylcellulose, hydroxyethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent. Freeze dried tablets may be formed in a freeze-dryer from a solution of the drug substance. Suitable filler can be included.

Formulations for rectal administration may be in the form of suppositories in which the compound of the present invention is admixed with low melting point, water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution.

Furthermore, the formulation may contain cosolvent, solubilising agent and/or complexation agents. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical, such as dermal, intradermal or ophthalmic administration include liquid or semisolid preparations such as liniments, lotions, gels, applicants, sprays, foams, film forming systems, microneedles, micro- or nano-emulsions, oil-in-water or water-in-oil emulsions such as creams, ointments or pastes; or solutions or suspensions such as drops.

For topical administration, the compound of formula I may typically be present in an amount of from 0.001 to 20% by weight of the composition, such as 0.01% to about 10%, but may also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, penetration enhancing agents, solubility enhancing agents preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of autoimmune or inflammatory diseases such as psoriasis, psoriatic arthritis, multiple sclerosis, rheumatoid arthritis, crohns disease, alopecia areata, contact dermatitis, spondyloarthritis; and cancers.

Methods of Preparation

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used. The compounds of the present invention or any intermediate may be purified if required using standard methods well known to a synthetic organist chemist, e.g. methods described in "Purification of Laboratory Chemicals", 6$^{th}$ ed. 2009, W. Amarego and C. Chai, Butterworth-Heinemann. Starting materials are either known compounds, commercially available, or they may be prepared by routine synthetic methods well known to a person skilled in the art.

Synthetic Routes

The following schemes illustrate the preparation of compounds of the formula (I), throughout which $R_1$, $R_2$, $R_3$, $R_4$, $R_5$ are as described above:

When X=N,

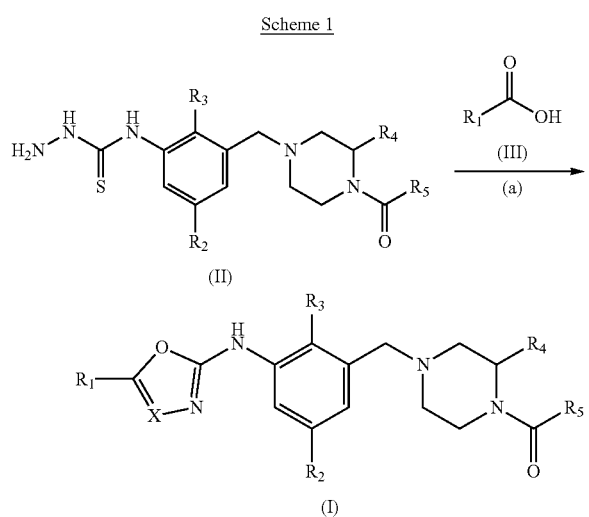

Acids suitable for use as compound (III) are commercially available, are known in the literature or can be prepared by standard methods.

Step (a): Acid (III) is reacted with aminothiourea (II) to give the compound of formula (I). This reaction is carried out by standard methods.

Coupling may be undertaken by using either;
(i) The acid chloride derivative of acid (III)+aminothiourea (II), with an excess of base in a suitable solvent, then desulfurative cyclisation with WSCDI or DCC in DCM, THF or DMSO with or without heating; or tosyl chloride and excess pyridine in THF at 65° C.
(ii) The acid (III)+aminothiourea (II), with WSCDI or DCC in DCM, THF or DMSO with or without heating; or tosyl chloride and excess pyridine in THF at 65° C.

Typically the conditions are as follows:
(i) acid chloride of acid (III) (generated in-situ or commercial), an excess of aminothiourea (II), optionally with an excess of tertiary amine such as TEA, Hünig's base or NMM, in DCM or THF, without heating for 1 to 24 hrs, then WSDCI in DCM or THF without heating for 1 to 16 hrs
(ii) acid (III), WSCDI or DCC, aminothiourea (II), in THF, DCM without heating or in DMSO at 60° C. for 1 to 16 hrs; or, acid (III), aminothiourea (II), with an excess of pyridine and tosyl chloride in THF at 65° C. for 1-2 hrs.

The preferred conditions are: 1.2 eq. acid (III), 1 eq. aminothiourea (II), 4 eq. WSCDI in DCM at room temperature for up to 16 hours.

Alternatively, when X=N or CH:
Compound (I) can be prepared as outlined in scheme 1.1

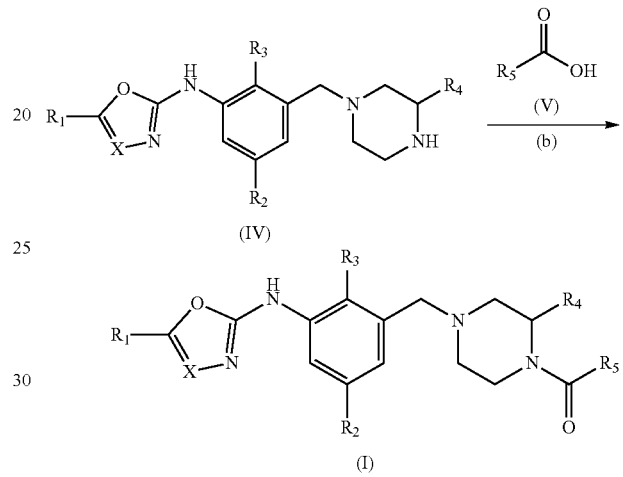

Acids suitable for use as compound (V) are commercially available or known in the literature.

Step (b): Acid (V) is reacted with amine (IV) to give the compound of formula (I). This reaction is carried out by standard methods.

Coupling may be undertaken by using either;
(i) The acid chloride derivative of acid (V)+amine (IV), with an excess of base in a suitable solvent, or
(ii) acid (V), amine (IV), HATU with an excess of NMM, TEA, Hünig's base in THF or DMF at room temperature for 4 to 16 hrs; or acid (V), WSCDI/DCC and HOBT/HOAT, amine (IV), with an excess of NMM, TEA, Hünig's base in THF, DCM or EtOAc, at room temperature for 4 to 16 hrs.

The preferred conditions are: 1.0 eq. acid (V), 1.0 eq. amine (IV), 1.5 eq. HATU and an excess of in DMF at room temperature for up to 16 hours.

Alternatively, when X=N or CH and $R_5$=ORa:
Compound (I) can be prepared as outlined in scheme 1.2

Scheme 1.2

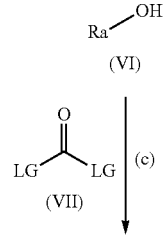

-continued

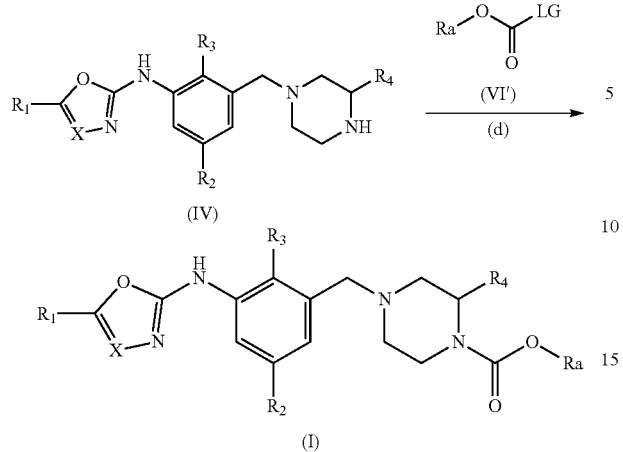

Alcohols suitable for use as compound (VI) are commercially available or are known in the literature.

LG represents a leaving group, typically chloro, compounds suitable for use as compound (VII) are known in the literature or commercially available.

Step (c): The alcohol (IV) is transformed in situ to the reactive intermediate (IV'), if LG is chloro then (IV') is a carbamoyl chloride.

Typical conditions are, (i) The alcohol (VI) in a suitable aprotic solvent with phosgene, triphosgene, diphosgene or CDI in the presence of a tertiary base, without heating for 1 to 24 hr.

Preferred conditions are: The alcohol (VI) in DCM with triphosgene (0.4 eq) with Hunig's base (2 eq.), without heating for 2 hr.

Step (d): The reactive intermediate (VI') is reacted with amine (IV). Typical conditions are, (i) The reactive intermediate (IV') in a suitable aprotic solvent with amine (IV) in the presence of a tertiary base like NMM, Hunig's base, TEA without heating for 1 to 24 hr.

Preferred conditions are: The reactive intermediate (VI') (1.3 eq.) with amine (IV) in with Hunig's base (3 eq) in DCM at low temperature for 2 hr.

When X=N or CH,

Scheme 1.2

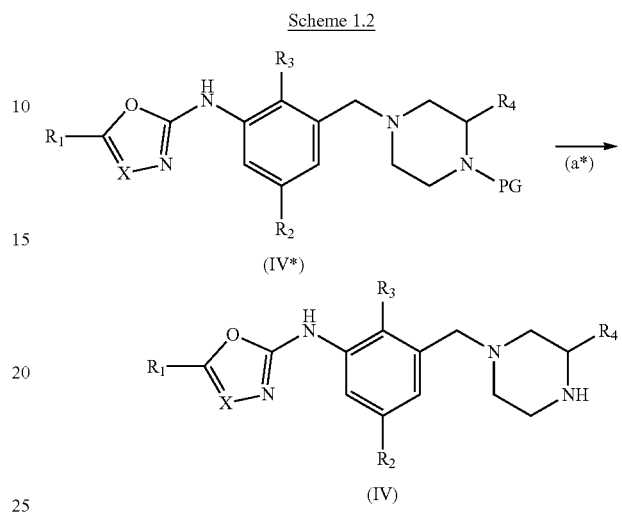

PG represents a suitable protecting group for nitrogen. Standard methodology for nitrogen protecting groups is used, described in for example "Greene's Protective Groups in Organic Synthesis" Fifth edition, Wiley, Ed. P. G. M. Wuts.

Those skilled in the art will appreciate that the compounds of formula (IV*) can have, but are not limited to, structures of the same formula as compound (I). (e.g. $R_5$ is O-tert-butyl or O-benzyl)

Step (a*): Deprotection of compound (IX) is undertaken using standard methodology, as described in "Greene's Protective Groups in Organic Synthesis" Fifth edition, Wiley, Ed. P. G. M. Wuts.

Preferred conditions are: when PG is Boc the is hydrogen chloride in a suitable solvent such as 1,4-dioxane at room temperature for 1-16 hours, or a solution of trifluoroacetic acid in dichloromethane for 1-2 hours.

Scheme 2

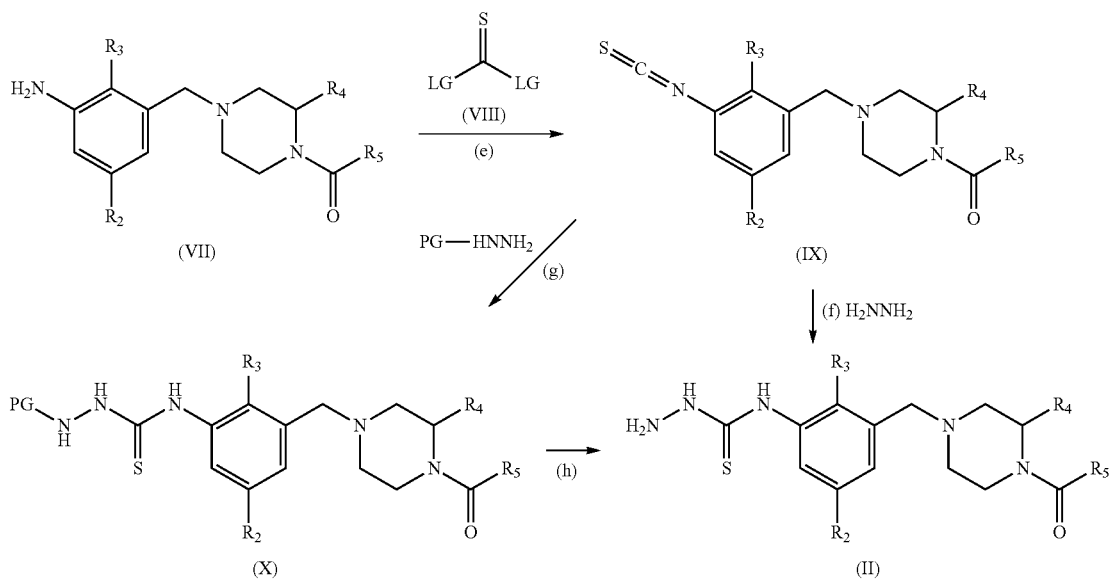

PG represents a suitable protecting group for nitrogen. Standard methodology for nitrogen protecting groups is used, such as that found in textbooks, e.g. "Greene's Protective Groups in Organic Synthesis" Fifth edition, Wiley, Ed. P. G. M. Wuts.

LG represents a leaving group, typically chloro, compounds suitable for use as compound (VII) are known in the literature or commercially available.

Step (e): Amine (VII) is reacted with thiocarbonyl compounds (VIII) to give compounds of formula (IX). This reaction is carried out by standard methods.

Typical conditions are,
(i) Amine (II) in a suitable aprotic solvent with thiocarbonyl dichloride, optionally in the prescence of base, without heating for 1-24 hrs.
(ii) Amine (II) in a suitable aprotic solvent with bis(2-pyridyloxy)methanethione and DMAP, without heating for 1-3 hrs.

Preferred conditions are: The amine and thiocarbonyl dichloride (1 eq) in chloroform and aqueous sodium hydrogen carbonate without heating for 1 hr.

Step (f): Isothiocyanate (IX) is reacted with commercially available hydrazine compositions, such as hydrazine hydrate or hydrazine hydrochloride, to give compounds of formula (II). This reaction is carried out by standard methods.

Preferred conditions are: Isothiocyanate with hydrazine hydrate (1.05 eq) in $CHCl_3$, without heating for 1-16 hrs.

Alternatively,
Compound (II) can be accessed via

Step (g): Isothiocyanate (IX) is reacted with commercially available protected hydrazine to give compounds of formula (II). This reaction is carried out by standard methods.

Preferred conditions are: Isothiocyanate with hydrazine hydrate (1.05 eq) in $CHCl_3$, without heating for 1-16 hrs.

Step (h): Deprotection of compound (IX) is undertaken using standard methodology, as described in "Greene's Protective Groups in Organic Synthesis" Fifth edition, Wiley, Ed. P. G. M. Wuts.

When PG is Boc the preferred method is hydrogen chloride in a suitable solvent such as 1,4-dioxane at room temperature for 1-16 hours, or a solution of trifluoroacetic acid in dichloromethane for 1-2 hours.

Scheme 3

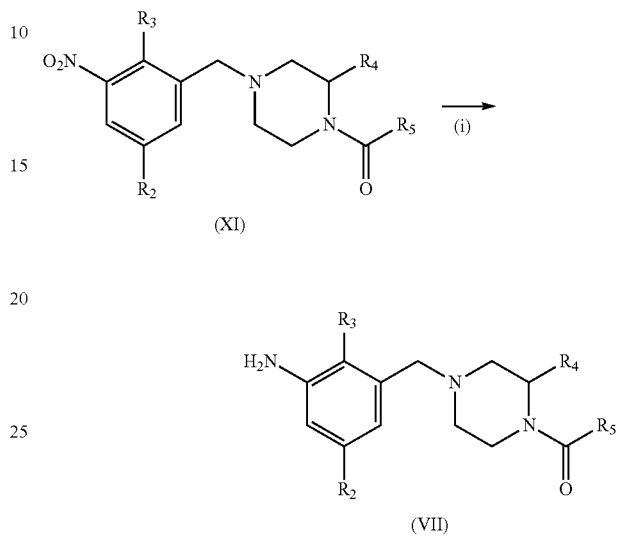

Step (i): Nitro compound (XI) is reacted under reducing conditions to give compounds of formula (VII). This reaction is carried out by standard methods.

Typical conditions are,
(i) Nitro compound (XI) and a suitable Pd catalyst in a protic solvent such as EtOH under a pressure of hydrogen gas, with heating for 4-24 hrs.
(ii) Nitro compound (XI) and Zn or Fe in AcOH with or without aprotic cosolvent without heating for 4-24 hrs.

Preferred conditions are: Nitro compound (XI) and Fe powder (2 eq) in AcOH without heating for 16 hrs.

Scheme 4

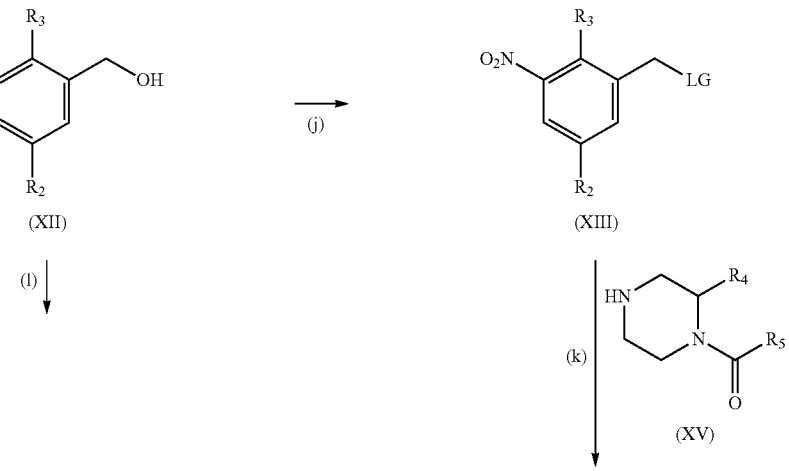

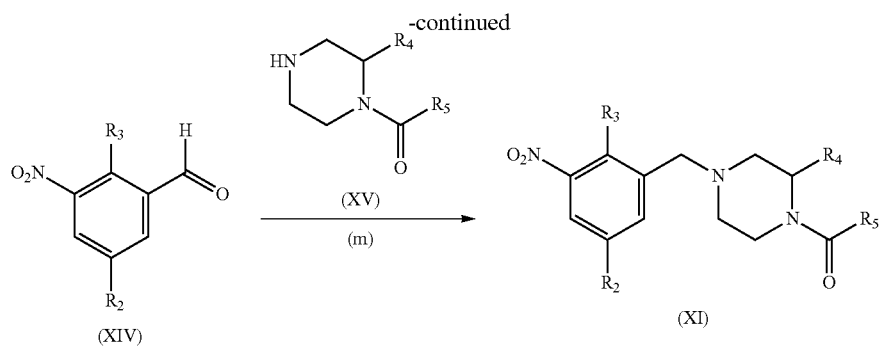

Step (j): Benzylic alcohol (XII) is reacted with a activating reagent to give compounds of the formula (XIII). If LG is a chloro, then (XIII) is a benzyl chloride. If LG is OSO$_2$CH$_3$, then (XIII) is a methanesulfonate.

Typical conditions are,
(i) Benzylic alcohol (XII) and thionyl chloride in a suitable solvent such as THF or DMF, with a base such as TEA or Hunig's base with or without heating for 1-24 hrs.
(ii) Benzylic alcohol (XII) and thionyl chloride in pyridine with or without heating for 1-24 hrs.
(iii) Benzylic alcohol (XII) and methanesulfonyl chloride in a suitable aprotic solvent with a base such as TEA or Hunig's base without heating for 1-24 hrs.

Preferred conditions are: Benzylic alcohol (XII), methanesulfonyl chloride (2 eq) and TEA (3 eq) in DCM at 0-5° C.

Step (k): Benzylic chloride or methanesulfonate (XIII) is reacted with amine (XV) to give compounds of the formula (XI).

Typical conditions are,
(i) Benzylic chloride (XIII), amine (XV) and TEA, Hunig's base, NMM or K$_2$CO$_3$ in suitable aprotic solvent, optionally with KI, with or without heating for 1-24 hrs.
(ii) Benzylic methanesulfonate (XIII), amine (XV) and TEA, Hunig's base, NMM or K$_2$CO$_3$ in suitable aprotic solvent with or without heating for 1-24 hrs.

Preferred conditions are: Benzylic methanesulfonate (XIII), amine (XV), K$_2$CO$_3$ (3 eq) in MeCN from 0-75° C. for 16 hrs.

Alternatively

Compound (II) can be accessed via

Step (l): Benzylic alcohol (XII) is reacted to give compounds of the formula (XIV).

Typical conditions are,
(i) Benzylic alcohol (XII) and MnO$_2$ in a suitable aprotic solvent with or without heating for 1-24 hrs.
(ii) Benzylic alcohol (XII), oxalyl chloride, DMSO and TEA in DCM at −78° C.
(iii) Benzylic alcohol (XII), PCC in a suitable aprotic solvent with or without heating for 1-24 hrs.

Preferred conditions are: Benzylic alcohol (XII) and PCC (1.3 eq) in DCM without heating for 3 hrs.

Step (m): Aldehyde (XIV) is reacted with amine (XV) to give compounds of formula (XI).

Typical conditions are,
(i) Aldehyde (XIV), amine (XV), Ti(OPr-i)$_4$ and NaBH$_4$ in a protic solvent such as MeOH without heating for 1-24 hrs.
(ii) Aldehyde (XIV), amine (XV) with NaHB(OAc)$_3$ in DCM without heating for 1-24 hrs.

Preferred conditions are: Aldehyde (XIV), amine (XV) (1.1 eq) and NaHB(OAc)$_3$ (2 eq) in DCM without heating for 4 hrs.

LG represents a leaving group, typically chloro, compounds suitable for use as compound (VII) are known in the literature or commercially available.

Step (c): The alcohol (IV) is transformed in situ to the reactive intermediate (IV'), if LG is chloro then (IV') is a carbamoyl chloride.

Typical conditions are, (i) The alcohol (VI) in a suitable aprotic solvent with phosgene, triphosgene, diphosgene or CDI in the presence of a tertiary base, without heating for 1 to 24 hr.

Preferred conditions are: The alcohol (VI) in DCM with triphosgene (0.4 eq) with Hunig's base (2 eq.), without heating for 2 hr.

Step (d): The reactive intermediate (VI') is reacted with amine (XVI). Typical conditions are, (i) The reactive intermediate (IV') in a suitable aprotic solvent with amine (XVI) in the presence of a tertiary base like NMM, Hunig's base, TEA without heating for 1 to 24 hr.

Preferred conditions are: The reactive intermediate (VI') (1.3 eq.) with amine (XVI) in with Hunig's base (3 eq) in DCM at low temperature for 2 hr.

Step (n): Carbamate (XVII) is reacted to give compounds of the formula (XV)

Typical conditions are, (i) Carbamate (XVII) in a solution of trifluoroacetic acid in dichloromethane for 1-2 hours.

(ii) Carbamate (XVII) and hydrogen chloride in either DCM or 1,4-dioxane for 1-16 hrs.

Preferred conditions are: Carbamate (XVII) and an excess of HCl in 1,4-dioxane, without heating for 16 hrs.

Scheme 6

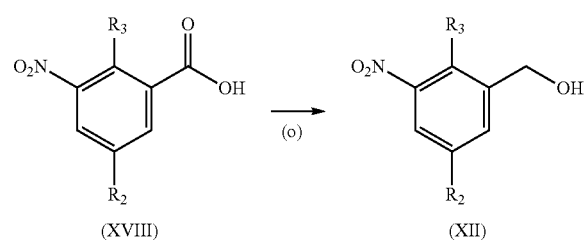

Acids suitable for use as compounds (XVIII) are commercially available, known in the literature or can be prepared from commercially available intermediates using methods outlined in, amongst others, Kuntz et al., J. Med. Chem (2016), 59, 1556-1564, Sun et al., PCT 2004073612, Jackson Bioorg Med Chem Lett. (2011), 21, 3227-3231, or defined as in Scheme 7.

Step (o): Acid (XVIII) is reacted to give compounds of the formula (XII).

Typical conditions are, (i) Acid (XVIII) and borane.tetrahyrofuran complex in suitable aprotic solvent such as THF with heating for 3-16 hrs.

(ii) Acid (XVIII) and LiAlH$_4$ in a suitable aprotic solvent without heating for 1-24 hrs.

Preferred conditions are: Acid (XVIII) and borane THF complex (3 eq) in THF with heat for 3 hrs.

Scheme 7

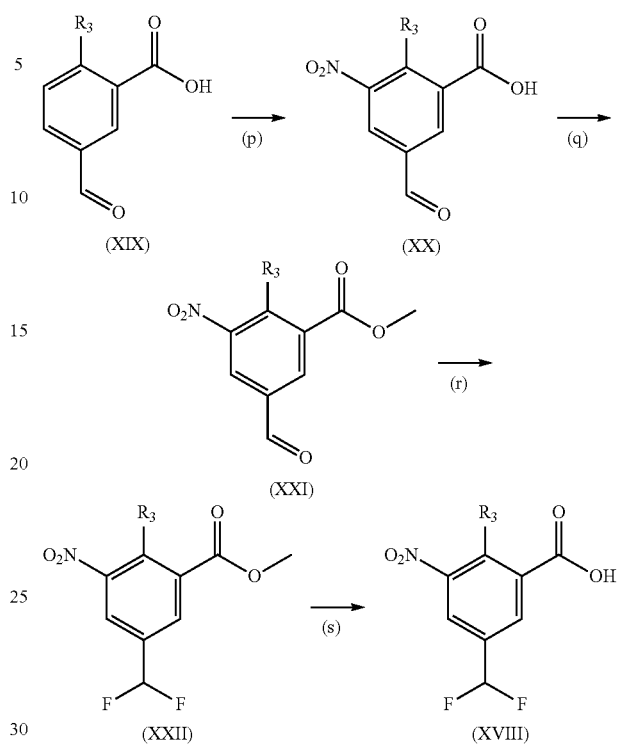

Step (p): Acid (XIX) is reacted to give compounds of formula (XX)

Typical conditions are,
(i) Acid (XIX), c.H$_2$SO$_4$ and c.HNO$_3$ without heating for 1-3 hrs.
(ii) Acid (XIX), c.H$_2$SO$_4$ and KNO$_3$ with heating for 2-16 hrs.

Preferred conditions are: Acid (XIX) in c.H$_2$SO$_4$ with mixture of c.HNO$_3$/c.H$_2$SO$_4$ without heating for 1 hr.

Step (q): Acid (XX) is reacted to give compounds of formula (XXI)

Typical conditions are,
(i) Acid (XX), TMSCHN$_2$ in a suitable aprotic solvent with MeOH and without heating for 2-16 hrs.
(ii) Acid (XX), MeI and K$_2$CO$_3$ or Na$_2$CO$_3$ in a suitable aprotic solvent without heating for 3-24 hrs.

Preferred conditions are: Acid (XX), MeI (2 eq) and K$_2$CO$_3$ (3 eq) in DMF at 0° C. for 3 hrs. Step (r): Aldehyde (XXI) is reacted to give compounds of formula (XXII)

Typical conditions are,
(i) Aldehyde (XXI) and DAST in a suitable solvent such as DCM without heating for 2-24 hrs
(ii) Aldehyde (XXI) and Deoxyfluor in a suitable solvent such as DCM, optionally with protic solvent such as EtOH, with or without heating.

Preferred conditions are: Aldehyde (XXI) and DAST (2 eq) in DCM without heating for 16 hrs.

Step (s): Ester (XXII) is reacted to give compounds of formula (XVIII) Deprotection of compound (XXII) is undertaken using standard methodology, as described in "Greene's Protective Groups in Organic Synthesis" Fifth edition, Wiley, Ed. P. G. M. Wuts.

Preferred conditions are: Ester (XXII) with LiOH in aqueous THF without heating for 5 hrs.

The following scheme illustrates the preparation of compounds of the formula (XXIII) with $R_1$, $R_2$, $R_3$, $R_4$ and $R_5$ as hereinbefore defined:

When X=CH,

Scheme 8

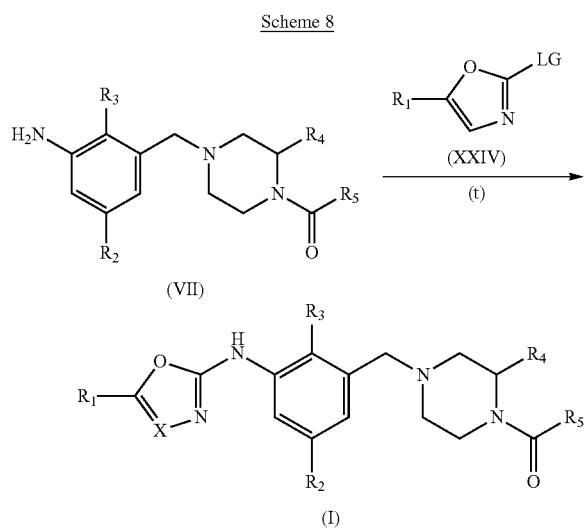

LG represents a leaving group, typically chloro, compounds suitable for use as compound (XXIV) are known in the literature or commercially available, or can be prepared from commercially available intermediates using methods outlined in the literature.

Step (t): Amine (VII) is reacted with oxazole (XXIV) to give compounds of formula (I') When LG is chloro or bromo, typical conditions are,
  (i) Amine (VII), oxazole (XXIV) in a suitable solvent with heating for 0.5-24 hrs.
  (ii) Amine (VII), oxazole (XXIV) in a suitable aprotic solvent, with strong base such as NaH, with heating for 1-24 hrs.

When LG is sulfur, typical conditions are,
  (i) Amine (VII), oxazole (XXIV), $POCl_3$ or $SOCl_2$ with base such as TEA or pyridine with heating for 1-24 hrs.
  (ii) Amine (VII), oxazole (XXIV) with mcpba or Oxone in suitable solvent with heating for 1-24 hrs.

Preferred conditions are: LG is chloro: Amine (VII) and oxazole (XXIV) in IPA with microwave irradiation for 30 min.

General Procedures, Preparations and Examples $^1$H nuclear magnetic resonance (NMR) spectra were recorded at 300 MHz unless otherwise specified. Chemical shift values (δ, in ppm) are quoted relative to internal tetramethylsilane (δ=0.00) standards. The value of a multiplet, either defined doublet (d), triplet (t), quartet (q)) or not (m) at the approximate midpoint is given unless a range is quoted. (br) indicates a broad peak, whilst (s) indicates a singlet. All NMR spectra are recorded in DMSO-$d_6$ unless another solvent is stated.

The organic solvents used were usually anhydrous. The solvent ratios indicated refer to vol:vol unless otherwise noted.

LCMS Method 1: KINETEX-1.7u XB-C18 column, 0.05% FA in water with acetonitrile

LCMS Method 2: ACQUITY UPLC BEH C18 column, 0.05% FA in water with acetonitrile

LCMS Method 3: Xbridge C18 column, 0.01M $NH_4CO_3$ in water with acetonitrile

UPLC-MS Method 4:
Column: Waters Acquity UPLC HSS T3 1.8 µm, 2.1×50 mm.
Column temperature: 60° C.
UV: PDA 210-400 nm.
Injection volume: 2 µl.
Eluents: A: 10 mM Ammonium acetate with 0.1% formic acid.
B: 100% Acetonitrile with 0.1% formic acid.

| Gradient: | Time | A % | B % | Flow |
|---|---|---|---|---|
| | 0.0 | 95 | 5 | 1.2 |
| | 0.9 | 5 | 95 | 1.2 |
| | 0.91 | 5 | 95 | 1.3 |
| | 1.2 | 5 | 95 | 1.3 |
| | 1.21 | 5 | 95 | 1.2 |
| | 1.4 | 95 | 5 | 1.2 |

MS: Electrospray switching between positive and negative ionisation.
Instruments: Waters Aquity UPLC, Waters SQD UPLC-MS Method 5:
Column: Acquity UPLC HSS T3 1.8 µm; 2.1×50 mm
Flow: 0.7 ml/min
Column temp: 40° C.
Mobile phases: A: 10 mM Ammonium acetate+0.1% formic acid
B: 100% Acetonitrile+0.1% formic acid
UV: 240-400 nm
Injection volume: 21 µl

| Gradient: | Time | A % | B % |
|---|---|---|---|
| | 0.0 | 99% A | 1% B |
| | 0.5 | 94% A | 6% B |
| | 1.0 | 94% A | 6% B |
| | 2.6 | 5% A | 95% B |
| | 3.8 | 5% A | 95% B |
| | 3.81 | 99% A | 1% B |
| | 4.8 | 99% A | 1% B |

UPLC (inlet method): XE Metode 7 CM
MS-method: PosNeg_50_1000
Instruments: Waters Acquity UPLC, Waters LCT Premier XE UPLC-MS Method 6:
Column: Acquity UPLC HSS T3 1.8 µm; 2.1×50 mm
Flow: 0.7 ml/min
Column temp: 30° C.
Mobile phases: A: 10 mM Ammonium acetate+0.1% formic acid
B: 100% Acetonitrile+0.1% formic acid
UV: 240-400 nm
Injection volume: 1 µl

| Gradient: | Time | A % | B % |
|---|---|---|---|
| | 0.0 | 99% A | 1% B |
| | 0.5 | 94% A | 6% B |
| | 1.0 | 94% A | 6% B |
| | 2.6 | 5% A | 95% B |
| | 3.8 | 5% A | 95% B |

| Gradient: | Time | A % | B % |
|---|---|---|---|
| | 3.81 | 99% A | 1% B |
| | 4.8 | 99% A | 1% B |

UPLC (inlet method): XEV Metode 1 CM
MS-method: Pos_50_1000 or Neg_50_1000
Instruments: Waters Acquity UPLC, Waters XEVO G2-XS QTof
Basic preparative HPLC conditions:
Column: XBridge Prep C18 5 μm OBD, 19×150 mm
Eluents: Ammonium formate (50 mM)/acetonitrile, 10-100% acetonitrile
Flow: 30 mL/min
Acidic preparative HPLC conditions:
Column: XTerra® RP-18 5 μm OBD, 19×150 mm
Eluents: 0.1% formic acid in water/acetonitrile, 10-100% acetonitrile
Flow: 30 mL/min

LIST OF ABBREVIATIONS

AcOH acetic acid
CDI 1,1'-carbonyldiimidazole
CHCl3 chloroform
c.HNO$_3$ concentrated nitric acid
c.H$_2$SO$_4$ concentrated sulfuric acid
DAST (diethylamino)sulfur trifluoride
DCC dicyclohexylcarbodiimide
DCM dichloromethane
Deoxyfluor bis(2-methoxyethyl)aminosulfur trifluoride
DMAP N,N-dimethyl-4-pyridinamine
DMF dimethylformamide
DMSO dimethylsulfoxide
EtOAc ethyl acetate
EtOH ethanol
FA Formic acid
Fe iron
HATU N,N,N',N'-tetramethyl-O-(1H-benzotriazol-1-yl)uronium hexafluorophosphate
HCl hydrogen chloride
HOAT 1-hydroxy-7-aza benzotriazole
HOBT 1-hydroxybenzotriazole
Hunig's base diisopropylethylamine
IPA propan-2-ol
K$_2$CO$_3$ potassium carbonate
KI potassium iodide
LiAlH$_4$ lithium aluminium hydride
LiOH lithium hydroxide
mcpba 3-chloroperbenzoic acid
MeCN acetonitrile
MeI iodomethane
MeOH methanol
NaBH$_4$ sodium borohydride
NaBH(OAc)$_3$ sodium triacetoxyborohydride
Na$_2$CO$_3$ sodium carbonate
NaH sodium hydride
NMM 4-methylmorpholine
Oxone potassium peroxymonosulfate
PCC pyridinium chlorochromate
Pd palladium
POCl$_3$ phosphorous oxychloride
SOCl$_2$ thionyl chloride
TEA triethylamine
THF tetra hydrofuran
Ti(OPr-i)$_4$ titanium isopropoxide
TMSCHN$_2$ trimethylsilyldiazomethane
TsCl tosyl chloride
WSCDI 3-(ethyliminomethyleneamino)-N,N-dimethyl-propan-1-amine hydrochloride
Zn zinc Scheme 9.1

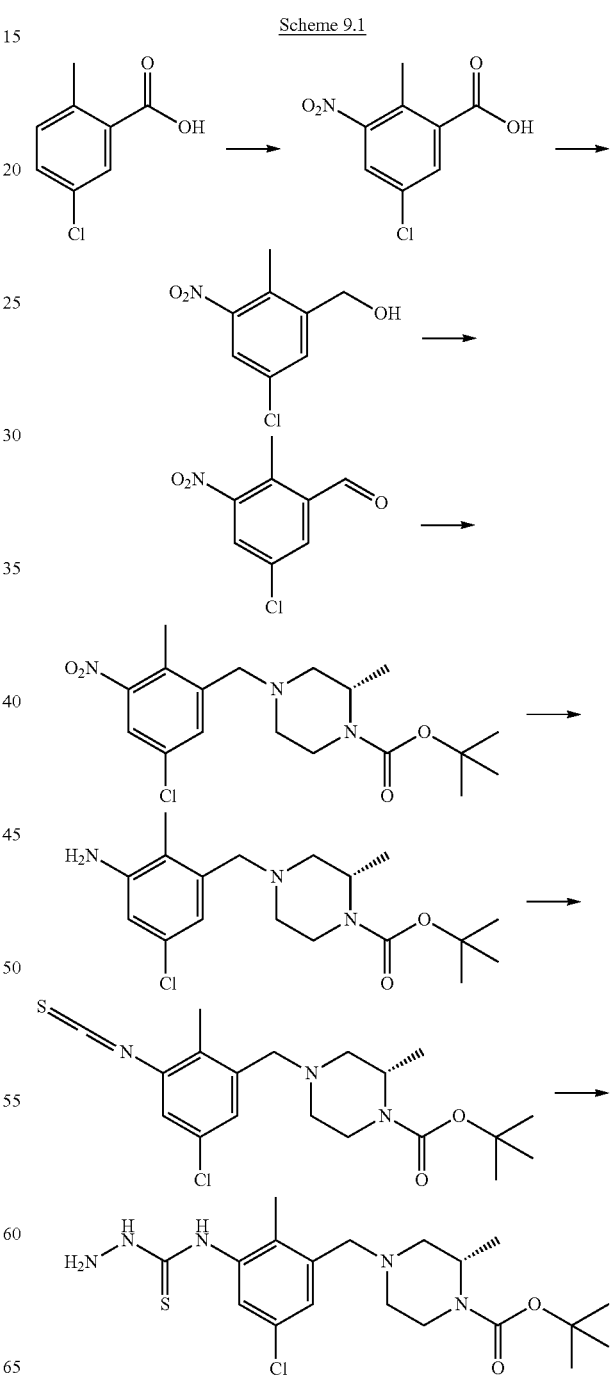

Preparation 1: 5-chloro-2-methyl-3-nitrobenzoic acid

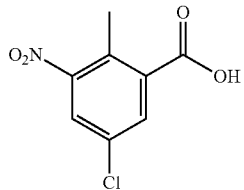

5-Chloro-2-methylbenzoic acid (75.0 g, 439 mmol) was added portion-wise to conc. sulphuric acid (525 ml, 7 vol) at 0° C. After complete addition a solution of conc. nitric acid (41.1 g, 978 mmol, 67%) in conc. sulphuric acid (82.5 ml) was added drop-wise maintaining internal temperature at 0° C. On complete addition the reaction mixture was stirred for an additional 30 mins at 0° C. The mixture was poured onto ice/water and the precipitate was filtered, washed with water, dried and filtered to afford title compound as an off-white solid. (80.0 g, 84.4%, as a mixture of isomers)

$^1$H NMR (400 MHz, CDCl$_3$) δ=8.18 (d, J=2.4 Hz, 1H), 7.90 (d, J=2.4 Hz, 1H), 2.66 (s, 3H). Peaks at 7.55 (d, J=8.3 Hz, 1H), 7.39 (d, J=8.3 Hz, 1H), 2.57 (s, 3H) relate to regioisomer. LCMS Method 1: m/z 214.03 [M−H$^+$]; RT=2.49 min.

Preparation 2: (5-chloro-2-methyl-3-nitro-phenyl)methanol

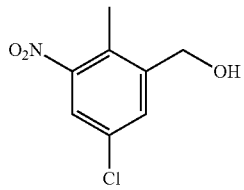

Borane tetrahydrofuran complex solution (1.11 L, 1.0 M in THF) was added to a solution of the acid from Preparation 1 (80.0 g, 371 mmol) drop-wise at 0° C. On complete addition the reaction mixture was warmed to room temperature then stirred at reflux for 3 h. The reaction mixture was cooled to room temperature. Methanol was added drop-wise until evolution of gas subsided. The reaction mixture was stirred at reflux for 2 h. The cooled reaction mixture was poured into water (500 mL) and extracted with ethyl acetate (2×1000 mL). The combined ethyl acetate layers were dried over sodium sulphate and evaporated under reduced pressure to afford title compound as a pale brown solid. (75.0 g, 100%)

$^1$H NMR (400 MHz, CDCl$_3$) δ=7.71 (br d, J=6.8 Hz, 2H), 7.34-7.40 (m, 0.24H), 7.27-7.32 (m, 0.24H), 4.77 (s, 2H), 4.58 (s, 0.5H), 2.47 (s, 1H), 2.33 (s, 3H).

Preparation 3: 5-chloro-2-methyl-3-nitro-benzaldehyde

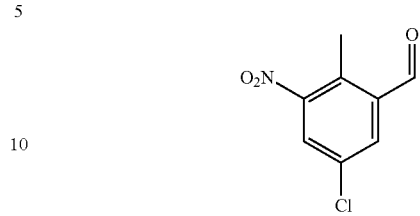

Pyridinium chlorochromate (104 g, 483 mmol) was slowly added to a stirred solution of alcohol from Preparation 2 (75.0 g, 372 mmol) in dichloromethane (200 mL). The reaction mixture was stirred at room temperature for 3 h then filtered through Celite®. The solvent was removed under reduced pressure. The obtained residue was purified by silica gel (100-200 mesh) column chromatography eluting with a gradient of 0-10% ethyl acetate in petroleum ether. Clean fractions were evaporated under reduced pressure to give the title compound as an off-white solid. (39.0 g, 52.5%)

$^1$H NMR (400 MHz, CDCl$_3$) δ=10.34 (s, 1H), 8.02 (d, J=2.0 Hz, 1H), 7.97 (d, J=2.4 Hz, 1H), 2.75 (s, 3H). LCMS Method 1: m/z 198.08 [M−H$^+$]; 82.8%; RT=2.74 min.

Preparation 4: tert-butyl (2S)-4-[(5-chloro-2-methyl-3-nitro-phenyl)methyl]-2-methyl-piperazine-1-carboxylate

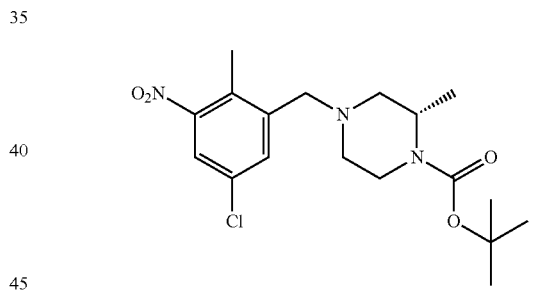

tert-Butyl (2S)-2-methylpiperazine-1-carboxylate (43.1 g, 215 mmol) was added to a solution of aldehyde from Preparation 3 (39.0 g, 195 mmol) in dichloromethane (780 mL). The reaction mixture was stirred at room temperature for 10 min then sodium triacetoxyborohydride (83.1 g, 391 mmol) was added portion-wise. On complete addition the reaction mixture was stirred at room temperature for 4 h. The reaction mixture was carefully quenched with water (200 mL) and extracted with dichloromethane (200 mL). The organic layer was dried over sodium sulphate and concentrated under reduced pressure. Trituration of the crude product with n-pentane afforded the title compound as an off-white solid. (43.0 g, 57.3%)

$^1$H NMR (300 MHz, DMSO-d$_6$) δ=7.92 (d, J=2.2 Hz, 1H), 7.68 (d, J=2.2 Hz, 1H), 4.09 (m, 1H), 3.67 (br d, J=13.1 Hz, 1H), 3.52 (s, 2H), 2.88-3.02 (m, 1H), 2.69 (br d, J=11.1 Hz, 1H), 2.57 (br d, J=11.3 Hz, 1H), 2.35 (s, 3H), 2.15 (dd, J=11.3, 3.6 Hz, 1H), 1.98 (td, J=11.7, 3.4 Hz, 1H), 1.39 (s, 9H), 1.13 (d, J=6.7 Hz, 3H). LCMS Method 1: m/z 384.66 [M+H$^+$]; RT=3.47 min.

Preparation 5: tert-butyl (2S)-4-[(3-amino-5-chloro-2-methyl-phenyl)methyl]-2-methyl-piperazine-1-carboxylate

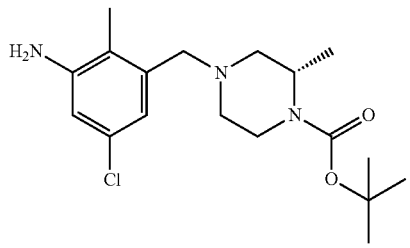 [SMILES: Cc1c(CN2CCN(C(=O)OC(C)(C)C)[C@@H](C)C2)cc(Cl)cc1[N+](=O)[O-]]

Iron powder (7.29 g, 130 mmol) was added to a solution of nitro compound from Preparation 4 (25.0 g, 65.3 mmol) in acetic acid (250 mL), portion-wise at room temperature. The reaction mixture was stirred for 16 h and then concentrated to low volume under reduced pressure. The crude product was diluted in dichloromethane (100 mL) and filtered through a pad of Celite®. The filtrate was concentrated and pH adjusted to pH 8 with saturated sodium hydrogen carbonate. The mixture was extracted with dichloromethane (3×200 mL). The combined organic layer was dried over sodium sulphate and evaporated under reduced pressure. The obtained residue was purified by silica gel (100-200 mesh) column chromatography eluting with a gradient of 20-30% ethyl acetate in petroleum ether. Clean fractions were evaporated under reduced pressure to give the title compound as an off-white solid. (18.0 g, 78.1%)

$^1$H NMR (400 MHz, DMSO-d$_6$) δ=6.59 (d, J=2.1 Hz, 1H), 6.47 (d, J=2.1 Hz, 1H), 5.10 (s, 2H), 4.07 (br s, 1H), 3.65 (br d, J=13.1 Hz, 1H), 3.21-3.31 (m, 2H), 2.91 (br t, J=11.4 Hz, 1H), 2.67 (br d, J=11.0 Hz, 1H), 2.56 (br d, J=11.3 Hz, 1H), 2.12 (s, 3H), 1.94-2.12 (m, 1H), 1.86 (td, J=11.6, 3.4 Hz, 1H), 1.39 (s, 9H), 1.11 (d, J=6.7 Hz, 3H). LCMS Method 1: m/z 354.27 [M+H$^+$]; RT=2.19 min.

Preparation 6: tert-butyl (2S)-4-[(5-chloro-3-isothiocyanato-2-methyl-phenyl)methyl]-2-methyl-piperazine-1-carboxylate

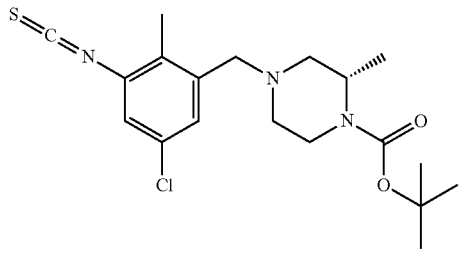 [SMILES: Cc1c(CN2CCN(C(=O)OC(C)(C)C)[C@@H](C)C2)cc(Cl)cc1N=C=S]

Thiocarbonyl dichloride (0.17 mL, 2.12 mmol) was added drop-wise to a rapidly stirred mixture of the product from Preparation 5 (750 mg, 2.12 mmol) in chloroform (70 mL) and saturated sodium hydrogen carbonate (70 mL). The reaction mixture was stirred at room temperature for 16 h. The reaction mixture was extracted with dichloromethane (2×50 mL). The combined organic layers were dried over magnesium sulphate and evaporated under reduced pressure to afford title compound as off-white solid. (839 mg, 100%)

$^1$H NMR (300 MHz, CDCl$_3$) δ=7.20 (d, J=2.2 Hz, 1H), 7.16 (d, J=2.2 Hz, 1H), 4.21 (s, 1H), 3.80 (d, J=13.1 Hz, 1H), 3.36 (s, 2H), 3.05 (td, J=12.7, 3.4 Hz, 1H), 2.67 (d, J=11.0 Hz, 1H), 2.54 (d, J=11.0 Hz, 1H), 2.34 (s, 3H), 2.20 (dd, J=11.1, 3.9 Hz, 1H), 2.01 (d, J=3.5 Hz, 1H), 1.46 (d, J=0.6 Hz, 9H), 1.21 (d, J=6.7 Hz, 3H). LCMS Method 4: m/z 396.2 [M+H$^+$]; RT=1.15 min.

Preparation 7: tert-butyl (2S)-4-[[3-(aminocarbamothioylamino)-5-chloro-2-methyl-phenyl]methyl]-2-methyl-piperazine-1-carboxylate

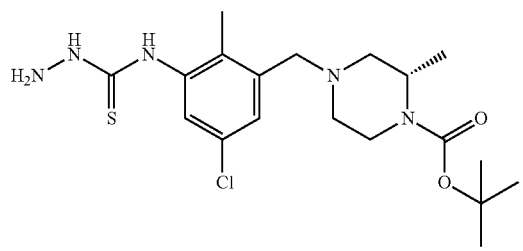 [SMILES: Cc1c(CN2CCN(C(=O)OC(C)(C)C)[C@@H](C)C2)cc(Cl)cc1NC(=S)NN]

The thioisocyanate from Preparation 6 (839 mg, 2.12 mmol), in chloroform (4 mL), was added to a solution of hydrazine hydrate (111 mg, 2.22 mmol) in chloroform (10 mL) over 10 min. The resulting mixture was stirred at room temperature for 16 h. The reaction mixture was evaporated under reduced pressure to afford title compound as pale yellow solid. (906 mg, 99%)

$^1$H NMR (300 MHz, CDCl$_3$) δ=8.97 (s, 1H), 7.59 (s, 1H), 7.26 (1H), 7.23 (s, 1H), 4.20 (s, 1H), 4.01 (s, 2H), 3.80 (d, J=13.1 Hz, 1H), 3.40 (s, 2H), 3.05 (td, J=12.7, 3.4 Hz, 1H), 2.71 (d, J=11.1 Hz, 1H), 2.57 (d, J=11.1 Hz, 1H), 2.25 (s, 3H), 2.18 (d, J=3.9 Hz, 1H), 2.01 (td, J=11.7, 3.5 Hz, 1H), 1.46 (s, 9H), 1.21 (d, J=6.7 Hz, 3H). LCMS Method 4: m/z 396.2 [M+H$^+$]; RT=0.74 min.

Scheme 9.2

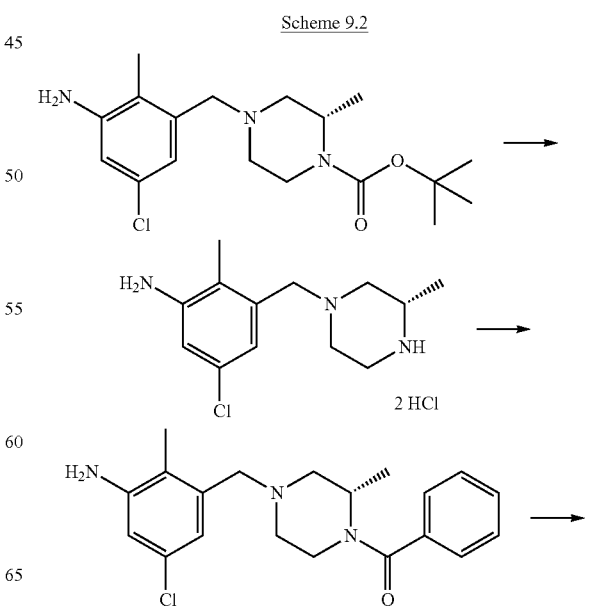

-continued

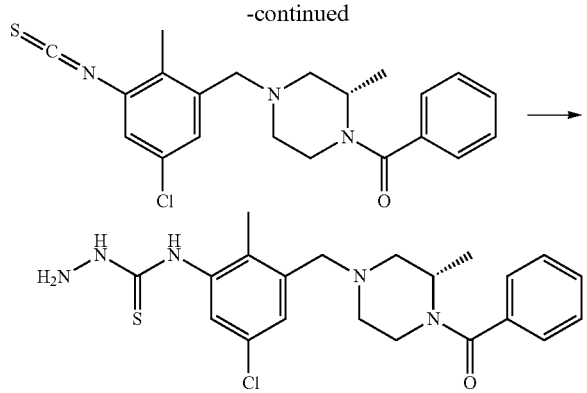

Preparation 8: 5-chloro-2-methyl-3-[[(3S)-3-methyl piperazin-1-yl]methyl]aniline dihydrochloride

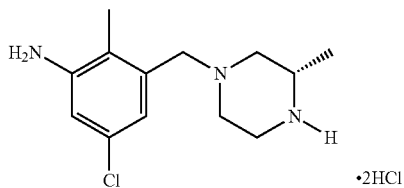 [SMILES: Cc1c(N)cc(Cl)cc1CN1CCN[C@@H](C)C1]

Hydrogen chloride (4M solution in 1,4-dioxane, 15 mL, 60 mmol) was added to a solution of the piperazine compound from Preparation 5 (3.00 g, 8.48 mmol) in dichloromethane (30 mL) and stirred at room temperature for 4 h. The reaction mixture was concentrated under reduced pressure to afford title compound as a colourless solid that was used without any purification. (2.77 g, 100%) LCMS Method 4: m/z 254.2 [M+H$^+$]; RT=0.42 min.

Preparation 9: [(2S)-4-[(3-amino-5-chloro-2-methyl-phenyl)methyl]-2-methyl-piperazin-1-yl]-phenyl-methanone

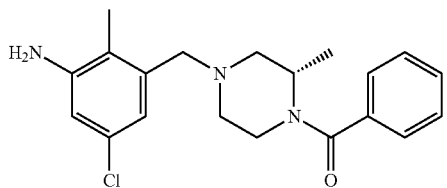 [SMILES: Cc1c(N)cc(Cl)cc1CN1CCN(C(=O)c2ccccc2)[C@@H](C)C1]

Benzoic acid (561 mg, 4.59 mmol) was added to a solution of the amine from Preparation 8 (1.50 g, 4.59 mmol) in ethyl acetate (25 mL). To this mixture was added triethylamine (3.84 mL, 27.6 mmol) and N,N,N',N'-tetramethyl-O-(1H-benzotriazol-1-yl)uronium hexafluorophosphate (1.83 g, 4.82 mmol). The resulting reaction mixture was stirred at room temperature for 16 h and then quenched with water and extracted with dichloromethane (2×30 mL). The combined organic layers was dried over magnesium sulphate and evaporated under reduced pressure. The obtained residue was purified by silica gel (100-200 mesh) column chromatography eluting with a gradient of 0-60% ethyl acetate in heptane. Clean fractions were evaporated under reduced pressure to give the title compound as a colourless solid. (1.36 g, 83.0%)

$^1$H NMR (300 MHz, DMSO-d6) δ=7.42-7.45 (m, 3H), 7.32-7.35 (m, 2H), 6.59 (d, J=2.2 Hz, 1H), 6.47 (d, J=2.2 Hz, 1H), 5.10 (s, 2H), 3.10 (bs, 1H), 2.71 (d, J=10.1 Hz, 1H), 2.61 (d, J=7.3 Hz, 1H), 2.12 (dd, J=11.3, 3.8 Hz, 1H), 2.01 (s, 3H), 1.95 (td, J=11.7, 3.5 Hz, 1H), 1.22 (d, J=6.7 Hz, 3H). LCMS Method 4: m/z 358.3 [M+H$^+$]; RT=0.42 min.

Preparation 10: [(2S)-4-[(5-chloro-3-isothiocyanato-2-methyl-phenyl)methyl]-2-methyl-piperazin-1-yl]-phenyl-methanone

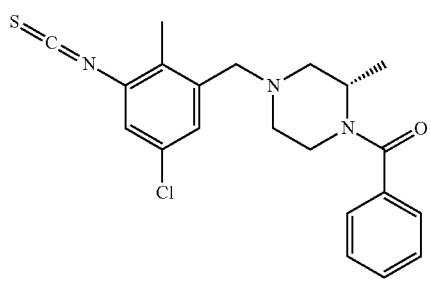 [SMILES: Cc1c(CN2CCN(C(=O)c3ccccc3)[C@@H](C)C2)cc(Cl)cc1N=C=S]

Using a procedure similar to that described for Preparation 6, but using the compound described in Preparation 9 (675 mg, 1.89 mmol), the title compound was prepared as a yellow oil. (750 mg, 99%)

$^1$H NMR (300 MHz, CDCl$_3$) δ=7.30-7.47 (m, 5H), 7.09-7.23 (m, 2H), 3.40 (s, 2H), 3.24 (s, 1H), 2.73 (s, 1H), 2.58 (s, 1H), 2.35 (s, 4H), 2.11 (d, J=13.6 Hz, 1H), 1.33 (d, J=6.8 Hz, 3H). LCMS Method 4: m/z 400.3 [M+H$^+$]; RT=1.04 min.

Preparation 11: 1-amino-3-[3-[[(3S)-4-benzoyl-3-methyl-piperazin-1-yl]methyl]-5-chloro-2-methyl-phenyl]thiourea

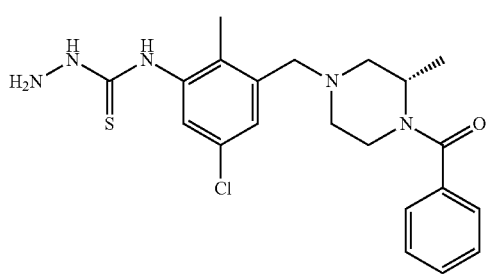 [SMILES: Cc1c(CN2CCN(C(=O)c3ccccc3)[C@@H](C)C2)cc(Cl)cc1NC(=S)NN]

Using a procedure similar to that described for Preparation 7, but using the compound described in Preparation 10 (550 mg, 1.37 mmol), the title compound was prepared as an off-white solid. (490 mg, 82%)

$^1$H NMR (300 MHz, CDCl$_3$) δ=8.97 (s, 1H), 7.59 (s, 1H), 7.38 (tdd, J=6.4, 2.8, 1.9 Hz, 5H), 7.20 (d, J=2.2 Hz, 1H), 4.06 (d, J=15.7 Hz, 2H), 3.43 (s, 2H), 3.23 (s, 1H), 2.76 (s, 1H), 2.63 (d, J=11.4 Hz, 1H), 2.24 (s, 4H), 2.11 (d, J=11.9 Hz, 1H), 1.32 (d, J=6.7 Hz, 2H). LCMS Method 4: m/z 432.2 [M+H$^+$]; RT=0.64 min.

Scheme 9.3

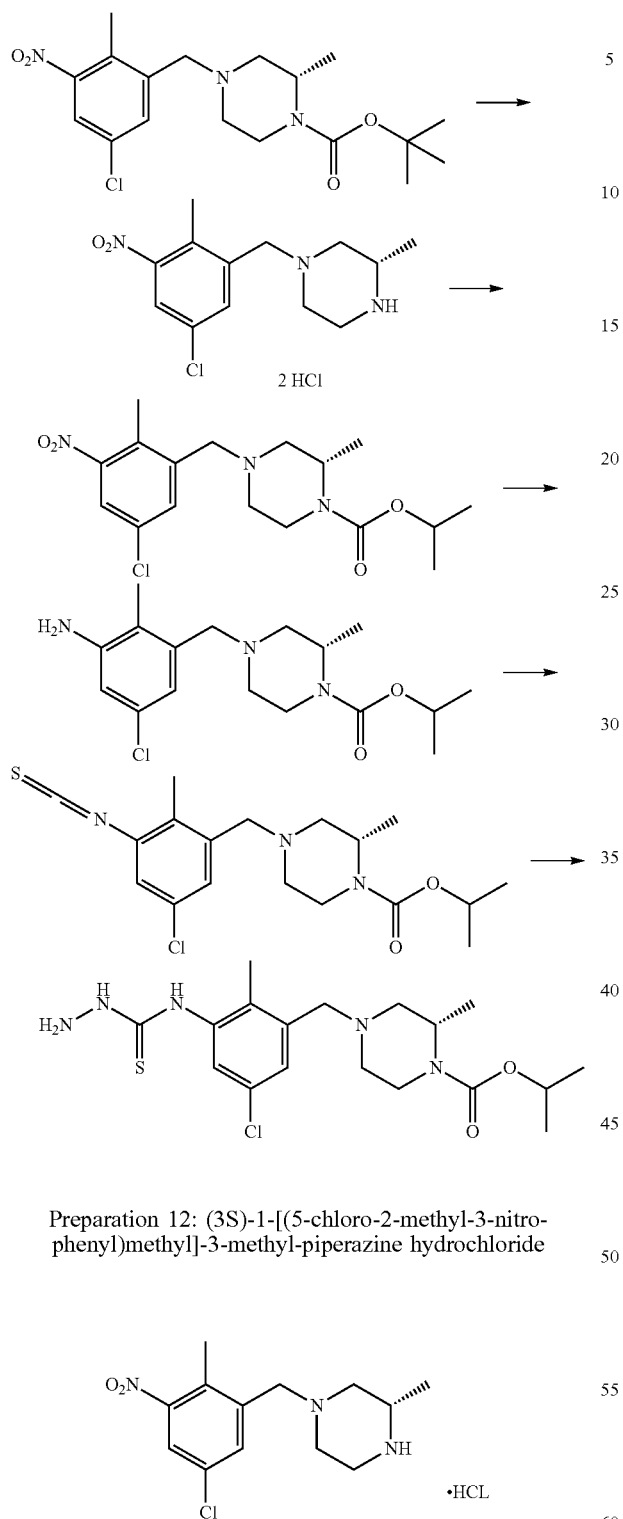

Preparation 12: (3S)-1-[(5-chloro-2-methyl-3-nitro-phenyl)methyl]-3-methyl-piperazine hydrochloride

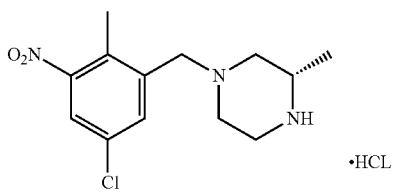 [SMILES: Cc1c(CN2CCN[C@@H](C)C2)cc(Cl)cc1[N+](=O)[O-]]

Hydrogen chloride (4M solution in 1,4-dioxane, 200 mL) was added to a solution of the piperazine compound from Preparation 4 (15.0 g, 39.2 mmol) in 1,4-dioxane (45 mL) at 0° C. The resulting mixture was stirred at room temperature for 16 h before being concentrated under reduced pressure to afford title compound as a colourless solid. (12.5 g, 100%)

$^1$H NMR (300 MHz, DMSO-d$_6$) δ=7.86-8.17 (m, 2H), 5.46 (br s, 2H), 4.10 (br s, 2H), 3.57 (s, 3H), 3.25 (br s, 2H), 2.40 (s, 3H), 1.25 (br d, J=6.6 Hz, 3H).

LCMS Method 1: m/z 284, 17 [M+H$^+$]; RT=2.04 min.

Preparation 13: isopropyl (2S)-4-[(5-chloro-2-methyl-3-nitro-phenyl)methyl]-2-methyl-piperazine-1-carboxylate

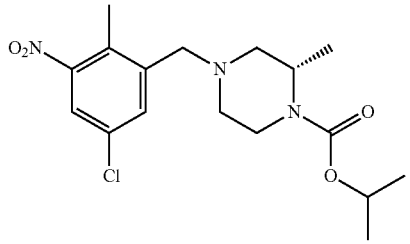 [SMILES: Cc1c(CN2CCN(C(=O)OC(C)C)[C@@H](C)C2)cc(Cl)cc1[N+](=O)[O-]]

Isopropyl chloroformate (2M solution in toluene, 3.66 mmol) was added drop-wise to a solution of the amine from Preparation 12 (900 mg, 2.81 mmol) and diisopropylethylamine (1.5 mL, 8.44 mmol) in dichloromethane (10 mL) at 0° C. The reaction mixture was stirred to room temperature over 2 h. The mixture was diluted with water (50 mL) and extracted with dichloromethane (2×50 mL). The combined organic layer was dried over sodium sulphate and evaporated under reduced pressure. The obtained residue was purified by silica gel (100-200 mesh) column chromatography eluting with a gradient of 10-20% ethyl acetate in petroleum ether. Clean fractions were evaporated under reduced pressure to give the title compound as a colourless oil. (600 mg, 57.7%)

$^1$H NMR (300 MHz, CDCl$_3$) δ=7.69 (d, J=2.1 Hz, 1H), 7.53 (d, J=2.1 Hz, 1H), 4.92-4.96 (m, 1H), 4.28-4.31 (m, 1H), 3.85-3.88 (m, 1H), 3.46 (s, 2H), 3.10-3.14 (m, 1H), 2.70-2.73 (m, 1H), 2.52-2.57 (m, 1H), 2.44 (s, 3H), 2.21-2.31 (m, 1H), 2.01-2.15 (m, 1H), 1.24 (m, 9H). LCMS Method 1: m/z 370.62 [M+H$^+$]; RT=3.18 min.

Preparation 14: isopropyl (2S)-4-[(3-amino-5-chloro-2-methyl-phenyl)methyl]-2-methyl-piperazine-1-carboxylate

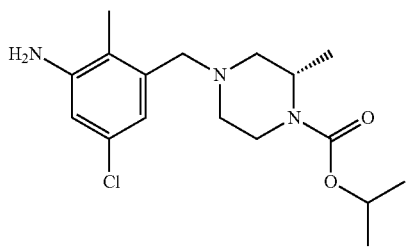

Using a procedure similar to that described for Preparation 5 but using the nitro compound from preparation 13 (3.30 g, 8.94 mmol), the title compound was prepared as a brown gum (2.60 g, 85.8%).

$^1$H NMR (400 MHz, DMSO-d$_6$) δ=6.59 (d, J=2.1 Hz, 1H), 6.47 (d, J=2.1 Hz, 1H), 5.10 (s, 2H), 4.75-4.79 (m, 1H), 4.11 (br s, 1H), 3.65-3.69 (m, 1H), 3.20-3.30 (m, 2H), 2.86-3.04 (m, 1H), 2.65-2.69 (m, 1H), 2.53-2.57 (m, 1H), 1.98-2.15 (m, 4H), 1.82-1.89 (m, 1H), 1.17 (d, J=6.1 Hz, 6H), 1.13 (d, J=6.7 Hz, 3H). LCMS Method 1: m/z 384. [M+H⁺]; 98.8%; RT=2.05 min.

Preparation 15: isopropyl (2S)-4-[(5-chloro-3-isothiocyanato-2-methyl-phenyl)methyl]-2-methyl-piperazine-1-carboxylate

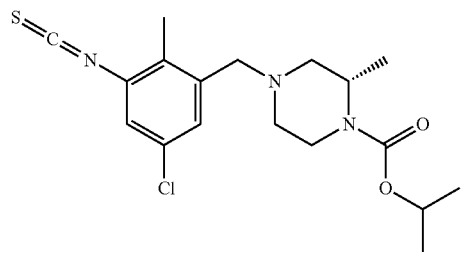 [SMILES: Cc1c(CN2CCN(C(=O)OC(C)C)[C@@H](C)C2)cc(Cl)cc1N=C=S]

Using a procedure similar to that described for Preparation 6, but using the compound described in Preparation 14 (1.00 g, 2.94 mmol), the title compound was prepared as a yellow oil. (1.11 g, 98.8%)

¹H NMR (300 MHz, CDCl₃) δ=7.20 (s, 1H), 7.17 (s, 1H), 4.92 (h, J=6.2 Hz, 1H), 4.26 (s, 1H), 3.86 (d, J=13.2 Hz, 1H), 3.37 (s, 2H), 3.08 (td, J=12.7, 3.4 Hz, 1H), 2.68 (d, J=11.0 Hz, 1H), 2.55 (d, J=11.1 Hz, 1H), 2.34 (s, 3H), 2.28-2.13 (m, 1H), 2.03 (td, J=11.6, 3.5 Hz, 1H), 1.24 (d, J=4.6, Hz, 6H) overlapping 1.22 (d, J=6.5, Hz, 3H). LCMS Method 4: m/z 382.1 [M+H⁺]; RT=1.08 min.

Preparation 16: isopropyl (2S)-4-[[3-(aminocarbamothioylamino)-5-chloro-2-methyl-phenyl]methyl]-2-methyl-piperazine-1-carboxylate

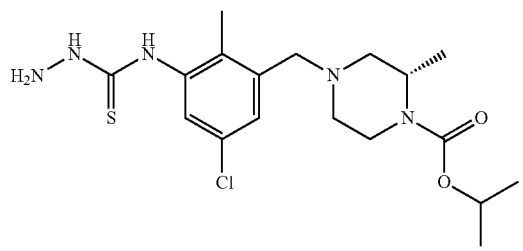 [SMILES: Cc1c(CN2CCN(C(=O)OC(C)C)[C@@H](C)C2)cc(Cl)cc1NC(=S)NN]

Using a procedure similar to that described for Preparation 7, but using the compound described in Preparation 15 (1.11 g, 2.91 mmol), the title compound was prepared as a yellow oil. (869 mg, 72.2%)

¹H NMR (300 MHz, CDCl₃) δ=7.59 (br s, 1H), 7.23 (s, 1H), 4.93 (p, J=6.2 Hz, 1H), 4.25 (s, 1H), 4.04 (s, 2H), 3.85 (d, J=13.2 Hz, 1H), 3.40 (s, 2H), 3.09 (td, J=12.9, 3.4 Hz, 1H), 2.72 (d, J=10.9 Hz, 1H), 2.58 (d, J=11.1 Hz, 1H), 2.25 (s, 4H), 2.13-1.88 (m, 1H), 1.24 (d, J=4.6, Hz, 6H) overlapping 1.22 (d, J=6.5, Hz, 3H). LCMS Method 4: m/z 414.1 [M+H⁺]; RT=0.66 min.

Scheme 9.4

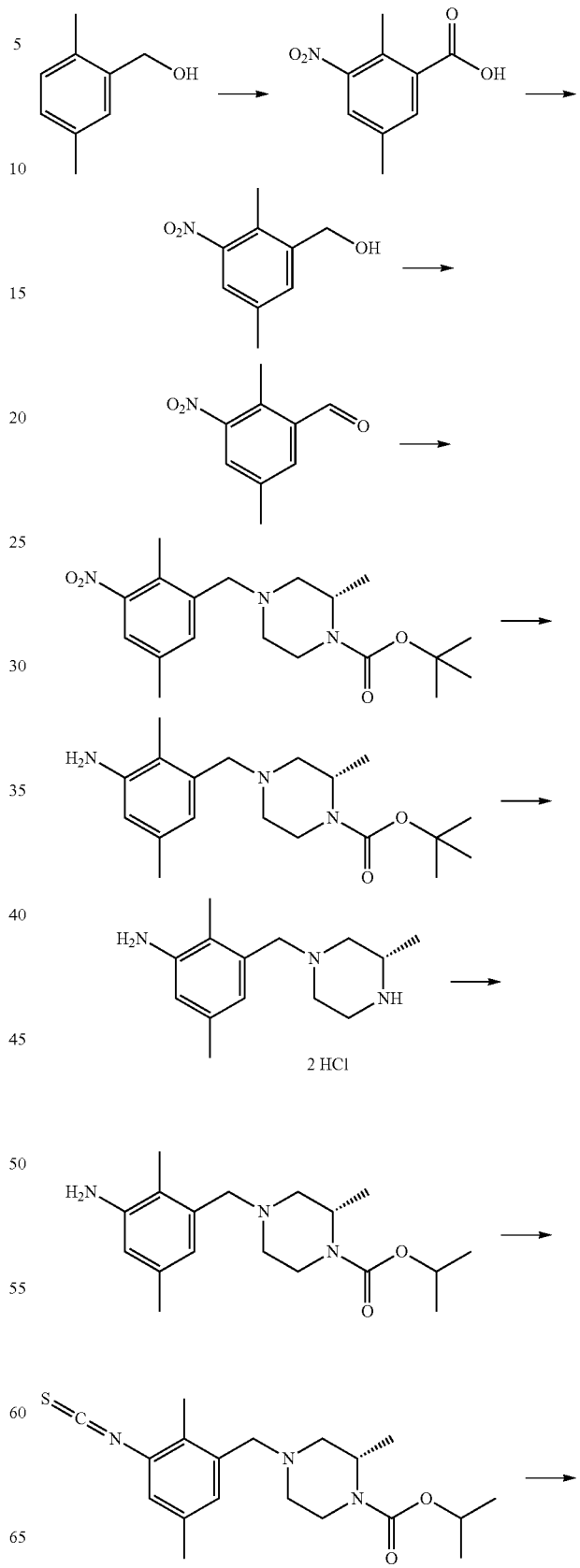

-continued

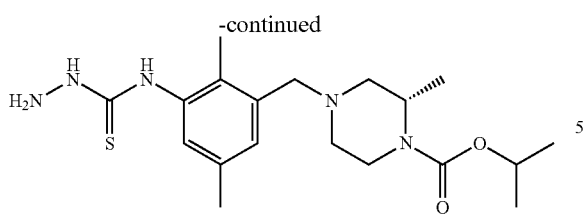

Preparation 17: 2,5-dimethyl-3-nitro-benzoic acid

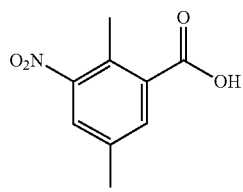

Using a procedure similar to that described for Preparation 1, but using 2,5-dimethylbenzoic acid (40.0 g, 266 mmol), the title compound was prepared as an off-white solid (37.0 g, 71.1%, mixture of isomers).

$^1$H NMR (400 MHz, acetone-d$_6$) δ=7.89 (s, 1H), 7.79 (s, 1H), 2.54 (s, 3H), 2.42 (s, 3H).

Preparation 18: (2,5-dimethyl-3-nitro-phenyl)methanol

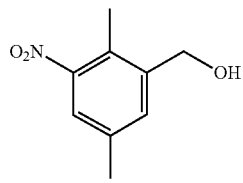

Using a procedure similar to that described for Preparation 2, but using the acid from Preparation 17 (37.0 g, 189 mmol), the title compound was prepared as a pale brown solid (15.9 g, 46.3%, mixture of isomers). Used directly without purification.

Preparation 19: 2,5-dimethyl-3-nitro-benzaldehyde

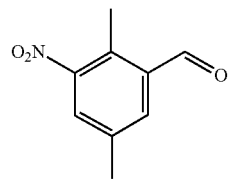

Using a procedure similar to that described for Preparation 3, but using the compound described in Preparation 18 (12.0 g, 66.2 mmol), the title compound was prepared as an off white solid (10.5 g, 88.4%).

$^1$H NMR (300 MHz, CDCl$_3$) δ=10.35 (s, 1H), 7.85 (s, 1H), 7.78 (s, 1H), 2.72 (s, 3H), 2.47 (s, 3H).

Preparation 20: tert-butyl (2S)-4-[(2,5-dimethyl-3-nitro-phenyl)methyl]-2-methyl-piperazine-1-carboxylate

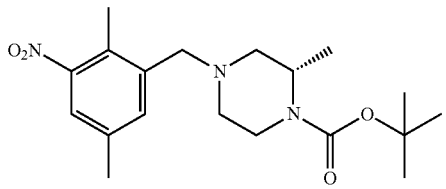

Using a procedure similar to that described for Preparation 4, but using the compound from Preparation 19 (10.5 g, 56.6 mmol), the title compound was prepared as a colourless gum (11.5 g, 54.0%).

$^1$H NMR (300 MHz, DMSO-d$_6$) δ=7.57 (s, 1H), 7.39 (s, 1H), 4.09 (br s, 1H), 3.64-3.67 (m, 1H), 3.40-3.53 (m, 2H), 2.86-2.99 (m, 1H), 2.67-2.69 (m, 1H), 2.57 (m, 1H), 2.25-2.40 (m, 5H), 2.11-2.14 (m, 1H), 1.86-2.00 (m, 1H), 1.39 (s, 9H), 1.12 (d, J=6.6 Hz, 3H). LCMS Method 1: m/z 364.91 [M+H$^+$]; RT=2.86 min.

Preparation 21: tert-butyl (2S)-4-[(3-amino-2,5-dimethyl-phenyl)methyl]-2-methyl-piperazine-1-carboxylate

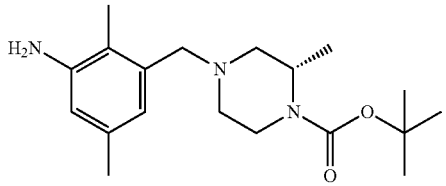 [SMILES: Cc1cc(CN2CCN(C(=O)OC(C)(C)C)[C@@H](C)C2)c(C)c([N+](=O)[O-])c1]

Using a procedure similar to that described for Preparation 5, but using the compound described in Preparation 20 (11.5 g, 31.7 mmol), the title compound was prepared as an off-white solid. (9.90 g, 93.8%).

$^1$H NMR (400 MHz, DMSO-d$_6$) δ=6.37 (s, 1H), 6.25 (s, 1H), 4.64 (br s, 2H), 4.06 (br s, 1H), 3.61-3.66 (m, 1H), 3.15-3.30 (m, 2H), 2.81-2.99 (m, 1H), 2.67 (br d, J=10.8 Hz, 1H), 2.57 (br d, J=11.2 Hz, 1H), 2.10 (s, 3H), 1.96-2.05 (m, 4H), 1.80 (td, J=11.6, 3.2 Hz, 1H), 1.38 (s, 9H), 1.10 (d, J=6.8 Hz, 3H). LCMS Method 1: m/z 334.15 [M+H$^+$]; RT=1.93 min.

Preparation 22: 2,5-dimethyl-3-[[(3S)-3-methylpiperazin-1-yl]methyl]aniline dihydrochloride

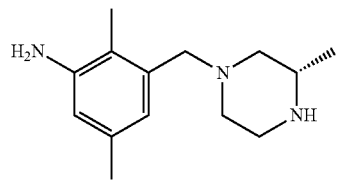

Using a procedure similar to that described for Preparation 12, but using the compound described in Preparation 21

(400 mg, 1.2 mmol) and replacing 1,4-dioxane with methanol as solvent, the title compound was prepared as an off-white solid taken directly into next step. (366 mg, 100%) LCMS Method 4: m/z 232.2 [M+H⁺]; RT=0.31 min.

Preparation 23: isopropyl (2S)-4-[(3-amino-2,5-dimethyl-phenyl)methyl]-2-methyl-piperazine-1-carboxylate

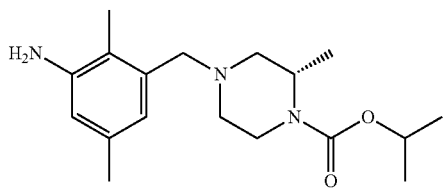

Using a procedure similar to that described for Preparation 13, but using the compound described in Preparation 22 (10.0 g, 32.6 mmol), the title compound was prepared as a brown oil. (5.60 g, 54.0%)

¹H NMR (500 MHz, DMSO-d₆) δ=6.37 (s, 1H), 6.25 (s, 1H), 4.76 (quin, J=6.2 Hz, 1H), 4.65 (s, 2H), 4.10 (br s, 1H), 3.68 (br d, J=12.8 Hz, 1H), 3.20-3.30 (m, 2H), 2.87-2.98 (m, 1H), 2.68 (br d, J=11.0 Hz, 1H), 2.58 (br d, J=11.3 Hz, 1H), 2.10 (s, 3H), 1.96-2.05 (m, 4H), 1.82 (td, J=11.7, 3.4 Hz, 1H), 1.17 (d, J=6.3 Hz, 6H), 1.12 (d, J=6.7 Hz, 3H). LCMS Method 2: m/z 320.38 [M+H⁺]; RT=1.24 min.

Preparation 24: isopropyl (2S)-4-[(3-isothiocyanato-2,5-dimethyl-phenyl)methyl]-2-methyl-piperazine-1-carboxylate

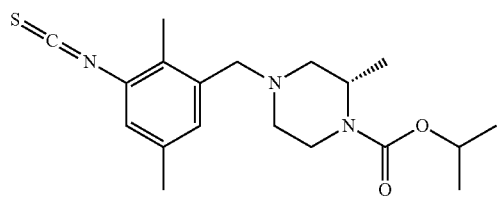 [SMILES: Cc1cc(CN2CCN(C(=O)OC(C)C)[C@@H](C)C2)c(C)c(N=C=S)c1]

Using a procedure similar to that described for Preparation 6, but using the compound described in Preparation 23 (3.52 g, 11.0 mmol), the title compound was prepared as a yellow oil and used directly in next step. (3.98 g, 100%) LCMS Method 4: m/z 362.2 [M+H⁺]; RT=1.06 min.

Preparation 25: isopropyl (2S)-4-[[3-(aminocarbamothioylamino)-2,5-dimethyl-phenyl]methyl]-2-methyl-piperazine-1-carboxylate

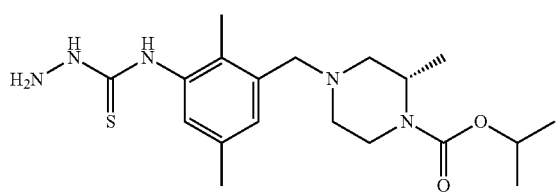 [SMILES: Cc1cc(CN2CCN(C(=O)OC(C)C)[C@@H](C)C2)c(C)c(NC(=S)NN)c1]

Using a procedure similar to that described for Preparation 7, but using the compound described in Preparation 24 (3.98 g, 11.0 mmol), the title compound was prepared as a yellow oil. (3.17 g, 73.2%)

¹H NMR (600 MHz, CDCl₃) δ=8.95 (s, 1H), 6.92-7.10 (m, 1H), 4.92 (p, J=6.2 Hz, 1H), 4.24 (s, 1H), 4.05 (s, 1H), 3.84 (d, J=13.2 Hz, 1H), 3.39 (s, 2H), 3.07 (td, J=12.8, 3.5 Hz, 1H), 2.72 (d, J=10.9 Hz, 1H), 2.58 (d, J=11.3 Hz, 1H), 2.32 (s, 3H), 2.25 (s, 3H), 2.22-2.10 (m, 1H), 2.00 (td, J=11.7, 3.6 Hz, 1H), 1.24 (dd, J=6.2, 1.6 Hz, 6H), 1.21 (d, J=6.7 Hz, 3H). LCMS Method 4: m/z 294.2 [M+H⁺]; RT=0.50 min.

Scheme 9.5

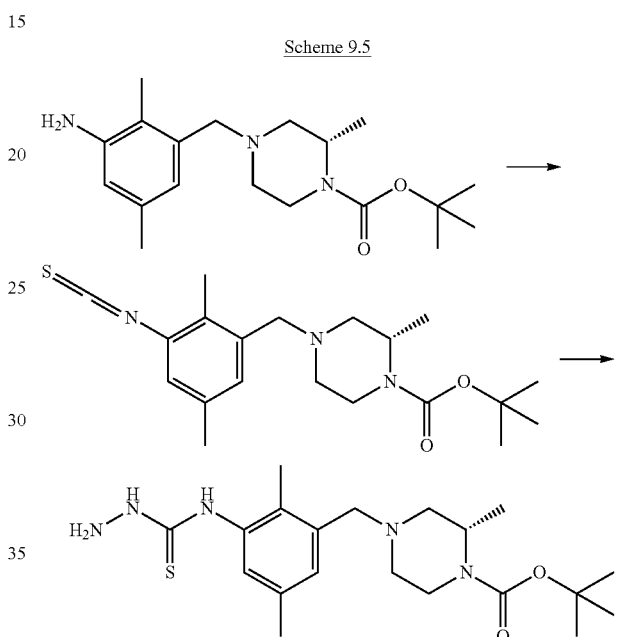

Preparation 26: tert-butyl (2S)-4-[(3-isothiocyanato-2,5-dimethyl-phenyl)methyl]-2-methyl-piperazine-1-carboxylate

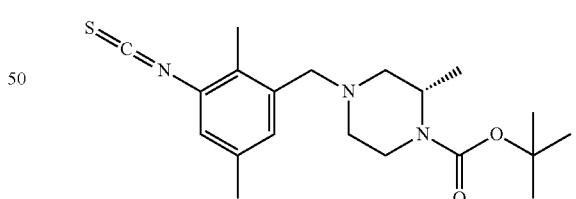

Using a procedure similar to that described for Preparation 6, but using the compound described in Preparation 21 (1.15 g, 3.45 mmol), the title compound was prepared as a yellow oil. (1.40 g, 100%)

¹H NMR (300 MHz, CDCl₃) δ=6.97 (m, 2H), 4.19 (s, 1H), 3.78 (d, J=13.0 Hz, 1H), 3.44-3.24 (m, 2H), 3.03 (td, J=12.7, 3.4 Hz, 1H), 2.66 (d, J=11.2 Hz, 1H), 2.54 (d, J=11.1 Hz, 1H), 2.35 (s, 3H), 2.28 (d, J=0.8 Hz, 3H), 2.21-2.09 (m, 1H), 2.03-1.90 (m, 1H), 1.45 (s, 9H), 1.19 (d, J=6.7 Hz, 3H). LCMS Method 4: m/z 376.2 [M+H⁺]; RT=1.12 min.

Preparation 27: tert-butyl (2S)-4-[[3-(aminocarbamothioylamino)-2,5-dimethyl-phenyl]methyl]-2-methyl-piperazine-1-carboxylate

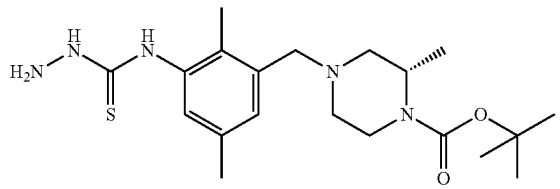 [SMILES: Cc1cc(CN2CCN(C(=O)OC(C)(C)C)[C@@H](C)C2)c(C)c(NC(=S)NN)c1]

Using a procedure similar to that described for Preparation 7, but using the compound described in Preparation 26 (1.40 g, 3.45 mmol), the title compound was prepared as a yellow oil. (1.50 g, 98.7%)

$^1$H NMR (300 MHz, DMSO-d6) δ=8.95 (s, 1H), 7.20 (s, 1H), 6.91 (s, 1H), 4.73 (s, 1H), 4.08 (s, 1H), 3.66 (d, J=13.0 Hz, 1H), 2.92 (t, J=12.1 Hz, 1H), 2.70 (d, J=11.5 Hz, 1H), 2.59 (d, J=11.4 Hz, 1H), 2.24 (s, 3H), 2.14 (s, 3H), 2.06 (dd, J=11.1, 4.0 Hz, 1H), 1.95-1.81 (m, 1H), 1.39 (s, 9H), 1.12 (d, J=6.7 Hz, 3H). LCMS Method 4: m/z 408.2 [M+H$^+$]; RT=0.54 min.

Scheme 9.6

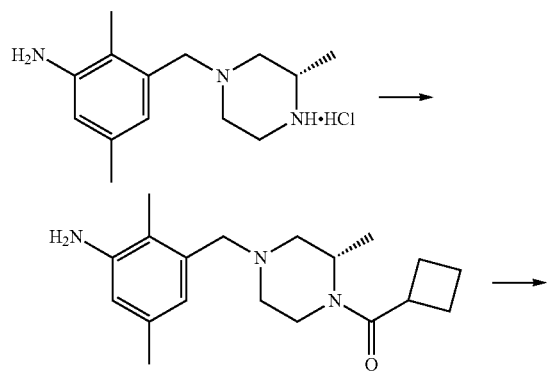

Preparation 28: cyclobutyl-[(2S)-4-[(3-isothiocyanato-2,5-dimethyl-phenyl)methyl]-2-methyl-piperazin-1-yl]methanone

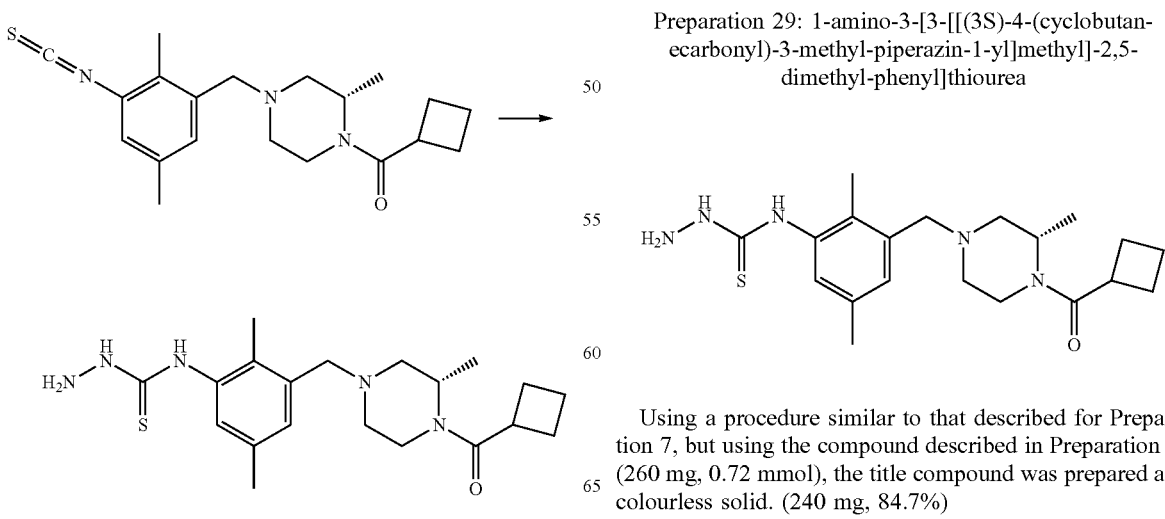

N,N,N',N'-tetramethyl-O-(1H-benzotriazol-1-yl)uronium hexafluorophosphate (478 mg, 1.26 mmol) was added to a solution of the product from Preparation 22 (280 mg, 0.91 mmol), cyclobutane carboxylic acid (105 mg, 1.05 mmol) and triethylamine (0.73 mL, 5.24 mmol) in dichloromethane (3.0 mL) and the reaction mixture was stirred at room temperature for 16 h. The reaction mixture was quenched with water and extracted with dichloromethane (2×50 mL). The combined organic layers were dried over magnesium sulphate, filtered and evaporated under reduced pressure. The obtained residue (270 mg) was dissolved in chloroform (10 mL) and saturated sodium hydrogen carbonate (10 mL) added. The resulting mixture was rapidly stirred while thiocarbonyl dichloride (0.069 mL, 0.89 mmol) was added drop-wise. The reaction mixture was stirred at room temperature for 16 h before being extracted with dichloromethane (2×50 mL). The combined organic layers were dried over magnesium sulphate and evaporated under reduced pressure to afford title compound as off-white solid. (260 mg, 80%)

$^1$H NMR (600 MHz, CDCl$_3$) δ=6.99 (s, 1H), 6.95 (s, 1H), 4.71 (s, 0.5H), 4.34-4.47 (m, 0.5H), 3.81-3.86 (m, 0.5H), 3.31-3.39 (m, 2.5H), 3.16-3.26 (m, 1.5H), 2.90 (td, J=12.9, 3.5 Hz, 0.5H), 2.70 (dd, J=32.9, 11.1 Hz, 1H), 2.59 (t, J=12.1 Hz, 1H), 2.46-2.26 (m, 2H) covering 2.35 (s, 3H), 2.28 (s, 3H), 2.12 (qq, J=12.4, 6.8, 5.2 Hz, 3H), 2.02-1.90 (m, 2H), 1.86 (tt, J=12.4, 6.1 Hz, 1H), 1.31-1.14 (m, 3H). LCMS Method 4: m/z 358.2 [M+H$^+$]; RT=1.00 min.

Preparation 29: 1-amino-3-[3-[[(3S)-4-(cyclobutanecarbonyl)-3-methyl-piperazin-1-yl]methyl]-2,5-dimethyl-phenyl]thiourea Using a procedure similar to that described for Preparation 7, but using the compound described in Preparation 28 (260 mg, 0.72 mmol), the title compound was prepared as a colourless solid. (240 mg, 84.7%)

LCMS Method 4: m/z 390.2 [M+H$^+$]; RT=0.46 min.

Scheme 9.7

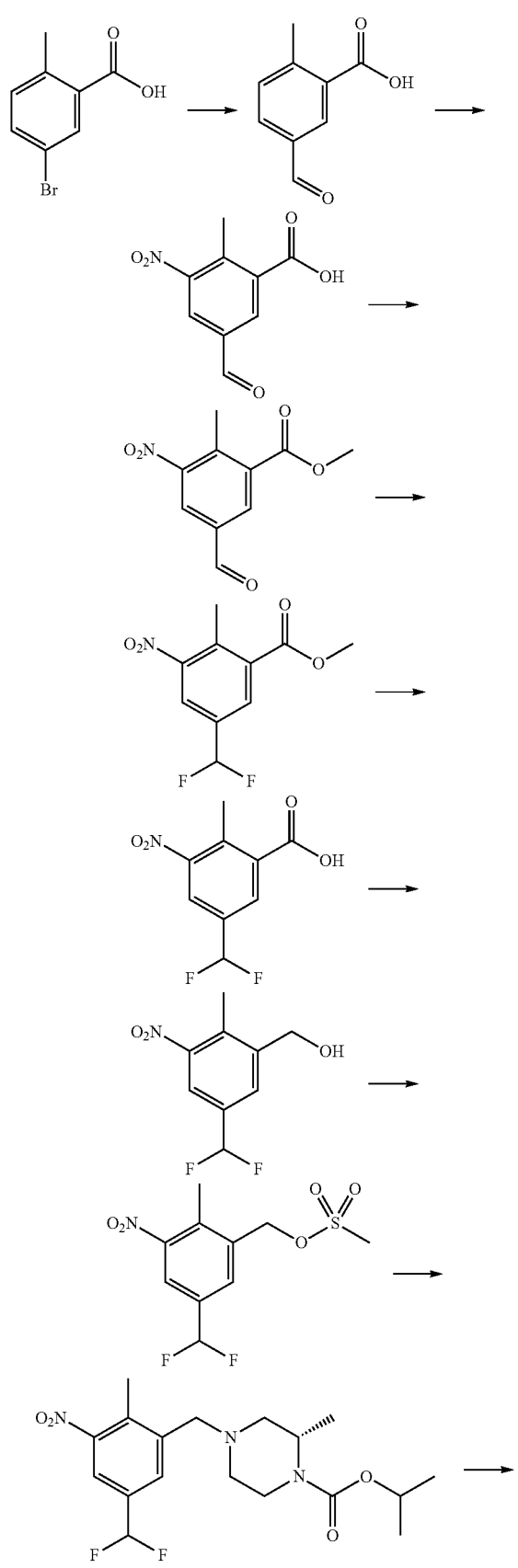

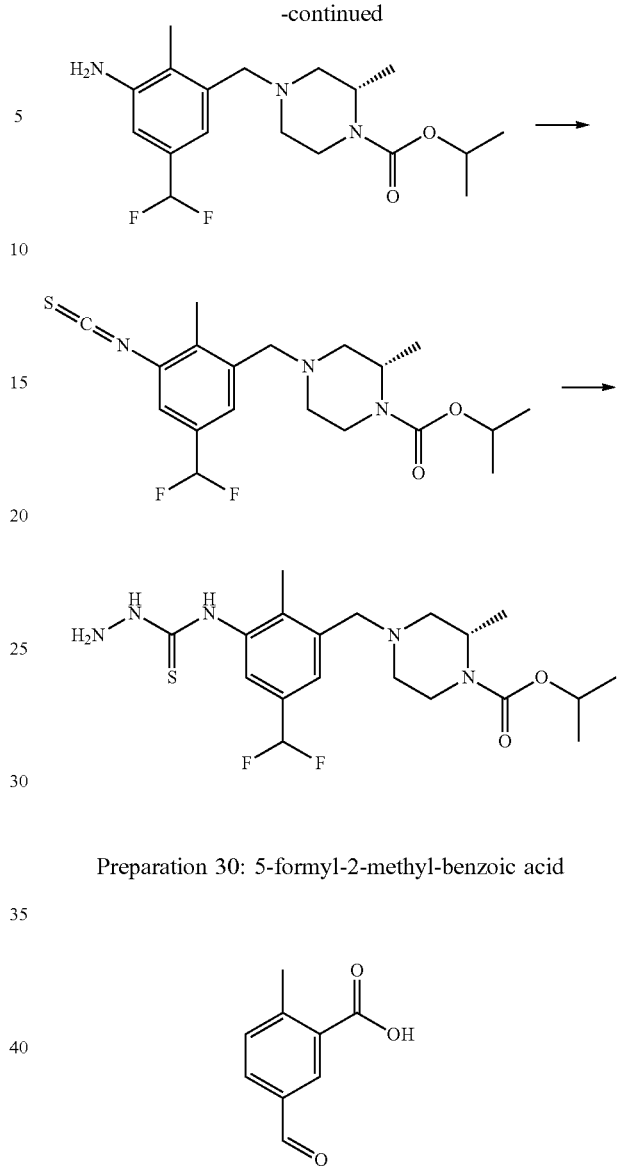

Preparation 30: 5-formyl-2-methyl-benzoic acid n-Butyllithium (139 mL, 348 mmol, 2.5M solution in tetrahydrofuran) was added drop-wise to a solution of 5-bromo-2-methylbenzoic acid (30.0 g, 139 mmol) in tetrahydrofuran (300 mL) at −78° C. The resulting mixture was stirred for 1 h and then dimethylformamide (54.0 mL, 697 mmol) was added drop-wise and stirring continue for a further 1 h at −78° C. The reaction mixture was then poured onto aqueous hydrogen chloride solution (500 mL, 1M) and extracted with ethyl acetate (2×1000 mL). The combined organic layer was dried over sodium sulphate and evaporated under reduced pressure to afford title compound as yellow solid that was used in the next step without purification. (12.0 g, 52.4%)

$^1$H NMR (500 MHz, DMSO-d$_6$): δ=13.16 (br s, 1H), 10.02 (s, 1H), 8.34 (d, J=1.8 Hz, 1H), 7.96 (dd, J=1.8, 7.9 Hz, 1H), 7.55 (d, J=7.9 Hz, 1H), 2.62 (s, 3H). LCMS Method 2: m/z 164.80 [M+H$^+$]; RT=1.43 min.

Preparation 31: 5-formyl-2-methyl-3-nitro-benzoic acid

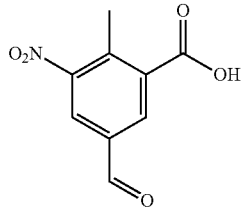

Using a procedure similar to that described for Preparation 1, but using the compound described in Preparation 30 (42.0 g, 256 mmol), the title compound was prepared as an off-white solid. (32.0 g, 59.8%)

$^1$H NMR (300 MHz, DMSO-$d_6$): δ=13.80 (br s, 1H), 10.07 (s, 1H), 8.49 (d, J=2.2 Hz, 2H), 2.61 (s, 3H). LCMS Method 1: m/z 208.32 [M–H$^+$]; RT=1.81 min.

Preparation 32: methyl 5-formyl-2-methyl-3-nitro-benzoate

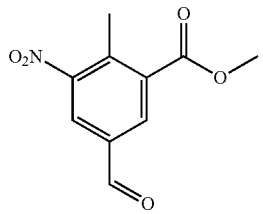 [SMILES: COC(=O)c1cc(C=O)cc([N+](=O)[O-])c1C]

Potassium carbonate (63.0 g, 459 mmol) was added portion-wise to a solution of product from Preparation 31 (32.0 g, 153 mmol) in dimethylformamide (200 mL) at 0° C. The reaction mixture was stirred for 10 min before methyl iodide (33.9 mL, 306.2 mmol) was added drop-wise maintaining temperature around 0° C. The reaction was stirred for 3 h and allowed to reach to room temperature before being poured onto ice/water (500 mL) and extracted with ethyl acetate (2×1000 mL). The combined organic layer was dried over sodium sulphate and evaporated under reduced pressure to afford title compound as a brown oil that was used in the next step without purification. (30.0 g, 87.8%)

$^1$H NMR (300 MHz, CDCl$_3$): δ=10.05 (s, 1H), 8.50 (s, 1H), 8.32 (s, 1H), 3.99 (s, 3H), 2.73 (s, 3H). LCMS Method 2: m/z 222.19 [M–H$^+$]; RT=2.33 min.

Preparation 33: methyl 5-(difluoromethyl)-2-methyl-3-nitro-benzoate

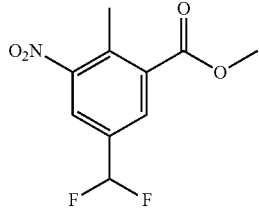 [SMILES: COC(=O)c1cc(C(F)F)cc([N+](=O)[O-])c1C]

N,N-Diethylaminosulfur trifluoride (35.0 mL, 269 mmol) was added to a solution of product from Preparation 32 (30.0 g, 134 mmol) in dichloromethane at −10° C. The resulting reaction mixture was stirred at room temperature for 16 h. The reaction mixture was quenched with saturated sodium hydrogen carbonate solution (500 mL) and extracted with dichloromethane (2×1000 mL). The combined organic layers were washed with saturated brine (500 mL) then dried over sodium sulphate and evaporated under reduced pressure. The obtained residue was purified by silica gel (100-200 mesh) column chromatography eluting with a gradient of 0-10% ethyl acetate in petroleum ether. Clean fractions were evaporated under reduced pressure to give the title compound as an off-white solid. (20.0 g, 60.7%)

$^1$H NMR (400 MHz, CDCl3): δ=8.15 (s, 1H), 8.00 (s, 1H), 6.87-6.52 (m, 1H), 3.97 (s, 3H), 2.68 (s, 3H).

Preparation 34: 5-(difluoromethyl)-2-methyl-3-nitro-benzoic acid

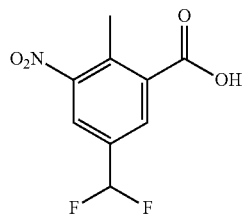 [SMILES: Cc1c(C(=O)O)cc(C(F)F)cc1[N+](=O)[O-]]

Lithium hydroxide hydrate (22.7 g, 542 mmol) was added to a solution of product from Preparation 33 (19.0 g, 77.5 mmol) in tetrahydrofuran (200 mL) and water (100 mL) portion-wise at room temperature. The reaction mixture was stirred for 5 h then neutralised with aqueous hydrogen chloride solution (1M). The precipitated solid was collected, washed with water and dried under reduced pressure to afford title compound as a colourless solid. (17.0 g, 94.9%)

$^1$H NMR (300 MHz, CDCl3): δ=8.30 (s, 1H), 8.04 (s, 1H), 6.95-6.50 (m, 1H), 2.74 (s, 3H). LCMS Method 2: m/z 230.10 [M–H$^+$]; RT=1.76 min.

Preparation 35: [5-(difluoromethyl)-2-methyl-3-nitro-phenyl]methanol

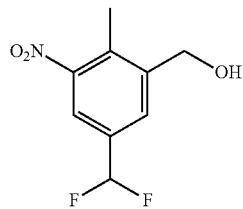

Using a procedure similar to that described for Preparation 2, but using the compound described in Preparation 34 (17.0 g, 73.6 mmol), the title compound was prepared as an off-white solid. (16.0 g, 100%)

$^1$H NMR (500 MHz, DMSO-$d_6$): δ=7.97 (s, 1H), 7.92 (s, 1H), 7.31-6.99 (m, 1H), 5.58 (t, J=5.4 Hz, 1H), 4.64 (d, J=5.3 Hz, 2H), 2.33 (s, 3H). LCMS Method 2: m/z 215.71 [M–H$^+$]; RT=1.81 min.

Preparation 36: [5-(difluoromethyl)-2-methyl-3-nitro-phenyl]methyl methanesulfonate

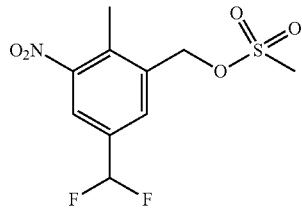 [SMILES: Cc1c(COS(C)(=O)=O)cc(C(F)F)cc1[N+](=O)[O-]]

Triethylamine (27.0 mL, 193 mmol) was added drop-wise to a solution of the product from Preparation 35 (14.0 g, 64.5 mmol) in dichloromethane (10 mL) at 0° C. After 10 min, methanesulfonyl chloride (10.0 mL, 129 mmol) was added drop-wise maintaining temperature at 0° C. The reaction mixture was stirred for 2 h then diluted with water (200 mL) and extracted with dichloromethane (2×200 mL). The combined organic layer was dried over sodium sulphate and evaporated under reduced pressure to afford title compound as a brown oil. Used without further purification. (18.0 g, 94.5%)

$^1$H NMR (400 MHz, CDCl$_3$): δ=7.92 (s, 1H), 7.72 (s, 1H), 6.86-6.52 (m, 1H), 4.68 (s, 2H), 3.14 (s, 3H), 2.58 (s, 3H).

Preparation 37: isopropyl (2S)-4-[[5-(difluoromethyl)-2-methyl-3-nitro-phenyl]methyl]-2-methyl-piperazine-1-carboxylate

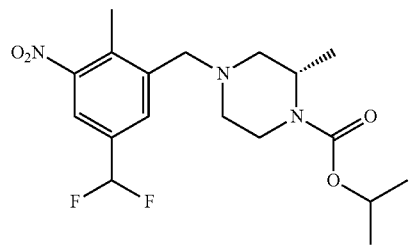 [SMILES: Cc1c(CN2CCN(C(=O)OC(C)C)[C@@H](C)C2)cc(C(F)F)cc1[N+](=O)[O-]]

Potassium carbonate (10.8 g, 79.3 mmol) was added portion-wise to a solution of product from Preparation 36 (7.80 g, 26.4 mmol) in acetonitrile (100 mL) at 0° C. Isopropyl (2S)-2-methylpiperazine-1-carboxylate hydrochloride from Preparation 49 (5.04 g, 26.4 mmol) was added portion-wise at 0° C. The reaction mixture was warmed to 75° C. and stirred for 16 h. The reaction mixture was quenched with water (200 mL) and extracted with ethyl acetate (2×300 mL). The combined organic layers were dried over sodium sulphate and evaporated under reduced pressure. The obtained residue was purified by silica gel (100-200 mesh) column chromatography eluting with a gradient of 0-15% ethyl acetate in petroleum ether. Clean fractions were evaporated under reduced pressure to give the title compound as a brown gum. (8.0 g, 79.2%)

$^1$H NMR (500 MHz, CDCl$_3$): δ=7.83 (s, 1H), 7.69 (s, 1H), 6.85-6.44 (m, 1H), 4.94-4.92 (m, 1H), 4.28 (br s, 1H), 3.88 (m, 1H), 3.53 (s, 2H), 3.12-3.10 (m, 1H), 2.70 (m, 1H), 2.56 (m, 1H), 2.52 (s, 3H), 2.27 (m, 1H), 2.12-2.10 (m, 1H), 1.27-1.22 (m, 9H). LCMS Method 2: m/z 386.37. [M+H$^+$]; RT=2.93 min.

Preparation 38: isopropyl (2S)-4-[[3-amino-5-(difluoromethyl)-2-methyl-phenyl]methyl]-2-methyl-piperazine-1-carboxylate

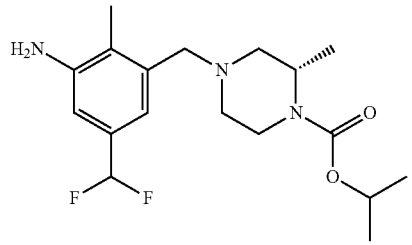

Using a procedure similar to that described for Preparation 5, but using the compound described in Preparation 37 (8.0 g, 20.7 mmol), the title compound was prepared as a yellow gum. (6.40 g, 86.0%)

$^1$H NMR (400 MHz, DMSO-d$_6$): δ=6.98-6.57 (m, 3H), 5.09 (s, 2H), 4.77 (m, 1H), 4.11 (br s, 1H), 3.69 (m, 1H), 3.34 (m, 2H), 3.02-2.88 (m, 1H), 2.68 (m, 1H), 2.57 (m, 1H), 2.12-2.02 (m, 4H), 1.9-1.86 (m, 1H), 1.19-1.08 (m, 9H). LCMS Method 3: m/z 356.2 [M+H$^+$]; RT=6.0 min.

Preparation 39: isopropyl (2S)-4-[[5-(difluoromethyl)-3-isothiocyanato-2-methyl-phenyl]methyl]-2-methyl-piperazine-1-carboxylate

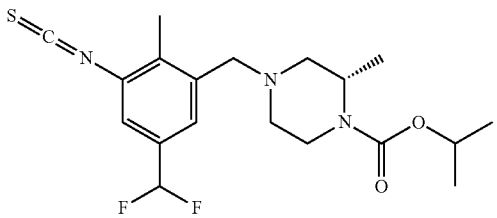 [SMILES: Cc1c(CN2CCN(C(=O)OC(C)C)[C@@H](C)C2)cc(C(F)F)cc1N=C=S]

Using a procedure similar to that described for Preparation 6, but using the compound described in Preparation 38 (430 mg, 1.21 mmol), the title compound was prepared as a yellow oil. (447 mg, 92.9%)

$^1$H NMR (300 MHz, CDCl$_3$): δ=7.33 (s, 1H), 7.31 (s, 1H), 6.58 (t, J=56.3 Hz, 1H), 4.92 (h, J=6.2 Hz, 1H), 4.26 (s, 1H), 3.86 (d, J=13.3 Hz, 1H), 3.44 (s, 2H), 3.09 (td, J=12.7, 3.5 Hz, 1H), 2.68 (d, J=11.0 Hz, 1H), 2.54 (d, J=11.1 Hz, 1H), 2.43 (s, 3H), 2.22 (dd, J=11.1, 3.9 Hz, 1H), 2.05 (td, J=11.6, 3.5 Hz, 1H), 1.24 (d, J=6.1 Hz, 6H) overlapping with 1.22 (d, J=6.1 Hz, 3H). LCMS Method 4: m/z 398.2 [M+H$^+$]; RT=1.01 min.

Preparation 40: isopropyl (2S)-4-[[3-(aminocarbamothioylamino)-5-(difluoromethyl)-2-methyl-phenyl]methyl]-2-methyl-piperazine-1-carboxylate

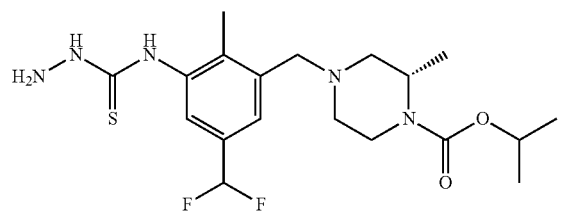 [SMILES: Cc1c(CN2CCN(C(=O)OC(C)C)[C@@H](C)C2)cc(C(F)F)cc1NC(=S)NN]

Using a procedure similar to that described for Preparation 7, but using the compound described in Preparation 39 (447 mg, 1.12 mmol), the title compound was prepared as a yellow oil. (357 mg, 73.9%)

$^1$H NMR (300 MHz, CDCl$_3$) δ=7.65 (br s, 1H), 7.39 (s, 1H), 6.63 (t, J=56.6 Hz, 1H), 4.93 (hept, J=6.2 Hz, 1H), 4.25 (s, 1H), 4.05 (s, 2H), 3.86 (d, J=13.1 Hz, 1H), 3.48 (s, 2H), 3.09 (td, J=12.8, 3.4 Hz, 1H), 2.72 (d, J=11.1 Hz, 1H), 2.58 (d, J=11.2 Hz, 1H), 2.33 (d, J=1.4 Hz, 3H), 2.21 (dd, J=11.2, 3.9 Hz, 1H), 2.13-1.94 (m, 1H), 1.24 (d, J=6.1 Hz, 6H) overlapping with 1.22 (d, J=6.1 Hz, 3H). LCMS Method 4: m/z 430.2 [M+H$^+$]; RT=0.62 min Scheme 9.8

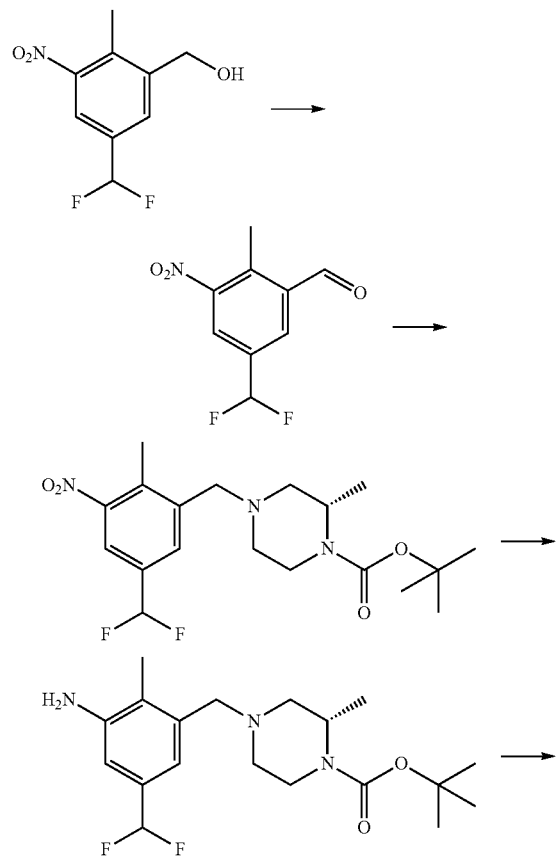

-continued

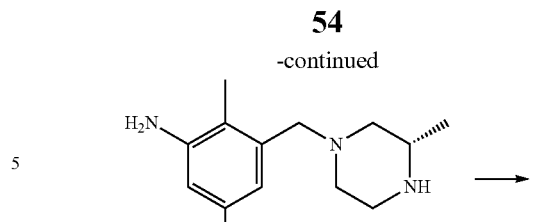

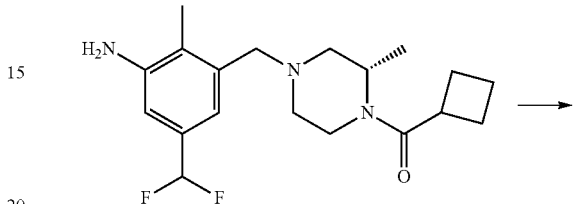

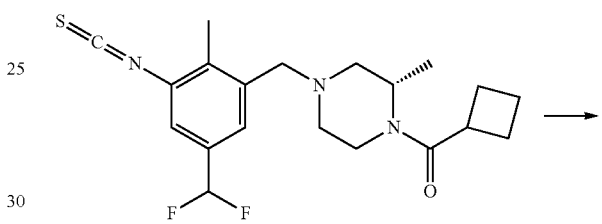

Preparation 41:
5-(difluoromethyl)-2-methyl-3-nitro-benzaldehyde

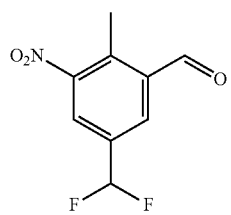

Using a procedure similar to that described for Preparation 3, but using the compound described in Preparation 35 (1.0 g, 4.60 mmol), the title compound was prepared as an off white solid (500 mg, 50.5%).

$^1$H NMR (300 MHz, CDCl$_3$) δ=10.42 (s, 1H), 8.19 (s, 1H), 8.13 (s, 1H), 6.52-6.98 (m, 1H), 2.83 (s, 3H). LCMS Method 1: m/z 356.2 [M+H$^+$]; RT=2.51 min.

Preparation 42: tert-butyl (2S)-4-[[5-(difluoromethyl)-2-methyl-3-nitro-phenyl]methyl]-2-methyl-piperazine-1-carboxylate

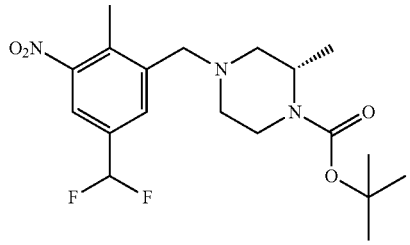 [SMILES: Cc1c(CN2CCN(C(=O)OC(C)(C)C)[C@@H](C)C2)cc(C(F)F)cc1[N+](=O)[O-]]

Using a procedure similar to that described for Preparation 4, but using the compound described in Preparation 41 (600 mg, 2.79 mmol), the title compound was prepared as an off white solid (700 mg, 62.8%).

$^1$H NMR (400 MHz, DMSO-d$_6$): δ=7.99 (s, 1H), 7.81 (s, 1H), 6.95-7.27 (m, 1H), 4.08-4.10 (m, 1H), 3.67-3.70 (m, 1H), 3.58 (s, 2H), 2.91-3.02 (m, 1H), 2.69-2.71 (m, 1H), 2.55-2.58 (m, 1H), 2.43 (s, 3H), 2.14-2.18 (m, 1H), 1.98-2.04 (m, 1H), 1.39 (s, 9H), 1.14 (d, J=6.4 Hz, 3H); LCMS Method 1: m/z 356.2 [M+H$^+$]; RT=3.11 min.

Preparation 43: tert-butyl (2S)-4-[[3-amino-5-(difluoromethyl)-2-methyl-phenyl]methyl]-2-methyl-piperazine-1-carboxylate

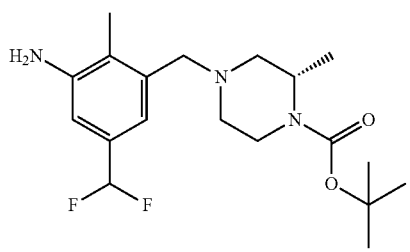

Using a procedure similar to that described for Preparation 5, but using the compound described in Preparation 42 (7.0 g, 17.5 mmol), the title compound was prepared as a tacky yellow solid (5.1 g, 79%).

$^1$H NMR (300 MHz, CDCl$_3$) δ=6.80 (s, 1H), 6.77 (s 1H), 6.40-6.64 (m, 1H), 4.18-4.20 (m, 1H), 3.76-3.80 (m, 3H), 3.36-3.45 (m, 2H), 3.00-3.06 (m, 1H), 2.68-2.70 (m, 1H), 2.55-2.58 (m, 1H), 2.20 (s, 3H) 2.14-2.17 (m, 1H), 1.95-2.00 (m, 1H), 1.45 (s, 9H), 1.19 (d, J=6.7 Hz, 3H). LCMS Method 2: m/z 270.2 [M+H$^+$]; RT=1.57 min.

Preparation 44: 5-(difluoromethyl)-2-methyl-3-[[(3S)-3-methylpiperazin-1-yl]methyl]aniline dihydrochloride

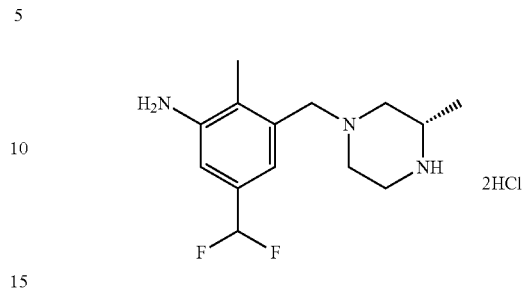

Using a procedure similar to that described for Preparation 8, but using the compound described in Preparation 43 (1.10 g, 2.98 mmol), the title compound was prepared as a colourless foam. (1.0 g, 100%) LCMS Method 4: m/z 270.2 [M+H$^+$]; RT=0.37 min.

Preparation 45: [(2S)-4-[[3-amino-5-(difluoromethyl)-2-methyl-phenyl]methyl]-2-methyl-piperazin-1-yl]-cyclobutyl-methanone

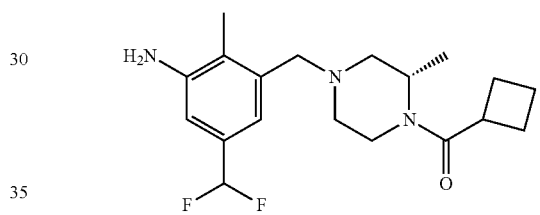

Using a procedure similar to that described for Preparation 9, but using the compound described in Preparation 44 (1.10 g, 2.98 mmol) and cyclobutane carboxylic acid, the title compound was prepared as a yellow oil. (1.03 g, 98%)

$^1$H NMR (600 MHz, CDCl$_3$) δ=6.79 (s, 1H), 6.77 (d, J=1.4 Hz, 1H), 6.52 (t, J=56.8 Hz, 1H), 4.71 (s, 0.5H), 4.36 (d, J=13.4 Hz, 0.5H), 3.83 (s, 0.5H), 3.46 (dd, J=12.9, 9.7 Hz, 1H), 3.35 (dd, J=15.1, 11.3 Hz, 1.5H), 3.17-3.25 (m, 1.5H), 2.87-2.93 (m, 0.5H). 2.76 (s, 0.5H), 2.67-2.72 (m, 0.5H), 2.61 (dd, J=27.1, 11.2 Hz, 1H), 2.38-2.43 (m, 0.5H), 2.25-2.35 (m, 1.5H), 2.19 (s, 3H), 2.05-2.17 (m, 3H), 1.90-2.01 (m, 2H), 1.81-1.89 (m, 1H), 1.19-1.27 (m, 3H). LCMS Method 4: m/z 352.2 [M+H$^+$]; RT=0.58 min.

Preparation 46: cyclobutyl-[(2S)-4-[[5-(difluoromethyl)-3-isothiocyanato-2-methyl-phenyl]methyl]-2-methyl-piperazin-1-yl]methanone

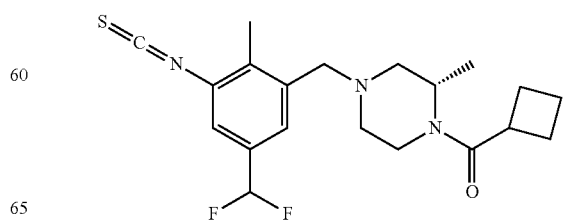

Using a procedure similar to that described for Preparation 6, but using the compound described in Preparation 45 (550 mg, 1.56 mmol), the title compound was prepared as a yellow oil. (588 mg, 95%)

¹H NMR (600 MHz, CDCl₃) δ=7.33 (s, 1H) overlapping with 7.31 (s, 1H), 6.58 (s, 1H), 4.74 (d, J=5.8 Hz, 1H), 4.36-4.41 (m, 0.5H), 3.85 (s, 0.5H), 3.38-3.48 (m, 2.5H), 3.16-3.28 (m, 1.5H), 2.89-2.95 (m, 0.5H), 2.75 (d, 0.5H), 2.68 (d, 0.5H), 2.58 (dd, J=21.4, 11.2 Hz, 1H), 2.43 (s, 3H) overlapping with 2.38-2.43 (m, 0.5H), 2.27-2.37 (m, 1.5H), 2.06-2.33 (m, 3H), 1.92-2.03 (m, 2H), 1.86 (d, J=10.1 Hz, 1H), 1.25 (dd, J=37.8, 6.8 Hz, 3H). LCMS Method 4: m/z 394.2 [M+H⁺]; RT=0.95 min.

Preparation 47: 1-amino-3-[3-[[(3S)-4-(cyclobutanecarbonyl)-3-methyl-piperazin-1-yl]methyl]-5-(difluoromethyl)-2-methyl-phenyl]thiourea

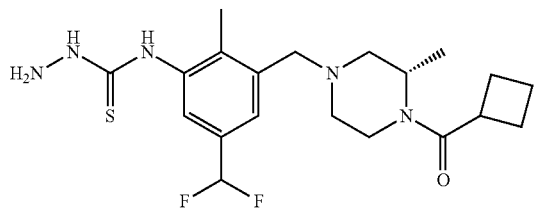 [SMILES: Cc1c(CN2CCN(C(=O)C3CCC3)[C@@H](C)C2)cc(C(F)F)cc1NC(=S)NN]

Using a procedure similar to that described for Preparation 7, but using the compound described in Preparation 46 (588 mg, 1.19 mmol), the title compound was prepared as a yellow oil. (617 mg, 97%)

¹H NMR (600 MHz, CDCl₃) δ=9.05 (s, 1H), 7.72 (s, 1H), 7.50 (s, 1H), 7.38 (s, 1H), 6.64 (t, J=56.6 Hz, 1H), 4.72 (s, 0.5H), 4.38 (d, J=13.4 Hz, 0.5H), 4.03 (s, 2H), 3.84 (s, 0.5H), 3.52 (dd, J=13.4, 8.5 Hz, 1H), 3.36-3.44 (m, 1.5H), 3.17-3.28 (m, 1.5H), 2.93 (td, J=12.9, 3.5 Hz, 0.5H), 2.71-2.80 (m, 1H), 2.62 (dd, J=25.7, 11.2 Hz, 1H), 2.38-2.45 (m, 0.5H), 2.27-2.35 (m, 1.5H) overlapping 2.33 (s, 3H), 1.92-2.22 (m, 5H), 1.86 (t, J=10.0 Hz, 1H), 1.17-1.30 (m, 3H). LCMS Method 4: m/z 426.3 [M+H⁺]; RT=0.56 min.

Scheme 9.9

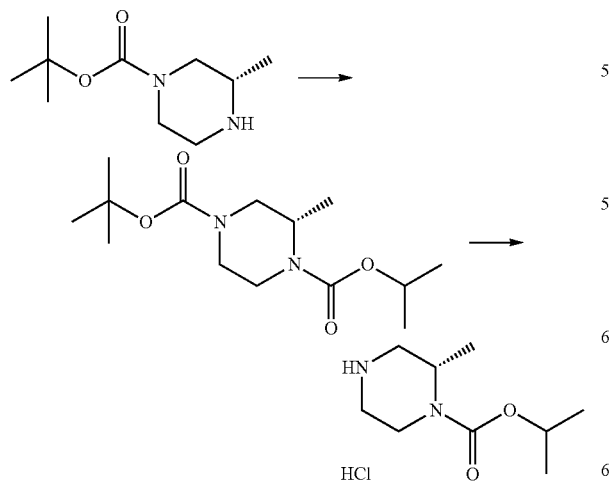

Preparation 48: 04-tert-butyl 01-isopropyl (2S)-2-methylpiperazine-1,4-dicarboxylate

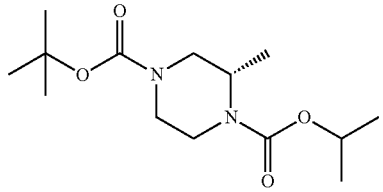 [SMILES: CC(C)OC(=O)N1CCN(C(=O)OC(C)(C)C)C[C@@H]1C]

Isopropyl chloroformate (39.0 mL, 78.0 mmol, 2M solution in toluene) was added drop-wise to a solution of diisopropylethylamine (34.0 mL, 195 mmol) and tert-butyl (3S)-3-methylpiperazine-1-carboxylate (13.0 g, 65.0 mmol) in dichloromethane (130 mL) at 0° C. The reaction mixture was allowed to warm to room temperature over 2 h. The mixture was diluted with water (200 mL) and extracted with dichloromethane (2×200 mL). The combined organic layer was dried over sodium sulphate and evaporated under reduced pressure. The obtained residue was purified by silica gel (100-200 mesh) column chromatography eluting with a gradient of 20-50% ethyl acetate in petroleum ether. Clean fractions were evaporated under reduced pressure to give the title compound as a colourless oil. (12.0 g, 64.5%)

¹H NMR (400 MHz, CDCl₃): δ=4.96-4.93 (m, 1H), 4.28 (m, 1H), 4.15-3.67 (m, 3H), 3.16-2.94 (m, 2H), 2.81 (m, 1H), 1.47 (s, 9H), 1.25 (d, J=6.2 Hz, 6H), 1.14 (d, J=6.7 Hz, 3H).

Preparation 49: isopropyl (2S)-2-methylpiperazine-1-carboxylate

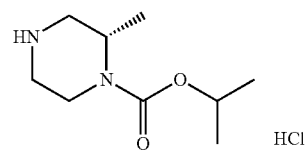

Using a procedure similar to that described for Preparation 8, but using the compound described in Preparation 48 (12.0 g, 41.9 mmol), the title compound was prepared as a colourless solid. (9.0 g, 96.4%)

¹H NMR (300 MHz, DMSO-d₆): δ=9.52 (br s, 2H), 4.85-4.73 (m, 1H), 4.38-4.24 (m, 1H), 3.91 (m, 1H), 3.26-3.12 (m, 2H), 3.10 (s, 1H), 3.08-2.98 (m, 1H), 2.92-2.75 (m, 1H), 1.27 (d, J=7.0 Hz, 3H), 1.20 (d, J=6.2 Hz, 6H).

Scheme 9.10

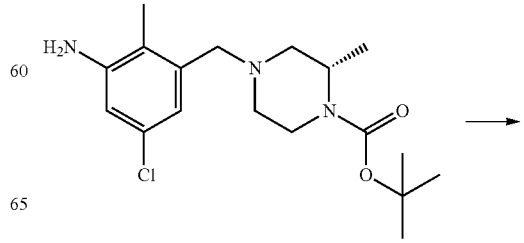

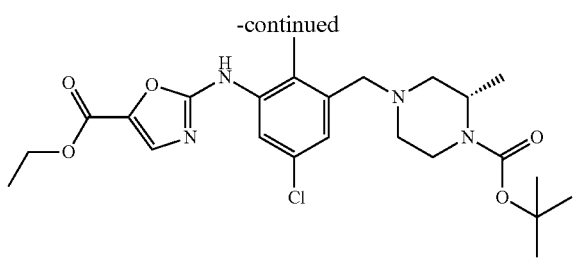

Preparation 50: ethyl 2-[3-[[(3S)-4-tert-butoxycarbonyl-3-methyl-piperazin-1-yl]methyl]-5-chloro-2-methyl-anilino]oxazole-5-carboxylate

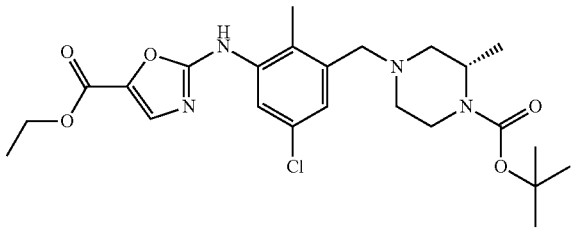 [SMILES: CCOC(=O)c1cnc(Nc2cc(Cl)cc(CN3CCN(C(=O)OC(C)(C)C)[C@@H](C)C3)c2C)o1]

Ethyl 2-chlorooxazole-5-carboxylate (372 mg, 2.12 mmol) was added to a solution of tert-butyl (2S)-4-[(3-amino-5-chloro-2-methyl-phenyl)methyl]-2-methyl-piperazine-1-carboxylate from Preparation 5 (500 mg, 1.41 mmol) in propan-2-ol (5.0 mL) and stirred under microwave irradiation at 160° C. for 30 min. The solvent was removed under reduced pressure and the obtained residue was purified by silica gel (100-200 mesh) column chromatography eluting with a gradient of 10-70% ethyl acetate in heptane. Clean fractions were evaporated under reduced pressure to give title compound as colourless oil. (130 mg, 18.7%)

LCMS Method 4: m/z 493.3 [M+H$^+$]; RT=0.94 min.

Preparation 51: 5-[3-[[(3S)-4-benzoyl-3-methyl-piperazin-1-yl]methyl]-5-chloro-2-methyl-anilino]-1,3,4-oxadiazole-2-carboxamide

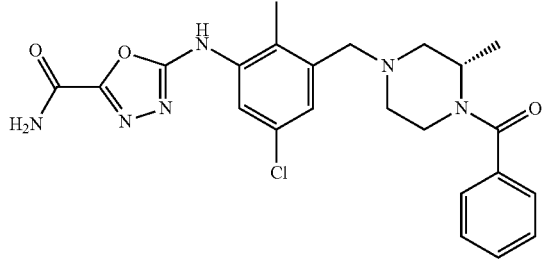 [SMILES: Cc1c(CN2CCN(C(=O)c3ccccc3)[C@@H](C)C2)cc(Cl)cc1Nc1nnc(C(N)=O)o1]

Oxamic acid (7.42 mg, 0.083 mmol) was added to a solution of product from Preparation 11 (30.0 mg, 0.069 mmol) in dichloromethane (0.6 mL) followed by 3-(ethyliminomethyleneamino)-N,N-dimethyl-propan-1-amine hydrochloride (53.3 mg, 0.278 mmol). The reaction was stirred at room temperature for 1 h until complete. The reaction mixture was concentrated under reduced pressure then dissolved in dimethylformamide (0.7 mL) and purified by basic preparative HPLC. Clean fractions were evaporated under reduced pressure to give title compound (6.0 mg, 18.4%). LCMS Method 4: m/z 469.2 [M+H$^+$]; RT=0.63 min.

Preparation 52: (1R)-1-[5-[2,5-dimethyl-3-[[(3S)-3-methylpiperazin-1-yl]methyl]anilino]-1,3,4-oxadiazol-2-yl]ethanol dihydrochloride

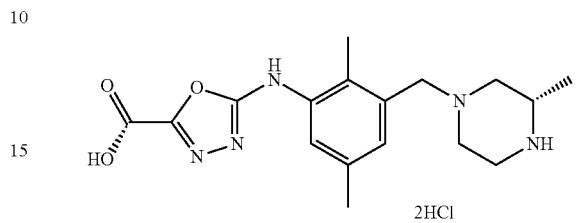

3-(Ethyliminomethyleneamino)-N,N-dimethyl-propan-1-amine hydrochloride (423 mg, 2.21 mmol) was added to a solution of tert-butyl (2S)-4-[[3-(aminocarbamothioylamino)-2,5-dimethyl-phenyl]methyl]-2-methyl-piperazine-1-carboxylate from Preparation 27 (300 mg, 0.74 mmol) and (2R)-2-hydroxypropanoic acid (66.3 mg, 0.74 mmol) in dichloromethane (10.0 mL) at room temperature and stirred for 2 h. The mixture was concentrated under reduced pressure and the obtained residue was purified by silica gel (100-200 mesh) column chromatography eluting with a gradient of 30-100% ethyl acetate in heptane. Clean fractions were evaporated under reduced pressure to give the tert-butyl carbamate intermediate as a colourless solid. Hydrogen chloride (4M in 1,4-dioxane, 1.0 mL) was added to a solution of the tert-butyl carbamate intermediate (75 mg, 0.17 mmol) in dichloromethane (3.0 mL) and stirred at room temperature for 2 hrs. Toluene (5 mL) was added and then the solvent was removed under reduced pressure to give title compound as colourless solid. (72 mg, 23%)

LCMS Method 4: m/z 346.2 [M+H$^+$]; RT=0.36 min.

Preparation 53: (1S)-1-[5-[2,5-dimethyl-3-[[(3S)-3-methylpiperazin-1-yl]methyl]anilino]-1,3,4-oxadiazol-2-yl]ethanol dihydrochloride

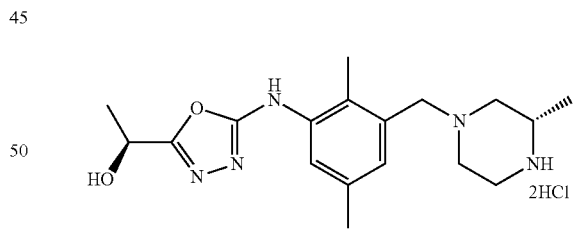

3-(Ethyliminomethyleneamino)-N,N-dimethyl-propan-1-amine hydrochloride (715 mg, 3.75 mmol) was added to a solution of tert-butyl (2S)-4-[[3-(aminocarbamothioylamino)-2,5-dimethyl-phenyl]methyl]-2-methyl-piperazine-1-carboxylate from Preparation 27 (545 mg, 1.34 mmol) and (2S)-2-hydroxypropanoic acid (120 mg, 1.34 mmol) in dichloromethane (10.0 mL) at room temperature and stirred for 16 h. The mixture was diluted with water (5 mL) and extracted with dichloromethane (2×10 mL). The combined organic layer was dried over sodium sulphate and evaporated under reduced pressure. The obtained residue was purified by silica gel (100-200 mesh) column chromatography eluting with a gradient of 0-80% ethyl acetate in heptane. Clean fractions were evaporated under reduced pressure to give the tert-butyl carbamate intermediate as a colourless solid. Hydrogen chloride (4M in 1,4-dioxane, 8.0 mL) was added to a solution of this intermediate material (280 mg, 0.63 mmol) in 1,4-dioxane (4.0 mL) and stirred at room temperature for 4 hrs. The solvent was removed under reduced pressure to give title compound as colourless solid. (263 mg, 47%)

LCMS Method 4: m/z 346.2 [M+H$^+$]; RT=0.37 min.

Preparation 54: 2-[5-[5-chloro-2-methyl-3-[[(3S)-3-methylpiperazin-1-yl]methyl]anilino]-1,3,4-oxadiazol-2-yl]acetonitrile dihydrochloride

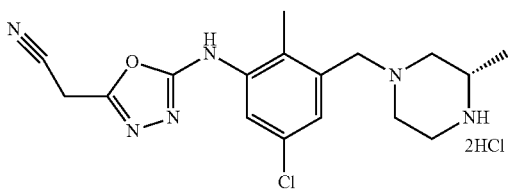 [SMILES: Cc1c(CN2CCN[C@@H](C)C2)cc(Cl)cc1Nc1nnc(CC#N)o1 ; "2HCl"]

Using a procedure similar to that described for Preparation 52, but using 2-cyanoacetic acid instead of (2R)-2-hydroxypropanoic acid and the thiosemicarbazide from Preparation 7 the title compound was prepared as a colourless solid. (112 mg, 61%) LCMS Method 4: m/z 341.2 [M+H$^+$]; RT=0.36 min.

Preparation 55: 3-[5-[2,5-dimethyl-3-[[(3S)-3-methylpiperazin-1-yl]methyl]anilino]-1,3,4-oxadiazol-2-yl]cyclobutanol dihydrochloride

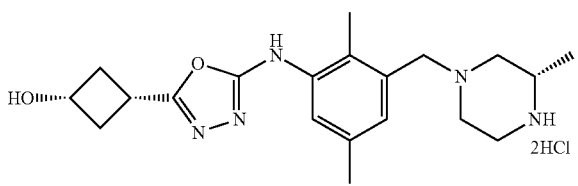 [SMILES: Cc1cc(CN2CCN[C@@H](C)C2)c(C)c(Nc2nnc([C@H]3C[C@@H](O)C3)o2)c1 ; "2HCl"]

Using a procedure similar to that described for Preparation 52, but using Cis-3-hydroxycyclobutanecarboxylic acid instead of (2R)-2-hydroxypropanoic acid the title compound was prepared as a colourless solid. (146 mg, 61%) LCMS Method 4: m/z 372.2 [M+H$^+$]; RT=0.36 min.

Scheme 9.11

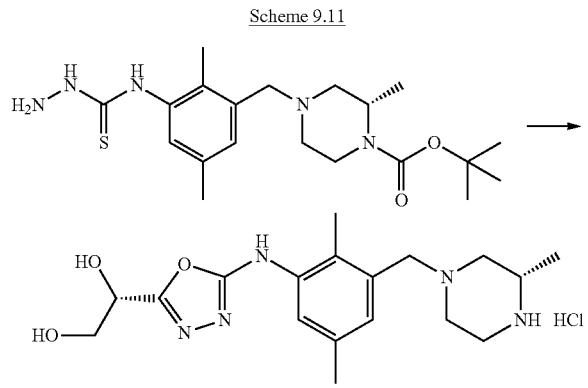

Preparation 56: (1S)-1-[5-[2,5-dimethyl-3-[[(3S)-3-methylpiperazin-1-yl]methyl]anilino]-1,3,4-oxadiazol-2-yl]ethane-1,2-diol hydrochloride

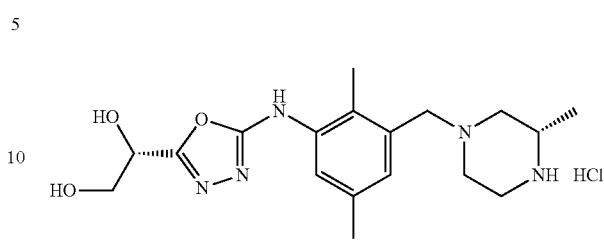

3-(Ethyliminomethyleneamino)-N,N-dimethyl-propan-1-amine hydrochloride (846 mg, 4.42 mmol) was added to a solution of product from Preparation 27 (600 mg, 1.47 mmol) and (4S)-2,2-dimethyl-1,3-dioxolane-4-carboxylic acid (323 mg, 2.21 mmol) dissolved in dry dichloromethane (30 mL) and stirred at room temperature for 12 h. The reaction mixture was quenched with water (30 mL) and extracted with dichloromethane (30 mL). The organic layer was collected and concentrated under reduced pressure. The obtained residue was purified by silica gel (100-200 mesh) column chromatography eluting with a gradient of 0-40% ethyl acetate in heptane. Clean fractions were evaporated under reduced pressure to give the intermediate product as a colourless oil. (600 mg, 81.2%) LCMS Method 4: m/z 502.4 [M+H$^+$]; RT=0.77 min. Hydrogen chloride (4M solution in 1,4-dioxane, 2.99 mL, 12 mmol) was added to a solution of the intermediate in methanol (5 mL) and stirred at room temperature for 3 h. The reaction mixture was concentrated under reduced pressure to afford title compound as a colourless foam that was used without any purification. (476 mg, 100%) LCMS Method 4: m/z 362.3 [M+H$^+$]; RT=0.33 min.

Scheme 9.12

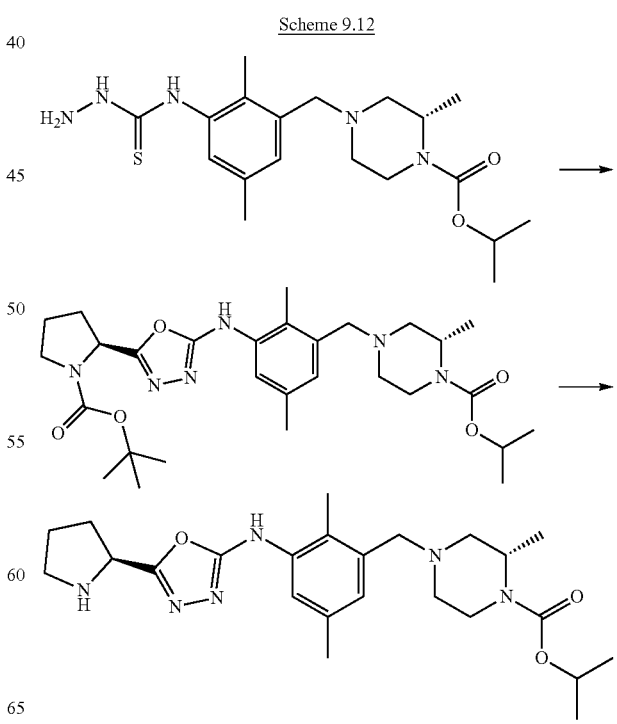

Preparation 57: isopropyl (2S)-4-[[3-[[5-[(2S)-1-tert-butoxycarbonylpyrrolidin-2-yl]-1,3,4-oxadiazol-2-yl]amino]-2,5-dimethyl-phenyl]methyl]-2-methyl-piperazine-1-carboxylate

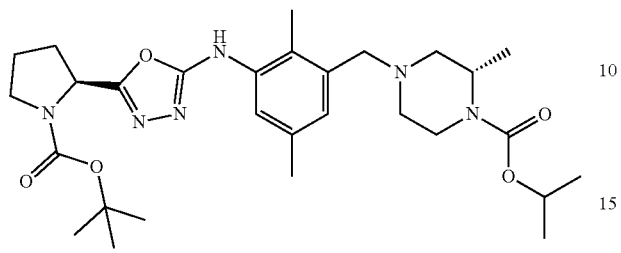

3-(Ethyliminomethyleneamino)-N,N-dimethyl-propan-1-amine hydrochloride (450 mg, 2.34 mmol) was added to a solution of product from Preparation 25 (264 mg, 0.67 mmol) and (2S)-1-tert-butoxycarbonylpyrrolidine-2-carboxylic acid (159 mg, 0.74 mmol) in dichloromethane (15 mL) and stirred at room temperature for 4.5 h. The mixture was concentrated to low volume and purified by silica gel (100-200 mesh) column chromatography eluting with a gradient of 0-80% ethyl acetate in heptanes. Clean fractions were combined and evaporated under reduced pressure to give the title compound as a colourless solid. (292 mg, 78%) LCMS Method 5: m/z 557.3 [M+H$^+$]; RT=2.23 min.

Preparation 58: isopropyl (2S)-4-[[2,5-dimethyl-3-[[5-[(2S)-pyrrolidin-2-yl]-1,3,4-oxadiazol-2-yl]amino]phenyl]methyl]-2-methyl-piperazine-1-carboxylate

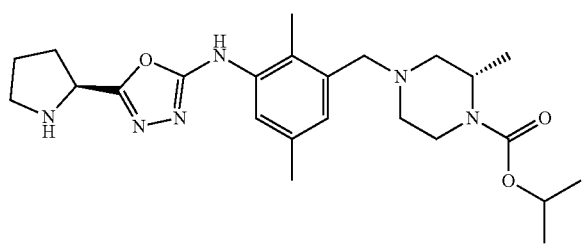 [SMILES: Cc1cc(CN2CCN(C(=O)OC(C)C)[C@@H](C)C2)c(C)c(Nc2nnc([C@@H]3CCCN3)o2)c1]

Hydrogen chloride (4M solution in 1,4-dioxane, 2.60 mL, 10.4 mmol) was added to a solution of the product from Preparation 57 (290 mg, 0.52 mmol) in methanol (4 mL) and stirred at room temperature for 2 h. The reaction mixture was concentrated under reduced pressure then partitioned between dichloromethane and saturated aqueous NaHCO$_3$. The organic layer was washed with brine, then dried over Na$_2$SO$_4$, filtered and concentrated to dryness. The residue was taken up in DMSO and purified by basic preparative HPLC. Clean fractions were combined and evaporated under reduced pressure to give the title compound as a colourless solid. (224 mg, 94%)

$^1$H NMR (600 MHz, DMSO-d$_6$) δ: 9.26 (s, 1H), 7.39 (d, J=1.7 Hz, 1H), 6.83 (d, J=1.7 Hz, 1H), 4.77 (hept, J=6.2 Hz, 1H), 4.26 (dd, J=8.1, 5.9 Hz, 1H), 4.12 (t, J=5.7 Hz, 1H), 3.70 (dt, J=13.1, 2.6 Hz, 1H), 3.38 (m, 2H), 2.95 (td, J 12.9, 3.4 Hz, 1H), 2.88 (ddd, J=10.0, 7.6, 5.7 Hz, 1H), 2.83 (dt, J=9.9, 6.9 Hz, 1H), 2.71 (ddt, J=11.2, 3.6, 1.9 Hz, 1H), 2.60 (dt, J=11.2, 1.9 Hz, 1H), 2.25 (s, 3H), 2.21 (s, 3H), 2.06 (m, 2H), 1.96 (m, 1H), 1.90 (td, J=11.7, 3.5 Hz, 1H), 1.81 (dddd, J=13.9, 12.0, 7.7, 5.9 Hz, 1H), 1.71 (m, 1H), 1.17 (dd, J=6.3, 0.9 Hz, 6H), 1.13 (d, J=6.7 Hz, 3H). LCMS Method 4: m/z 457.4 [M+H$^+$]; RT=0.45 min.

Scheme 9.13

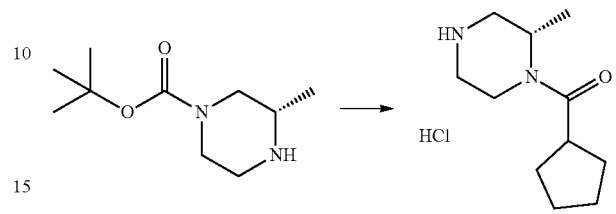

Preparation 59: cyclopentyl-[(2S)-2-methylpiperazin-1-yl]methanone hydrochloride

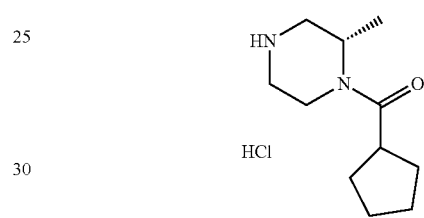

Cyclopentanecarbonyl chloride (12.3 mL, 101 mmol) was added dropwise to a solution of tert-butyl (3S)-3-methylpiperazine-1-carboxylate (18.4 g, 92 mmol) and triethylamine (46.1 mL, 243 mmol) in dichloromethane (270 mL) at 0° C. On complete addition the reaction mixture was stirred to room temperature over 2 h. The mixture was concentrated to dryness and the residue dissolved in ethyl acetate (150 ml) and washed successively with 10% citric acid (aq), saturated NaHCO$_3$ (aq). The organic layer was filtered through a small plug of silica then concentrated in vacuo to leave crude intermediate material. This intermediate material (27.0 g) was dissolved in dichloromethane and using a procedure similar to that described for Preparation 8, the title compound was prepared as an off white solid (21.0 g, 95%). LCMS Method 4: m/z 197.2 [M+H$^+$]; RT=0.35 min.

Scheme 9.14

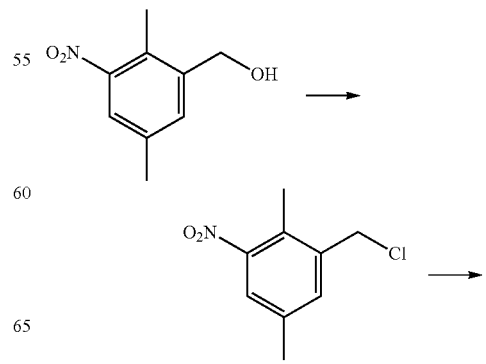

-continued

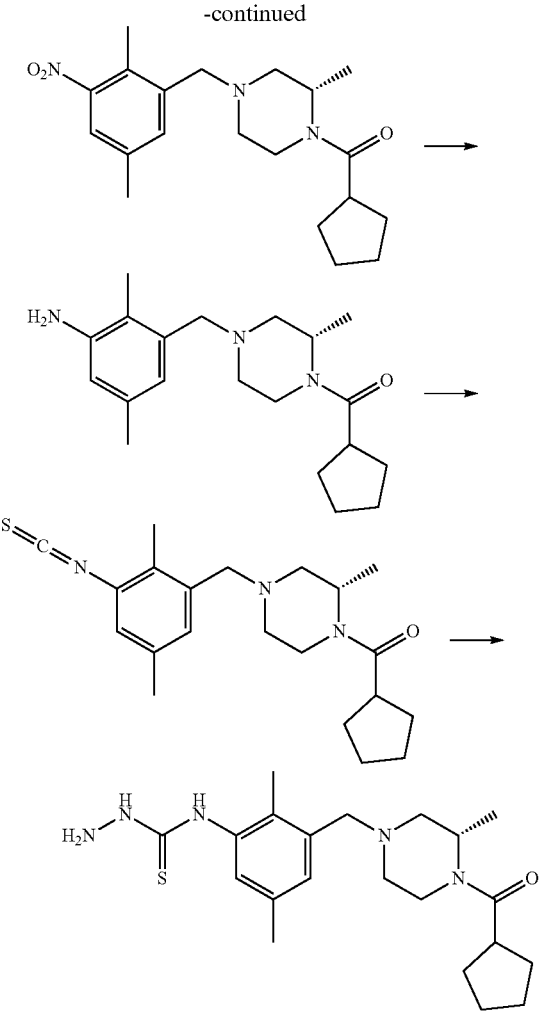

Preparation 60:
1-(chloromethyl)-2,5-dimethyl-3-nitro-benzene

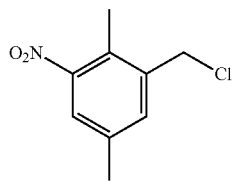

Methanesulfonyl chloride (3.3 mL, 42 mmol) was added to a solution of product from Preparation 18 (5.1 g, 28 mmol) and triethylamine (7.9 mL, 56 mmol) in dichloromethane (25 mL) at room temperature and stirred for 72 h. The mixture was diluted with dichloromethane (25 mL) and washed successively with HCl (0.5 M aq, 5 mL), saturated NaHCO$_3$ (aq, 5 mL), water and brine. The organic layer was dried over Na$_2$SO$_4$, filtered and concentrated in vacuo to afford the title compound as an off white solid. (5.6 g, 100%).
$^1$H NMR (600 MHz, CDCl$_3$) δ: 7.57 (d, J=1.8 Hz, 1H), 7.37 (d, J=1.8 Hz, 1H), 4.61 (s, 2H), 2.49 (s, 3H), 2.39 (s, 3H).

Preparation 61: cyclopentyl-[(2S)-4-[(2,5-dimethyl-3-nitro-phenyl)methyl]-2-methyl-2piperazin-1-yl]methanone

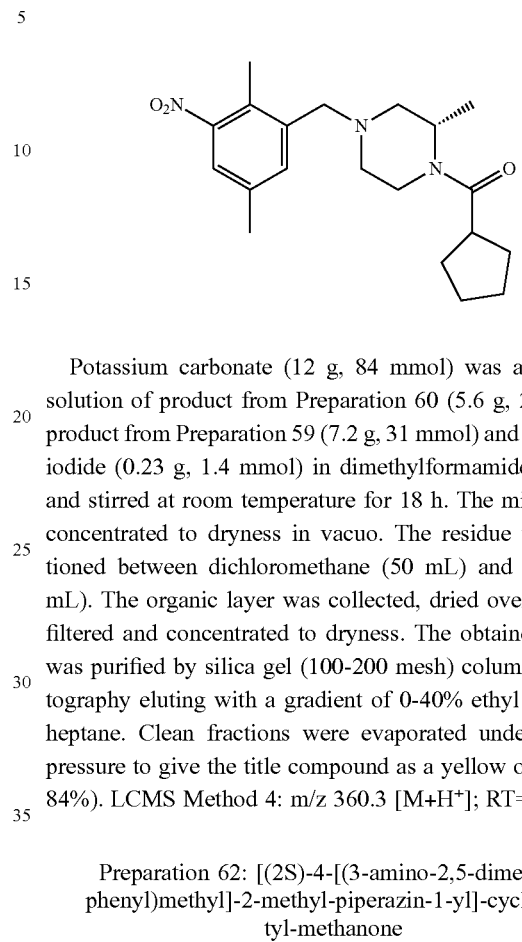

Potassium carbonate (12 g, 84 mmol) was added to a solution of product from Preparation 60 (5.6 g, 28 mmol), product from Preparation 59 (7.2 g, 31 mmol) and potassium iodide (0.23 g, 1.4 mmol) in dimethylformamide (20 mL) and stirred at room temperature for 18 h. The mixture was concentrated to dryness in vacuo. The residue was partitioned between dichloromethane (50 mL) and water (10 mL). The organic layer was collected, dried over Na$_2$SO$_4$, filtered and concentrated to dryness. The obtained residue was purified by silica gel (100-200 mesh) column chromatography eluting with a gradient of 0-40% ethyl acetate in heptane. Clean fractions were evaporated under reduced pressure to give the title compound as a yellow oil (8.43 g, 84%). LCMS Method 4: m/z 360.3 [M+H$^+$]; RT=0.90 min.

Preparation 62: [(2S)-4-[(3-amino-2,5-dimethyl-phenyl)methyl]-2-methyl-piperazin-1-yl]-cyclopentyl-methanone

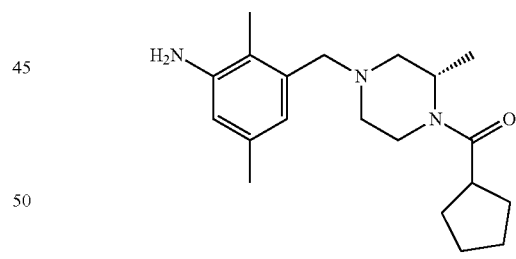

Iron powder (19.6 g, 352 mmol) was added to a solution of product from Preparation 61 (8.43 g, 23.4 mmol) in acetic acid (210 mL) and stirred at room temperature for 18 h. The mixture was filtered through a Celite® pad, washing the pad with methanol. The combined filtrate and methanol washings were concentrated to dryness. The crude residue was dissolved in water (20 mL) and basified to pH 12 with 4N NaOH (aq). The aqueous phase was extracted with dichloromethane (3×100 mL). The combined extracts were washed successively with saturated NaHCO$_3$ (aq) and brine, then dried over Na$_2$SO$_4$, filtered and concentrated in vacuo to leave the product as pale yellow oil (7.66 g, 99%). LCMS Method 4: m/z 330.3 [M+H$^+$]; RT=0.57 min.

Preparation 63: cyclopentyl-[(2S)-4-[(3-isothiocyanato-2,5-dimethyl-phenyl)methyl]-2-methyl-piperazin-1-yl]methanone

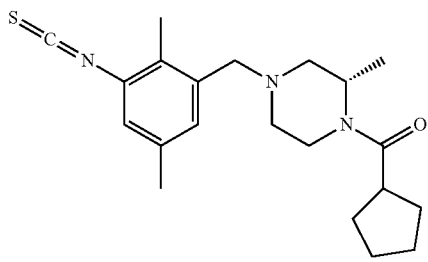 [SMILES: Cc1cc(CN2CCN(C(=O)C3CCCC3)[C@@H](C)C2)c(C)c(N=C=S)c1]

Using a procedure similar to that described for Preparation 6, but using the compound described in Preparation 62 (6.00, 18.2 mmol), the title compound was prepared as a yellow oil (6.76 g, 99%). LCMS Method 4: m/z 330.3 [M+H⁺]; RT=1.05 min.

Preparation 64: 1-amino-3-[3-[[(3S)-4-(cyclopentanecarbonyl)-3-methyl-piperazin-1-yl]methyl]-2,5-dimethyl-phenyl]thiourea

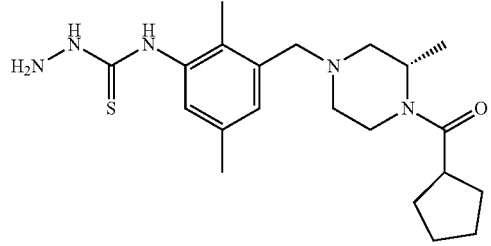 [SMILES: Cc1cc(CN2CCN(C(=O)C3CCCC3)[C@@H](C)C2)c(C)c(NC(=S)NN)c1]

Using a procedure similar to that described for Preparation 7, but using the compound described in Preparation 63 (6.00, 18.2 mmol), the title compound was prepared as a yellow oil (6.06 g, 82%). LCMS Method 4: m/z 330.3 [M+H⁺]; RT=0.54 min.

Scheme 9.15

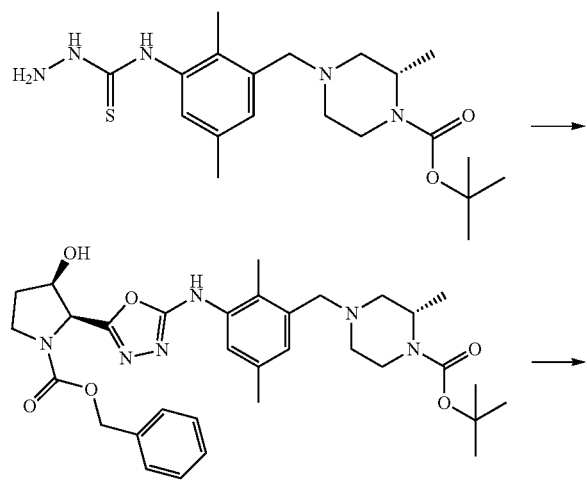

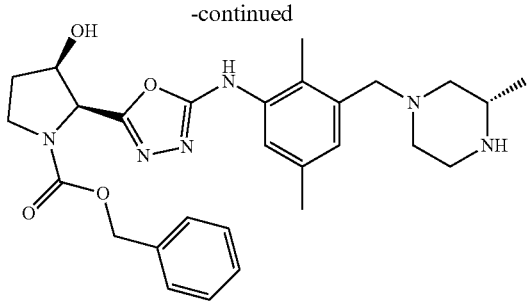

Preparation 65: tert-butyl (2S)-4-[[3-[[5-[(2S,3R)-1-benzyloxycarbonyl-3-hydroxy-pyrrolidin-2-yl]-1,3,4-oxadiazol-2-yl]amino]-2,5-dimethyl-phenyl]methyl]-2-methyl-piperazine-1-carboxylate

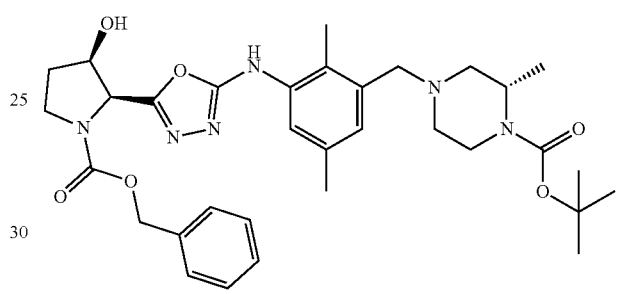

Using a similar procedure to that described in Example 31, but using (2S,3R)-1-benzyloxycarbonyl-3-hydroxy-pyrrolidine-2-carboxylic acid (0.89 g, 3.36 mmol) and product from Preparation 27 (1.14 g, 2.80 mmol). The obtained residue was purified by silica gel (100-200 mesh) column chromatography eluting with a gradient of 0-100% ethyl acetate in heptane. Clean fractions were evaporated under reduced pressure to give the title compound as a colourless oil (0.85 g, 49%). LCMS Method 4: m/z 621.5 [M+H⁺]; RT=0.74 min.

Preparation 66: benzyl (2S,3R)-2-[5-[2,5-dimethyl-3-[[(3S)-3-methylpiperazin-1-yl]methyl]anilino]-1,3,4-oxadiazol-2-yl]-3-hydroxy-pyrrolidine-1-carboxylate

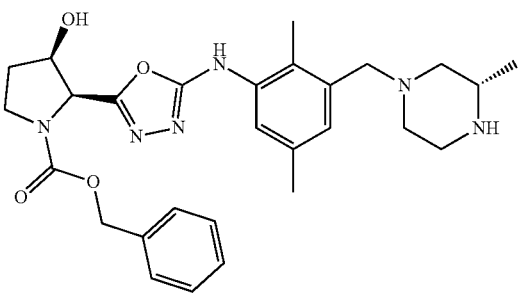 [SMILES: Cc1cc(CN2CCN[C@@H](C)C2)c(C)c(Nc2nnc([C@@H]3[C@H](O)CCN3C(=O)OCc3ccccc3)o2)c1]

Hydrogen chloride (4M solution in 1,4-dioxane, 6.85 mL, 27.3 mmol) was added to a solution of product from Preparation 65 (0.85 g, 1.37 mmol) in methanol (5 mL) and stirred at room temperature for 2 h. The reaction mixture was concentrated under reduced pressure then azeotroped with toluene. The residue was purified by basic HPLC. Clean fractions were evaporated under reduced pressure to afford the title compound as a colourless solid. (443 mg, 62%) LCMS Method 4: m/z 521.3 [M+H⁺]; RT=0.56 min.

General Routes to Exemplified Compounds:

All exemplified oxadiazole compounds can be accessed through either of the two general routes described in Scheme 10.1.

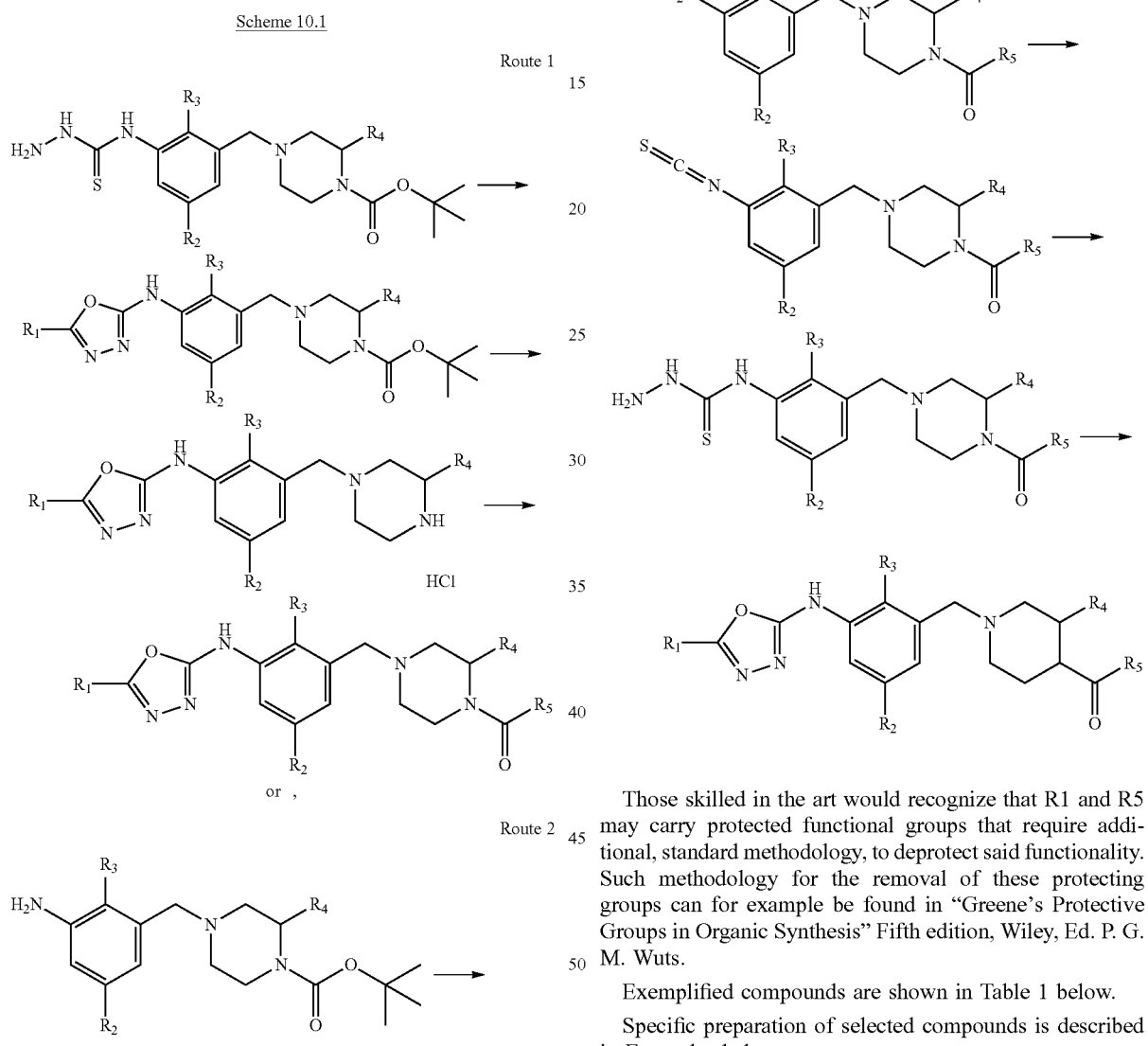

Those skilled in the art would recognize that R1 and R5 may carry protected functional groups that require additional, standard methodology, to deprotect said functionality. Such methodology for the removal of these protecting groups can for example be found in "Greene's Protective Groups in Organic Synthesis" Fifth edition, Wiley, Ed. P. G. M. Wuts.

Exemplified compounds are shown in Table 1 below.

Specific preparation of selected compounds is described in Examples below.

TABLE 1

| Example | Structure | Name | Mass ion | Rt |
|---|---|---|---|---|
| 1 | 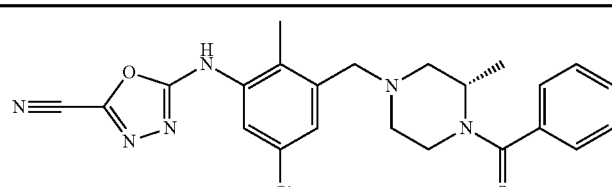 | 5-[3-[[(3S)-4-benzoyl-3-methyl-piperazin-1-yl]methyl]-5-chloro-2-methyl-anilino]-1,3,4-oxadiazole-2-carbonitrile | 450.16 | 2.44 |

TABLE 1-continued

| Example | Structure | Name | Mass ion | Rt |
|---|---|---|---|---|
| 2 | 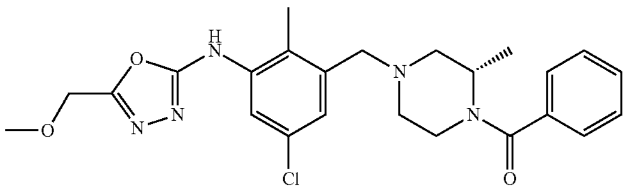 [SMILES: COCc1nnc(Nc2cc(Cl)cc(CN3CCN(C(=O)c4ccccc4)[C@@H](C)C3)c2C)o1] | [(2S)-4-[[5-chloro-3-[[5-(methoxymethyl)-1,3,4-oxadiazol-2-yl]amino]-2-methyl-phenyl]methyl]-2-methyl-piperazin-1-yl]-phenyl-methanone | 469.19 | 2.21 |
| 3 | 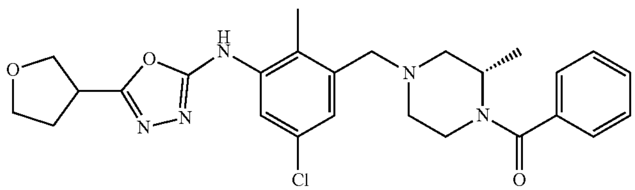 [SMILES: Cc1c(CN2CCN(C(=O)c3ccccc3)[C@@H](C)C2)cc(Cl)cc1Nc1nnc(C2CCOC2)o1] | [(2S)-4-[[5-chloro-2-methyl-3-[(5-tetrahydrofuran-3-yl-1,3,4-oxadiazol-2-yl)amino]phenyl]methyl]-2-methyl-piperazin-1-yl]-phenyl-methanone | 495.20 | 2.19 |
| 4 | 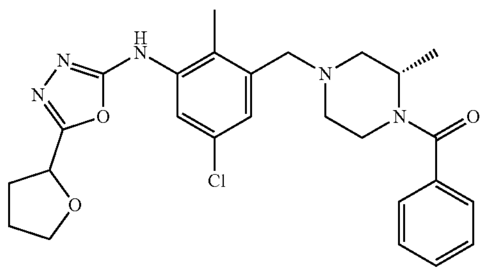 [SMILES: Cc1c(CN2CCN(C(=O)c3ccccc3)[C@@H](C)C2)cc(Cl)cc1Nc1nnc(C2CCCO2)o1] | [(2S)-4-[[5-chloro-2-methyl-3-[(5-tetrahydrofuran-2-yl-1,3,4-oxadiazol-2-yl)amino]phenyl]methyl]-2-methyl-piperazin-1-yl]-phenyl-methanone | 495.20 | 2.29 |
| 5 | 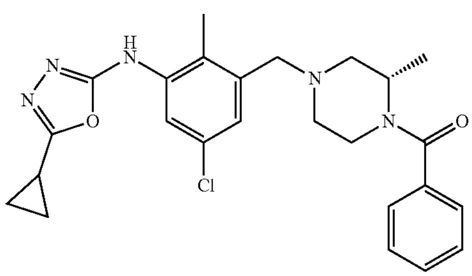 [SMILES: Cc1c(CN2CCN(C(=O)c3ccccc3)[C@@H](C)C2)cc(Cl)cc1Nc1nnc(C2CC2)o1] | [(2S)-4-[[5-chloro-3-[(5-cyclopropyl-1,3,4-oxadiazol-2-yl)amino]-2-methyl-phenyl]methyl]-2-methyl-piperazin-1-yl]-phenyl-methanone | 465.19 | 2.31 |
| 6 | 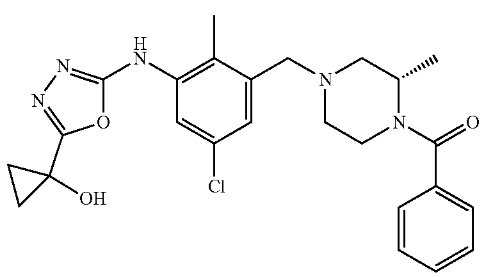 [SMILES: Cc1c(CN2CCN(C(=O)c3ccccc3)[C@@H](C)C2)cc(Cl)cc1Nc1nnc(C2(O)CC2)o1] | [(2S)-4-[[5-chloro-3-[[5-(1-hydroxycyclopropyl)-1,3,4-oxadiazol-2-yl]amino]-2-methyl-phenyl]methyl]-2-methyl-piperazin-1-yl]-phenyl-methanone | 481.19 | 2.10 |
| 7 | 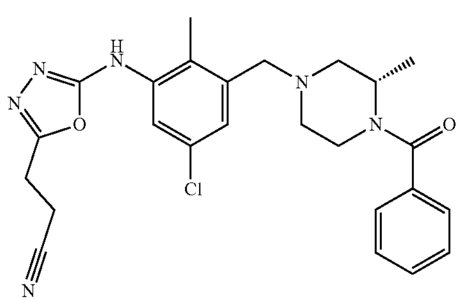 [SMILES: Cc1c(CN2CCN(C(=O)c3ccccc3)[C@@H](C)C2)cc(Cl)cc1Nc1nnc(CCC#N)o1] | 3-[5-[3-[[(3S)-4-benzoyl-3-methyl-piperazin-1-yl]methyl]-5-chloro-2-methyl-anilino]-1,3,4-oxadiazol-2-yl]propanenitrile | 478.19 | 2.17 |

TABLE 1-continued

| Example | Structure | Name | Mass ion | Rt |
|---|---|---|---|---|
| 8 | 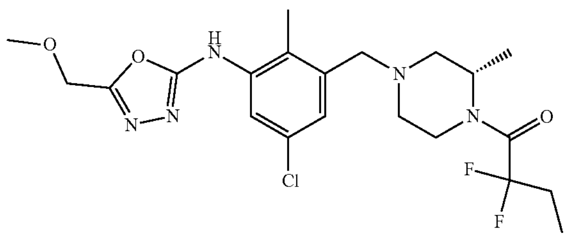 [SMILES: CCC(F)(F)C(=O)N1CCN(Cc2cc(Cl)cc(Nc3nnc(COC)o3)c2C)C[C@@H]1C] | 1-[(2S)-4-[[5-chloro-3-[[5-(methoxymethyl)-1,3,4-oxadiazol-2-yl]amino]-2-methyl-phenyl]methyl]-2-methyl-piperazin-1-yl]-2,2-difluoro-butan-1-one | 471.18 | 2.44 |
| 9 | 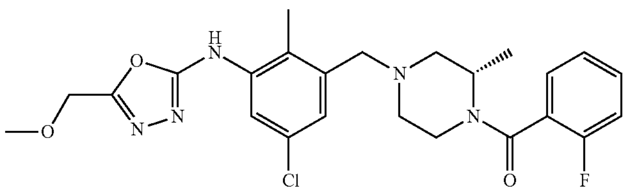 [SMILES: COCc1nnc(Nc2cc(Cl)cc(CN3CCN(C(=O)c4ccccc4F)[C@@H](C)C3)c2C)o1] | [(2S)-4-[[5-chloro-3-[[5-(methoxymethyl)-1,3,4-oxadiazol-2-yl]amino]-2-methyl-phenyl]methyl]-2-methyl-piperazin-1-yl]-(2-fluorophenyl)methanone | 487.18 | 2.27 |
| 10 | 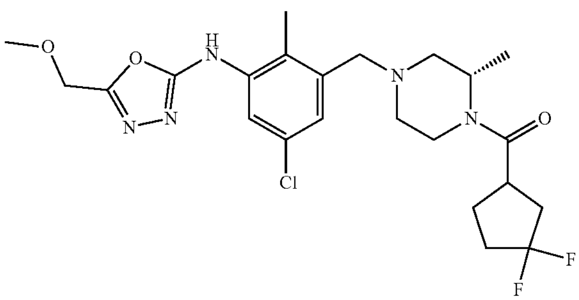 [SMILES: COCc1nnc(Nc2cc(Cl)cc(CN3CCN(C(=O)C4CCC(F)(F)C4)[C@@H](C)C3)c2C)o1] | [(2S)-4-[[5-chloro-3-[[5-(methoxymethyl)-1,3,4-oxadiazol-2-yl]amino]-2-methyl-phenyl]methyl]-2-methyl-piperazin-1-yl]-(3,3-difluorocyclopentyl)methanone | 497.20 | 2.24 |
| 11 | 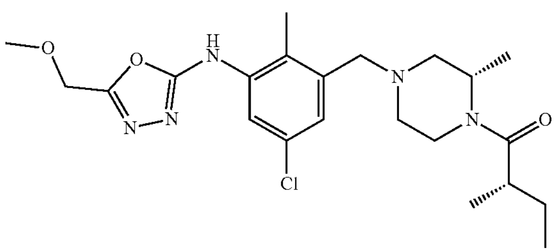 [SMILES: CC[C@H](C)C(=O)N1CCN(Cc2cc(Cl)cc(Nc3nnc(COC)o3)c2C)C[C@@H]1C] | (2S)-1-[(2S)-4-[[5-chloro-3-[[5-(methoxymethyl)-1,3,4-oxadiazol-2-yl]amino]-2-methyl-phenyl]methyl]-2-methyl-piperazin-1-yl]-2-methyl-butan-1-one | 449.22 | 2.17 |
| 12 | 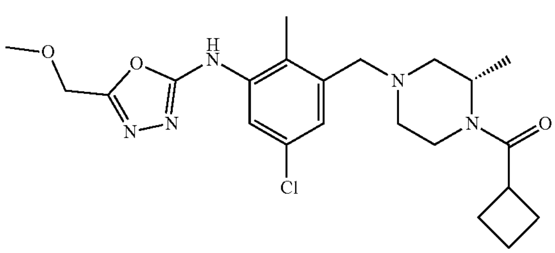 [SMILES: COCc1nnc(Nc2cc(Cl)cc(CN3CCN(C(=O)C4CCC4)[C@@H](C)C3)c2C)o1] | [(2S)-4-[[5-chloro-3-[[5-(methoxymethyl)-1,3,4-oxadiazol-2-yl]amino]-2-methyl-phenyl]methyl]-2-methyl-piperazin-1-yl]-cyclobutyl-methanone | 447.20 | 2.11 |
| 13 | 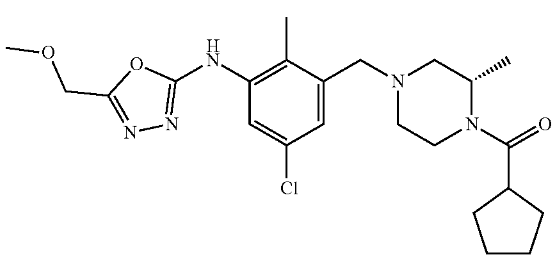 [SMILES: COCc1nnc(Nc2cc(Cl)cc(CN3CCN(C(=O)C4CCCC4)[C@@H](C)C3)c2C)o1] | [(2S)-4-[[5-chloro-3-[[5-(methoxymethyl)-1,3,4-oxadiazol-2-yl]amino]-2-methyl-phenyl]methyl]-2-methyl-piperazin-1-yl]-cyclopentyl-methanone | 461.22 | 2.23 |

TABLE 1-continued

| Example | Name | Mass ion | Rt |
|---|---|---|---|
| 14 | cyclobutyl-[(2S)-4-[[2,5-dimethyl-3-[(5-methyl-1,3,4-oxadiazol-2-yl)amino]phenyl]methyl]-2-methyl-piperazin-1-yl]methanone | 398.25 | 1.80 |
| 15 | 2-[5-[3-[[(3S)-4-(cyclobutanecarbonyl)-3-methyl-piperazin-1-yl]methyl]-2,5-dimethyl-anilino]-1,3,4-oxadiazol-2-yl]acetonitrile | 422.24 | 1.82 |
| 16 | 2-[5-[3-[[(3S)-4-(cyclopropanecarbonyl)-3-methyl-piperazin-1-yl]methyl]-2,5-dimethyl-anilino]-1,3,4-oxadiazol-2-yl]acetonitrile | 408.22 | 1.72 |
| 17 | 2-[5-[3-[[(3S)-4-(3,3-difluorocyclopentanecarbonyl)-3-methyl-piperazin-1-yl]methyl]-2,5-dimethyl-anilino]-1,3,4-oxadiazol-2-yl]acetonitrile | 472.24 | 1.94 |
| 18 | 2-[5-[5-chloro-3-[[4-(cyclopentanecarbonyl)-3-methyl-piperazin-1-yl]methyl]-2-methyl-anilino]-1,3,4-oxadiazol-2-yl]acetonitrile | 456.20 | 2.22 |
| 19 | cyclobutyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone | 428.26 | 1.75 |

TABLE 1-continued

| Example | Structure | Name | Mass ion | Rt |
|---|---|---|---|---|
| 20 | 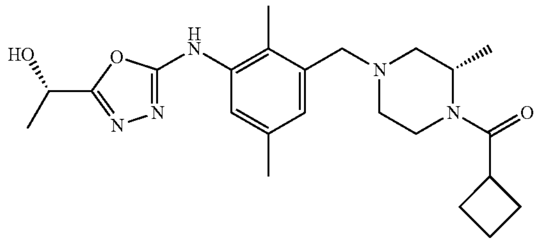 [SMILES: Cc1cc(CN2CCN(C(=O)C3CCC3)[C@@H](C)C2)c(C)c(Nc2nnc([C@H](C)O)o2)c1] | cyclobutyl-[(2S)-4-[[3-[[5-[(1S)-1-hydroxyethyl]-1,3,4-oxadiazol-2-yl]amino]-2,5-dimethyl-phenyl]methyl]-2-methyl-piperazin-1-yl]methanone | 428.26 | 1.75 |
| 21 | 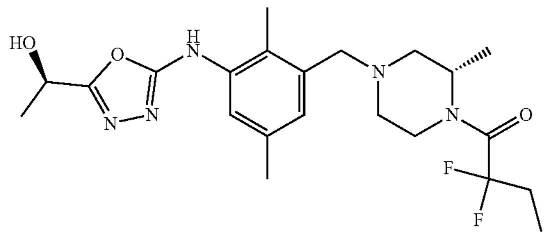 [SMILES: CCC(F)(F)C(=O)N1CCN(Cc2cc(C)cc(Nc3nnc([C@@H](C)O)o3)c2C)C[C@@H]1C] | 2,2-difluoro-1-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]butan-1-one | 451.24 | 1.99 |
| 22 | 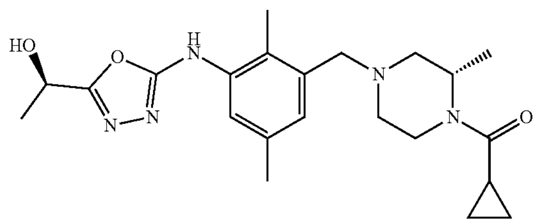 [SMILES: Cc1cc(CN2CCN(C(=O)C3CC3)[C@@H](C)C2)c(C)c(Nc2nnc([C@@H](C)O)o2)c1] | cyclopropyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone | 413.24 | 1.66 |
| 23 | 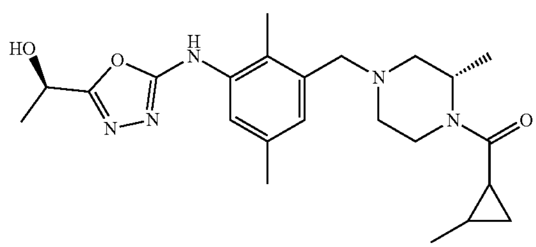 [SMILES: Cc1cc(CN2CCN(C(=O)C3CC3C)[C@@H](C)C2)c(C)c(Nc2nnc([C@@H](C)O)o2)c1] | [(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]-(2-methylcyclopropyl)methanone | 428.27 | 1.74 |
| 24 | 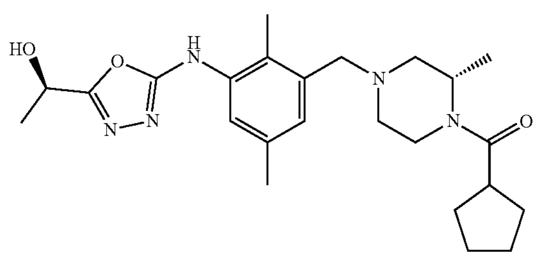 [SMILES: Cc1cc(CN2CCN(C(=O)C3CCCC3)[C@@H](C)C2)c(C)c(Nc2nnc([C@@H](C)O)o2)c1] | cyclopentyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone | 442.28 | 1.82 |
| 25 | 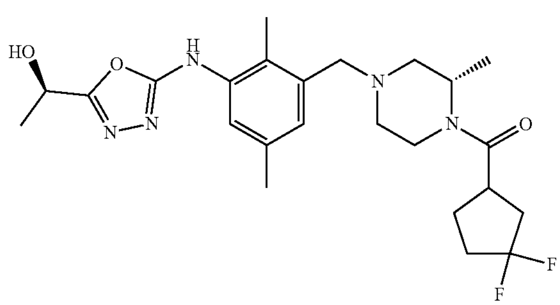 [SMILES: Cc1cc(CN2CCN(C(=O)C3CCC(F)(F)C3)[C@@H](C)C2)c(C)c(Nc2nnc([C@@H](C)O)o2)c1] | (3,3-difluorocyclopentyl)-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone | 478.25 | 1.85 |

TABLE 1-continued

| Example | Name | Mass ion | Rt |
|---|---|---|---|
| 26 | 2-cyclobutyl-1-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]ethanone | 442.28 | 1.83 |
| 27 | cyclobutyl-[(2S)-4-[[5-(difluoromethyl)-3-[[5-[(1S)-1-hydroxyethyl]-1,3,4-oxadiazol-2-yl]amino]-2-methyl-phenyl]methyl]-2-methyl-piperazin-1-yl]methanone | 464.25 | 1.90 |
| 28 | tert-butyl (2S)-4-[[3-[[5-[(1S)-1-hydroxyethyl]-1,3,4-oxadiazol-2-yl]amino]-2,5-dimethyl-phenyl]methyl]-2-methyl-piperazine-1-carboxylate | 446.26 | 1.90 |
| 29 | tert-butyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate | 471.28 | 1.91 |
| 30 | tert-butyl (2S)-4-[[2,5-dimethyl-3-[[5-(3-methyltriazol-4-yl)-1,3,4-oxadiazol-2-yl]amino]phenyl]methyl]-2-methyl-piperazine-1-carboxylate | 483.27 | 2.06 |
| 31 | tert-butyl (2S)-4-[[2,5-dimethyl-3-[[5-(2-methylpyrazol-3-yl)-1,3,4-oxadiazol-2-yl]amino]phenyl]methyl]-2-methyl-piperazine-1-carboxylate | 482.28 | 2.13 |

TABLE 1-continued

| Example | Structure | Name | Mass ion | Rt |
|---|---|---|---|---|
| 32 | 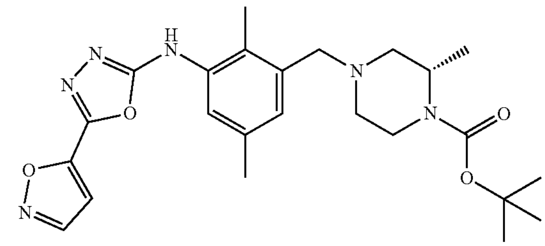 [SMILES: Cc1cc(CN2CCN(C(=O)OC(C)(C)C)[C@@H](C)C2)c(C)c(Nc2nnc(-c3ccno3)o2)c1] | tert-butyl (2S)-4-[[3-[(5-isoxazol-5-yl-1,3,4-oxadiazol-2-yl)amino]-2,5-dimethyl-phenyl]methyl]-2-methyl-piperazine-1-carboxylate | 469.25 | 2.14 |
| 33 | 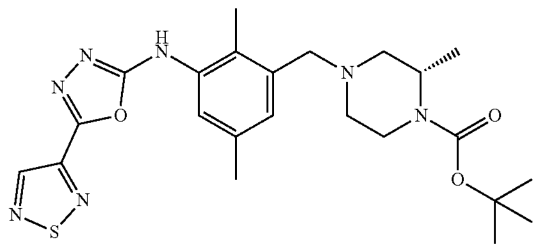 [SMILES: Cc1cc(CN2CCN(C(=O)OC(C)(C)C)[C@@H](C)C2)c(C)c(Nc2nnc(-c3cnsn3)o2)c1] | tert-butyl (2S)-4-[[2,5-dimethyl-3-[[5-(1,2,5-thiadiazol-3-yl)-1,3,4-oxadiazol-2-yl]amino]phenyl]methyl]-2-methyl-piperazine-1-carboxylate | 486.22 | 2.21 |
| 34 | 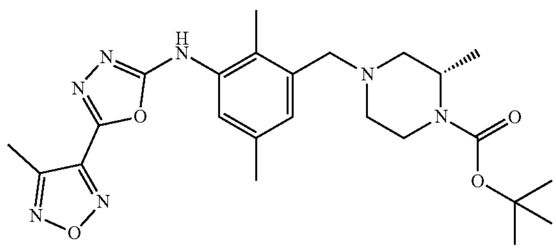 [SMILES: Cc1cc(CN2CCN(C(=O)OC(C)(C)C)[C@@H](C)C2)c(C)c(Nc2nnc(-c3nonc3C)o2)c1] | tert-butyl (2S)-4-[[2,5-dimethyl-3-[[5-(4-methyl-1,2,5-oxadiazol-3-yl)-1,3,4-oxadiazol-2-yl]amino]phenyl]methyl]-2-methyl-piperazine-1-carboxylate | 484.26 | 2.38 |
| 35 | 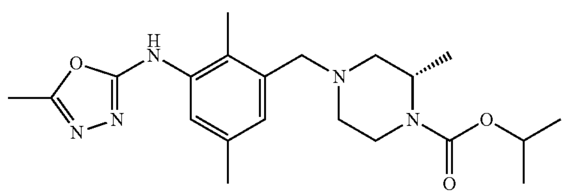 [SMILES: Cc1cc(CN2CCN(C(=O)OC(C)C)[C@@H](C)C2)c(C)c(Nc2nnc(C)o2)c1] | isopropyl (2S)-4-[[2,5-dimethyl-3-[(5-methyl-1,3,4-oxadiazol-2-yl)amino]phenyl]methyl]-2-methyl-piperazine-1-carboxylate | 402.24 | 1.89 |
| 36 | 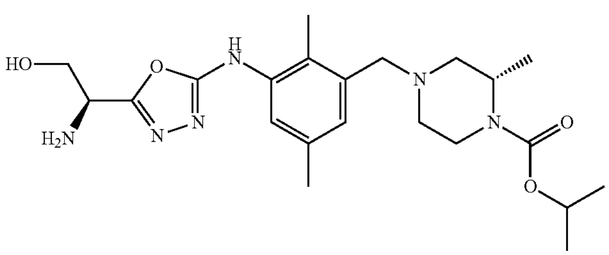 [SMILES: Cc1cc(CN2CCN(C(=O)OC(C)C)[C@@H](C)C2)c(C)c(Nc2nnc([C@@H](N)CO)o2)c1] | isopropyl (2S)-4-[[3-[[5-[(1S)-1-amino-2-hydroxy-ethyl]-1,3,4-oxadiazol-2-yl]amino]-2,5-dimethyl-phenyl]methyl]-2-methyl-piperazine-1-carboxylate | 446.26 | 1.65 |
| 37 | 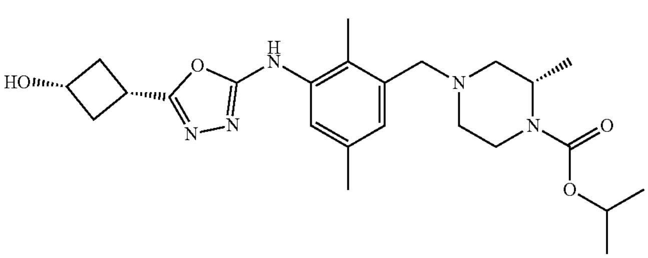 [SMILES: Cc1cc(CN2CCN(C(=O)OC(C)C)[C@@H](C)C2)c(C)c(Nc2nnc([C@H]3C[C@@H](O)C3)o2)c1] | isopropyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate | 457.27 | 1.84 |

TABLE 1-continued

| Example | Structure | Name | Mass ion | Rt |
|---|---|---|---|---|
| 38 | 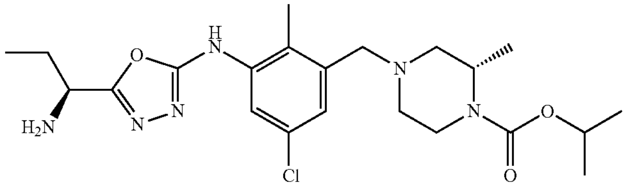 [SMILES: CC[C@H](N)c1nnc(Nc2cc(Cl)cc(CN3CCN(C(=O)OC(C)C)[C@@H](C)C3)c2C)o1] | isopropyl (2S)-4-[[3-[[5-[(1S)-1-aminopropyl]-1,3,4-oxadiazol-2-yl]amino]-5-chloro-2-methyl-phenyl]methyl]-2-methyl-piperazine-1-carboxylate | 465.23 | 1.91 |
| 39 | 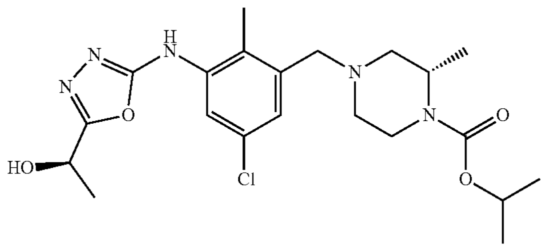 [SMILES: Cc1c(CN2CCN(C(=O)OC(C)C)[C@@H](C)C2)cc(Cl)cc1Nc1nnc([C@@H](C)O)o1] | isopropyl (2S)-4-[[5-chloro-3-[[5-[(1R)-1-hydroxyethyl]-1,3,4-oxadiazol-2-yl]amino]-2-methyl-phenyl]methyl]-2-methyl-piperazine-1-carboxylate | 452.21 | 2.06 |
| 40 | 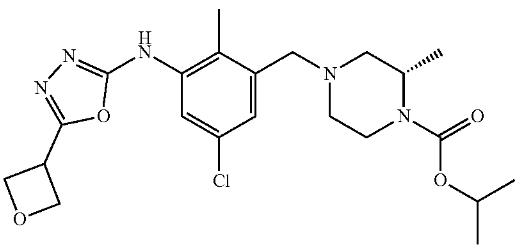 [SMILES: Cc1c(CN2CCN(C(=O)OC(C)C)[C@@H](C)C2)cc(Cl)cc1Nc1nnc(C2COC2)o1] | isopropyl (2S)-4-[[5-chloro-2-methyl-3-[[5-(oxetan-3-yl)-1,3,4-oxadiazol-2-yl]amino]phenyl]methyl]-2-methyl-piperazine-1-carboxylate | 463.20 | 2.17 |
| 41 | 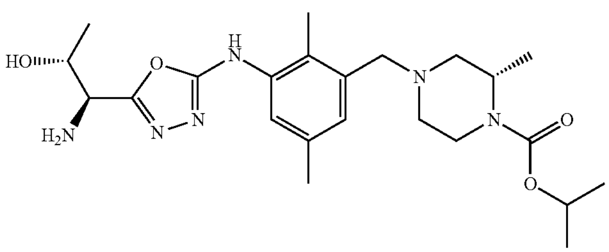 [SMILES: Cc1cc(CN2CCN(C(=O)OC(C)C)[C@@H](C)C2)c(C)c(Nc2nnc([C@@H](N)[C@@H](C)O)o2)c1] | isopropyl (2S)-4-[[3-[[5-[(1S,2R)-1-amino-2-hydroxy-propyl]-1,3,4-oxadiazol-2-yl]amino]-2,5-dimethyl-phenyl]methyl]-2-methyl-piperazine-1-carboxylate | 461.29 | 1.68 |
| 42 | 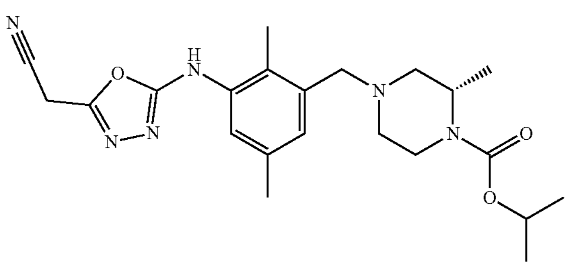 [SMILES: Cc1cc(CN2CCN(C(=O)OC(C)C)[C@@H](C)C2)c(C)c(Nc2nnc(CC#N)o2)c1] | isopropyl (2S)-4-[[3-[[5-(cyanomethyl)-1,3,4-oxadiazol-2-yl]amino]-2,5-dimethyl-phenyl]methyl]-2-methyl-piperazine-1-carboxylate | 426.24 | 1.93 |
| 43 | 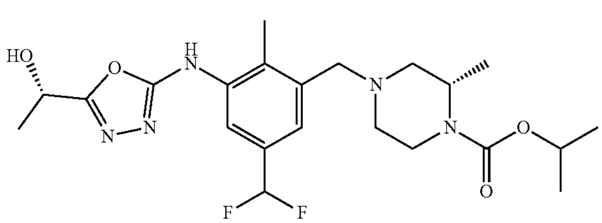 [SMILES: Cc1c(CN2CCN(C(=O)OC(C)C)[C@@H](C)C2)cc(C(F)F)cc1Nc1nnc([C@H](C)O)o1] | isopropyl (2S)-4-[[5-(difluoromethyl)-3-[[5-[(1S)-1-hydroxyethyl]-1,3,4-oxadiazol-2-yl]amino]-2-methyl-phenyl]methyl]-2-methyl-piperazine-1-carboxylate | 468.23 | 2.00 |

TABLE 1-continued

| Example | Name | Mass ion | Rt |
|---|---|---|---|
| 44 | isopropyl (2S)-4-[[5-chloro-2-methyl-3-[(5-tetrahydropyran-3-yl-1,3,4-oxadiazol-2-yl)amino]phenyl]methyl]-2-methyl-piperazine-1-carboxylate | 491.23 | 2.35 |
| 45 | isopropyl (2S)-4-[[5-chloro-3-[[5-(1-hydroxycyclopropyl)-1,3,4-oxadiazol-2-yl]amino]-2-methyl-phenyl]methyl]-2-methyl-piperazine-1-carboxylate | 463.20 | 2.11 |
| 46 | isopropyl (2S)-4-[[5-chloro-3-[[5-[1-(hydroxymethyl)cyclopropyl]-1,3,4-oxadiazol-2-yl]amino]-2-methyl-phenyl]methyl]-2-methyl-piperazine-1-carboxylate | 477.21 | 2.13 |
| 47 | isopropyl (2S)-4-[[5-chloro-2-methyl-3-[[5-(2,2,2-trifluoro-1-hydroxy-ethyl)-1,3,4-oxadiazol-2-yl]amino]phenyl]methyl]-2-methyl-piperazine-1-carboxylate | 505.17 | 2.35 |
| 48 | isopropyl (2S)-4-[[5-chloro-2-methyl-3-[[5-(2-oxopyrrolidin-3-yl)-1,3,4-oxadiazol-2-yl]amino]phenyl]methyl]-2-methyl-piperazine-1-carboxylate | 490.21 | 2.01 |
| 49 | isopropyl (2S)-4-[[3-[[5-[(1S)-1-aminoethyl]-1,3,4-oxadiazol-2-yl]amino]-2,5-dimethyl-phenyl]methyl]-2-methyl-piperazine-1-carboxylate | 431.27 | 1.68 |

TABLE 1-continued

| Example | Structure | Name | Mass ion | Rt |
|---|---|---|---|---|
| 50 | 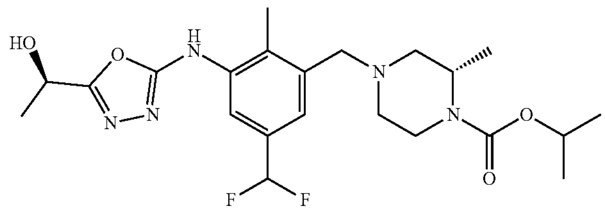 [SMILES: Cc1c(CN2CCN(C(=O)OC(C)C)[C@@H](C)C2)cc(C(F)F)cc1Nc1nnc([C@@H](C)O)o1] | isopropyl (2S)-4-[[5-(difluoromethyl)-3-[[5-[(1R)-1-hydroxyethyl]-1,3,4-oxadiazol-2-yl]amino]-2-methyl-phenyl]methyl]-2-methyl-piperazine-1-carboxylate | 468.23 | 2.00 |
| 51 | 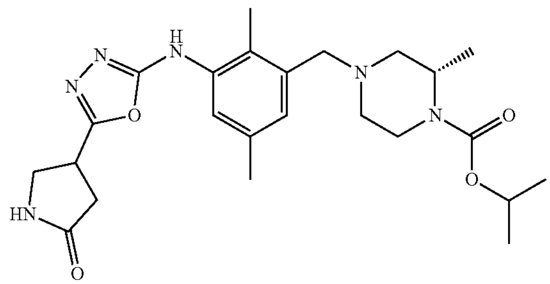 [SMILES: Cc1cc(CN2CCN(C(=O)OC(C)C)[C@@H](C)C2)c(C)c(Nc2nnc(C3CNC(=O)C3)o2)c1] | isopropyl (2S)-4-[[2,5-dimethyl-3-[[5-(5-oxopyrrolidin-3-yl)-1,3,4-oxadiazol-2-yl]amino]phenyl]methyl]-2-methyl-piperazine-1-carboxylate | 471.27 | 1.78 |
| 52 | 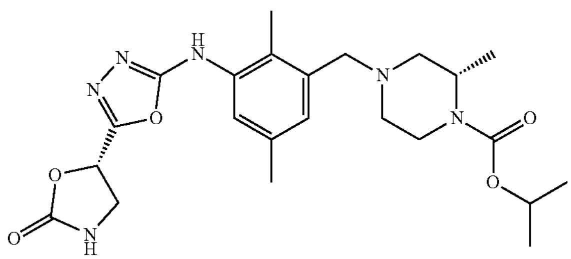 [SMILES: Cc1cc(CN2CCN(C(=O)OC(C)C)[C@@H](C)C2)c(C)c(Nc2nnc([C@@H]3CNC(=O)O3)o2)c1] | isopropyl (2S)-4-[[2,5-dimethyl-3-[[5-[(5S)-2-oxooxazolidin-5-yl]-1,3,4-oxadiazol-2-yl]amino]phenyl]methyl]-2-methyl-piperazine-1-carboxylate | 473.25 | 1.82 |
| 53 | 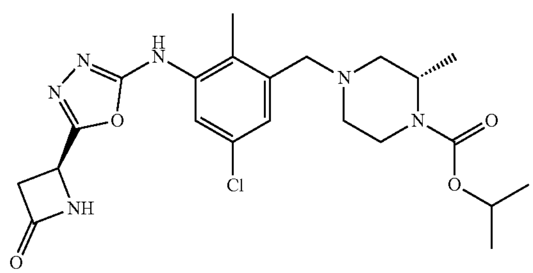 [SMILES: Cc1c(CN2CCN(C(=O)OC(C)C)[C@@H](C)C2)cc(Cl)cc1Nc1nnc([C@@H]2CC(=O)N2)o1] | isopropyl (2S)-4-[[5-chloro-2-methyl-3-[[5-[(2S)-4-oxoazetidin-2-yl]-1,3,4-oxadiazol-2-yl]amino]phenyl]methyl]-2-methyl-piperazine-1-carboxylate | 476.19 | 2.04 |
| 54 | 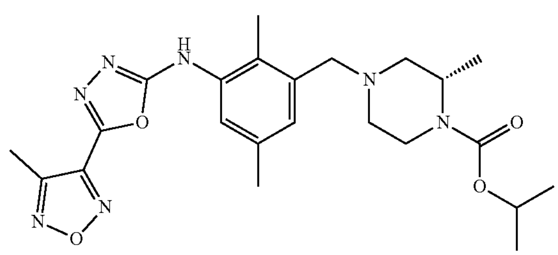 [SMILES: Cc1cc(CN2CCN(C(=O)OC(C)C)[C@@H](C)C2)c(C)c(Nc2nnc(-c3nonc3C)o2)c1] | isopropyl (2S)-4-[[2,5-dimethyl-3-[[5-(4-methyl-1,2,5-oxadiazol-3-yl)-1,3,4-oxadiazol-2-yl]amino]phenyl]methyl]-2-methyl-piperazine-1-carboxylate | 470.25 | 2.29 |
| 55 | 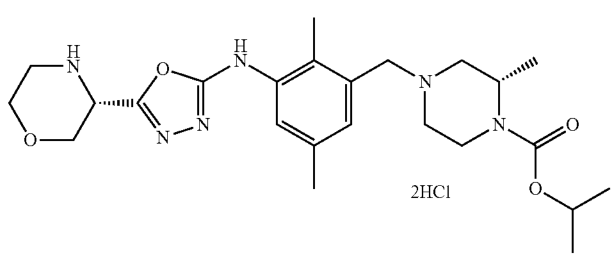 [SMILES: Cc1cc(CN2CCN(C(=O)OC(C)C)[C@@H](C)C2)c(C)c(Nc2nnc([C@@H]3COCCN3)o2)c1] | isopropyl (2S)-4-[[2,5-dimethyl-3-[[5-[(3S)-morpholin-3-yl]-1,3,4-oxadiazol-2-yl]amino]phenyl]methyl]-2-methyl-piperazine-1-carboxylate dihydrochloride | 473.28 | 1.72 |

TABLE 1-continued

| Example | Structure | Name | Mass ion | Rt |
|---|---|---|---|---|
| 56 | 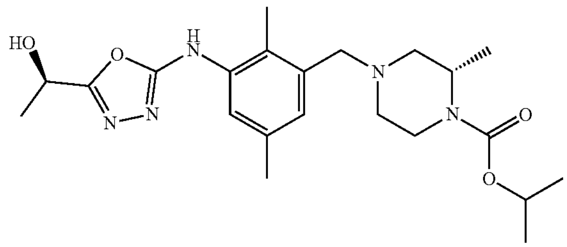 [SMILES: Cc1cc(CN2CCN(C(=O)OC(C)C)[C@@H](C)C2)c(C)c(Nc2nnc([C@@H](C)O)o2)c1] | isopropyl (2S)-4-[[3-[[5-[(1R)-1-hydroxyethyl]-1,3,4-oxadiazol-2-yl]amino]-2,5-dimethyl-phenyl]methyl]-2-methyl-piperazine-1-carboxylate | 432.26 | 1.83 |
| 57 | 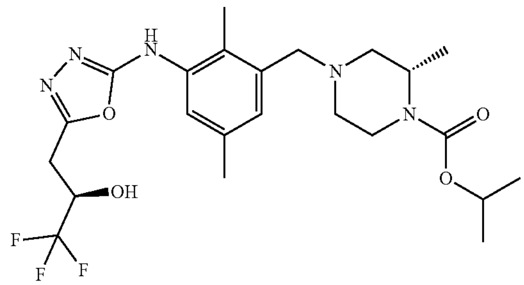 [SMILES: Cc1cc(CN2CCN(C(=O)OC(C)C)[C@@H](C)C2)c(C)c(Nc2nnc(C[C@@H](O)C(F)(F)F)o2)c1] | isopropyl (2S)-4-[[2,5-dimethyl-3-[[5-[(2R)-3,3,3-trifluoro-2-hydroxy-propyl]-1,3,4-oxadiazol-2-yl]amino]phenyl]methyl]-2-methyl-piperazine-1-carboxylate | 500.25 | 2.00 |
| 58 | 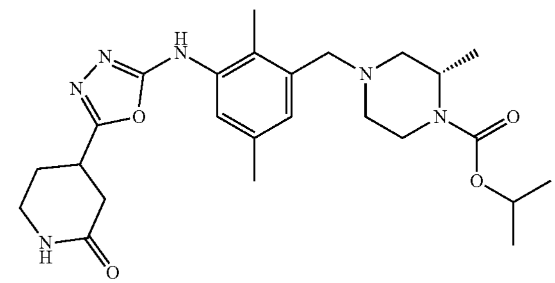 [SMILES: Cc1cc(CN2CCN(C(=O)OC(C)C)[C@@H](C)C2)c(C)c(Nc2nnc(C3CCNC(=O)C3)o2)c1] | isopropyl (2S)-4-[[2,5-dimethyl-3-[[5-(2-oxo-4-piperidyl)-1,3,4-oxadiazol-2-yl]amino]phenyl]methyl]-2-methyl-piperazine-1-carboxylate | 485.29 | 1.79 |
| 59 | 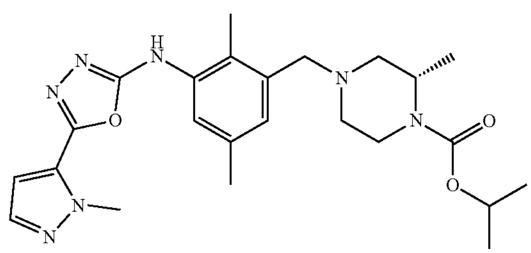 [SMILES: Cc1cc(CN2CCN(C(=O)OC(C)C)[C@@H](C)C2)c(C)c(Nc2nnc(-c3ccnn3C)o2)c1] | isopropyl (2S)-4-[[2,5-dimethyl-3-[[5-(2-methylpyrazol-3-yl)-1,3,4-oxadiazol-2-yl]amino]phenyl]methyl]-2-methyl-piperazine-1-carboxylate | 468.27 | 2.05 |
| 60 | 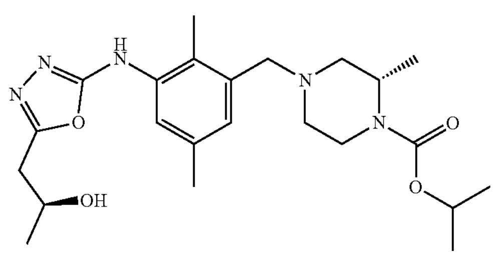 [SMILES: Cc1cc(CN2CCN(C(=O)OC(C)C)[C@@H](C)C2)c(C)c(Nc2nnc(C[C@H](C)O)o2)c1] | isopropyl (2S)-4-[[3-[[5-[(2S)-2-hydroxypropyl]-1,3,4-oxadiazol-2-yl]amino]-2,5-dimethyl-phenyl]methyl]-2-methyl-piperazine-1-carboxylate | 446.28 | 1.83 |
| 61 | 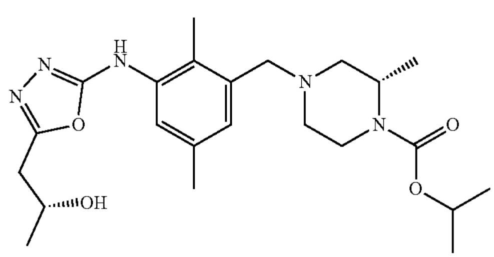 [SMILES: Cc1cc(CN2CCN(C(=O)OC(C)C)[C@@H](C)C2)c(C)c(Nc2nnc(C[C@@H](C)O)o2)c1] | isopropyl (2S)-4-[[3-[[5-[(2R)-2-hydroxypropyl]-1,3,4-oxadiazol-2-yl]amino]-2,5-dimethyl-phenyl]methyl]-2-methyl-piperazine-1-carboxylate | 446.28 | 1.83 |

TABLE 1-continued

| Example | Structure | Name | Mass ion | Rt |
|---|---|---|---|---|
| 62 | 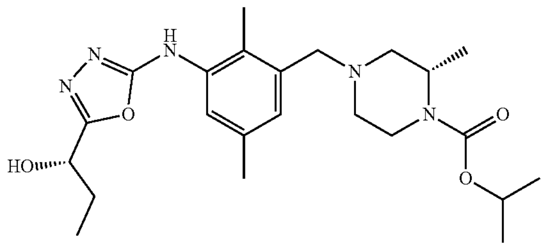 [SMILES: CC[C@H](O)c1nnc(Nc2cc(C)cc(CN3CCN(C(=O)OC(C)C)[C@@H](C)C3)c2C)o1] | isopropyl (2S)-4-[[3-[[5-[(1S)-1-hydroxypropyl]-1,3,4-oxadiazol-2-yl]amino]-2,5-dimethyl-phenyl]methyl]-2-methyl-piperazine-1-carboxylate | 446.28 | 1.89 |
| 63 | 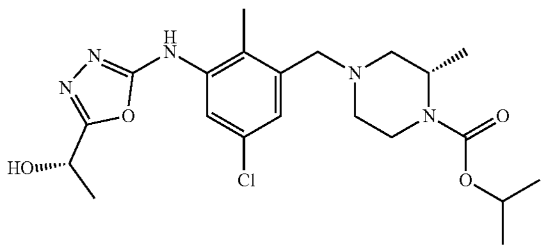 [SMILES: Cc1c(CN2CCN(C(=O)OC(C)C)[C@@H](C)C2)cc(Cl)cc1Nc1nnc([C@H](C)O)o1] | isopropyl (2S)-4-[[5-chloro-3-[[5-[(1S)-1-hydroxyethyl]-1,3,4-oxadiazol-2-yl]amino]-2-methyl-phenyl]methyl]-2-methyl-piperazine-1-carboxylate | 451.20 | 2.08 |
| 64 | 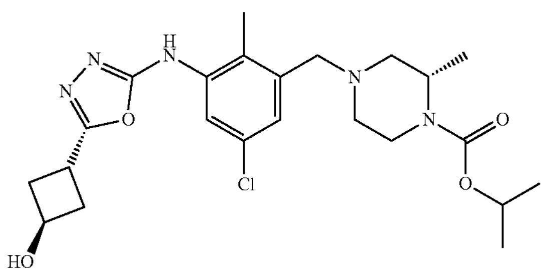 | isopropyl (2S)-4-[[5-chloro-3-[[5-(3-hydroxycyclobutyl)-1,3,4-oxadiazol-2-yl]amino]-2-methyl-phenyl]methyl]-2-methyl-piperazine-1-carboxylate | 477.21 | 2.07 |
| 65 | 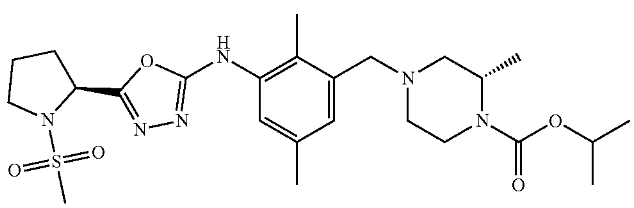 [SMILES: Cc1cc(CN2CCN(C(=O)OC(C)C)[C@@H](C)C2)c(C)c(Nc2nnc([C@@H]3CCCN3S(C)(=O)=O)o2)c1] | isopropyl (2S)-4-[[2,5-dimethyl-3-[[5-[(2S)-1-methylsulfonylpyrrolidin-2-yl]-1,3,4-oxadiazol-2-yl]amino]phenyl]methyl]-2-methyl-piperazine-1-carboxylate | 534.26 | 1.95 |
| 66 | 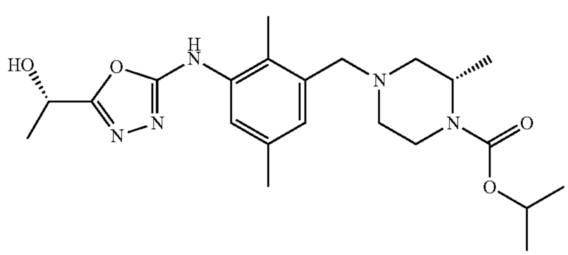 [SMILES: Cc1cc(CN2CCN(C(=O)OC(C)C)[C@@H](C)C2)c(C)c(Nc2nnc([C@H](C)O)o2)c1] | isopropyl (2S)-4-[[3-[[5-[(1S)-1-hydroxyethyl]-1,3,4-oxadiazol-2-yl]amino]-2,5-dimethyl-phenyl]methyl]-2-methyl-piperazine-1-carboxylate | 432.26 | 1.83 |
| 67 | 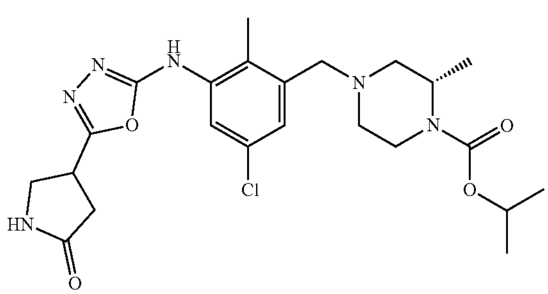 | isopropyl (2S)-4-[[5-chloro-2-methyl-3-[[5-(5-oxopyrrolidin-3-yl)-1,3,4-oxadiazol-2-yl]amino]phenyl]methyl]-2-methyl-piperazine-1-carboxylate | 490.21 | 1.99 |

TABLE 1-continued

| Example | Structure | Name | Mass ion | Rt |
|---|---|---|---|---|
| 68 | 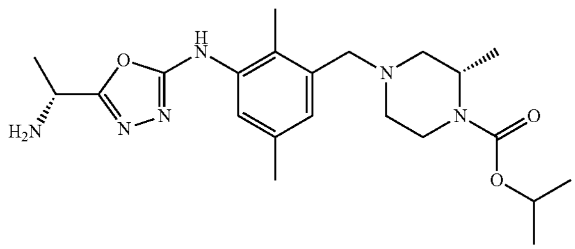 [SMILES: Cc1cc(CN2CCN(C(=O)OC(C)C)[C@@H](C)C2)c(C)c(Nc2nnc([C@@H](C)N)o2)c1] | isopropyl (2S)-4-[[3-[[5-[(1R)-1-aminoethyl]-1,3,4-oxadiazol-2-yl]amino]-2,5-dimethyl-phenyl]methyl]-2-methyl-piperazine-1-carboxylate | 431.27 | 1.68 |
| 69 | 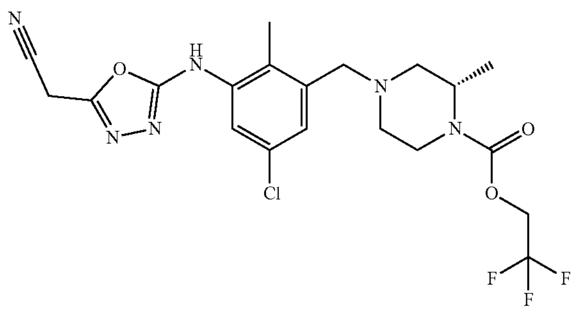 [SMILES: Cc1c(CN2CCN(C(=O)OCC(F)(F)F)[C@@H](C)C2)cc(Cl)cc1Nc1nnc(CC#N)o1] | 2,2,2-trifluoroethyl (2S)-4-[[5-chloro-3-[[5-(cyanomethyl)-1,3,4-oxadiazol-2-yl]amino]-2-methyl-phenyl]methyl]-2-methyl-piperazine-1-carboxylate | 486.14 | 2.39 |
| 70 | 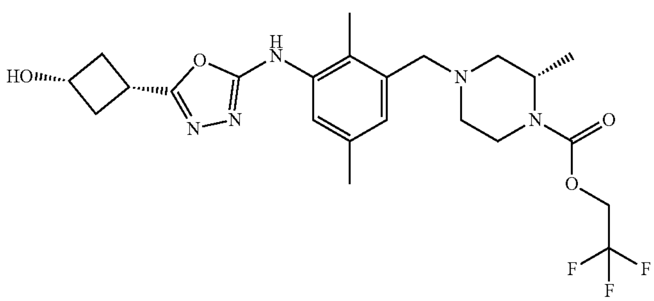 [SMILES: Cc1cc(CN2CCN(C(=O)OCC(F)(F)F)[C@@H](C)C2)c(C)c(Nc2nnc([C@H]3C[C@@H](O)C3)o2)c1] | 2,2,2-trifluoroethyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate | 497.22 | 1.96 |
| 71 | 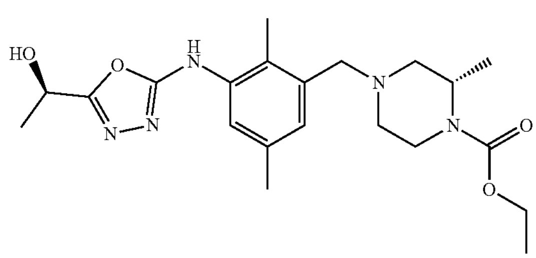 [SMILES: CCOC(=O)N1CCN(Cc2cc(C)cc(Nc3nnc([C@@H](C)O)o3)c2C)C[C@@H]1C] | ethyl (2S)-4-[[3-[[5-[(1R)-1-hydroxyethyl]-1,3,4-oxadiazol-2-yl]amino]-2,5-dimethyl-phenyl]methyl]-2-methyl-piperazine-1-carboxylate | 417.24 | 1.73 |
| 72 | 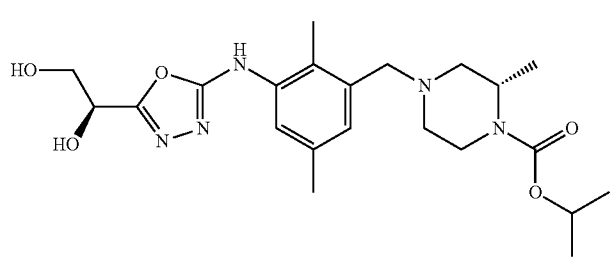 [SMILES: Cc1cc(CN2CCN(C(=O)OC(C)C)[C@@H](C)C2)c(C)c(Nc2nnc([C@@H](O)CO)o2)c1] | isopropyl (2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate | 448.25 | 1.74 |

TABLE 1-continued

| Example | Structure | Name | Mass ion | Rt |
|---|---|---|---|---|
| 73 | 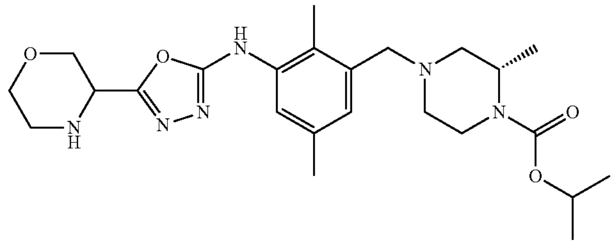 [SMILES: Cc1cc(CN2CCN(C(=O)OC(C)C)[C@@H](C)C2)c(C)c(Nc2nnc(C3COCCN3)o2)c1] | isopropyl (2S)-4-[[5-chloro-2-methyl-3-[(5-morpholin-3-yl-1,3,4-oxadiazol-2-yl)amino]phenyl]methyl]-2-methyl-piperazine-1-carboxylate | 492.22 | 1.90 |
| 74 | 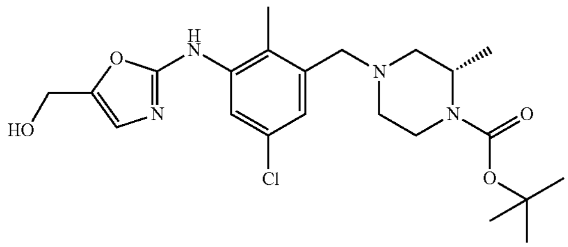 [SMILES: Cc1c(CN2CCN(C(=O)OC(C)(C)C)[C@@H](C)C2)cc(Cl)cc1Nc1ncc(CO)o1] | tert-butyl (2S)-4-[[5-chloro-3-[[5-(hydroxymethyl)oxazol-2-yl]amino]-2-methyl-phenyl]methyl]-2-methyl-piperazine-1-carboxylate | | 2.21 |
| 75 | 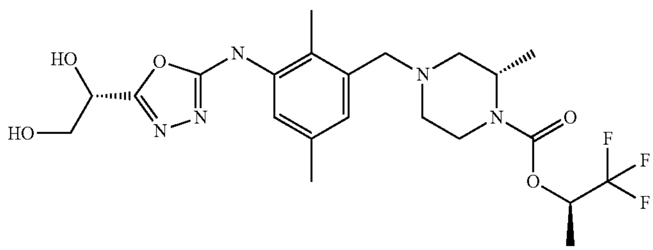 [SMILES: Cc1cc(CN2CCN(C(=O)O[C@H](C)C(F)(F)F)[C@@H](C)C2)c(C)c(Nc2nnc([C@@H](O)CO)o2)c1] | [(1R)-2,2,2-trifluoro-1-methyl-ethyl](2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate | 502.2 | 1.88$^a$ |
| 76 | 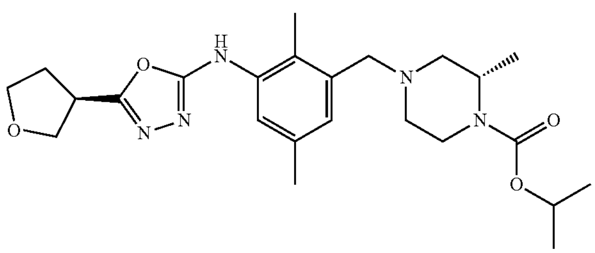 [SMILES: Cc1cc(CN2CCN(C(=O)OC(C)C)[C@@H](C)C2)c(C)c(Nc2nnc([C@@H]3CCOC3)o2)c1] | isopropyl (2S)-4-[[2,5-dimethyl-3-[[5-[(3S)-tetrahydrofuran-2-yl]-1,3,4-oxadiazol-2-yl]amino]phenyl]methyl]-2-methyl-piperazine-1-carboxylate | 458.2 | 1.92 |
| 77 | 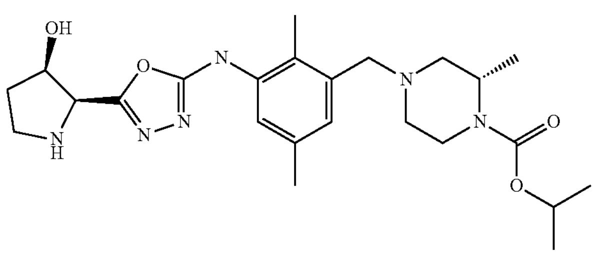 [SMILES: Cc1cc(CN2CCN(C(=O)OC(C)C)[C@@H](C)C2)c(C)c(Nc2nnc([C@H]3NCC[C@H]3O)o2)c1] | isopropyl (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate | 473.2 | 1.67 |
| 78 | 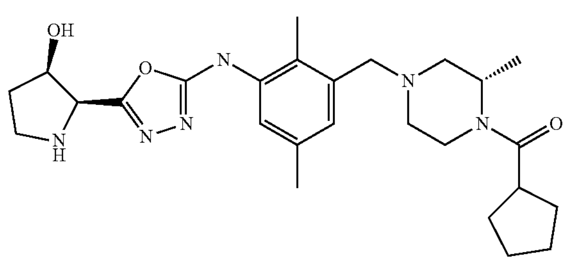 [SMILES: Cc1cc(CN2CCN(C(=O)C3CCCC3)[C@@H](C)C2)c(C)c(Nc2nnc([C@H]3NCC[C@H]3O)o2)c1] | cyclopentyl-[(2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazin-1-yl]methanone | 483.3 | 1.63$^a$ |

TABLE 1-continued

| Example | Structure | Name | Mass ion | Rt |
|---|---|---|---|---|
| 79 | 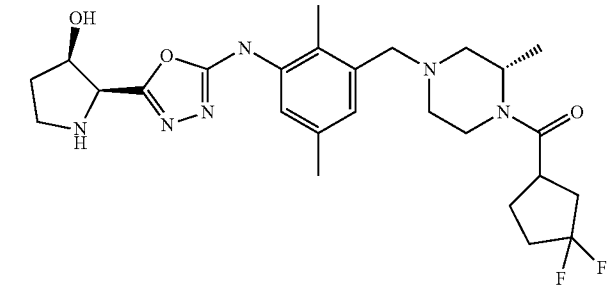 [SMILES: Cc1cc(CN2CCN(C(=O)C3CCC(F)(F)C3)[C@@H](C)C2)c(C)c(Nc2nnc([C@H]3NCC[C@H]3O)o2)c1] | (3,3-difluorocyclopentyl)-[(2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazin-1-yl]methanone | 519.3 | 0.55[b] |
| 80 | 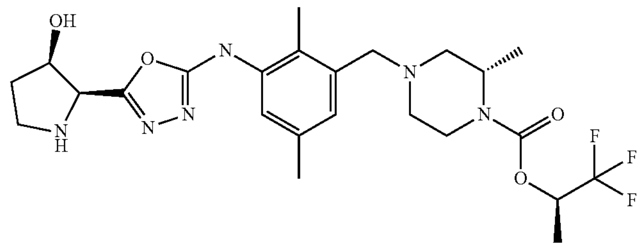 [SMILES: Cc1cc(CN2CCN(C(=O)O[C@H](C)C(F)(F)F)[C@@H](C)C2)c(C)c(Nc2nnc([C@H]3NCC[C@H]3O)o2)c1] | [(1R)-2,2,2-trifluoro-1-methyl-ethyl](2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate | 527.4 | 0.71[b] |
| 81 | 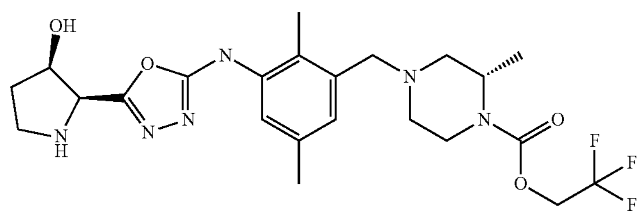 [SMILES: Cc1cc(CN2CCN(C(=O)OCC(F)(F)F)[C@@H](C)C2)c(C)c(Nc2nnc([C@H]3NCC[C@H]3O)o2)c1] | 2,2,2-trifluoroethyl (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate | 513.2 | 0.68[b] |
| 82 | 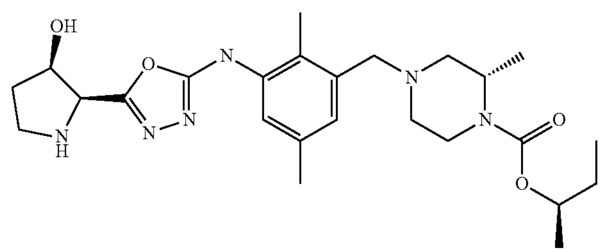 [SMILES: CC[C@@H](C)OC(=O)N1CCN(Cc2cc(C)cc(Nc3nnc([C@H]4NCC[C@H]4O)o3)c2C)C[C@@H]1C] | [(1R)-1-methylpropyl] (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate | 487.4 | 0.71[b] |
| 83 | 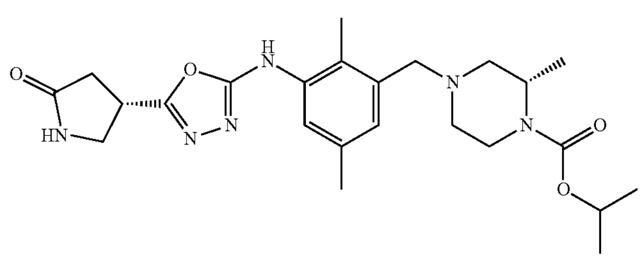 [SMILES: Cc1cc(CN2CCN(C(=O)OC(C)C)[C@@H](C)C2)c(C)c(Nc2nnc([C@@H]3CNC(=O)C3)o2)c1] | isopropyl (2S)-4-[[2,5-dimethyl-3-[[5-[(3S)-5-oxopyrrolidin-3-yl]-1,3,4-oxadiazol-2-yl]amino]phenyl]methyl]-2-methyl-piperazine-1-carboxylate | 471.1 | 1.79 |

RT quoted for UPLC-MS Method 5 unless [a] UPLC-MS method 6 or [b] UPLC-MS Method 4

Example 1: 5-[3-[[(3S)-4-benzoyl-3-methyl-piperazin-1-yl]methyl]-5-chloro-2-methyl-anilino]-1,3,4-oxadiazole-2-carbonitrile

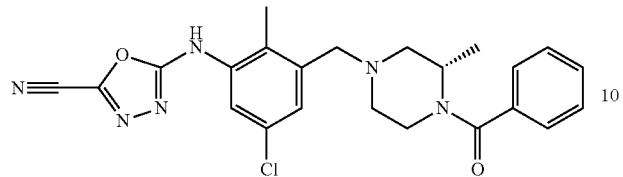

2,2,2-Trifluoracetic anhydride (0.006 mL, 0.043 mmol) was added to a solution of 5-[3-[[(3S)-4-benzoyl-3-methyl-piperazin-1-yl]methyl]-5-chloro-2-methyl-anilino]-1,3,4-oxadiazole-2-carboxamide from Preparation 51 (4.0 mg, 0.008 mmol) and pyridine (0.014 mL, 0.17 mmol) in 1,4-dioxane (0.2 mL). After 2 h of stirring at room temperature a further aliquot of 2,2,2-trifluoracetic anhydride (0.006 mL, 0.043 mmol) was added. The reaction mixture was stirred for 4 h and then was concentrated under reduced pressure. The crude material was then dissolved in dimethylformamide (0.7 mL) and purified by basic preparative HPLC. Clean fractions were evaporated under reduced pressure to give title compound (1.7 mg, 39%).

$^1$H NMR (600 MHz, DMSO-d6) δ 7.70 (d, J=2.3 Hz, 1H), 7.49-7.40 (m, 3H), 7.40-7.30 (m, 2H), 7.03 (d, J=2.3 Hz, 1H), 3.42 (s, 2H), 2.74 (s, 1H), 2.23 (s, 3H), 2.21-2.14 (m, 1H), 2.02 (td, J=11.6, 3.4 Hz, 1H), 1.23 (d, J=6.6 Hz, 3H).
UPLC-MS Method 5: m/z 450.2 [M+H$^+$]; RT=2.44 min.

Example 2: [(2S)-4-[[5-chloro-3-[[5-(methoxymethyl)-1,3,4-oxadiazol-2-yl]amino]-2-methyl-phenyl]methyl]-2-methyl-piperazin-1-yl]-phenyl-methanone

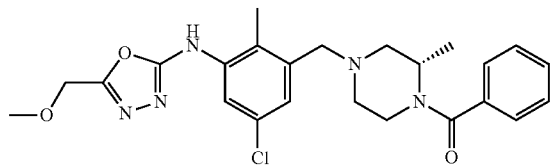 [SMILES: COCc1nnc(Nc2cc(Cl)cc(CN3CCN(C(=O)c4ccccc4)[C@@H](C)C3)c2C)o1]

2-Methoxyacetyl chloride (7.91 mg, 0.073 mmol) was added to a solution of product from Preparation 11 (30.0 mg, 0.069 mmol) and triethylamine (7.73 mg, 0.076 mmol) in tetrahydrofuran (2.0 mL) at 0° C. After 16 h at room temperature a further aliquot of both triethylamine (7.73 mg, 0.076 mmol) and 2-methoxyacetyl chloride (7.91 mg, 0.073 mmol) were added. On completion the reaction mixture was filtered and concentrated under reduced pressure. The crude intermediate was dissolved in dichloromethane (3.0 mL) and to this added 3-(ethyliminomethyleneamino)-N,N-dimethyl-propan-1-amine hydrochloride (26.6 mg, 0.139 mmol). The reaction mixture was stirred at room temperature for 16 h. The solvent was removed under reduced pressure. The obtained residue was purified by silica gel (100-200 mesh) column chromatography eluting with a gradient of 35-100% ethyl acetate in heptane. Clean fractions were evaporated under reduced pressure to give the title compound as a colourless solid. (7.0 mg, 21%)

$^1$H NMR (300 MHz, DMSO-d6) δ 9.72 (s, 1H), 7.82 (d, 2.2 Hz, 1H), 7.44 (q, J=2.8, 2.3 Hz, 3H), 7.35 (dd, J=6.5, 3.2 Hz, 2H), 7.11 (d, J=2.3 Hz, 1H), 4.53 (s, 2H), 3.45 (s, 2H), 3.33 (s, 3H), 3.14 (s, 3H), 2.73 (br s, 1H), 2.62 (d, J=11.0 Hz, 1H), 2.25 (s, 3H), 2.18 (dd, J=11.2, 3.8 Hz, 1H), 2.09-2.01 (m, 1H), 1.23 (d, J=6.3 Hz, 3H).
UPLC-MS Method 5: m/z [M+H$^+$]; RT=2.2 min Example 3: [(2S)-4-[[5-chloro-2-methyl-3-[(5-tetrahydrofuran-3-yl-1,3,4-oxadiazol-2-yl)amino]phenyl]methyl]-2-methyl-piperazin-1-yl]-phenyl-methanone

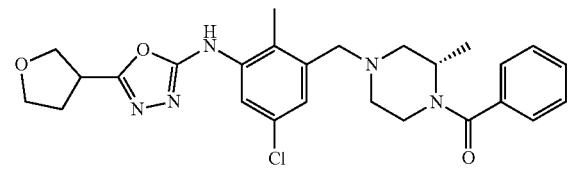 [SMILES: Cc1c(CN2CCN(C(=O)c3ccccc3)[C@@H](C)C2)cc(Cl)cc1Nc1nnc(C2CCOC2)o1]

3-(Ethyliminomethyleneamino)-N,N-dimethyl-propan-1-amine hydrochloride (14.2 mg, 4 eq) was added to a solution of the product from Preparation 11 (8.0 mg,) and tetrahydrofuran-3-carboxylic acid (2.58 mg, 1.2 eq) in dichloromethane (0.3 mL) and stirred at room temperature for 2 h. The reaction mixture was concentrated under reduced pressure then re-dissolved in dimethylformamide (0.3 mL) and purified by basic preparative HPLC. Clean fractions were evaporated under reduced pressure to give title compound (0.8 mg, 9%).

$^1$H NMR (600 MHz, DMSO-d6) δ=9.59 (s, 1H), 7.84 (d, J=2.3 Hz, 1H), 7.43-7.45 (m, 3H), 7.35 (ddd, J=4.9, 3.7, 1.8 Hz, 2H), 7.09 (d, J=2.3 Hz, 1H), 3.99 (dd, J=8.6, 7.7 Hz, 1H), 3.83-3.89 (m, 2H), 3.77 (td, J=8.0, 6.6 Hz, 1H), 3.65 (ddt, J=8.8, 7.5, 5.7 Hz, 1H), 3.44 (s, 2H), 3.04-3.24 (br s, 1H), 2.73 (d, J=14.6 Hz, 1H), 2.59-2.64 (m, 1H), 2.26-2.33 (m, 1H), 2.25 (s, 3H), 2.08-2.21 (m, 3H), 2.02 (td, J=11.6, 3.3 Hz, 1H), 1.23 (d, J=6.7 Hz, 3H).
UPLC-MS Method 5: m/z 496.2 [M+H$^+$]; RT=2.19 min.

Example 19: cyclobutyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone

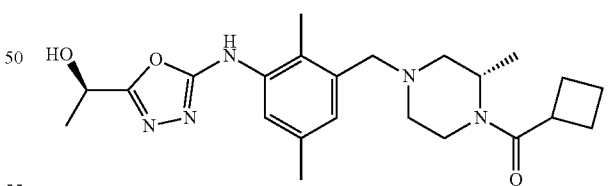

3-(ethyliminomethyleneamino)-N,N-dimethyl-propan-1-amine hydrochloride (216 mg, 1.13 mmol) was added to a solution of 1-amino-3-[3-[[(3S)-4-(cyclobutanecarbonyl)-3-methyl-piperazin-1-yl]methyl]-2,5-dimethyl-phenyl]thiourea from Preparation 29 (220 mg, 0.56 mmol) and (2R)-2-hydroxypropanoic acid (61.0 mg, 0.68 mmol) in dichloromethane (8.0 mL) at room temperature. The reaction was stirred for 1.5 h and then purified by automated silica gel chromatography. Clean fractions were evaporated under reduced pressure to give the title compound as an off-white solid (21.0 mg, 8.7%).

$^1$H NMR (600 MHz, DMSO-d6) δ=9.34 (s, 1H), 7.38 (s, 1H), 6.84 (s, 1H), 5.78 (d, J=5.5 Hz, 1H), 4.79 (qd, J=6.6, 5.3 Hz, 1H), 4.50 (s, 1H), 3.46-3.32 (m, 3H), 3.27 (dq, J=16.9, 8.2 Hz, 1H), 3.08 (t, J=12.0 Hz, 1H), 2.71 (dd, J=24.2, 11.7 Hz, 2H), 2.60 (s, 1H), 2.25 (s, 3H), 2.21 (s, 3H), 2.20-1.96 (m, 5H), 1.95-1.76 (m, 2H), 1.72 (d, J=9.6 Hz, 1H), 1.44 (d, J=6.6 Hz, 3H), 1.18 (d, J=6.5 Hz, 1H), 1.08 (d, J=6.7 Hz, 2H). UPLC-MS Method 5: RT=1.75 min.

Example 20: cyclobutyl-[(2S)-4-[[3-[[5-[(1S)-1-hydroxyethyl]-1,3,4-oxadiazol-2-yl]amino]-2,5-dimethyl-phenyl]methyl]-2-methyl-piperazin-1-yl]methanone

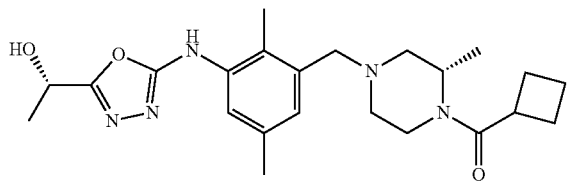 [SMILES: Cc1cc(CN2CCN(C(=O)C3CCC3)[C@@H](C)C2)c(C)c(Nc2nnc([C@H](C)O)o2)c1]

N,N,N',N'-tetramethyl-O-(1H-benzotriazol-1-yl)uronium hexafluorophosphate (136 mg, 0.36 mmol) was added to a solution of (1S)-1-[5-[2,5-dimethyl-3-[[(3S)-3-methylpiperazin-1-yl]methyl]anilino]-1,3,4-oxadiazol-2-yl]ethanol hydrochloride from Preparation 53 (100 mg, 0.24 mmol), cyclobutanecarboxylic acid (28.7 mg, 0.29 mmol) and diisopropylethylamine (0.21 mL, 1.20 mmol) in dimethylformamide (4.0 mL) and the resulting mixture was stirred at room temperature for 13 h. The reaction mixture was quenched with water and extracted with dichloromethane (2×50 mL). The combined extracted organic layers were dried over sodium sulphate and then evaporated under reduced pressure. The obtained residue was purified by silica gel (100-200 mesh) column chromatography eluting with a gradient of 0-100% ethyl acetate in heptane. Clean fractions were evaporated under reduced pressure to give the title compound as a colourless solid (25.0 mg, 24.5%).

$^1$H NMR (600 MHz, DMSO-d6) δ=9.34 (s, 1H), 7.38 (d, J=1.7 Hz, 1H), 6.85 (d, J=1.7 Hz, 1H), 5.79 (d, J=5.5 Hz, 1H), 4.85-4.70 (m, 1H), 4.09 (q, J=5.9 Hz, 1H), 3.66 (dt, J=13.1, 2.6 Hz, 1H), 3.39 (d, J=13.0 Hz, 1H), 2.97-2.85 (m, 1H), 2.69 (ddt, J=11.1, 3.5, 1.9 Hz, 1H), 2.59 (dt, J=11.3, 1.9 Hz, 1H), 2.25 (s, 3H), 2.21 (s, 3H), 2.07 (dd, J=11.3, 3.9 Hz, 1H), 1.88 (td, J=11.7, 3.5 Hz, 1H), 1.44 (d, J=6.6 Hz, 3H), 1.12 (d, J=6.8 Hz, 3H). UPLC-MS Method 5: RT=1.75 min.

Example 21: 2,2-difluoro-1-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]butan-1-one

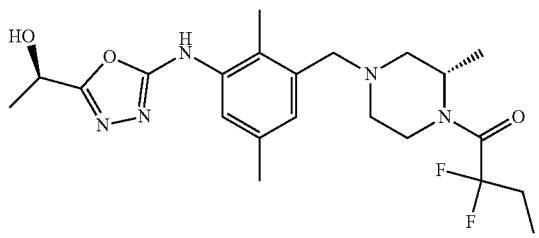 [SMILES: CCC(F)(F)C(=O)N1CCN(Cc2cc(C)cc(Nc3nnc([C@@H](C)O)o3)c2C)C[C@@H]1C]

N,N,N',N'-tetramethyl-O-(1H-benzotriazol-1-yl)uronium hexafluorophosphate (8.7 mg, 0.023 mmol) was added to a solution of (1R)-1-[5-[2,5-dimethyl-3-[[(3S)-3-methylpiperazin-1-yl]methyl]anilino]-1,3,4-oxadiazol-2-yl]ethanol hydrochloride from Preparation 52 (8.0 mg, 0.019 mmol), 2,2-difluorobutanoic acid (2.37 mg, 0.019 mmol) and triethylamine (11.6 mg, 0.11 mmol) in dimethylformamide (0.5 mL) After 3 h stirring the reaction mixture was purified by basic preparative HPLC. Clean fractions were evaporated under reduced pressure to give title compound as a colourless solid (0.8 mg, 9%).

$^1$H NMR (600 MHz, DMSO-d6) δ=9.35 (s, 1H), 7.40 (s, 1H), 6.85 (s, 1H), 5.79 (d, J=5.5 Hz, 1H), 4.74-4.84 (m, 1H), 4.52 (s, 0.5H), 4.33 (s, 0.5H), 4.14 (d, J=13.5 Hz, 0.5H), 3.88 (d, J=13.7 Hz, 0.5H), 3.28-3.43 (m, 3H), 2.97 (t, J=12.7 Hz, 0.5H), 2.80 (t, J=15.3 Hz, 1H), 2.68 (d, J=11.4 Hz, 1H), 2.25 (s, 3H), 2.22 (s, 3H), 2.03-2.18 (m, 3.5H), 1.94 (dt, J=28.0, 11.9 Hz, 1H), 1.44 (d, J=6.6 Hz, 3H), 1.23 (dd, J=65.2, 6.6 Hz, 3H), 0.97 (q, J=7.5 Hz, 3H). UPLC-MS Method 5: RT=1.99 min.

Example 22: cyclopropyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone

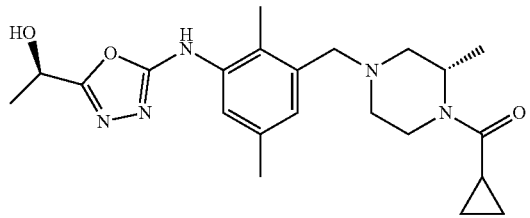 [SMILES: Cc1cc(CN2CCN(C(=O)C3CC3)[C@@H](C)C2)c(C)c(Nc2nnc([C@@H](C)O)o2)c1]

Using a procedure similar to that described for Example 21, but using cyclopropanecarboxylic acid (1.65 mg, 0.19 mmol) the title compound was prepared. After 3 h stirring the reaction mixture was purified by basic preparative HPLC. Clean fractions were evaporated under reduced pressure to give title compound as a colourless solid (0.8 mg, 10%).

$^1$H NMR (600 MHz, DMSO-d6) δ=9.35 (s, 1H), 7.39 (s, 1H), 6.86 (m, 1H), 5.79 (d, J=5.5 Hz, 1H), 4.74-4.82 (m, 1H), 4.49 (br s, 1H), 4.07 (br d, J=39.4 Hz, 1H), 3.39 (q, J=13.0 Hz, 2H), 2.76 (d, J=10.8 Hz, 1H), 2.62-2.57 (m, 4H), 2.26 (s, 3H), 2.23 (s, 3H), 2.01-2.18 (m, 1H), 1.84-1.97 (m, 2H), 1.44 (d, J=6.6 Hz, 3H), 1.05-1.30 (m, 3H), 0.68 (br d, J=9.5 Hz, 4H). UPLC-MS Method 5: RT=1.66 min.

Example 23: [(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]-(2-methylcyclopropyl)methanone

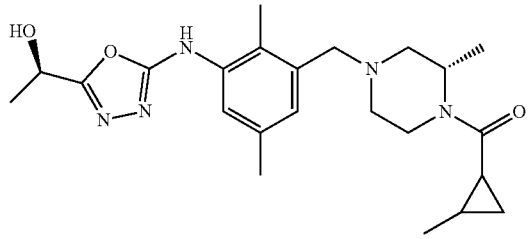 [SMILES: Cc1cc(CN2CCN(C(=O)C3CC3C)[C@@H](C)C2)c(C)c(Nc2nnc([C@@H](C)O)o2)c1]

Using a procedure similar to that described for Example 21, but using 2-methylcyclopropanecarboxylic acid the title compound was prepared. After 3 h stirring the reaction mixture was purified by basic preparative HPLC. Clean fractions were evaporated under reduced pressure to give title compound as a colourless solid (4.5 mg, 54%).

$^1$H NMR (600 MHz, DMSO-d6) δ=9.35 (s, 1H), 7.39 (s, 1H), 6.86 (s, 1H), 5.79 (d, J=5.5 Hz, 1H), 4.78 (qd, J=6.6, 5.3 Hz, 1H), 4.40-4.50 (m, 1H), 4.04 (d, J=47.1 Hz, 1H), 3.39 (ddd, J=28.7, 13.0, 4.9 Hz, 2H), 2.75 (d, J=10.7 Hz, 1H), 2.58-2.69 (s, 1H), 2.26 (s, 3H), 2.22 (s, 3H), 1.80-2.20 (m, 2H), 1.65 (s, 1H), 1.44 (d, J=6.6 Hz, 3H), 1.07-1.28 (m, 4H), 1.06 (d, J=3.5 Hz, 3H), 0.52 (s, 1H). UPLC-MS Method 5: RT=1.74 min.

Example 25: (3,3-difluorocyclopentyl)-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone

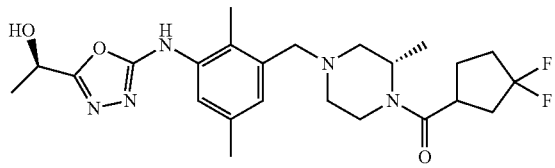 [SMILES: Cc1cc(CN2CCN(C(=O)C3CCC(F)(F)C3)[C@@H](C)C2)c(C)c(Nc2nnc([C@@H](C)O)o2)c1]

Using a procedure similar to that described for Example 21, but using 3,3-difluorocyclopentanecarboxylic acid the title compound was prepared. After 3 h stirring the reaction mixture was purified by basic preparative HPLC. Clean fractions were evaporated under reduced pressure to give title compound as a colourless solid (5.7 mg, 63%).

$^1$H NMR (600 MHz, DMSO-d6) δ=9.35 (s, 1H), 7.39 (s, 1H), 6.85 (s, 1H), 5.79 (d, J=5.5 Hz, 1H), 4.79 (qd, J=6.6, 5.4 Hz, 1H), 4.53 (s, 0.5H), 4.14-4.21 (m, 1H), 3.71 (t, J=15.5 Hz, 0.5H), 3.34-3.42 (m, 2H), 3.14-3.31 (m, 1.5H), 2.71-2.81 (m, 1.5H), 2.62 (d, J=6.6 Hz 1H), 2.28-2.44 (m, 0.5H), 2.25 (s, 3H), 2.22 (s, 3H), 1.98-2.15 (m, 4H), 1.89-1.99 (m, 1H), 1.77-1.85 (m, 1H), 1.63-1.75 (m, 0.5H), 1.44 (d, J=6.6 Hz, 3H), 1.09-1.25 (m, 3H). UPLC-MS Method 5: RT=1.75 min.

Example 26: 2-cyclobutyl-1-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]ethanone

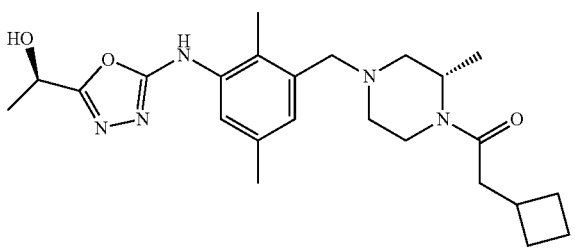 [SMILES: Cc1cc(CN2CCN(C(=O)CC3CCC3)[C@@H](C)C2)c(C)c(Nc2nnc([C@@H](C)O)o2)c1]

Using a procedure similar to that described for Example 21, but using 2-cyclobutylacetic acid the title compound was prepared. After 3 h stirring the reaction mixture was purified by basic preparative HPLC. Clean fractions were evaporated under reduced pressure to give title compound as a colourless solid (3.5 mg, 42%).

$^1$H NMR (600 MHz, DMSO-d6) δ=9.35 (s, 1H), 7.39 (d, J=1.8 Hz, 1H), 6.85 (d, J=1.8 Hz, 1H), 5.79 (d, J=5.5 Hz, 1H), 4.79 (qd, J=6.6, 5.5 Hz, 1H), 4.50 (s, 0.5H), 4.13 (d, J=13.3 Hz, 0.5H), 4.06 (s, 0.5H), 3.62 (d, J=13.2 Hz, 0.5H), 3.37 (q, 2H), 3.16 (t, J=12.6 Hz, 1H), 2.72 (d, J=11.2 Hz, 1.5H), 2.54-2.64 (m, 1.5H), 2.37-2.46 (m, 1H), 2.32 (dt, J=22.9, 7.9 Hz, 1H), 2.25 (s, 3H), 2.21 (s, 3H), 2.06-2.12 (m, 0.5H), 2.01 (s, 2.5H), 1.88-1.94 (m, 0.5H), 1.74-1.85 (m, 2.5H), 1.62 (dq, J=12.0, 8.5 Hz, 2H), 1.44 (d, J=6.6 Hz, 3H), 1.13 (dd, J=78.2, 6.6 Hz, 3H). UPLC-MS Method 5: RT=1.83 min.

Example 27: cyclobutyl-[(2S)-4-[[5-(difluoromethyl)-3-[[5-[(1S)-1-hydroxyethyl]-1,3,4-oxadiazol-2-yl]amino]-2-methyl-phenyl]methyl]-2-methyl-piperazin-1-yl]methanone

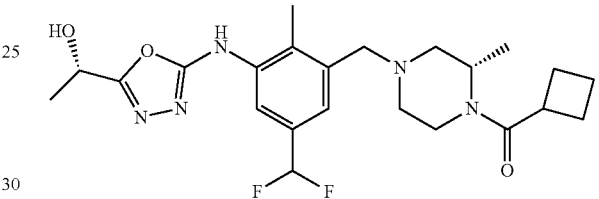

Using a procedure similar to that described for Example 19, but using 1-amino-3-[3-[[(3S)-4-(cyclobutanecarbonyl)-3-methyl-piperazin-1-yl]methyl]-5-(difluoromethyl)-2-methyl-phenyl]thiourea from Preparation 47 (300 mg, 0.2390 mmol) and (2S)-2-hydroxypropanoic acid the title compound was prepared as a colourless solid (40.0 mg, 15.3%).

$^1$H NMR (600 MHz, DMSO-d6) δ=9.61 (s, 1H), 7.91 (s, 1H), 7.23 (s, 1H), 7.00 (t, J=56.0 Hz, 1H), 5.83 (d, J=5.4 Hz, 1H), 4.81 (td, J=6.6, 5.5 Hz, 1H), 4.51 (s, 0.5H), 4.16 (d, J=13.0 Hz, 0.5H), 3.90 (s, 0.5H), 3.42-3.49 (m, 2.5H), 3.25-3.34 (m, 1H), 3.10 (m, 0.5H), 2.68-2.80 (m, 1.5H), 2.60 (m, 1H), 2.31 (s, 3H), 1.99-2.22 (m, 5H), 1.89 (qq, J=17.9, 9.5 Hz, 2H), 1.73 (dd, J=12.1, 7.4 Hz, 1H), 1.45 (d, J=6.6 Hz, 3H), 1.15 (dd, J=55.9, 6.6 Hz, 3H). UPLC-MS Method 5: RT=1.90 min.

Example 31: tert-butyl (2S)-4-[[2,5-dimethyl-3-[[5-(2-methylpyrazol-3-yl)-1,3,4-oxadiazol-2-yl]amino]phenyl]methyl]-2-methyl-piperazine-1-carboxylate

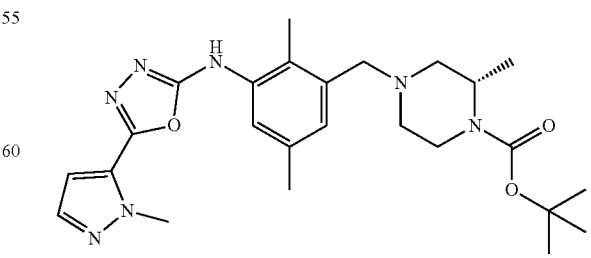

3-(ethyliminomethyleneamino)-N,N-dimethyl-propan-1-amine hydrochloride was added to a solution of tert-butyl (2S)-4-[[3-(aminocarbamothioylamino)-2,5-dimethyl-phenyl]methyl]-2-methyl-piperazine-1-carboxylate from Preparation 27 (8.55 mg, 0.021 mmol) and 2-methylpyrazole-3-carboxylic acid (3.17 mg, 0.025 mmol) in dichloromethane (1.0 mL). After 3 h the reaction mixture was quenched with water (0.5 mL) and extracted with dichloromethane (2.0 mL). The organic layer was collected and concentrated under reduced pressure. The residue was dissolved in dimethylformamide (0.4 mL) and purified basic preparative HPLC. Clean fractions were evaporated under reduced pressure to give title compound as a colourless solid (1.0 mg, 10%).

$^1$H NMR (600 MHz, DMSO-d6) δ=9.68 (s, 1H), 7.60 (d, J=2.0 Hz, 1H), 7.44 (s, 1H), 6.89 (s, 1H), 6.74 (d, J=2.0 Hz, 1H), 4.15 (s, 3H), 4.09 (s, 1H), 3.67 (d, J=13.2 Hz, 2H), 3.36-3.47 (m, 2H), 2.91 (t, J=13.4 Hz, 1H), 2.70 (d, J=11.2 Hz, 1H), 2.60 (dd, J=11.5, 2.2 Hz, 1H), 2.27 (s, 3H), 2.24 (s, 3H), 2.08 (dd, J=11.4, 3.8 Hz, 1H), 1.89 (td, J=11.7, 3.5 Hz, 1H), 1.39 (s, 9H), 1.12 (d, J=6.6 Hz, 3H). UPLC-MS Method 5: RT=2.13 min.

Example 33: tert-butyl (2S)-4-[[2,5-dimethyl-3-[[5-(1,2,5-thiadiazol-3-yl)-1,3,4-oxadiazol-2-yl]amino]phenyl]methyl]-2-methyl-piperazine-1-carboxylate

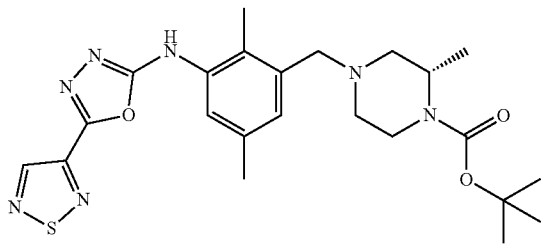 [SMILES: Cc1cc(CN2CCN(C(=O)OC(C)(C)C)[C@@H](C)C2)c(C)c(Nc2nnc(-c3cnsn3)o2)c1]

3-(Ethyliminomethyleneamino)-N,N-dimethyl-propan-1-amine hydrochloride was added to a solution of tert-butyl (2S)-4-[[3-(aminocarbamothioylamino)-2,5-dimethyl-phenyl]methyl]-2-methyl-piperazine-1-carboxylate from Preparation 27 (8.55 mg, 0.021 mmol) and 1,2,5-thiadiazole-3-carboxylic acid (3.25 mg, 0.025 mmol) in dichloromethane (1.0 mL). After 3 h the reaction mixture was quenched with water (0.5 mL) and extracted with dichloromethane (2.0 mL). The organic layer was collected and concentrated under reduced pressure. The residue was dissolved in dimethylformamide (0.4 mL) and purified basic preparative HPLC. Clean fractions were evaporated under reduced pressure to give title compound as a colourless solid (1.94 mg, 19%).

$^1$H NMR (600 MHz, DMSO-d6) δ=9.95 (s, 1H), 9.37 (s, 1H), 7.41 (s, 1H), 6.93 (s, 1H), 4.09 (s, 1H), 3.62-3.72 (m, 1H), 3.39 (q, J=19.7 Hz, 2H), 2.93 (t, J=12.6 Hz, 1H), 2.71 (d, J=11.7 Hz, 1H), 2.60 (dt, J=11.3, 1.9 Hz, 1H), 2.28 (s, 3H), 2.25 (s, 3H), 2.22 (d, J=17.0 Hz, 1H), 2.09 (dd, J=11.4, 4.0 Hz, 2H), 1.90 (td, J=11.7, 3.5 Hz, 1H), 1.39 (s, 9H), 1.13 (d, J=6.7 Hz, 3H). UPLC-MS Method 5: RT=2.21 min.

Example 34: tert-butyl (2S)-4-[[2,5-dimethyl-3-[[5-(4-methyl-1,2,5-oxadiazol-3-yl)-1,3,4-oxadiazol-2-yl]amino]phenyl]methyl]-2-methyl-piperazine-1-carboxylate

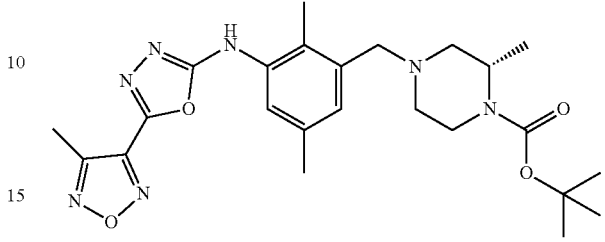

3-(Ethyliminomethyleneamino)-N,N-dimethyl-propan-1-amine hydrochloride was added to a solution of tert-butyl (2S)-4-[[3-(aminocarbamothioylamino)-2,5-dimethyl-phenyl]methyl]-2-methyl-piperazine-1-carboxylate from Preparation 27 (8.55 mg, 0.021 mmol) and 4-methyl-1,2,5-oxadiazole-3-carboxylic acid (3.20 mg, 0.025 mmol) in dichloromethane (1.0 mL). After 3 h the reaction mixture was quenched with water (0.5 mL) and extracted with dichloromethane (2.0 mL). The organic layer was collected and concentrated under reduced pressure. The residue was dissolved in dimethylformamide (0.4 mL) and purified basic preparative HPLC. Clean fractions were evaporated under reduced pressure to give title compound as a colourless solid (1.4 mg, 13%).

$^1$H NMR (600 MHz, DMSO-d6) δ=10.07 (s, 1H), 7.39 (s, 1H), 6.94 (s, 1H), 4.09 (s, 1H), 3.67 (d, J=12.8 Hz, 1H), 3.36-3.44 (m, 2H), 2.91 (t, J=13.1 Hz, 1H), 2.70 (d, J=11.2 Hz, 1H), 2.64 (s, 3H), 2.60 (dt, J=11.5, 2.0 Hz, 1H), 2.28 (s, 3H), 2.25 (s, 3H), 2.09 (dd, J=11.3, 3.9 Hz, 1H), 1.90 (td, J=11.7, 3.5 Hz, 1H), 1.39 (s, 9H), 1.12 (d, J=6.7 Hz, 3H). UPLC-MS Method 5: RT=2.38 min.

Example 36: isopropyl (2S)-4-[[3-[[5-[(1S)-1-amino-2-hydroxy-ethyl]-1,3,4-oxadiazol-2-yl]amino]-2,5-dimethyl-phenyl]methyl]-2-methyl-piperazine-1-carboxylate

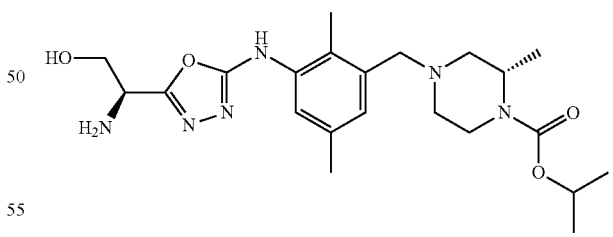

3-(Ethyliminomethyleneamino)-N,N-dimethyl-propan-1-amine hydrochloride (73.1 mg, 0.38 mmol) was added to a solution of isopropyl (2S)-4-[[3-(aminocarbamothioylamino)-2,5-dimethyl-phenyl]methyl]-2-methyl-piperazine-1-carboxylate from Preparation 25 (50.0 mg, 0.127 mmol) and (2S)-2-(tert-butoxycarbonylamino)-3-hydroxy-propanoic acid (28.7 mg, 0.14 mmol) in dichloromethane (3.0 mL) and stirred for 12 h. The reaction mixture was quenched with water (2.0 mL) and extracted with dichloromethane (5.0 mL). The organic layer was collected and concentrated under reduced pressure. The obtained residue was purified by silica gel (100-200 mesh) column chromatography eluting with a gradient of 0-90% ethyl acetate in heptane. Clean fractions were evaporated under reduced pressure to give intermediate compound, isopropyl-(2S)-4-[[3-[[5-[(1S)-1-(tert-butoxycarbonylamino)-2-hydroxy-ethyl]-1,3,4-oxadiazol-2-yl]amino]-2,5-dimethyl-phenyl]methyl]-2-methyl-piperazine-1-carboxylate (33.0 mg, 0.60 mmol, 47.5%). Hydrogen chloride (0.6 mL, 4M in dioxane) was added to a solution of intermediate isopropyl-(2S)-4-[[3-[[5-[(1S)-1-(tert-butoxycarbonylamino)-2-hydroxy-ethyl]-1,3,4-oxadiazol-2-yl]amino]-2,5-dimethyl-phenyl]methyl]-2-methyl-piperazine-1-carboxylate in dichloromethane (5.0 mL) and stirred for 1 h. The suspension was diluted with methanol and purified on 1 g SCX column, eluting with methanol, then methanolic ammonia (2N). Clean fractions were evaporated under reduced pressure to give title compound as colourless solid (25.0 mg, 0.056 mmol, 44% overall).

¹H NMR (600 MHz, DMSO-d6) δ=9.30 (s, 1H), 7.39 (d, J=1.6 Hz, 1H), 6.83 (d, J=1.7 Hz, 1H), 5.01 (s, 1H), 4.77 (hept, J=6.3 Hz, 1H), 4.12 (s, 1H), 4.01 (t, J=5.9 Hz, 1H), 3.70 (dt, J=12.9, 2.6 Hz, 1H), 3.63 (dd, J=5.9, 2.4 Hz, 2H), 3.32-3.41 (m, 3H), 2.91-3.00 (m, 1H), 2.71 (ddt, J=11.0, 3.3, 1.8 Hz, 1H), 2.60 (dt, J=11.3, 1.9 Hz, 1H), 2.25 (s, 3H), 2.21 (s, 3H), 2.08 (dd, J=11.4, 3.9 Hz, 1H), 1.90 (td, J=11.7, 3.6 Hz, 1H), 1.17 (dd, J=6.2, 1.1 Hz, 6H), 1.13 (d, J=6.8 Hz, 3H). UPLC-MS Method 5: RT=1.68 min.

Example 38: isopropyl (2S)-4-[[3-[[5-[(1S)-1-aminopropyl]-1,3,4-oxadiazol-2-yl]amino]-5-chloro-2-methyl-phenyl]methyl]-2-methyl-piperazine-1-carboxylate

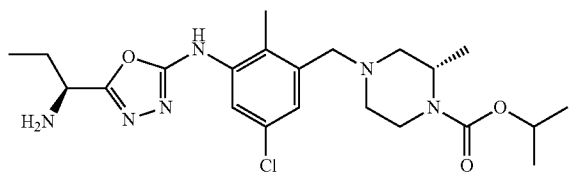 [SMILES: CC[C@H](N)c1nnc(Nc2cc(Cl)cc(CN3CCN(C(=O)OC(C)C)[C@@H](C)C3)c2C)o1]

3-(Ethyliminomethyleneamino)-N,N-dimethyl-propan-1-amine hydrochloride (27.8 mg, 0.15 mmol) was added to a solution isopropyl (2S)-4-[[3-(aminocarbamothioylamino)-5-chloro-2-methyl-phenyl]methyl]-2-methyl-piperazine-1-carboxylate from Preparation 16 (15.0 mg, 0.036 mmol) and (2R)-2-(tert-butoxycarbonylamino)butanoic acid (7.73 mg, 0.038 mmol) in dichloromethane (1.0 mL) and stirred for 12 h. The reaction mixture was purified by silica gel (100-200 mesh) column chromatography eluting with of 33% ethyl acetate in heptane. Clean fractions were evaporated under reduced pressure to give intermediate compound, isopropyl (2S)-4-[[3-[[5-[(1S)-1-(tert-butoxycarbonylamino)propyl]-1,3,4-oxadiazol-2-yl]amino]-5-chloro-2-methyl-phenyl]methyl]-2-methyl-piperazine-1-carboxylate. (15 mg, 73%)

Hydrogen chloride (0.6 mL, 4M in dioxane) was added to a solution of intermediate isopropyl (2S)-4-[[3-[[5-[(1S)-1-(tert-butoxycarbonylamino)propyl]-1,3,4-oxadiazol-2-yl]amino]-5-chloro-2-methyl-phenyl]methyl]-2-methyl-piperazine-1-carboxylate (15 mg, 0.026 mmol) in dichloromethane (1.0 mL) and stirred for 5 h. The reaction was evaporated under reduced pressure and the residue obtained was purified by silica gel (100-200 mesh) column chromatography eluting with dichloromethane/methanol/ammonia (95/5/0.5). Clean fractions were evaporated under reduced pressure to give title compound as colourless solid (7.0 mg, 57% overall).

¹H NMR (300 MHz, DMSO-d6) δ=9.56 (s, 1H), 7.83 (d, J=2.2 Hz, 1H), 7.08 (d, J=2.3 Hz, 1H), 4.77 (hept, J=6.1 Hz, 1H), 4.12 (s, 1H), 3.86 (t, J=6.8 Hz, 1H), 3.71 (d, J=12.8 Hz, 1H), 3.42 (s, 2H), 2.98 (dd, J=13.0, 9.8 Hz, 1H), 2.71 (d, J=11.3 Hz, 1H), 2.58 (d, J=11.3 Hz, 1H), 2.24 (s, 3H), 2.11 (dd, J=11.3, 3.8 Hz, 1H), 1.95 (td, J=11.4, 3.2 Hz, 1H), 1.59-1.85 (m, 2H), 1.17 (d, J=6.2 Hz, 6H), 1.14 (d, J=6.7 Hz, 3H), 0.90 (t, J=7.4 Hz, 3H). UPLC-MS Method 5: RT=1.91 min.

Example 41: isopropyl (2S)-4-[[3-[[5-[(1S,2R)-1-amino-2-hydroxy-propyl]-1,3,4-oxadiazol-2-yl]amino]-2,5-dimethyl-phenyl]methyl]-2-methyl-piperazine-1-carboxylate

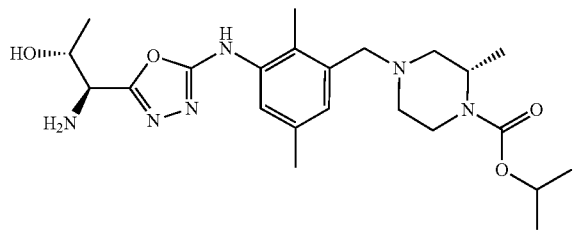 [SMILES: Cc1cc(CN2CCN(C(=O)OC(C)C)[C@@H](C)C2)c(C)c(Nc2nnc([C@@H](N)[C@@H](C)O)o2)c1]

3-(Ethyliminomethyleneamino)-N,N-dimethyl-propan-1-amine hydrochloride (73.1 mg, 0.38 mmol) was added to a solution of isopropyl (2S)-4-[[3-(aminocarbamothioylamino)-2,5-dimethyl-phenyl]methyl]-2-methyl-piperazine-1-carboxylate from Preparation 25 (50.0 mg, 0.127 mmol) and (2S,3R)-2-(tert-butoxycarbonylamino)-3-hydroxy-butanoic acid (30.6 mg, 0.14 mmol) in dichloromethane (5.0 mL) and stirred for 12 h. h The reaction mixture was quenched with water (2.0 mL) and extracted with dichloromethane (5.0 mL). The organic layer was collected and concentrated under reduced pressure. The obtained residue was purified by silica gel (100-200 mesh) column chromatography eluting with a gradient of 0-90% ethyl acetate in heptane. Clean fractions were evaporated under reduced pressure to give intermediate compound, isopropyl-(2S)-4-[[3-[[5-[(1S,2R)-1-(tert-butoxycarbonylamino)-2-hydroxy-propyl]-1,3,4-oxadiazol-2-yl]amino]-2,5-dimethyl-phenyl]methyl]-2-methyl-piperazine-1-carboxylate (33.0 mg, 0.058 mmol, 46.3%). Hydrogen chloride (0.6 mL, 4M in dioxane) was added to a solution of the intermediate isopropyl-(2S)-4-[[3-[[5-[(1S,2R)-1-(tert-butoxycarbonylamino)-2-hydroxy-propyl]-1,3,4-oxadiazol-2-yl]amino]-2,5-dimethyl-phenyl]methyl]-2-methyl-piperazine-1-carboxylate in dichloromethane and stirred for 12 h. The suspension was diluted with methanol and purified on 1 g SCX column, eluting with methanol, then methanolic ammonia (2N). Clean fractions were evaporated under reduced pressure to give title compound as colourless solid (23.0 mg, 40% overall).

¹H NMR (600 MHz, DMSO-d6) δ=9.28 (s, 1H), 7.39 (d, J=1.7 Hz, 1H), 6.83 (d, J=1.7 Hz, 1H), 4.93 (s, 1H), 4.77 (hept, J=6.2 Hz, 1H), 4.10-4.14 (m, 1H), 3.82 (q, J=6.1 Hz, 1H), 3.79 (d, J=5.5 Hz, 1H), 3.70 (dt, J=13.0, 2.7 Hz, 1H), 3.36 (q, J=15.7 Hz, 2H), 2.93-2.98 (m, 1H), 2.70 (ddt, J=11.1, 3.4, 1.8 Hz, 1H), 2.59 (dt, J=11.4, 1.8 Hz, 1H), 2.25 (s, 3H), 2.21 (s, 3H), 2.08 (dd, J=11.4, 3.8 Hz, 1H), 1.89 (td, J=11.6, 3.5 Hz, 1H), 1.17 (dd, J=6.3, 1.0 Hz, 6H), 1.13 (d, J=6.7 Hz, 3H), 1.09 (d, J=6.2 Hz, 3H). UPLC-MS Method 5: RT=1.68 min.

Example 43: isopropyl (2S)-4-[[5-(difluoromethyl)-3-[[5-[(1S)-1-hydroxyethyl]-1,3,4-oxadiazol-2-yl]amino]-2-methyl-phenyl]methyl]-2-methyl-piperazine-1-carboxylate

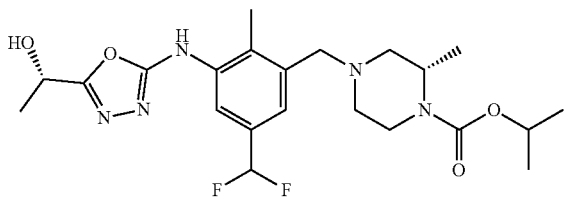 [SMILES: Cc1c(CN2CCN(C(=O)OC(C)C)[C@@H](C)C2)cc(C(F)F)cc1Nc1nnc([C@H](C)O)o1]

3-(Ethyliminomethyleneamino)-N,N-dimethyl-propan-1-amine hydrochloride (78.1 mg, 0.41 mmol) was added to a solution of isopropyl (2S)-4-[[3(aminocarbamothioylamino)-5-(difluoromethyl)-2-methyl-phenyl]methyl]-2-methyl-piperazine-1-carboxylate Preparation 40 (50.0 mg, 0.116 mmol) and (2S)-2-hydroxypropanoic acid (12.6 mg, 0.14 mmol). After 5 h stirring the reaction mixture was purified by basic preparative HPLC. Clean fractions were evaporated under reduced pressure to give title compound as a colourless solid (16.0 mg, 29.4%).

¹H NMR (600 MHz, DMSO-d6) δ=9.63 (s, 1H), 7.90 (s, 1H), 7.24 (s, 1H), 7.00 (t, J=56.0 Hz, 1H), 5.83 (d, J=5.4 Hz, 1H) 4.72-4.88 (m, 2H), 4.12 (q, J=6.5, 6.0 Hz, 1H), 3.72 (dt, J=13.1, 2.7 Hz, 1H), 3.47 (s, 2H), 2.92-3.06 (m, 1H), 2.71 (ddt, J=11.2, 3.5, 1.8 Hz, 1H), 2.59 (dt, J=11.4, 2.0 Hz, 1H), 2.31 (d, J=1.5 Hz, 3H), 2.12 (dd, J=11.3, 3.9 Hz, 1H), 1.97 (td, J=11.7, 3.5 Hz, 1H), 1.45 (d, J=6.6 Hz, 3H), 1.17 (d, J=6.2 Hz, 6H), 1.14 (d, J=6.7 Hz, 3H). UPLC-MS Method 5: RT=2.00 min.

Example 48: isopropyl (2S)-4-[[5-chloro-2-methyl-3-[[5-(2-oxopyrrolidin-3-yl)-1,3,4-oxadiazol-2-yl]amino]phenyl]methyl]-2-methyl-piperazine-1-carboxylate

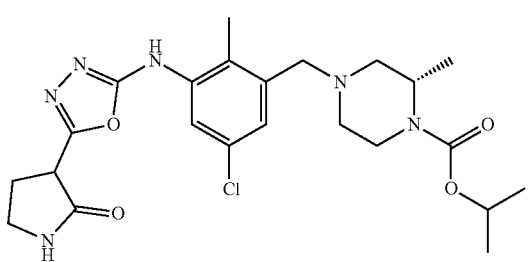 [SMILES: Cc1c(CN2CCN(C(=O)OC(C)C)[C@@H](C)C2)cc(Cl)cc1Nc1nnc(C2CCNC2=O)o1]

3-(ethyliminomethyleneamino)-N,N-dimethyl-propan-1-amine hydrochloride (14.8 mg, 0.077 mmol) was added to a solution of isopropyl (2S)-4-[[3-(aminocarbamothioylamino)-5-chloro-2-methyl-phenyl]methyl]-2-methyl-piperazine-1-carboxylate from Preparation 16 (8.0 mg, 0.019 mmol) and 2-oxopyrrolidine-3-carboxylic acid (3.0 mg, 0.023 mmol) in dichloromethane (0.8 mL). After 5 h stirring the reaction mixture was purified by basic preparative HPLC. Clean fractions were evaporated under reduced pressure to give title compound as a colourless solid (4.8 mg, 46%).

¹H NMR (600 MHz, DMSO-d6) δ=9.67 (s, 1H), 8.10 (s, 1H), 7.83 (d, J=2.3 Hz, 1H), 7.09 (d, J=2.3 Hz, 1H), 4.77 (hept, J=6.3 Hz, 1H), 4.12 (s, 1H), 3.97 (t, J=9.3 Hz, 1H), 3.59-3.77 (m, 1H), 3.42 (s, 2H), 2.98 (t, J=12.5 Hz, 1H), 2.74-2.68 (m, 1H), 2.61-2.55 (m, 2H), 2.54 (s, 29H), 2.51 (s, 6H), 2.47 (ddd, J=12.5, 7.8, 3.1 Hz, 1H), 2.41-2.32 (m, 1H), 2.11 (dd, J=11.3, 3.9 Hz, 1H), 1.95 (td, J=11.6, 3.5 Hz, 1H), 1.26-1.06 (m, 9H). UPLC-MS Method 5: RT=2.01 min.

Example 52: isopropyl (2S)-4-[[2,5-dimethyl-3-[[5-[(5S)-2-oxooxazolidin-5-yl]-1,3,4-oxadiazol-2-yl]amino]phenyl]methyl]-2-methyl-piperazine-1-carboxylate

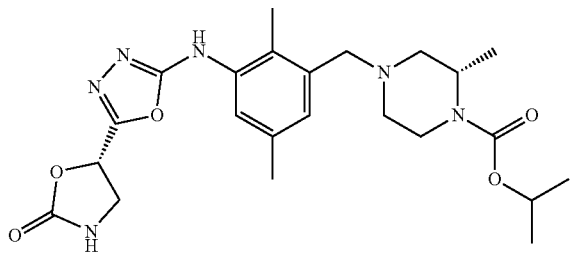 [SMILES: Cc1cc(CN2CCN(C(=O)OC(C)C)[C@@H](C)C2)c(C)c(Nc2nnc([C@@H]3CNC(=O)O3)o2)c1]

3-(Ethyliminomethyleneamino)-N,N-dimethyl-propan-1-amine hydrochloride (195 mg, 1.02 mmol) was added to a solution of (2S)-4-[[3-(aminocarbamothioylamino)-2,5-dimethyl-phenyl]methyl]-2-methyl-piperazine-1-carboxylate (100 mg, 0.25 mmol) and (5S)-2-oxooxazolidine-5-carboxylic acid from Preparation 25 (48.1 mg, 0.33 mmol) in dichloromethane (10 mL) and stirred at room temperature for 48 h. The reaction mixture was quenched with water (2.0 mL) and extracted with dichloromethane (5.0 mL). The organic layer was collected and concentrated under reduced pressure. The obtained residue was purified by silica gel (100-200 mesh) column chromatography eluting with a gradient of 0-90% ethyl acetate in heptane, then by acidic preparative HPLC to afford title compound as colourless solid (20.0 mg, 16.6%).

¹H NMR (600 MHz, DMSO-d6) δ=9.61 (s, 1H), 7.99 (s, 1H), 7.37 (d, J=1.7 Hz, 1H), 6.88 (d, J=1.8 Hz, 1H), 5.78 (dd, J=9.2, 5.7 Hz, 1H), 4.77 (hept, J=6.2 Hz, 1H), 4.12 (s, 1H), 3.88 (t, J=9.3 Hz, 1H), 3.81 (dd, J=9.3, 5.8 Hz, 1H), 3.70 (dt, J=13.0, 2.7 Hz, 1H), 3.34-3.41 (m, 2H), 2.96 (td, J=12.9, 3.3 Hz, 1H), 2.71 (ddt, J=11.2, 3.7, 1.9 Hz, 1H), 2.59 (dt, J=11.4, 1.8 Hz, 1H), 2.26 (s, 3H), 2.22 (s, 3H), 2.03-2.13 (m, 1H), 1.90 (td, J=11.6, 3.5 Hz, 1H), 1.17 (d, J=6.3, 1.0 Hz, 6H), 1.13 (d, J=6.7 Hz, 3H). UPLC-MS Method 5: RT=1.82 min.

Example 53: isopropyl (2S)-4-[[5-chloro-2-methyl-3-[[5-[(2S)-4-oxoazetidin-2-yl]-1,3,4-oxadiazol-2-yl]amino]phenyl]methyl]-2-methyl-piperazine-1-carboxylate

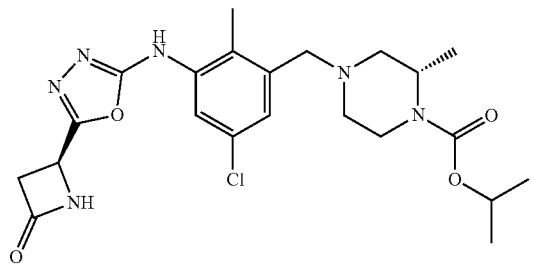 [SMILES: Cc1c(CN2CCN(C(=O)OC(C)C)[C@@H](C)C2)cc(Cl)cc1Nc1nnc([C@@H]2CC(=O)N2)o1]

3-(Ethyliminomethyleneamino)-N,N-dimethyl-propan-1-amine hydrochloride (18.5 mg, 0.097 mmol) was added to a solution of isopropyl (2S)-4-[[3-(aminocarbamothioylamino)-5-chloro-2-methyl-phenyl]methyl]-2-methyl-piperazine-1-carboxylate from Preparation 16 (10.0 mg, 0.024 mmol) and 4-oxoazetidine-2-carboxylic acid (3.6 mg, 0.031 mmol) in dichloromethane (0.6 mL). After 2 h stirring the reaction mixture was purified by basic preparative HPLC. Clean fractions were evaporated under reduced pressure to give title compound as a colourless solid (4.9 mg, 42%).

$^1$H NMR (300 MHz, DMSO-d6) δ=8.56 (s, 1H), 7.83 (d, J=2.2 Hz, 1H), 7.07 (d, J=2.3 Hz, 1H), 6.70 (br s, 1H), 4.74-4.82 (m, 2H), 4.13 (s, 1H), 3.71 (d, J=12.8 Hz, 1H), 3.36-3.44 (m, 3H), 3.15 (dd, J=14.8, 2.5 Hz, 1H), 2.91-3.07 (m, 1H), 2.71 (d, J=11.1 Hz, 1H), 2.58 (d, J=11.4 Hz, 1H), 2.24 (s, 3H), 2.02-2.17 (m, 1H), 1.95 (td, J=11.5, 3.3 Hz, 1H), 1.17 (d, J=6.2 Hz, 6H), 1.14 (d, J=6.6 Hz, 3H). UPLC-MS Method 5: RT=2.04 min.

Example 55: isopropyl (2S)-4-[[2,5-dimethyl-3-[[5-[(3S)-morpholin-3-yl]-1,3,4-oxadiazol-2-yl]amino]phenyl]methyl]-2-methyl-piperazine-1-carboxylate dihydrochloride

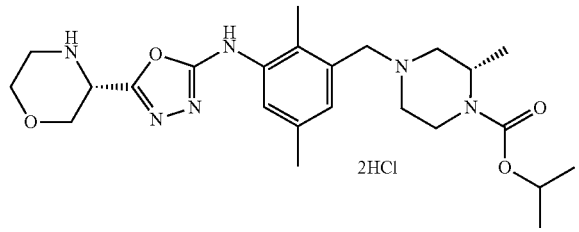 [SMILES: Cc1cc(CN2CCN(C(=O)OC(C)C)[C@@H](C)C2)c(C)c(Nc2nnc([C@@H]3COCCN3)o2)c1]

3-(Ethyliminomethyleneamino)-N,N-dimethyl-propan-1-amine hydrochloride (97.4 mg, 0.51 mmol) was added to a solution of (2S)-4-[[3-(aminocarbamothioylamino)-2,5-dimethyl-phenyl]methyl]-2-methyl-piperazine-1-carboxylate from Preparation 25 (50.0 mg, 0.127 mmol) and (3S)-4-tert-butoxycarboylmorpholine-3-carboxylic acid (38.2 mg, 0.16 mmol) in dichloromethane (3.0 mL) and stirred for 2.5 h.

The mixture was concentrated under reduced pressure and the obtained residue was purified by silica gel (100-200 mesh) column chromatography eluting with a gradient of 10-100% ethyl acetate in heptane. Clean fractions were evaporated under reduced pressure to give intermediate compound tert-butyl 3-[5-[3-[[(3S)-4-isopropoxycarbonyl-3-methyl-piperazin-1-yl]methyl]-2,5-dimethyl-anilino]-1,3,4-oxadiazol-2-yl]morpholine-4-carboxylate (56.0 mg, 0.098 mmol, 77%). Hydrogen chloride (1.5 mL, 4M in dioxane) was added to a solution of intermediate tert-butyl 3-[5-[3-[[(3S)-4-isopropoxycarbonyl-3-methyl-piperazin-1-yl]methyl]-2,5-dimethyl-anilino]-1,3,4-oxadiazol-2-yl]morpholine-4-carboxylate (52.0 mg, 0.091 mmol) in dichloromethane (5.0 mL) and stirred for 3 h. Toluene (3.0 mL) was added and the solid was collected and dried under reduced pressure to give title compound as colourless salt. (52.0 mg, 0,091 mmol, 77% overall).

$^1$H NMR (600 MHz, DMSO-d6) δ=10.59 (s, 1H), 10.42 (s, 1H), 10.22 (s, 1H), 9.86 (s, 1H), 7.51 (s, 1H), 7.45 (s, 1H), 4.88 (d, J=7.7 Hz, 1H), 4.80 (hept, J=6.3 Hz, 1H), 4.30-4.45 (m, 2H), 4.23 (dd, J=12.4, 3.6 Hz, 1H), 3.89-4.02 (m, 3H), 3.84 (ddd, J=12.3, 9.2, 2.8 Hz, 2H), 3.66-3.72 (m, 0.5H), 3.45-3.51 (m, 0.5H), 3.36 (s, 2H), 3.23 (d, J=12.0 Hz, 2H), 3.13 (dd, J=31.5, 12.5 Hz, 2H), 2.30 (s, 3H), 2.28 (s, 3H), 1.32 (d, J=7.2 Hz, 3H), 1.20 (d, J=6.3 Hz, 6H). UPLC-MS Method 5: RT=1.72 min.

Example 56: isopropyl (2S)-4-[[3-[[5-[(1R)-1-hydroxyethyl]-1,3,4-oxadiazol-2-yl]amino]-2,5-dimethyl-phenyl]methyl]-2-methyl-piperazine-1-carboxylate

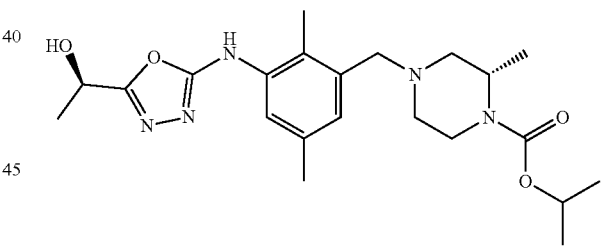

3-(Ethyliminomethyleneamino)-N,N-dimethyl-propan-1-amine hydrochloride (219 mg, 1.14 mmol) was added to a solution of (2S)-4-[[3-(aminocarbamothioylamino)-2,5-dimethyl-phenyl]methyl]-2-methyl-piperazine-1-carboxylate from Preparation 25 (150 mg, 0.38 mmol) and (2R)-2-hydroxypropanoic acid (41.2 mg, 0.46 mmol) in dichloromethane (15 mL). After 1 h stirring the reaction mixture was purified by basic preparative HPLC. Clean fractions were evaporated under reduced pressure to give title compound as a colourless solid (16.0 mg, 29.4%).

$^1$H NMR (600 MHz, DMSO-d6) δ=9.34 (s, 1H), 7.38 (s, 1H), 6.84 (s, 1H), 5.78 (d, J=5.5 Hz, 1H), 4.74-4.82 (m, 2H), 4.12 (s, 1H), 3.70 (d, J=12.9 Hz, 1H), 3.37 (q, J=15.4 Hz, 2H), 2.95 (t, J=12.2 Hz, 1H), 2.69-2.72 (m, 1H), 2.58-2.62 (m, 1H), 2.25 (s, 3H), 2.21 (s, 3H), 2.08 (d, J=8.2 Hz, 1H), 1.90 (td, J=11.7, 3.5 Hz, 1H), 1.44 (d, J=6.6 Hz, 3H), 1.17 (dd, J=6.2, 1.0 Hz, 6H), 1.13 (d, J=6.7 Hz, 3H). UPLC-MS Method 5: RT=1.83 min.

Example 63: isopropyl (2S)-4-[[5-chloro-3-[[5-[(1S)-1-hydroxyethyl]-1,3,4-oxadiazol-2-yl]amino]-2-methyl-phenyl]methyl]-2-methyl-piperazine-1-carboxylate

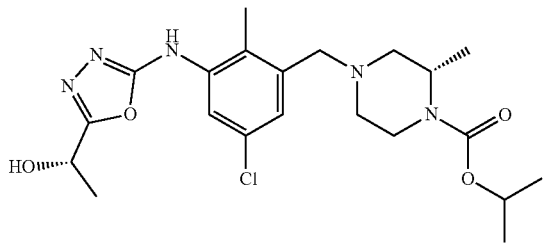 [SMILES: Cc1c(CN2CCN(C(=O)OC(C)C)[C@@H](C)C2)cc(Cl)cc1Nc1nnc([C@H](C)O)o1]

3-(Ethyliminomethyleneamino)-N,N-dimethyl-propan-1-amine hydrochloride (14.8 mg, 0.077 mmol) was added to a solution of isopropyl (2S)-4-[[3-(aminocarbamothioylamino)-5-chloro-2-methyl-phenyl]methyl]-2-methyl-piperazine-1-carboxylate from Preparation 16 (8.0 mg, 0.019 mmol) and (2S)-2-hydroxypropanoic acid (3.0 mg, 0.023 mmol) in dichloromethane (0.8 mL). After 5 h stirring the reaction mixture was purified by basic preparative HPLC. Clean fractions were evaporated under reduced pressure to give title compound as a colourless solid (2.6 mg, 12%).

$^1$H NMR (600 MHz, DMSO-d6) δ=9.66 (s, 1H), 7.83 (d, J=2.2 Hz, 1H), 7.10 (d, J=2.3 Hz, 1H), 5.84 (d, J=5.5 Hz, 1H), 4.80-4.85 (m, 1H), 4.77 (h, J=6.3 Hz, 1H), 4.13 (s, 1H), 3.70-3.73 (m, 1H), 3.42 (s, 2H), 2.98 (t, J=12.4 Hz, 1H), 2.71 (d, J=11.3 Hz, 1H), 2.59 (dt, J=13.1, 2.7 Hz, 1H), 2.24 (s, 3H), 2.11 (dd, J=11.4, 3.9 Hz, 1H), 1.95 (td, J=11.7, 3.6 Hz, 1H), 1.46 (d, J=6.6 Hz, 3H), 1.17 (dd, J=6.2, 0.8 Hz, 6H), 1.14 (d, J=6.7 Hz, 3H). UPLC-MS Method 5: RT=2.08 min.

Example 65: isopropyl (2S)-4-[[2,5-dimethyl-3-[[5-[(2S)-1-methylsulfonylpyrrolidin-2-yl]-1,3,4-oxadiazol-2-yl]amino]phenyl]methyl]-2-methyl-piperazine-1-carboxylate

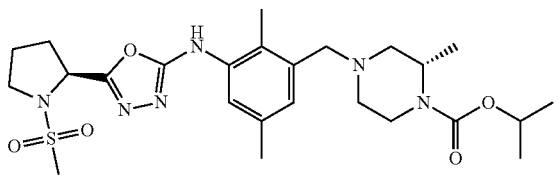 [SMILES: Cc1cc(CN2CCN(C(=O)OC(C)C)[C@@H](C)C2)c(C)c(Nc2nnc([C@@H]3CCCN3S(C)(=O)=O)o2)c1]

Methanesulfonyl chloride (4.57 mg, 0.04 mmol) was added to a solution of pyrrolidine compound from Preparation 58 (19.0 mg, 0.04 mmol) and diisopropylethylamine (0.04 mL, 0.21 mmol) in dimethylformamide (0.8 mL) and stirred at room temperature for 0.5 h. The mixture was purified directly by acidic preparative HPLC. Clean fractions were evaporated under reduced pressure to give title compound. (4.3 mg, 24%).

$^1$H NMR (600 MHz, DMSO-d$_6$) δ=9.40 (s, 1H), 7.39 (d, J=1.7 Hz, 1H), 6.84 (d, J=1.7 Hz, 1H), 5.03 (dd, J=8.2, 4.0 Hz, 1H), 4.77 (hept, J=6.2 Hz, 1H), 4.12 (dq, J=10.7, 6.2 Hz, 1H), 3.70 (dt, J=13.1, 2.7 Hz, 1H), 3.40 (m, 4H), 3.02 (s, 3H), 2.96 (td, J=12.9, 3.4 Hz, 1H), 2.71 (ddt, J=11.1, 3.6, 1.9 Hz, 1H), 2.60 (dt, J=11.2, 1.8 Hz, 1H), 2.29 (m, 1H), 2.25 (s, 3H), 2.22 (s, 3H), 2.11 (m, 2H), 2.01 (m, 2H), 1.90 (td, J=11.7, 3.5 Hz, 1H), 1.17 (dd, J=6.2, 1.0 Hz, 6H), 1.13 (d, J=6.7 Hz, 3H). UPLC-MS Method 5: m/z 535.3 [M+H$^+$]; RT=1.95 min.

Example 66: isopropyl (2S)-4-[[3-[[5-[(1S)-1-hydroxyethyl]-1,3,4-oxadiazol-2-yl]amino]-2,5-dimethyl-phenyl]methyl]-2-methyl-piperazine-1-carboxylate

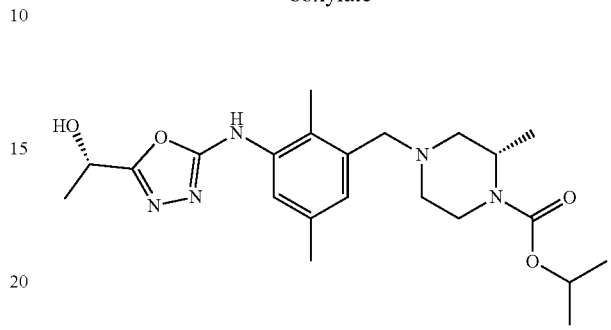

3-(Ethyliminomethyleneamino)-N,N-dimethyl-propan-1-amine hydrochloride (292 mg, 1.52 mmol) was added to a solution of (2S)-4-[[3-(aminocarbamothioylamino)-2,5-dimethyl-phenyl]methyl]-2-methyl-piperazine-1-carboxylate from Preparation 25 (200 mg, 0.51 mmol) and (2S)-2-hydroxypropanoic acid (50.0 mg, 0.56 mmol) in dichloromethane (5 mL). After 3 h the reaction mixture was quenched with water (2.0 mL) and extracted with dichloromethane (5.0 mL). The organic layer was collected and concentrated under reduced pressure. The obtained residue was purified by silica gel (100-200 mesh) column chromatography eluting with a gradient of 0-85% ethyl acetate in heptanes. Clean fractions were evaporated under reduced pressure to give title compound as a colourless solid. (124 mg, 56.6%) NMR and MS data as shown below.

Alternative Preparation 3-(Ethyliminomethyleneamino)-N,N-dimethyl-propan-1-amine hydrochloride (11.7 g, 60.9 mmol) was added to a solution of (2S)-4-[[3-(aminocarbamothioylamino)-2,5-dimethyl-phenyl]methyl]-2-methyl-piperazine-1-carboxylate from Preparation 25 (6.00 g, 15.2 mmol) and (2S)-2-hydroxypropanoic acid (2.20 g, 24.1 mmol) in acetonitrile (15 mL) at 0° C. The reaction mixture was stirred at room temperature for 48 h. Lithium hydroxide solution (91.5 mL, 1.0 M) was added to the reaction mixture and stirred for 10 min. To the reaction mixture was added water (100 mL) followed by acetic acid (5.23 mL, 91.5 mmol). The mixture was reduced to low volume in vacuo. The aqueous residue was neutralised with saturated NaHCO$_3$ (aq) and extracted with ethyl acetate (3×250 mL). The combined organic layers were washed with saturated brine, dried over MgSO$_4$, filtered and concentrated in vacuo. The obtained residue was purified by silica gel (100-200 mesh) column chromatography eluting with a gradient of 20-100% ethyl acetate in heptanes. Clean fractions were evaporated under reduced pressure to give title compound as a colourless non-crystalline solid. (3.05 g, 46.4%) This obtained material (2.58 g, 5.98 mmol) was dissolved in diethyl ether (25.8 mL, 10 mL/g). The mixture was left to crystallize over 12 h. The crystals were collected and dried in vacuo to give the title material as a crystalline solid. (2.31 g, melting point 120-121° C., 89.5%).

$^1$H NMR (600 MHz, DMSO-d6) δ=9.34 (s, 1H), 7.38 (d, J=1.7 Hz, 1H), 6.85 (d, J=1.7 Hz, 1H), 5.79 (d, J=5.5 Hz,

1H), 4.69-4.78 (m, 2H), 4.12 (s, 1H), 3.70 (dt, J=13.0, 2.7 Hz, 1H), 3.33-3.43 (m, 2H), 2.90-3.02 (m, 1H), 2.71 (ddt, J=11.1, 3.6, 1.9 Hz, 1H), 2.60 (dt, J=11.2, 2.0 Hz, 1H), 2.25 (s, 3H), 2.21 (s, 3H), 2.08 (dd, J=11.3, 3.8 Hz, 1H), 1.90 (td, J=11.7, 3.5 Hz, 1H), 1.44 (d, J=6.6 Hz, 3H), 1.17 (dd, J=6.2, 1.0 Hz, 6H), 1.13 (d, J=6.7 Hz, 3H). UPLC-MS Method 5: RT=1.83 min.

Example 67: isopropyl (2S)-4-[[5-chloro-2-methyl-3-[[5-(5-oxopyrrolidin-3-yl)-1,3,4-oxadiazol-2-yl]amino]phenyl]methyl]-2-methyl-piperazine-1-carboxylate

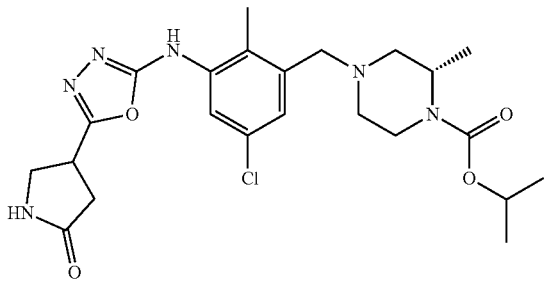 [SMILES: Cc1c(CN2CCN(C(=O)OC(C)C)[C@@H](C)C2)cc(Cl)cc1Nc1nnc(C2CNC(=O)C2)o1]

3-(ethyliminomethyleneamino)-N,N-dimethyl-propan-1-amine hydrochloride (14.8 mg, 0.077 mmol) was added to a solution of isopropyl (2S)-4-[[3-(aminocarbamothioylamino)-5-chloro-2-methyl-phenyl]methyl]-2-methyl-piperazine-1-carboxylate from Preparation 16 (8.0 mg, 0.019 mmol) and 2-oxopyrrolidine-4-carboxylic acid (3.0 mg, 0.023 mmol) in dichloromethane (0.8 mL). After 5 h stirring the reaction mixture was purified by basic preparative HPLC. Clean fractions were evaporated under reduced pressure to give title compound as a colourless solid (2.6 mg, 27%).
$^1$H NMR (600 MHz, DMSO-d6) δ=9.62 (s, 1H), 7.81-7.85 (m, 2H), 7.09 (d, J=2.3 Hz, 1H), 4.77 (hept, J=6.3 Hz, 1H), 4.13 (s, 1H), 3.88 (dddd, J=9.5, 8.3, 6.8, 5.7 Hz, 1H), 3.69-3.73 (m, 1H), 3.63-3.67 (m, 1H), 3.46-3.54 (m, 1H), 3.42 (s, 2H), 2.98 (t, J=12.4 Hz, 1H), 2.71 (d, J=11.4 Hz, 1H), 2.56-2.66 (m, 3H), 2.24 (s, 3H), 2.11 (dd, J=11.4, 3.9 Hz, 1H), 1.95 (td, J=11.6, 3.5 Hz, 1H), 1.17 (dd, J=6.2, 0.9 Hz, 6H), 1.14 (d, J=6.8 Hz, 3H). UPLC-MS Method 5: RT=1.99 min.

Example 68: isopropyl (2S)-4-[[3-[[5-[(1R)-1-aminoethyl]-1,3,4-oxadiazol-2-yl]amino]-2,5-dimethyl-phenyl]methyl]-2-methyl-piperazine-1-carboxylate

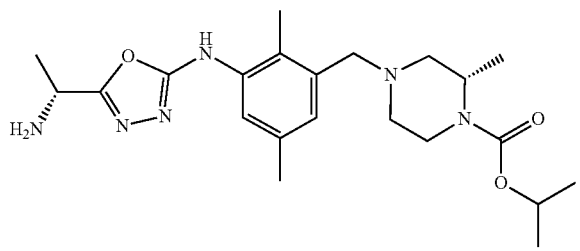 [SMILES: Cc1cc(CN2CCN(C(=O)OC(C)C)[C@@H](C)C2)c(C)c(Nc2nnc([C@@H](C)N)o2)c1]

3-(Ethyliminomethyleneamino)-N,N-dimethyl-propan-1-amine hydrochloride (46.4 mg, 0.24 mmol) was added to a solution of (2S)-4-[[3-(aminocarbamothioylamino)-2,5-dimethyl-phenyl]methyl]-2-methyl-piperazine-1-carboxylate from Preparation 25 (32.0 mg, 0.08 mmol) and (2R)-2-(tert-butoxycarbonylamino)propanoic acid (16.9 mg, 0.09 mmol) in dichloromethane (3.0 mL) and stirred for 2.5 h. The reaction mixture was quenched with water (2.0 mL) and extracted with dichloromethane (5.0 mL). The organic layer was collected and concentrated under reduced pressure. The obtained residue was purified by silica gel (100-200 mesh) column chromatography eluting with a gradient of 0-70% ethyl acetate in heptane. Clean fractions were evaporated under reduced pressure to give intermediate compound isopropyl (2S)-4-[[3-[[5-[(1R)-1-(tert-butoxycarbonylamino)ethyl]-1,3,4-oxadiazol-2-yl]amino]-2,5-dimethyl-phenyl]methyl]-2-methyl-piperazine-1-carboxylate (21.0 mg, 0.04 mmol, 48.7%). Hydrogen chloride (0.6 mL, 4M in dioxane) was added to a solution of the intermediate isopropyl (2S)-4-[[3-[[5-[(1R)-1-(tert-butoxycarbonylamino)ethyl]-1,3,4-oxadiazol-2-yl]amino]-2,5-dimethyl-phenyl]methyl]-2-methyl-piperazine-1-carboxylate (21.0 mg, 0.04 mmol) in dichloromethane (5.0 mL) and stirred for 2 h. The resulting suspension was diluted with methanol and purified on 1 g SCX column, eluting with methanol followed by methanolic ammonia (2N). Clean fractions were evaporated under reduced pressure to give title compound as a colourless solid (16.0 mg, 0.037 mmol, 93.9%).
$^1$H NMR (300 MHz, CDCl$_3$) δ=7.53 (d, J=1.7 Hz, 1H), 6.97-7.04 (m, 1H), 6.75 (d, J=1.7 Hz, 1H), 5.04 (d, J=8.6 Hz, 1H), 4.77-4.97 (m, 2H), 4.17 (s, 1H), 3.76 (d, J=13.1 Hz, 1H), 3.32 (s, 2H), 2.98 (td, J=12.7, 3.4 Hz, 1H), 2.64 (d, J=11.3 Hz, 1H), 2.50 (dt, J=11.0, 1.8 Hz, 1H), 2.25 (s, 3H), 2.22 (s, 3H), 2.09 (dd, J=11.2, 3.9 Hz, 1H), 1.85-1.96 (m, 1H), 1.50 (d, J=6.9 Hz, 3H), 1.16 (d, J=6.2 Hz, 6H), 1.12 (d, J=6.7 Hz, 3H). UPLC-MS Method 5: RT=1.68 min.

Example 69: 2,2,2-trifluoroethyl (2S)-4-[[5-chloro-3-[[5-(cyanomethyl)-1,3,4-oxadiazol-2-yl]amino]-2-methyl-phenyl]methyl]-2-methyl-piperazine-1-carboxylate

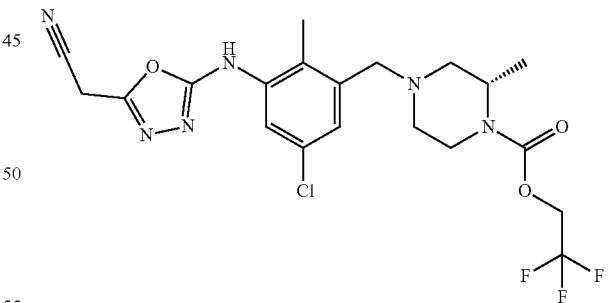

2,2,2-trifluoroethyl carbonochloridate (4.12 mg, 0.025 mmol) was added to a solution of 2-[5-[5-chloro-2-methyl-3-[[(3S)-3-methylpiperazin-1-yl]methyl]anilino]-1,3,4-oxadiazol-2-yl]acetonitrile dihydrochloride from Preparation 54 (10.0 mg, 0.023 mmol) and triethylamine (0.016 mL, 0.115 mmol) in dichloromethane (0.7 mL). The reaction was complete after 1 h. The reaction mixture was evaporated under reduced pressure then diluted with dimethylformamide (0.4 mL). To this was added lithium hydroxide solution (0.03 mL, 1N) and the reaction was stirred for 1 h. The reaction was purified by basic HPLC. Clean fractions were evaporated under reduced pressure to give title compound as a colourless solid (0.8 mg, 8%).

$^1$H NMR (600 MHz, DMSO-d6) δ=9.81 (s, 1H), 7.77 (d, J=2.2 Hz, 1H), 7.14 (d, J=2.2 Hz, 1H), 4.65-4.76 (m, 2H), 4.50 (s, 2H), 4.15 (s, 1H), 3.73 (d, J=13.1 Hz, 1H), 3.44 (s, 2H), 3.09 (s, 1H), 2.75 (d, J=11.4 Hz, 1H), 2.61-2.64 (m, 1H), 2.25 (s, 3H), 2.16 (dd, J=11.5, 3.9 Hz, 1H), 2.00 (td, J=11.8, 3.5 Hz, 1H), 1.18 (d, J=6.8 Hz, 3H). UPLC-MS Method 5: RT=2.39 min.

Example 70: 2,2,2-trifluoroethyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate

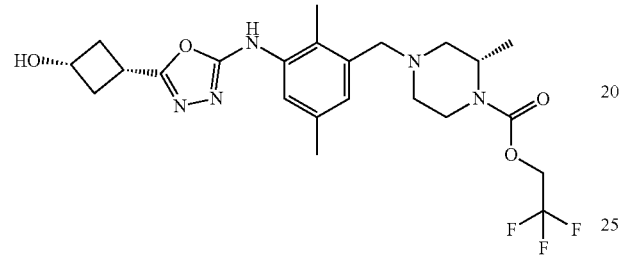

A solution of 2,2,2-trifluoroethyl carbonochloridate in dichloromethane (0.15 mL, 0.18 M, 0.027 mmol) was added to a solution of 3-[5-[2,5-dimethyl-3-[[(3S)-3-methylpiperazin-1-yl]methyl]anilino]-1,3,4-oxadiazol-2-yl]cyclobutanol dihydrochloride from Preparation 55 (12.0 mg, 0.027 mmol) and triethylamine (0.03 mL, 0.22 mmol) in dichloromethane (0.8 mL). The resulting mixture was stirred for 30 min, a further aliquot of 2,2,2-trifluoroethyl carbonochloridate in dichloromethane (0.15 mL, 0.18 M, 0.027 mmol) was added and stirring continued. After 1 h the reaction mixture was evaporated under reduced pressure then diluted with dimethylformamide (0.6 mL) and purified by basic HPLC. Clean fractions were evaporated under reduced pressure to give title compound as a colourless solid (1.0 mg, 11%).

$^1$H NMR (600 MHz, DMSO-d6) δ=9.23 (s, 1H), 7.41 (s, 1H), 6.83 (s, 1H), 5.31 (d, J=6.5 Hz, 1H), 4.64-4.77 (m, 2H), 4.06-4.15 (m, 2H), 3.72 (d, J=13.1 Hz, 1H), 3.38 (q, J=12.8 Hz, 2H), 3.04 (td, J=10.8, 10.1, 5.7 Hz, 2H), 2.73-2.76 (m, 1H), 2.63 (dt, J=11.1, 1.7 Hz, 1H), 2.54-2.61 (m, 2H), 2.25 (s, 3H), 2.21 (s, 3H), 2.06-2.13 (m, 3H), 1.94 (td, J=11.7, 3.6 Hz, 1H), 1.17 (d, J=6.7 Hz, 3H). UPLC-MS Method 5: RT=1.96 min.

Example 71: ethyl (2S)-4-[[3-[[5-[(1R)-1-hydroxyethyl]-1,3,4-oxadiazol-2-yl]amino]-2,5-dimethyl-phenyl]methyl]-2-methyl-piperazine-1-carboxylate

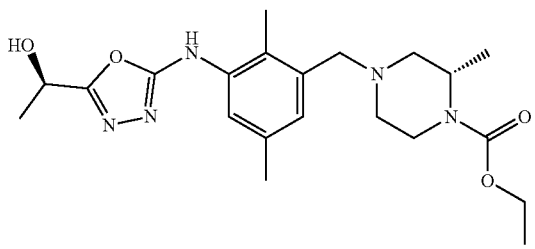

Ethyl carbonochloridate in dichloromethane (0.024 mL, 0.024 mmol) was added to a solution of (1R)-1-[5-[2,5-dimethyl-3-[[(3S)-3-methylpiperazin-1-yl]methyl]anilino]-1,3,4-oxadiazol-2-yl]ethanol dihydrochloride from Preparation 52 (10.0 mg, 0.024 mmol) and triethylamine (14.5 mg, 0.143 mmol) in dichloromethane (0.7 mL). After 2 h the reaction mixture was evaporated under reduced pressure and then diluted with dimethylformamide (0.6 mL) and purified by basic HPLC. Clean fractions were evaporated under reduced pressure to give title compound as a colourless solid (0.5 mg, 5%).

$^1$H NMR (600 MHz, DMSO-d6) δ=7.38 (d, J=1.7 Hz, 1H), 6.84 (d, J=1.6 Hz, 1H), 5.84 (s, 1H), 4.78 (q, J=6.6 Hz, 1H), 4.10-4.15 (m, 1H), 4.03 (qq, J=10.8, 7.1 Hz, 2H), 3.71 (d, J=13.0 Hz, 1H), 2.93-3.02 (m, 1H), 2.71 (d, J=12.0 Hz, 1H), 2.56-2.66 (m, 1H), 2.25 (s, 3H), 2.21 (s, 3H), 2.08 (dd, J=11.3, 3.9 Hz, 1H), 1.99 (dt, J=18.9, 7.0 Hz, 1H), 1.90 (td, J=11.7, 3.5 Hz, 1H), 1.44 (d, J=6.6 Hz, 3H), 1.17 (t, J=7.1 Hz, 3H), 1.13 (d, J=6.7 Hz, 3H). UPLC-MS Method 5: RT=1.73 min.

Example 72: isopropyl (2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate

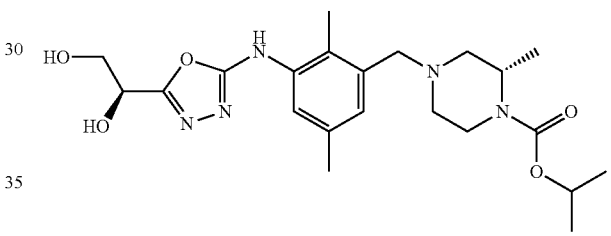

3-(Ethyliminomethyleneamino)-N,N-dimethyl-propan-1-amine hydrochloride (29.2 mg, 0.15 mmol) was added to a solution of isopropyl(2S)-4-[[3(aminocarbamothioylamino)-2,5-dimethyl-phenyl]methyl]-2-methyl-piperazine-1-carboxylate (20.0 mg, 0.051 mmol) and 4S)-2,2-dimethyl-1,3-dioxolane-4-carboxylic acid Preparation 25 (8.17 mg, 0.056 mmol) dissolved in dry dichloromethane (5 mL) and stirred at room temperature for 12 h. The reaction mixture was quenched with water (2.0 mL) and extracted with dichloromethane (5.0 mL). The organic layer was collected and concentrated under reduced pressure. The obtained residue was purified by silica gel (100-200 mesh) column chromatography eluting with a gradient of 10-100% ethyl acetate in heptane. Clean fractions were evaporated under reduced pressure to give intermediate compound isopropyl (2S)-4-[[3-[[5-[(4S)-2,2-dimethyl-1,3-dioxolan-4-yl]-1,3,4-oxadiazol-2-yl]amino]-2,5-dimethyl-phenyl]methyl]-2-methyl-piperazine-1-carboxylate (22.0 mg, 0.045 mmol, 88.8%). Hydrogen chloride (0.6 mL, 4M in dioxane) was added to a solution of the intermediate isopropyl-(2S)-4-[[3-[[5-[(4S)-2,2-dimethyl-1,3-dioxolan-4-yl]-1,3,4-oxadiazol-2-yl]amino]-2,5-dimethyl-phenyl]methyl]-2-methyl-piperazine-1-carboxylate (22.0 mg, 0.045 mmol, 88.8%) in dichloromethane (5.0 mL). After 1 h the solvent was removed under reduced pressure and the residue was dissolved in toluene and evaporated under reduced pressure (2×20 mL). The crude product was purified by basic HPLC. Clean fractions were evaporated under reduced pressure to give title compound as a colourless solid (9.0 mg, 39.5%).

$^1$H NMR (600 MHz, DMSO-d6) δ=7.39 (d, J=1.7 Hz, 1H), 6.84 (d, J=1.7 Hz, 1H), 5.92 (s, 1H), 4.98 (s, 1H), 4.77 (h, J=6.3 Hz, 1H), 4.61 (t, J=6.7 Hz, 1H), 4.12 (dt, J=11.5, 4.6 Hz, 1H), 3.70 (dt, J=13.1, 2.6 Hz, 1H), 3.65 (d, J=6.6 Hz, 2H), 3.39 (m, 2H), 2.93-2.98 (m, 1H), 2.65-2.75 (m, 1H), 2.60 (dt, J=11.2, 1.9 Hz, 1H), 2.25 (s, 3H), 2.21 (s, 3H), 2.02-2.12 (m, 1H), 1.90 (td, J=11.7, 3.5 Hz, 1H), 1.17 (d, J=6.2 Hz, 6H), 1.13 (d, J=6.7 Hz, 3H). UPLC-MS Method 5: RT=1.74 min.

Example 74: tert-butyl (2S)-4-[[5-chloro-3-[[5-(hydroxymethyl)oxazol-2-yl]amino]-2-methyl-phenyl]methyl]-2-methyl-piperazine-1-carboxylate

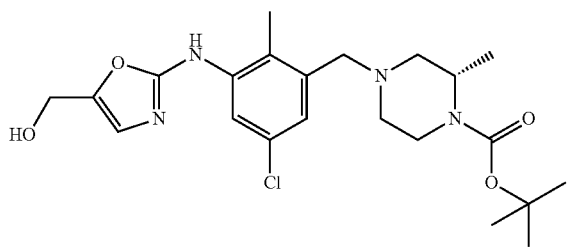 [SMILES: Cc1c(CN2CCN(C(=O)OC(C)(C)C)[C@@H](C)C2)cc(Cl)cc1Nc1ncc(CO)o1]

Lithium aluminium hydride (2.3 M in THF, 0.026 mL, 0.061 mmol) was added to a solution of ethyl 2-[3-[[(3S)-4-tert-butoxycarbonyl-3-methyl-piperazin-1-yl]methyl]-5-chloro-2-methyl-anilino]oxazole-5-carboxylate Preparation 50 (130 mg, 0.26 mmol) in tetrahydrofuran at 0° C. After 1 h of stirring the mixture was quenched with water and extracted with ethyl acetate (3×10 mL). The organic phase was washed with brine and water, dried over magnesium sulphate and evaporated under reduced pressure. The residue was purified by basic HPLC. Clean fractions were evaporated under reduced pressure to give title compound (4.0 mg, 21.8%).

$^1$H NMR (600 MHz, DMSO-d6) δ=9.22 (s, 1H), 7.97 (d, J=2.2 Hz, 1H), 7.01 (d, J=2.2 Hz, 1H), 6.78 (s, 1H), 5.19 (t, J=5.4 Hz, 1H), 4.37 (d, J=4.7 Hz, 2H), 4.09 (m, 1H), 3.67 (dt, J=13.1, 2.7 Hz, 1H), 3.44-3.36 (m, 2H), 2.93 (t, J=12.2, 1H), 2.69 (dp, J=11.2, 1.9 Hz, 1H), 2.58 (dt, J=11.3, 1.9 Hz, 1H), 2.22 (s, 3H), 2.09 (dd, J=11.3, 3.9 Hz, 1H), 1.92 (td, J=11.6, 3.5 Hz, 1H), 1.39 (s, 9H), 1.13 (d, J=6.7 Hz, 3H). UPLC-MS Method 5: RT=2.21 min.

Example 75: [(1R)-2,2,2-trifluoro-1-methyl-ethyl] (2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate

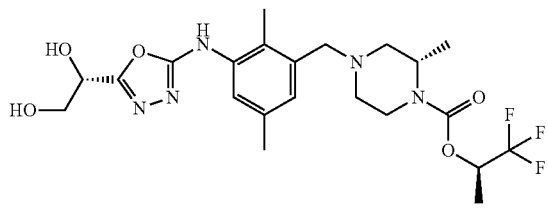 [SMILES: Cc1cc(CN2CCN(C(=O)O[C@H](C)C(F)(F)F)[C@@H](C)C2)c(C)c(Nc2nnc([C@@H](O)CO)o2)c1]

Bis(trichloromethyl) carbonate (150 mg, 0.49 mmol) was added to a solution of (2R)-1,1,1-trifluoropropan-2-ol (160 mg, 1.40 mmol) and triethylamine (0.17 mL, 1.20 mmol) in dichloromethane (6.0 mL) at 0° C. On complete addition the reaction mixture was warmed to room temperature over 4 hr, whereupon the complete reaction mixture was added to a solution of product from Preparation 56 (476 mg, 1.20 mmol) and triethylamine (1.67 mL, 12.0 mmol) in dimethylformamide (20 mL) at room temperature. The reaction was stirred for 18 h then the solvent was removed in vacuo. The residue was dissolved in water (40 mL) and extracted with ethyl acetate (2×40 mL). The combined organic layers were dried over Na$_2$SO$_4$, filtered and concentrated in vacuo. The obtained residue was purified by silica gel (100-200 mesh) column chromatography eluting with a gradient of 0-100% ethyl acetate in heptane. Clean fractions were evaporated under reduced pressure to give the title compound as a colourless non-crystalline solid (140 mg, 23.3%).

$^1$H NMR (600 MHz, DMSO-d$_6$) δ=9.35 (s, 1H), 7.40 (s, 1H), 6.85 (s, 1H), 5.91 (d, J=5.2 Hz, 1H), 5.33 (p, J=6.7 Hz, 1H), 4.96 (t, J=6.0 Hz, 1H), 4.61 (td, J=6.6, 5.2 Hz, 1H), 4.15 (s, 1H), 3.70 (d, J=13.2 Hz, 1H), 3.65 (t, J=6.3 Hz, 2H), 3.33-3.45 (m, 2H), 3.05 (bs, 1H), 2.72-2.77 (m, 1H), 2.64 (d, J=11.4 Hz, 1H), 2.25 (s, 3H), 2.21 (s, 3H), 2.13 (d, J=11.5 Hz, 1H), 1.89-1.97 (m, 1H), 1.35 (d, J=6.6 Hz, 3H), 1.16 (d, J=6.7 Hz, 3H). UPLC-MS Method 6: m/z 502.2 [M+H$^+$]; RT=1.88 min.

Example 76: isopropyl (2S)-4-[[2,5-dimethyl-3-[[5-[(3R)-tetrahydrofuran-3-yl]-1,3,4-oxadiazol-2-yl]amino]phenyl]methyl]-2-methyl-piperazine-1-carboxylate

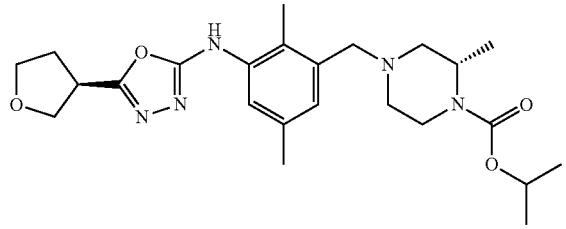 [SMILES: Cc1cc(CN2CCN(C(=O)OC(C)C)[C@@H](C)C2)c(C)c(Nc2nnc([C@@H]3CCOC3)o2)c1]

3-(Ethyliminomethyleneamino)-N,N-dimethyl-propan-1-amine hydrochloride (29.2 mg, 0.15 mmol) was added to a solution of product from Preparation 25 (15.0 mg, 0.04 mmol) and (3R)-tetrahydrofuran-3-carboxylic acid (6.20 mg, 0.05 mmol) in dichloromethane at room temperature. The mixture was stirred for 1 h then concentrated to dryness in vacuo. The residue was re-dissolved in 1,4-dioxan (0.5 mL) and lithium hydroxide solution added (0.2 mL, 1.0 M). The mixture was stirred for 0.5 h. The reaction mixture was purified by basic preparative HPLC. Clean fractions were evaporated under reduced pressure to give title compound as a colourless oil (16 mg, 91%).

$^1$H NMR (600 MHz, DMSO-d$_6$) δ: 7.39 (s, 1H), 6.83 (s, 1H), 4.77 (hept, J=6.2 Hz, 1H), 4.11 (hept, J=8.9, 6.6 Hz, 1H), 3.97 (dd, J=8.6, 7.6 Hz, 1H), 3.84 (ddd, J=10.8, 8.3, 5.8 Hz, 2H), 3.77 (td, J=7.9, 6.6 Hz, 1H), 3.70 (dt, J=12.9, 2.6 Hz, 1H), 3.62 (ddt, J=8.9, 7.6, 5.8 Hz, 1H), 3.34-3.41 (m, 2H), 2.95 (m, 1H), 2.70 (ddt, J=11.1, 3.4, 1.8 Hz, 1H), 2.59 (dt, J=11.2, 1.8 Hz, 1H), 2.25-2.31 (m, 1H), 2.24 (s, 3H), 2.20 (s, 3H), 2.15 (ddt, J=12.4, 7.7, 6.2 Hz, 1H), 2.06-2.10 (m, 1H), 1.89 (td, J=11.7, 3.5 Hz, 1H), 1.17 (dd, J=6.2, 1.1 Hz, 6H), 1.13 (d, J=6.7 Hz, 3H). UPLC-MS Method 5: m/z 458.2 [M+H$^+$]; RT=1.92 min.

Example 77: isopropyl (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate

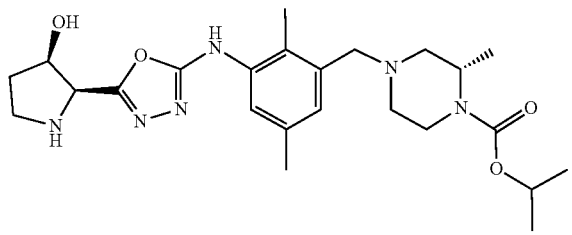 [SMILES: Cc1cc(CN2CCN(C(=O)OC(C)C)[C@@H](C)C2)c(C)c(Nc2nnc([C@H]3NCC[C@H]3O)o2)c1]

3-(Ethyliminomethyleneamino)-N,N-dimethyl-propan-1-amine hydrochloride (1.0 g, 5.0 mmol) was added to a solution of product from Preparation 25 (500 mg, 1.0 mmol) and (2S,3R)-1-tert-butoxycarbonyl-3-hydroxy-pyrrolidine-2-carboxylic acid (300 mg, 1.0 mmol) in dichloromethane (40 mL) and stirred at room temperature for 1.5 h. The mixture was concentrated to dryness in vacuo. The obtained residue was purified by silica gel (100-200 mesh) column chromatography eluting with a gradient of 0-100% ethyl acetate in heptanes. Clean fractions were combined and concentrated in vacuo to leave intermediate product as colourless oil. LCMS Method 4: m/z 473.4 [M+H$^+$]; RT=0.68 min.

Hydrogen chloride (4M solution in 1,4-dioxane, 2.27 mL, 9.08 mmol) was added to a solution of this piperazine intermediate (520 mg, 0.91 mmol) in methanol (2 mL) and stirred at room temperature for 2 h. The reaction mixture was concentrated under reduced pressure and was purified by silica gel (100-200 mesh) column chromatography eluting with a gradient of 0-100% ethyl acetate in heptanes. Fractions were pooled and concentrated in vacuo and the residue obtained was re-purified by basic HPLC (10-100% MeCN). Clean fractions were combined and evaporated under reduced pressure to give the title compound as a colourless non-crystalline solid. (208 mg, 48.4%)

$^1$H NMR (600 MHz, DMSO-d$_6$) δ: 9.23 (s, 1H), 7.41 (s, 1H), 6.82 (s, 1H), 4.98 (d, J=4.9 Hz, 1H), 4.77 (hept, J=6.3 Hz, 1H), 4.35 (p, J=5.4 Hz, 1H), 4.17 (d, J=5.7 Hz, 1H), 4.12 (d, J=6.4 Hz, 1H), 3.69 (m, 1H), 3.32-3.42 (m, 2H), 3.09 (ddd, J=9.9, 8.1, 5.8 Hz, 1H), 2.95 (m, 1H), 2.82 (ddd, J=9.9, 8.1, 6.3 Hz, 1H), 2.71 (d, J=10.6 Hz, 1H), 2.60 (dt, J=11.2, 1.7 Hz, 1H), 2.24 (s, 3H), 2.21 (s, 3H), 2.08 (dd, J=11.4, 3.9 Hz, 1H), 1.96 (ddt, J=12.2, 8.0, 6.0 Hz, 1H), 1.89 (td, J=11.7, 3.5 Hz, 1H), 1.77 (dddd, J=12.6, 8.0, 6.3, 4.9 Hz, 1H), 1.17 (d, J=6.2 Hz, 6H), 1.13 (d, J=6.7 Hz, 3H). LCMS Method 5: m/z 473.2 [M+H$^+$]; RT=1.67 min.

Example 78: cyclopentyl-[(2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazin-1-yl]methanone

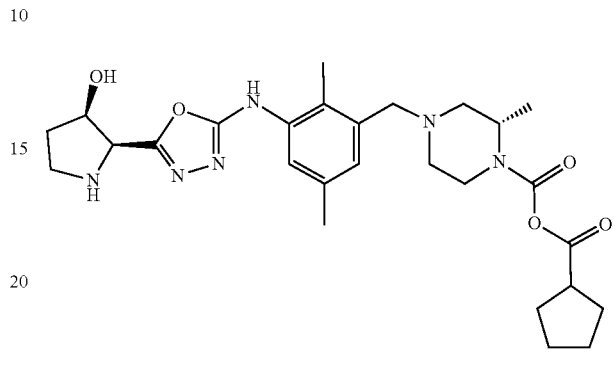

3-(Ethyliminomethyleneamino)-N,N-dimethyl-propan-1-amine hydrochloride (1.21 g, 6.30 mmol) was added to a solution of product from Preparation 64 (635 mg, 1.58 mmol) and (2S,3R)-1-tert-butoxycarbonyl-3-hydroxy-pyrrolidine-2-carboxylic acid (437 mg, 1.89 mmol) in dichloromethane (10 mL) and stirred at room temperature for 2 h. The reaction mixture was quenched with aqueous brine (10 mL) and extracted with dichloromethane (40 mL). The organic layer was dried over Na$_2$SO$_4$, filtered and concentrated in vacuo. The residue was dissolved in 2M AcOH/MeOH and loaded onto 10 g SCX cartridge. Washed with methanol then eluted with 2N NH3/MeOH. Relevant fractions were combined and concentrated in vacuo. The residue was re-purified by silica gel (100-200 mesh) column chromatography eluting with a gradient of 0-20% of a 4% methanolic ammonia solution in ethyl acetate. Relevant fractions were combined and concentrated in vacuo to leave the intermediate material as a colourless oil (724 mg, 1.24 mmol, 78%). LCMS Method 4: m/z 473.4 [M+H$^+$]; RT=0.67 min. Trifluoroacetic acid (4.0 mL, 52.2 mmol) was added to a solution of this intermediate (724 mg, 1.24 mmol) in acetonitrile (4.0 mL) and stirred for 1 h, then concentrated to dryness. The residue was dissolved in 2M AcOH/MeOH and loaded onto 10 g SCX cartridge. Washed with methanol then eluted with 2N ammonia in methanol. Relevant fractions were combined and concentrated in vacuo. The residue was dissolved in acetonitrile and purified by basic preparative HPLC. Clean fractions were evaporated under reduced pressure to give the title compound (349 mg, 58.2%).

$^1$H NMR (600 MHz, DMSO-d$_6$) δ: 9.23 (s, 1H), 7.41 (s, 1H), 6.82 (s, 1H), 4.99 (d, J=4.9 Hz, 1H), 4.54 (d, J=7.4 Hz, 0.5H), 4.35 (p, J=5.3 Hz, 1H), 4.20 (m, 0.5H) overlapping 4.17 (d, J=5.7 Hz, 1H), 3.73 (d, J=13.3 Hz, 0.5H), 3.16 (t, J=12.6 Hz, 0.5H), 3.09 (ddd, J=10.0, 8.1, 5.7 Hz, 1H), 2.91 (q, J=7.1 Hz, 1H), 2.83 (ddd, J=10.0, 8.2, 6.3 Hz, 1H), 2.77 (m, 0.5H) overlapping 2.73 (d, J=11.0 Hz, 1H), 2.63 (m, 1H), 2.25 (s, 3H), 2.23 (s, 3H), 2.04 (m, 1H), 1.96 (ddt, J=12.3, 8.2, 6.0 Hz, 1H), 1.86 (m, 0.5H), 1.77 (dddd, J=12.8, 8.1, 6.3, 4.9 Hz, 1H), 1.70 (m, 2H), 1.57 (m, 3H), 1.50 (m, 2H), 1.15 (dd, J=82.7, 6.6 Hz, 3H).). LCMS Method 6: m/z 483.3 [M+H$^+$]; RT=1.63 min.

Example 80: [(1R)-2,2,2-trifluoro-1-methyl-ethyl] (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate

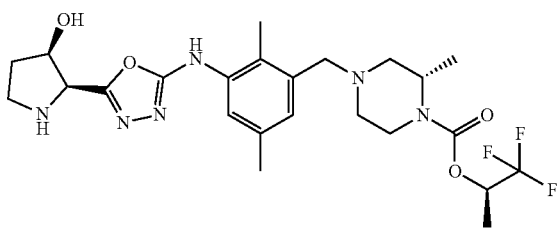 [SMILES: Cc1cc(CN2CCN(C(=O)O[C@H](C)C(F)(F)F)[C@@H](C)C2)c(C)c(Nc2nnc([C@H]3NCC[C@H]3O)o2)c1]

Using a procedure similar to that described in Example 75, but using the product from Preparation 66 (30.0 mg, 0.06 mmol) and (2R)-1,1,1-trifluoropropan-2-ol (24.0 mg, 0.21 mmol), the intermediate compound was prepared. The crude intermediate product was purified by basic HPLC. The clean fractions were combined and concentrated in vacuo to leave the intermediate product as a colourless foam (17.0 mg, 44%). 10% palladium on carbon (4.0 mg, 0.04 mmol) was added to a solution of the isolated intermediate (17.0 mg, 0.026 mmol) in ethanol (2 mL) under an atmosphere of hydrogen and the reaction mixture was stirred for 2 h at room temperature. The reaction mixture was filtered through a Celite® pad and concentrated in vacuo. The obtained residue was dissolved in methanol and purified by basic HPLC. The clean fractions were combined and concentrated in vacuo to leave the title product as a colourless non-crystalline solid (8.0 mg, 62%).

$^1$H NMR (600 MHz, DMSO-d6) δ=9.23 (s, 1H), 7.41 (d, J=1.7 Hz, 1H), 6.82 (d, J=1.7 Hz, 1H), 5.33 (hept, J=6.8 Hz, 1H), 4.98 (d, J=4.9 Hz, 1H), 4.35 (p, J=5.3 Hz, 1H), 4.17 (d, J=5.7 Hz, 1H) overlapping 4.14 (d, J=9.2 Hz, 1H), 3.70 (d, J=13.1 Hz, 1H), 3.41 (d, J=13.0 Hz, 1H), 3.36 (m, 2H), 3.09 (ddd, J=10.0, 8.1, 5.7 Hz, 1H), 3.05 (m, 1H), 2.82 (ddd, J=10.0, 8.1, 6.3 Hz, 1H), 2.74 (ddt, J=11.2, 3.5, 1.8 Hz, 1H), 2.63 (m, 1H), 2.24 (s, 3H), 2.22 (s, 3H), 2.12 (dd, J=12.0, 4.0 Hz, 1H), 1.95 (m, 2H), 1.77 (dddd, J=12.8, 8.1, 6.2, 4.8 Hz, 1H), 1.35 (dd, J=6.6 Hz, 3H), 1.16 (d, J=6.7 Hz, 3H). UPLC-MS Method 4: RT=0.71 min.

Example 81: 2,2,2-trifluoroethyl (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate

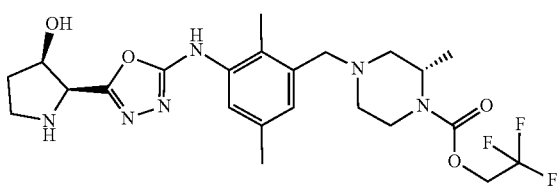 [SMILES: Cc1cc(CN2CCN(C(=O)OCC(F)(F)F)[C@@H](C)C2)c(C)c(Nc2nnc([C@H]3NCC[C@H]3O)o2)c1]

Using a procedure as described in Example 80, using the product from Preparation 66 (29.0 mg, 0.06 mmol) and 2,2,2-trifluoroethanol (70.0 mg, 0.7 mmol), followed by the intermediate deprotection with palladium on carbon and basic HPLC purification, the title compound was isolated as a colourless non-crystalline solid. (4.0 mg, 14% overall)

$^1$H NMR (600 MHz, DMSO-d6) δ=9.22 (s, 1H), 7.41 (d, J=1.7 Hz, 1H), 6.82 (d, J=1.7 Hz, 1H), 4.97 (d, J=4.8 Hz, 1H), 4.68 (m, 2H), 4.35 (p, J=5.4 Hz, 1H), 4.17 (d, J=5.7 Hz, 1H), 3.72 (d, J=13.0 Hz, 1H), 3.38 (d, J=4.9 Hz, 1H), 3.36 (m, 2H), 3.09 (ddd, J=9.8, 8.0, 5.6 Hz, 1H), 2.80 (m, 2H), 2.64 (d, J=11.3 Hz, 1H), 2.24 (s, 3H), 2.22 (s, 3H), 2.12 (dd, J=11.4, 3.8 Hz, 1H), 1.95 (m, 2H), 1.77 (m, 1H), 1.17 (d, J=6.7 Hz, 3H). UPLC-MS Method 4: RT=0.68 min.

Example 82: [(1R)-1-methylpropyl] (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate

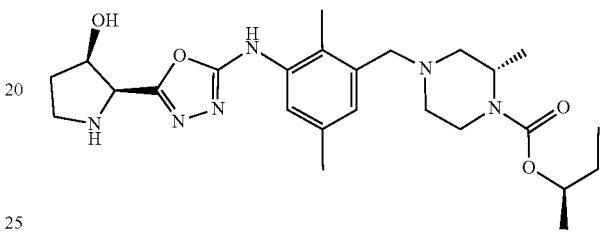

Using a procedure as described in Example 80, using the product from Preparation 66 (30.0 mg, 0.06 mmol) and (2R)-butan-2-ol (90.0 mg, 1.21 mmol), followed by the intermediate deprotection with palladium on carbon and basic HPLC purification, the title compound was isolated as a colourless non-crystalline solid. (4.0 mg, 14% overall) $^1$H NMR (600 MHz, DMSO-d6) δ=9.23 (s, 1H), 7.41 (d, J=1.7 Hz, 1H), 6.82 (d, J=1.7 Hz, 1H), 4.98 (d, J=4.8 Hz, 1H), 4.61 (hept, J=6.2 Hz, 1H), 4.35 (p, J=5.3 Hz, 1H), 4.17 (d, J=5.8 Hz, 1H), 4.14 (t, J=5.6 Hz, 1H), 3.71 (dt, J=13.0, 2.7 Hz, 1H), 3.40 (m, 2H), 3.09 (ddd, J=10.1, 8.1, 5.8 Hz, 1H), 2.96 (m, 1H), 2.82 (ddd, J=10.0, 8.2, 6.3 Hz, 1H), 2.71 (m, 1H), 2.60 (dt, J=11.1, 1.9 Hz, 1H), 2.24 (s, 3H), 2.22 (s, 3H), 2.08 (dd, J=11.3, 3.9 Hz, 1H), 1.96 (m, 1H), 1.89 (td, J=11.7, 3.5 Hz, 1H), 1.77 (dddd, J=12.7, 8.1, 6.3, 4.9 Hz, 1H), 1.51 (m, 2H), 1.14 (m, 6H), 0.85 (t, J=7.4 Hz, 3H). UPLC-MS Method 4: RT=0.71 min.

Example 83: isopropyl (2S)-4-[[2,5-dimethyl-3-[[5-[(3S)-5-oxopyrrolidin-3-yl]-1,3,4-oxadiazol-2-yl]amino]phenyl]methyl]-2-methyl-piperazine-1-carboxylate

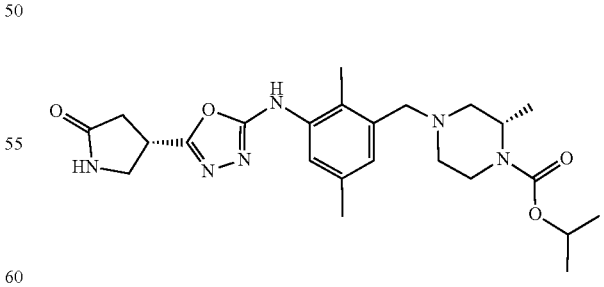

Using a procedure similar to that described for Example 3, but with the product from Preparation 27 (750 mg, 1.91 mmol) and (3S)-5-oxopyrrolidine-3-carboxylic acid (295 mg, 2.29 mmol) the title compound was prepared. The obtained residue was purified by silica gel (100-200 mesh) column chromatography eluting with a gradient of 0-15% methanol in ethyl acetate. Clean fractions were evaporated under reduced pressure to give title compound as a colourless non-crystalline solid (700 mg, 78%). The obtained product (15 mg) was dissolved in ethyl acetate (0.1 mL) which crystallized immediately. The crystalline material was collected and dried under pressure, before being used to seed the remaining product (650 mg) in ethyl acetate (5 mL). The precipitated material was collected and dried under pressure to give the title compound as a crystalline solid. (625 mg, melting point 169-170° C., 93%)

$^1$H NMR (600 MHz, DMSO-d6) δ=9.33 (s, 1H), 7.80 (s, 1H), 7.39 (d, J=1.7 Hz, 1H), 6.84 (d, J=1.7 Hz, 1H), 4.77 (hept, J=6.3 Hz, 1H), 4.11 (m, 1H), 3.85 (m, 1H), 3.70 (dt, J=13.0, 2.6 Hz, 1H), 3.63 (m, 1H), 3.45 (dd, J=9.7, 5.7 Hz, 1H), 3.38 (m, 2H), 2.95 (td, J=12.9, 3.3 Hz, 1H), 2.70 (dp, J=11.2, 1.8 Hz, 1H), 2.59 (m, 2H), 2.46 (dd, J=16.5, 6.7 Hz, 1H), 2.24 (s, 3H), 2.21 (s, 3H), 2.08 (dd, J=11.3, 3.9 Hz, 1H), 1.90 (td, J=11.7, 3.5 Hz, 1H), 1.17 (dd, J=6.2, 1.0 Hz, 6H), 1.12 (d, J=6.7 Hz, 3H).

UPLC-MS Method 5: RT=1.79 min.

ROR-Gamma Binding Assay

This assay is used to evaluate the binding affinity of compounds to the ligand-binding pocket of the human RORgt nuclear receptor based on displacement of a radioligand. The $EC_{50}$ values are calculated using a four parameter fit. Compounds binding with high affinity to RORgt will have low $EC_{50}$ values.

The assay is a Scintillation Proximity Assay (SPA) that involves competition between an unlabeled test compound and tritium-labeled 25-hydroxycholesterol for binding to RORgT ligand binding domain (LBD) protein immobilized on the surface of SPA beads. These beads contain a scintillant that emits light if excited by a radioactive particle, and this light is detected using a scintillation counter. In this assay, tritium-labelled 25-hydroxycholesterol is used as radiotracer.

400 nL of titrated test and reference compounds in DMSO were transferred by the Echo liquid handling system to a 384-well assay plate followed by addition of 5 μL [3H]-25-Hydroxycholesterol (Perkin Elmer) and 35 μL diluted RORgT LBD protein with the following amino acid sequence (HIS-FLG-tag): MAHHHHHHGS DYKDDDDKGS SGASLTEIEH LVQSVCKSYR ETCQLRLEDL LRQRSNIFSR EEVTGYQRKS MWEMWERCAH HLTEAIQYVV EFAKRLSGFM ELCQNDQIVL LKAGAMEVVL VRMCRAYNAD NRTVFFEGKY GGMELFRALG CSELISSIFD FSHSL-SALHF SEDEIALYTA LVLINAHRPG LQEKRKVEQL QYNLELAFHH HLCKTHRQSI LAKLPPKGKL RSLCSQHVER LQIFQHLHPI VVQAAFPPLY KELF-STETES PVGLSK (SEQ ID NO: 1) (Purchased from Proteros Biostructures GmbH). After 30 min of preincubation, 40 μL of HIS-TAG PVT SPA beads (Perkin Elmer) were added. The plates were then incubated for minimum 4 hours at room temperature in darkness before measuring the SPA signal using a MicroBeta plate scintillation counter. Final assay conditions were: 50 mM HEPES pH 7.4, 150 mM NaCl, 5 mM MgCl2, 0.1% BSA, 4 μg/well HIS-TAG PVT SPA Beads, 30 ng/well RORgT LBD (equal to a final concentration of 12 nM), 15 nM [$^3$H]-25-Hydroxycholesterol, 0.5% DMSO and varying concentrations of test compound in a total volume of 80 μL/well. $EC_{50}$ values were calculated using a 4-parameter non-linear regression curve-fitting model.

The exemplified compounds were tested in the ROR-gamma binding assay.

Results are shown in Table 2.

Human PBMC IL-17A Assay

This assay measures the IL-17A inhibitory potential of test compounds in Human peripheral mononuclear cells.

Peripheral blood mononuclear cells (PBMC) were isolated from human buffy coats using density grade centrifugation (Lymphoprep, Medinor), washed twice in PBS and frozen at −150° C. for later use.

Test compounds were diluted in DMSO and 70 nL of titrated test and reference compounds were transferred by the Echo liquid handling system to a 384-well assay plate in to give a final concentration of 0.1% DMSO in the wells.

The PBMC were thawed, washed and suspended in RPMI-1640 supplemented with pen/strep, glutamax and 10% bovine calf serum. The cells were mixed with antiCD3/antiCD28-coated beads (1 cells pr one bead) (Milteney T-cell expansion kit), and immediately thereafter the cells were pipetted to the plate at 130,000c/well. The plate was incubated for 3 days in humidified air/$CO_2$ (95%/5%) On day 3 the level of IL-17A in the culture supernatant is measured using alpha-LISA kit (Perkin Elmer). Cell viability was measured by adding 6 uL pr well Prestoblue© (Life Technologies) and incubating for 2 hours followed by fluorescent measurement (Ex535/Em615). $EC_{50}$ values were calculated using a 4-parameter non-linear regression curve-fitting model. Donors may be pre-screened in order to select PBMC with a high secretion of IL-17A.

The exemplified compounds were tested in the Human PBMC IL-17A assay.

Results are shown in Table 2.

Human Whole Blood IL-17A Assay

The EC50 value reported from this assay is a measure of the potency of the tested compound in inhibiting IL-17A levels in the blood after three days of incubation.

Test compounds were diluted in DMSO and 80 nL of titrated compound is transferred by the Echo liquid handling system to a 384-well assay plate to give a final concentration of 0.1% DMSO in the wells.

Freshly drawn human peripheral blood stabilized with heparin was diluted 1:1 with X-vivo 15 medium (Lonza) added pen/strep and glutamax. *Staphylococcus* enterotoxin B (Sigma) at 300 ng/mL was added to the diluted blood just prior to pipetting into wells, 80 uL per well. The plates were incubated for 3 days at 37° C. in humidified air/$CO_2$ (95%/5%). After 3 days of incubation, the level of IL-17A was measured using an alpha-LISA kit (Perkin Elmer).

$EC_{50}$ values were calculated using a 4-parameter non-linear regression curve-fitting model.

The exemplified compounds were tested in the Human whole blood IL-17A assay.

Results are shown in Table 2.

Human Liver Microsomes (HLM) Assay

Compounds of the invention were tested in the Human liver microsomes (HLM) assay. Incubations of test compounds in DMSO, diluted with phosphate buffer, pH 7.4, at 0.5 μM were carried out with human liver microsomes (0.5 mg/mL). The percentage of organic solvent in the incubations was 1%. The human liver microsomal suspension in phosphate buffer was mixed with NADPH (1 mM) and preheated to 37° C. before test compound was added. Aliquots were taken at 0, 5, 10, 20, 30 and 40 minutes, and reactions were terminated by addition of cold acetonitrile containing analytical internal standard (IS).

The results were expressed as apparent clearance ($Cl_{app}$) (mL/min/kg) and hepatic extraction ratio ($E_h$) (%) calculated from the elimination rate constant (k) (min$^{-1}$) of test compound depletion. Apparent clearance is a measure of compound elimination from the liver.

TABLE 2

| Example | ROR-gamma binding (nM) | Human PBMC IL-17a (nM) | Human Whole blood IL-17A (nM) |
|---|---|---|---|
| 1 | 40.2 | 3,030 | NT |
| 2 | 29 | 137 | 454 |
| 3 | 22.3 | 51.1 | 204 |
| 4 | 29.9 | 34.7 | 428 |
| 5 | 22.6 | 69.7 | 385 |
| 6 | 31.7 | 234 | 504 |
| 7 | 33 | 49.8 | 219 |
| 8 | 69 | 251 | 497 |
| 9 | 23.5 | 99.3 | 254 |
| 10 | 45.4 | 173 | 296 |
| 11 | 28.1 | 92.6 | 132 |
| 12 | 40.4 | 128 | 302 |
| 13 | 14.7 | 48.9 | 112 |
| 14 | 61.1 | 185 | 372 |
| 15 | 63.8 | 101 | 421 |
| 16 | 223 | 237 | 206 |
| 17 | 54.5 | 230 | 131 |
| 18 | 21.2 | 69.8 | 203 |
| 19 | 92.3 | 117 | 216 |
| 20 | 113 | 189 | 259 |
| 21 | 71.7 | 180 | 251 |
| 22 | 169 | 254 | 355 |
| 23 | 125 | 368 | 238 |
| 24 | 38.6 | 35.9 | 112 |
| 25 | 159 | 258 | 191 |
| 26 | 58.2 | 91.3 | 119 |
| 27 | 95.9 | 425 | 457 |
| 28 | 35.5 | 107 | NT |
| 29 | 37.8 | 117 | 422 |
| 30 | 31.2 | 93.6 | 239 |
| 31 | 32.4 | 63.5 | 231 |
| 32 | 26.4 | 101 | 392 |
| 33 | 23.3 | 45.2 | 126 |
| 34 | 24.6 | 24.8 | 83.7 |
| 35 | 33.9 | 106 | 499 |
| 36 | 84.1 | 366 | 451 |
| 37 | 40.8 | 43.7 | 426 |
| 38 | 49.7 | 58.5 | 403 |
| 39 | 29.2 | 38.2 | 377 |
| 40 | 21.2 | 212 | 365 |
| 41 | 91.1 | 215 | 373 |
| 42 | 48 | 34.2 | 359 |
| 43 | 53.9 | 63.5 | 332 |
| 44 | 22.7 | 26 | 330 |
| 45 | 42 | 39.9 | 330 |
| 46 | 37.1 | 103 | 322 |
| 47 | 26.6 | 63.2 | 307 |
| 48 | 37.2 | 191 | 296 |
| 49 | 90.5 | 218 | 275 |
| 50 | 31.6 | 86.5 | 272 |
| 51 | 64.4 | 216 | 266 |
| 52 | 42.1 | 134 | 256 |
| 53 | 68.2 | 93.9 | 247 |
| 54 | 16.3 | 28.1 | 176 |
| 55 | 39 | 62.3 | 36.8 |
| 56 | 36.5 | 51.9 | 92.2 |
| 57 | 23.8 | 46.5 | 96.7 |
| 58 | 54.4 | 373 | 215 |
| 59 | 25.7 | 123 | 211 |
| 60 | 38.3 | 106 | 195 |
| 61 | 42.3 | 106 | 101 |
| 62 | 20.7 | 67.6 | 103 |
| 63 | 34.8 | 62.1 | 187 |
| 64 | 50.6 | 131 | 191 |
| 65 | 47.9 | 58.7 | 107 |
| 66 | 54.8 | 77.6 | 140 |
| 67 | 62.2 | 47.2 | 597 |
| 68 | 103 | 182 | 552 |
| 69 | 70 | 308 | NT |
| 70 | 52.2 | 78.5 | 227 |
| 71 | 62 | 223 | 307 |
| 72 | 81.6 | 262 | 258 |
| 73 | 55.9 | 59.8 | 270 |
| 74 | 71.8 | 408 | 946 |
| 75 | 32.4 | 52.9 | 158 |
| 76 | 25.6 | 60.5 | 112 |
| 77 | 61.2 | 180 | 368 |
| 78 | 72.5 | 95.9 | 157 |
| 79 | 274 | 1,220 | 3,530 |
| 80 | 22.3 | 70 | NT |
| 81 | 110 | 1,520 | NT |
| 82 | 32 | 46 | NT |
| 83 | 67 | 123 | 240 |

The Following are Further Embodiments of the Invention

Embodiment 1. A compound according to general formula (I)

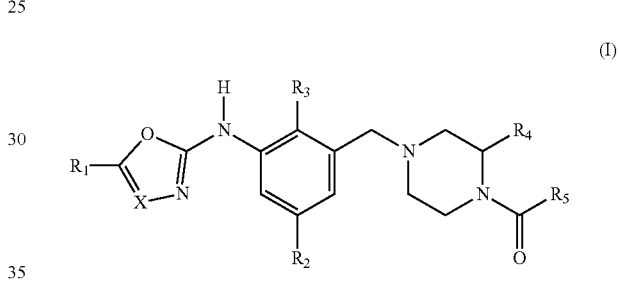

(I)

wherein X represents N or CH;

$R_1$ is selected from the group consisting of —CN, ($C_1$-$C_6$)alkyl, ($C_3$-$C_7$)cycloalkyl, (3-7 membered)heterocycloalkyl, (5-6 membered)heteroaryl, ($C_3$-$C_7$)cycloalkyl($C_1$-$C_4$)alkyl, (3-7 membered)heterocycloalkyl-($C_1$-$C_4$)alkyl and (5-6 membered)heteroaryl-($C_1$-$C_4$)alkyl, wherein said ($C_1$-$C_6$)alkyl, ($C_3$-$C_7$)cycloalkyl, (3-7 membered)heterocycloalkyl, (5-6-membered)heteroaryl, ($C_3$-$C_7$)cycloalkyl($C_1$-$C_4$) alkyl, (3-7 membered)heterocycloalkyl-($C_1$-$C_4$)alkyl and (5-6 membered)heteroaryl-($C_1$-$C_4$)alkyl is optionally substituted with one or more substituents independently selected from $R_6$;

$R_2$ is selected from the group consisting of halogen, cyano, ($C_1$-$C_4$)alkyl and ($C_3$-$C_7$)cycloalkyl, wherein said ($C_1$-$C_4$)alkyl and ($C_3$-$C_7$)cycloalkyl is optionally substituted with one or more substituents independently selected from —OH and halogen;

$R_3$ is selected from the group consisting of halogen, cyano, ($C_1$-$C_4$)alkyl, ($C_1$-$C_4$)haloalkyl and ($C_3$-$C_7$)cycloalkyl;

$R_4$ is selected from the group consisting of ($C_1$-$C_4$)alkyl and ($C_1$-$C_4$)haloalkyl;

$R_5$ is selected from the group consisting of ($C_1$-$C_6$)alkyl, ($C_3$-$C_7$)cycloalkyl, ($C_1$-$C_6$)alkyl-($C_3$-$C_7$)cycloalkyl, ($C_3$-$C_7$) cycloalkyl-($C_1$-$C_6$)alkyl, (3-7 membered)heterocycloalkyl, phenyl, (5-6 membered)heteroaryl and —$OR_a$; wherein said ($C_1$-$C_6$)alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl, (3-7 membered) heterocycloalkyl, phenyl, (5-6 membered)heteroaryl and —$OR_a$ is optionally substituted with one or more substituents independently selected from $R_7$;

$R_6$ represents the group consisting of —OH, —CN, halogen, =O, —S(O)$_2$R$_b$, —NR$_c$R$_d$, —NR$_c$C(O)R$_d$, —C(O)NR$_c$R$_d$, —S(O)$_2$NR$_c$R$_d$, —NR$_c$S(O)$_2$R$_b$, —OR$_b$, —C(O)R$_b$, (C$_1$-C$_4$)alkyl, hydroxy(C$_1$-C$_4$)alkyl, halo(C$_1$-C$_4$)alkyl, (C$_3$-C$_7$)cycloalkyl, (3-7 membered)heterocycloalkyl and (5-6 membered)heteroaryl;

$R_7$ represents the group consisting of —OH, —CN, halogen, (C$_1$-C$_4$)alkyl, (C$_3$-C$_7$)cycloalkyl and (C$_1$-C$_6$)alkyl-(C$_3$-C$_7$)cycloalkyl-;

$R_a$ represents (C$_1$-C$_6$)alkyl, (C$_3$-C$_7$)cycloalkyl, (C$_1$-C$_6$)alkyl-(C$_3$-C$_7$)cycloalkyl- or (C$_3$-C$_7$)-cycloalkyl(C$_1$-C$_6$)alkyl;

$R_b$ represents (C$_1$-C$_6$)alkyl or (C$_3$-C$_7$)cycloalkyl;

$R_c$ and $R_d$ each independently represents H, (C$_1$-C$_6$)alkyl or (C$_3$-C$_7$)cycloalkyl;

or pharmaceutically acceptable salts, hydrates or solvates thereof.

Embodiment 2. The compound according to embodiment 1 wherein X represents N.

Embodiment 3. The compound according to any one of embodiments 1-2 wherein $R_1$ is selected from the group consisting of —CN, (C$_1$-C$_6$)alkyl, (C$_3$-C$_7$)cycloalkyl, (3-7 membered)heterocycloalkyl and 5-membered heteroaryl wherein said (C$_1$-C$_6$)alkyl, (C$_3$-C$_7$)cycloalkyl, (3-7 membered)heterocycloalkyl and 5-membered heteroaryl is optionally substituted with one or more substituents independently selected from $R_6$.

Embodiment 4. The compound according to any one of embodiments 1-3 wherein $R_1$ is selected from the group consisting of (C$_1$-C$_6$)alkyl, (C$_3$-C$_7$)cycloalkyl, (3-7 membered)heterocycloalkyl, wherein said (C$_1$-C$_6$)alkyl, (C$_3$-C$_7$)cycloalkyl, (3-7 membered)heterocycloalkyl is optionally substituted with one or more substituents independently selected from $R_6$; wherein $R_6$ represents the group consisting of —OH, halogen, =O, —S(O)$_2$R$_b$, —NR$_c$R$_d$, and —OR$_b$; $R_b$ represents methyl or ethyl; $R_c$ and $R_d$ independently represents hydrogen, methyl or ethyl.

Embodiment 5. The compound according to any one of embodiments 1-4 wherein $R_1$ is selected from the group consisting of (3-7 membered)heterocycloalkyl, wherein said (3-7 membered)heterocycloalkyl is optionally substituted with one or more substituents independently selected from $R_6$; wherein $R_6$ represents —S(O)$_2$R$_b$ and $R_b$ represents (C$_1$-C$_4$)alkyl.

Embodiment 6. The compound according to any one of embodiments 1-5 wherein $R_1$ is selected from the group consisting of (C$_1$-C$_4$)alkyl, wherein said (C$_1$-C$_4$)alkyl is optionally substituted with one or more —OH.

Embodiment 7. The compound according to any one of embodiments 1-6 wherein $R_1$ is selected from (5-6 membered)heteroaryl, wherein said (5-6-membered)heteroaryl is optionally substituted with one or more substituents independently selected from (C$_1$-C$_4$)alkyl.

Embodiment 8. The compound according to any one of embodiments 1-7 wherein $R_1$ is selected from (3-7 membered)heterocycloalkyl, wherein said (3-7 membered)heterocycloalkyl is optionally substituted with one or more substituents independently selected from (C$_1$-C$_4$)alkyl.

Embodiment 9. The compound according to any one of embodiments 1-8 wherein $R_1$ represents cyclopropyl, cyclobutyl, oxetanyl, azetidinyl and pyrrolidinyl, wherein said cyclopropyl, cyclobutyl, oxetanyl, azetidinyl and pyrrolidinyl is optionally substituted with one or more —OH or =O.

Embodiment 10. The compound according to any one of embodiments 1-9 wherein $R_1$ is selected from the group consisting of (C$_1$-C$_4$)alkyl and pyrrolidinyl, wherein said (C$_1$-C$_4$)alkyl and pyrrolidinyl is optionally substituted with one or more —OH.

Embodiment 11. The compound according to any one of embodiments 1-10 wherein $R_1$ is selected from the group consisting of methyl, ethyl, propyl and pyrrolidinyl, wherein said methyl, ethyl, propyl and pyrrolidinyl is optionally substituted with one or more —OH.

Embodiment 12. The compound according to any one of embodiments 1-11 wherein $R_1$ represents —CN, methyl, ethyl, propyl, cyclopropyl, cyclobutyl, oxetanyl, tetrahydrofuranyl, tetrahydropyranyl, azetidinyl, pyrrolidinyl, oxazolidinyl, morpholinyl, piperidinyl, triazolyl, pyrrazolyl, isoxazolyl, thiadiazolyl or oxadiazolyl, wherein said methyl, ethyl, propyl, cyclopropyl, cyclobutyl, oxetanyl, tetrahydrofuranyl, tetrahydropyranyl, azetidinyl, pyrrolidinyl, oxazolidinyl, morpholinyl, piperidinyl, triazolyl, pyrrazolyl, isoxazolyl, thiadiazolyl or oxadiazolyl is optionally substituted with one or more —OH, —S(O)$_2$CH$_3$, —NH$_2$, —CN, =O, fluoro, methyl, methoxy or hydroxymethyl, Embodiment 13. The compound according to any one of embodiments 1-12 wherein $R_2$ is selected from the group consisting of halogen and (C$_1$-C$_4$)alkyl, wherein said (C$_1$-C$_4$)alkyl is optionally substituted with one or more substituents independently selected from halogen.

Embodiment 14. The compound according to any one of embodiments 1-13 wherein $R_2$ represents (C$_1$-C$_4$)alkyl.

Embodiment 15. The compound according to any one of embodiments 1-14 wherein $R_2$ represents methyl.

Embodiment 16. The compound according to any one of embodiments 1-15 wherein $R_2$ and $R_3$ both represent methyl.

Embodiment 17. The compound according to any one of embodiments 1-16 wherein each of $R_2$, $R_3$ and $R_4$ represent methyl.

Embodiment 18. The compound according to any one of embodiments 1-17 wherein X represents N and each of $R_2$, $R_3$ and $R_4$ represent methyl.

Embodiment 19. The compound according to any one of embodiments 1-18 wherein $R_2$ represents chloro or difluoromethyl.

Embodiment 20. The compound according to any one of embodiments 1-19 wherein $R_2$ represents chloro, methyl or difluoromethyl.

Embodiment 21. The compound according to any one of embodiments 1-20 wherein $R_3$ represents (C$_1$-C$_4$)alkyl.

Embodiment 22. The compound according to any one of embodiments 1-21 wherein $R_3$ represents methyl.

Embodiment 23. The compound according to embodiments 1-22 wherein $R_4$ represents (C$_1$-C$_4$)alkyl.

Embodiment 24. The compound according to any one of embodiments 1-23 wherein $R_4$ represents methyl.

Embodiment 25. The compound according to any one of embodiments 1-24 wherein $R_5$ is selected from the group consisting of (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl, phenyl and —OR$_a$; wherein said (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl, phenyl and —OR$_a$ is optionally substituted with one or more substituents independently selected from $R_7$.

Embodiment 26. The compound according to any one of embodiments 1-25 wherein $R_5$ is selected from the group consisting of (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl and —OR$_a$; wherein said (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl and —OR$_a$ is optionally substituted with one or more substituents independently selected from $R_7$; wherein $R_7$ represent halogen and $R_a$ represents $(C_1-C_6)$alkyl.

Embodiment 27. The compound according to any one of embodiments 1-26 wherein $R_5$ is selected from the group consisting of $(C_1-C_6)$alkyl and —$OR_a$; wherein said $(C_1-C_6)$alkyl and —$OR_a$ is optionally substituted with one or more substituents independently selected from $R_7$; wherein $R_a$ represents $(C_1-C_6)$alkyl and $R_7$ represent halogen.

Embodiment 28. The compound according to any one of embodiments 1-27 wherein $R_5$ is selected from the group consisting of $(C_1-C_6)$alkyl and —$OR_a$; wherein said $(C_1-C_6)$alkyl and —$OR_a$ is optionally substituted with one or more fluoro and wherein $R_a$ represents ethyl, propyl or isopropyl.

Embodiment 29. The compound according to any one of embodiments 1-28 wherein $R_5$ represents phenyl; wherein said phenyl is optionally substituted with one or more substituents independently selected from $R_7$.

Embodiment 30. The compound according to any one of embodiments 1-29 wherein $R_5$ represents phenyl; wherein said phenyl is optionally substituted with one or more halogen.

Embodiment 31. The compound according to any one of embodiments 1-30 wherein $R_5$ represents cyclopentyl; wherein said cyclopentyl is optionally substituted with one or more fluoro.

Embodiment 32. The compound according to any one of embodiments 1-31 wherein $R_5$ represents phenyl, propyl, butyl, ethoxy, iso-propyloxy, tert-butyloxy, cyclopropyl, cyclobutyl, cyclopentyl, methylcyclopropyl or cyclobutylmethyl.

Embodiment 33. The compound according to any one of embodiments 1-32 wherein $R_5$ represents phenyl, propyl, butyl, ethoxy, iso-propyloxy, tert-butyloxy, cyclopropyl, cyclobutyl, cyclopentyl, methylcyclopropyl or cyclobutylmethyl; wherein said phenyl, propyl, butyl, ethoxy, iso-propyloxy, tert-butyloxy, cyclopropyl, cyclobutyl, cyclopentyl, methylcyclopropyl or cyclobutylmethyl is optionally substituted with one or more fluoro.

Embodiment 34. The compound according to any one of embodiments 1-33 wherein $R_6$ represents the group consisting of —OH, —CN, halogen, =O, —$S(O)_2R_b$, —$NR_cR_d$, —$OR_b$, $(C_1-C_4)$alkyl and hydroxy$(C_1-C_4)$alkyl.

Embodiment 35. The compound according to any one of embodiments 1-34 wherein $R_6$ represents —OH, —CN, fluoro, —NH2, =O, —$S(O)_2CH_3$, methyl, methoxy or hydroxymethyl.

Embodiment 36. The compound according to any one of embodiments 1-35 wherein $R_6$ represents —OH.

Embodiment 37. The compound according to any one of embodiments 1-36 wherein $R_7$ represents halogen.

Embodiment 38. The compound according to any one of embodiments 1-37 wherein $R_7$ represents fluoro.

Embodiment 39. The compound according to any one of embodiments 1-38 wherein $R_7$ represents fluoro or —OH.

Embodiment 40. The compound according to any one of embodiments 1-39 wherein $R_a$ represents $(C_1-C_6)$alkyl optionally substituted with one or more halogen.

Embodiment 41. The compound according to any one of embodiments 1-40 wherein $R_b$ represents $(C_1-C_6)$alkyl.

Embodiment 42. The compound according to any one of embodiments 1-41 wherein $R_b$ represents methyl.

Embodiment 43. The compound according to any one of embodiments 1-42 wherein $R_c$ and $R_d$ each independently represents H or $(C_1-C_6)$alkyl.

Embodiment 44. The compound according to any one of embodiments 1-43 wherein $R_c$ and $R_d$ each independently represents H or methyl.

Embodiment 45. The compound according to any one of embodiments 1-44 wherein $R_1$ is selected from the group consisting of $(C_1-C_4)$alkyl and pyrrolidinyl, wherein said $(C_1-C_4)$alkyl and pyrrolidinyl is optionally substituted with one or more —OH; and wherein $R_2$ represents halogen or $(C_1-C_4)$alkyl which is optionally substituted with one or more halogen; $R_3$ represents $(C_1-C_4)$alkyl; $R_4$ represents $(C_1-C_4)$alkyl; $R_5$ is selected from the group consisting of $(C_1-C_6)$alkyl, $(C_3-C_7)$cycloalkyl, $(C_1-C_6)$alkyl-$(C_3-C_7)$cycloalkyl, $(C_3-C_7)$cycloalkyl-$(C_1-C_6)$alkyl and —$OR_a$; wherein said $(C_1-C_6)$alkyl, $(C_3-C_7)$cycloalkyl, $(C_1-C_6)$alkyl-$(C_3-C_7)$cycloalkyl, $(C_3-C_7)$cycloalkyl-$(C_1-C_6)$alkyl and —$OR_a$ is optionally substituted with one or more substituents independently selected from $R_7$; wherein $R_7$ represent halogen and $R_a$ represents $(C_1-C_6)$alkyl and X represents N; or pharmaceutically acceptable salts, hydrates or solvates thereof.

Embodiment 46. The compound according to any one of embodiments 1-45 wherein $R_1$ is selected from the group consisting of $(C_1-C_4)$alkyl and pyrrolidinyl, wherein said $(C_1-C_4)$alkyl and pyrrolidinyl is optionally substituted with one or more —OH; wherein X represents N; wherein each of $R_2$, $R_3$ and $R_4$ represent methyl; and wherein $R_5$ is selected from the group consisting of $(C_1-C_6)$alkyl and —$OR_a$, said $(C_1-C_6)$alkyl and —$OR_a$ optionally being substituted with one or more substituents independently selected from $R_7$ and wherein $R_7$ represents fluoro and $R_a$ represents ethyl, propyl or isopropyl or pharmaceutically acceptable salts, hydrates or solvates thereof.

Embodiment 47. The compound according to any one of embodiments 46 wherein $R_1$ is selected from the group consisting of $(C_1-C_6)$alkyl, $(C_3-C_7)$cycloalkyl, (3-7 membered)heterocycloalkyl, wherein said $(C_1-C_6)$alkyl, $(C_3-C_7)$cycloalkyl, (3-7 membered)heterocycloalkyl is optionally substituted with one or more substituents independently selected from $R_6$; wherein $R_6$ represents the group consisting of —OH, halogen, =O, —$S(O)_2R_b$, —$NR_cR_d$, and —$OR_b$; $R_b$ represents methyl or ethyl; $R_c$ and $R_d$ independently represents hydrogen, methyl or ethyl; and wherein $R_2$ represents halogen or $(C_1-C_4)$alkyl which is optionally substituted with one or more halogen; $R_3$ represents $(C_1-C_4)$alkyl; $R_4$ represents $(C_1-C_4)$alkyl; $R_5$ is selected from the group consisting of $(C_1-C_6)$alkyl, $(C_3-C_7)$cycloalkyl, $(C_1-C_6)$alkyl-$(C_3-C_7)$cycloalkyl, $(C_3-C_7)$cycloalkyl-$(C_1-C_6)$alkyl and —$OR_a$; wherein said $(C_1-C_6)$alkyl, $(C_3-C_7)$cycloalkyl, $(C_1-C_6)$alkyl-$(C_3-C_7)$cycloalkyl, $(C_3-C_7)$cycloalkyl-$(C_1-C_6)$alkyl and —$OR_a$ is optionally substituted with one or more substituents independently selected from $R_7$; wherein $R_7$ represent halogen and $R_a$ represents $(C_1-C_6)$alkyl and X represents N; or pharmaceutically acceptable salts, hydrates or solvates thereof.

Embodiment 48. The compound according to any one of embodiments 1-47 wherein $R_1$ is selected from the group consisting of $(C_1-C_6)$alkyl, $(C_3-C_7)$cycloalkyl, (3-7 membered)heterocycloalkyl, wherein said $(C_1-C_6)$alkyl, $(C_3-C_7)$cycloalkyl, (3-7 membered)heterocycloalkyl is optionally substituted with one or more substituents independently selected from $R_6$; wherein $R_6$ represents the group consisting of —OH, halogen, =O, —$S(O)_2R_b$, —$NR_cR_d$, and —$OR_b$; $R_b$ represents methyl or ethyl; $R_c$ and $R_d$ independently represents hydrogen, methyl or ethyl; and wherein $R_2$ represents $(C_1-C_4)$alkyl which is optionally substituted with one or more halogen; $R_3$ represents $(C_1-C_4)$alkyl; $R_4$ represents $(C_1-C_4)$alkyl; $R_5$ is selected from the group consisting of ($C_1$-$C_6$)alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl and —$OR_a$; wherein said ($C_1$-$C_6$)alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl and —$OR_a$ is optionally substituted with one or more substituents independently selected from $R_7$; wherein $R_7$ represent halogen and $R_a$ represents ($C_1$-$C_6$)alkyl and X represents N; or pharmaceutically acceptable salts, hydrates or solvates thereof.

Embodiment 49. The compound according to any one of embodiments 1-48 wherein $R_1$ is selected from the group consisting of ($C_1$-$C_6$)alkyl, ($C_3$-$C_7$)cycloalkyl, (3-7 membered)heterocycloalkyl, wherein said ($C_1$-$C_6$)alkyl, ($C_3$-$C_7$)cycloalkyl, (3-7 membered)heterocycloalkyl is optionally substituted with one or more substituents independently selected from $R_6$; wherein $R_6$ represents the group consisting of —OH, halogen, =O, —$NH_2$ and —$OR_b$; $R_b$ represents methyl or ethyl; and wherein $R_2$ represents ($C_1$-$C_4$)alkyl which is optionally substituted with one or more halogen; $R_3$ represents ($C_1$-$C_4$)alkyl; $R_4$ represents ($C_1$-$C_4$)alkyl; $R_5$ is selected from the group consisting of ($C_1$-$C_6$)alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl and —$OR_a$; wherein said ($C_1$-$C_6$)alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl and —$OR_a$ is optionally substituted with one or more substituents independently selected from $R_7$; wherein $R_7$ represent halogen and $R_a$ represents ($C_1$-$C_6$)alkyl and X represents N; or pharmaceutically acceptable salts, hydrates or solvates thereof.

Embodiment 50. The compound according to any one of embodiments 1-49 wherein $R_1$ is selected from the group consisting of —CN, ($C_1$-$C_6$)alkyl, ($C_3$-$C_7$)cycloalkyl, (3-7 membered) heterocycloalkyl and 5-membered heteroaryl wherein said ($C_1$-$C_6$)alkyl, ($C_3$-$C_7$)cycloalkyl, (3-7 membered) heterocycloalkyl and 5-membered heteroaryl is optionally substituted with one or more substituents independently selected from $R_6$; $R_6$ represents the group consisting of —OH, halogen, =O, —$S(O)_2R_b$, —$NR_cR_d$, and —$OR_b$; $R_b$ represents ($C_1$-$C_4$)alkyl; $R_c$ and $R_d$ independently represents H or ($C_1$-$C_6$)alkyl; and wherein $R_2$ represents halogen or ($C_1$-$C_4$)alkyl which is optionally substituted with one or more halogen; $R_3$ represents ($C_1$-$C_4$)alkyl; $R_4$ represents ($C_1$-$C_4$)alkyl; X represents N; $R_5$ represents phenyl; wherein said phenyl is optionally substituted with one or more substituents independently selected from $R_7$; wherein $R_7$ represents CN, halogen or ($C_1$-$C_4$)alkyl, or pharmaceutically acceptable salts, hydrates or solvates thereof.

Embodiment 51. The compound according to any one of embodiments 1-50 wherein $R_1$ is selected from (5-membered)heteroaryl, wherein said (5-membered)heteroaryl is optionally substituted with one or more substituents independently selected from ($C_1$-$C_4$)alkyl; and wherein $R_2$ represents halogen or ($C_1$-$C_4$)alkyl which is optionally substituted with one or more halogen; $R_3$ represents ($C_1$-$C_4$)alkyl; $R_4$ represents ($C_1$-$C_4$)alkyl; $R_5$ is selected from the group consisting of ($C_1$-$C_6$)alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl and —$OR_a$; wherein said ($C_1$-$C_6$)alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl and —$OR_a$ is optionally substituted with one or more substituents independently selected from $R_7$; wherein $R_7$ represent halogen; $R_a$ represents ($C_1$-$C_6$)alkyl and wherein X represents N. or pharmaceutically acceptable salts, hydrates or solvates thereof.

Embodiment 52. The compound according to any one of embodiments 1-51 wherein $R_1$ is selected from the group consisting of (3-7 membered)heterocycloalkyl, wherein said (3-7 membered)heterocycloalkyl is optionally substituted with one or more substituents independently selected from $R_6$; wherein $R_6$ represents —$S(O)_2R_b$ and $R_b$ represents ($C_1$-$C_4$)alkyl; and wherein $R_2$ represents halogen or ($C_1$-$C_4$) alkyl which is optionally substituted with one or more halogen; $R_3$ represents ($C_1$-$C_4$)alkyl; $R_4$ represents ($C_1$-$C_4$) alkyl; $R_5$ is selected from the group consisting of ($C_1$-$C_6$) alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl and —$OR_a$; wherein said ($C_1$-$C_6$)alkyl, ($C_3$-$C_7$)cycloalkyl, ($C_1$-$C_6$)alkyl-($C_3$-$C_7$)cycloalkyl, ($C_3$-$C_7$)cycloalkyl-($C_1$-$C_6$)alkyl and —$OR_a$ is optionally substituted with one or more substituents independently selected from $R_7$; wherein $R_7$ represent halogen; $R_a$ represents ($C_1$-$C_6$)alkyl and wherein X represents N. or pharmaceutically acceptable salts, hydrates or solvates thereof.

Embodiment 53. A compound according to any one of embodiments 1-52 selected from the list consisting of 5-[3-[[(3S)-4-benzoyl-3-methyl-piperazin-1-yl]methyl]-5-chloro-2-methyl-anilino]-1,3,4-oxadiazole-2-carbonitrile,

[(2S)-4-[[5-chloro-3-[[5-(methoxymethyl)-1,3,4-oxadiazol-2-yl]amino]-2-methyl-phenyl]methyl]-2-methyl-piperazin-1-yl]-phenyl-methanone,

[(2S)-4-[[5-chloro-2-methyl-3-[(5-tetrahydrofuran-3-yl-1,3,4-oxadiazol-2-yl)amino]phenyl]methyl]-2-methyl-piperazin-1-yl]-phenyl-methanone,

[(2S)-4-[[5-chloro-2-methyl-3-[(5-tetrahydrofuran-2-yl-1,3,4-oxadiazol-2-yl)amino]phenyl]methyl]-2-methyl-piperazin-1-yl]-phenyl-methanone,

[(2S)-4-[[5-chloro-3-[(5-cyclopropyl-1,3,4-oxadiazol-2-yl)amino]-2-methyl-phenyl]methyl]-2-methyl-piperazin-1-yl]-phenyl-methanone,

[(2S)-4-[[5-chloro-3-[[5-(1-hydroxycyclopropyl)-1,3,4-oxadiazol-2-yl]amino]-2-methyl-phenyl]methyl]-2-methyl-piperazin-1-yl]-phenyl-methanone, 3-[5-[3-[[(3S)-4-benzoyl-3-methyl-piperazin-1-yl]methyl]-5-chloro-2-methyl-anilino]-1,3,4-oxadiazol-2-yl]propanenitrile, 3-[5-[3-[[(3S)-4-benzoyl-3-methyl-piperazin-1-yl]methyl]-5-chloro-2-methyl-anilino]-1,3,4-oxadiazol-2-yl]propanenitrile, 1-[(2S)-4-[[5-chloro-3-[[5-(methoxymethyl)-1,3,4-oxadiazol-2-yl]amino]-2-methyl-phenyl]methyl]-2-methyl-piperazin-1-yl]-2,2-difluoro-butan-1-one,

[(2S)-4-[[5-chloro-3-[[5-(methoxymethyl)-1,3,4-oxadiazol-2-yl]amino]-2-methyl-phenyl]methyl]-2-methyl-piperazin-1-yl]-(2-fluorophenyl)methanone,

[(2S)-4-[[5-chloro-3-[[5-(methoxymethyl)-1,3,4-oxadiazol-2-yl]amino]-2-methyl-phenyl]methyl]-2-methyl-piperazin-1-yl]-(3,3-difluorocyclopentyl)methanone, (2S)-1-[(2S)-4-[[5-chloro-3-[[5-(methoxymethyl)-1,3,4-oxadiazol-2-yl]amino]-2-methyl-phenyl]methyl]-2-methyl-piperazin-1-yl]-2-methyl-butan-1-one,

[(2S)-4-[[5-chloro-3-[[5-(methoxymethyl)-1,3,4-oxadiazol-2-yl]amino]-2-methyl-phenyl]methyl]-2-methyl-piperazin-1-yl]-cyclobutyl-methanone,

[(2S)-4-[[5-chloro-3-[[5-(methoxymethyl)-1,3,4-oxadiazol-2-yl]amino]-2-methyl-phenyl]methyl]-2-methyl-piperazin-1-yl]-cyclopentyl-methanone, cyclobutyl-[(2S)-4-[[2,5-dimethyl-3-[(5-methyl-1,3,4-oxadiazol-2-yl)amino]phenyl]methyl]-2-methyl-piperazin-1-yl]methanone, 2-[5-[3-[[(3S)-4-(cyclobutanecarbonyl)-3-methyl-piperazin-1-yl]methyl]-2,5-dimethyl-anilino]-1,3,4-oxadiazol-2-yl]acetonitrile, 2-[5-[3-[[(3S)-4-(cyclopropanecarbonyl)-3-methyl-piperazin-1-yl]methyl]-2,5-dimethyl-anilino]-1,3,4-oxadiazol-2-yl]acetonitrile, 2-[5-[3-[[(3S)-4-(3,3-difluorocyclopentanecarbonyl)-3-methyl-piperazin-1-yl]methyl]-2,5-dimethyl-anilino]-1,3,4-oxadiazol-2-yl]acetonitrile, 2-[5-[5-chloro-3-[[4-(cyclopentanecarbonyl)-3-methyl-piperazin-1-yl]methyl]-2-methyl-anilino]-1,3,4-oxadiazol-2-yl]acetonitrile, cyclobutyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone, cyclobutyl-[(2S)-4-[[3-[[5-[(1S)-1-hydroxyethyl]-1,3,4-oxadiazol-2-yl]amino]-2,5-dimethyl-phenyl]methyl]-2-methyl-piperazin-1-yl]methanone, 2,2-difluoro-1-[(2S)-4-[[3-[[[5-[(1R)-1-hydroxyethyl]-1,3,4-oxadiazol-2-yl]amino]-2,5-dimethyl-phenyl]methyl]-2-methyl]-piperazin-1-yl]butan-1-one, cyclopropyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone,

[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]-(2-methylcyclopropyl)methanone, cyclopentyl-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]methanone, (3,3-difluorocyclopentyl)-[(2S)-4-[[13-[[5-[(1R)-1-hydroxyethyl]-1,3,4-oxadiazol-2-yl]amino]-2,5-dimethyl-phenyl]methyl]-2-methyl-piperazin-1-yl]methanone, 2-cyclobutyl-1-[(2S)-4-[[3-[[5-[(1R)-1-hydroxyethyl]-1,3,4-oxadiazol-2-yl]amino]-2,5-dimethyl-phenyl]methyl]-2-methyl-piperazin-1-yl]ethanone, cyclobutyl-[(2S)-4-[[5-(difluoromethyl)-3-[[5-[(1S)-1-hydroxyethyl]-1,3,4-oxadiazol-2-yl]amino]-2-methyl-phenyl]methyl]-2-methyl-piperazin-1-yl]methanone, tert-butyl (2S)-4-[[3-[[5-[(1S)-1-hydroxyethyl]-1,3,4-oxadiazol-2-yl]amino]-2,5-dimethyl-phenyl]methyl]-2-methyl-piperazine-1-carboxylate, tert-butyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate, tert-butyl (2S)-4-[[2,5-dimethyl-3-[[5-(3-methyltriazol-4-yl)-1,3,4-oxadiazol-2-yl]amino]phenyl]methyl]-2-methyl-piperazine-1-carboxylate, tert-butyl (2S)-4-[[2,5-dimethyl-3-[[5-(2-methylpyrazol-3-yl)-1,3,4-oxadiazol-2-yl]amino]phenyl]methyl]-2-methyl-piperazine-1-carboxylate, tert-butyl (2S)-4-[[3-[(5-isoxazol-5-yl-1,3,4-oxadiazol-2-yl)amino]-2,5-dimethyl-phenyl]methyl]-2-methyl-piperazine-1-carboxylate, tert-butyl (2S)-4-[[2,5-dimethyl-3-[[5-(1,2,5-thiadiazol-3-yl)-1,3,4-oxadiazol-2-yl]amino]phenyl]methyl]-2-methyl-piperazine-1-carboxylate, tert-butyl (2S)-4-[[2,5-dimethyl-3-[[5-(4-methyl-1,2,5-oxadiazol-3-yl)-1,3,4-oxadiazol-2-yl]amino]phenyl]methyl]-2-methyl-piperazine-1-carboxylate, isopropyl (2S)-4-[[2,5-dimethyl-3-[(5-methyl-1,3,4-oxadiazol-2-yl)amino]phenyl]methyl]-2-methyl-piperazine-1-carboxylate, isopropyl (2S)-4-[[3-[[5-[(1S)-1-amino-2-hydroxy-ethyl]-1,3,4-oxadiazol-2-yl]amino]-2,5-dimethyl-phenyl]methyl]-2-methyl-piperazine-1-carboxylate, isopropyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate, isopropyl (2S)-4-[[3-[[5-[(1S)-1-aminopropyl]-1,3,4-oxadiazol-2-yl]amino]-5-chloro-2-methyl-phenyl]methyl]-2-methyl-piperazine-1-carboxylate, isopropyl (2S)-4-[[5-chloro-3-[[5-[(1R)-1-hydroxyethyl]-1,3,4-oxadiazol-2-yl]amino]-2-methyl-phenyl]methyl]-2-methyl-piperazine-1-carboxylate, isopropyl (2S)-4-[[5-chloro-2-methyl-3-[[5-(oxetan-3-yl)-1,3,4-oxadiazol-2-yl]amino]phenyl]methyl]-2-methyl-piperazine-1-carboxylate, isopropyl (2S)-4-[[3-[[5-[(1S,2R)-1-amino-2-hydroxy-propyl]-1,3,4-oxadiazol-2-yl]amino]-2,5-dimethyl-phenyl]methyl]-2-methyl-piperazine-1-carboxylate, isopropyl (2S)-4-[[3-[[5-(cyanomethyl)-1,3,4-oxadiazol-2-yl]amino]-2,5-dimethyl-phenyl]methyl]-2-methyl-piperazine-1-carboxylate, isopropyl (2S)-4-[[5-(difluoromethyl)-3-[[5-[(1S)-1-hydroxyethyl]-1,3,4-oxadiazol-2-yl]amino]-2-methyl-phenyl]methyl]-2-methyl-piperazine-1-carboxylate, isopropyl (2S)-4-[[5-chloro-2-methyl-3-[(5-tetrahydropyran-3-yl-1,3,4-oxadiazol-2-yl)amino]phenyl]methyl]-2-methyl-piperazine-1-carboxylate, isopropyl (2S)-4-[[5-chloro-3-[[5-(1-hydroxycyclopropyl)-1,3,4-oxadiazol-2-yl]amino]-2-methyl-phenyl]methyl]-2-methyl-piperazine-1-carboxylate, isopropyl (2S)-4-[[5-chloro-3-[[5-[1-(hydroxymethyl)cyclopropyl]-1,3,4-oxadiazol-2-yl]amino]-2-methyl-phenyl]methyl]-2-methyl-piperazine-1-carboxylate, isopropyl (2S)-4-[[5-chloro-2-methyl-3-[[15-(2,2,2-trifluoro-1-hydroxy-ethyl)-1,3,4-oxadiazol-2-yl]amino]phenyl]methyl]-2-methyl-piperazine-1-carboxylate, isopropyl (2S)-4-[[5-chloro-2-methyl-3-[[5-(2-oxopyrrolidin-3-yl)-1,3,4-oxadiazol-2-yl]amino]phenyl]methyl]-2-methyl-piperazine-1-carboxylate, isopropyl (2S)-4-[[3-[[5-[(1S)-1-aminoethyl]-1,3,4-oxadiazol-2-yl]amino]-2,5-dimethyl-phenyl]methyl]-2-methyl-piperazine-1-carboxylate, isopropyl (2S)-4-[[5-(difluoromethyl)-3-[[5-[(1R)-1-hydroxyethyl]-1,3,4-oxadiazol-2-yl]amino]-2-methyl-phenyl]methyl]-2-methyl-piperazine-1-carboxylate, isopropyl (2S)-4-[[2,5-dimethyl-3-[[5-(5-oxopyrrolidin-3-yl)-1,3,4-oxadiazol-2-yl]amino]phenyl]methyl]-2-methyl-piperazine-1-carboxylate, isopropyl (2S)-4-[[2,5-dimethyl-3-[[5-[(5S)-2-oxooxazolidin-5-yl]-1,3,4-oxadiazol-2-yl]amino]phenyl]methyl]-2-methyl-piperazine-1-carboxylate, isopropyl (2S)-4-[[5-chloro-2-methyl-3-[[5-[(2S)-4-oxoazetidin-2-yl]-1,3,4-oxadiazol-2-yl]amino]phenyl]methyl]-2-methyl-piperazine-1-carboxylate, isopropyl (2S)-4-[[2,5-dimethyl-3-[[5-(4-methyl-1,2,5-oxadiazol-3-yl)-1,3,4-oxadiazol-2-yl]amino]phenyl]methyl]-2-methyl-piperazine-1-carboxylate, isopropyl (2S)-4-[[2,5-dimethyl-3-[[5-[(3S)-morpholin-3-yl]-1,3,4-oxadiazol-2-yl]amino]phenyl]methyl]-2-methyl-piperazine-1-carboxylate dihydrochloride, isopropyl (2S)-4-[[3-[[5-[(1R)-1-hydroxyethyl]-1,3,4-oxadiazol-2-yl]amino]-2,5-dimethyl-phenyl]methyl]-2-methyl-piperazine-1-carboxylate, isopropyl (2S)-4-[[2,5-dimethyl-3-[[5-[(2R)-3,3,3-trifluoro-2-hydroxy-propyl]-1,3,4-oxadiazol-2-yl]amino]phenyl]methyl]-2-methyl-piperazine-1-carboxylate, isopropyl (2S)-4-[[2,5-dimethyl-3-[[5-(2-oxo-4-piperidyl)-1,3,4-oxadiazol-2-yl]amino]phenyl]methyl]-2-methyl-piperazine-1-carboxylate, isopropyl (2S)-4-[[2,5-dimethyl-3-[[5-(2-methylpyrazol-3-yl)-1,3,4-oxadiazol-2-yl]amino]phenyl]methyl]-2-methyl-piperazine-1-carboxylate, isopropyl (2S)-4-[[3-[[5-[(2S)-2-hydroxypropyl]-1,3,4-oxadiazol-2-yl]amino]-2,5-dimethyl-phenyl]methyl]-2-methyl-piperazine-1-carboxylate,
isopropyl (2S)-4-[[3-[[5-[(2R)-2-hydroxypropyl]-1,3,4-oxadiazol-2-yl]amino]-2,5-dimethyl-phenyl]methyl]-2-methyl-piperazine-1-carboxylate,
isopropyl (2S)-4-[[3-[[5-[(1S)-1-hydroxypropyl]-1,3,4-oxadiazol-2-yl]amino]-2,5-dimethyl-phenyl]methyl]-2-methyl-piperazine-1-carboxylate,
isopropyl (2S)-4-[[5-chloro-3-[[5-[(1S)-1-hydroxyethyl]-1,3,4-oxadiazol-2-yl]amino]-2-methyl-phenyl]methyl]-2-methyl-piperazine-1-carboxylate,
isopropyl (2S)-4-[[5-chloro-3-[[5-(3-hydroxycyclobutyl)-1,3,4-oxadiazol-2-yl]amino]-2-methyl-phenyl]methyl]-2-methyl-piperazine-1-carboxylate,
isopropyl (2S)-4-[[2,5-dimethyl-3-[[5-[(2S)-1-methylsulfonylpyrrolidin-2-yl]-1,3,4-oxadiazol-2-yl]amino]phenyl]methyl]-2-methyl-piperazine-1-carboxylate,
isopropyl (2S)-4-[[3-[[5-[(1S)-1-hydroxyethyl]-1,3,4-oxadiazol-2-yl]amino]-2,5-dimethyl-phenyl]methyl]-2-methyl-piperazine-1-carboxylate,
isopropyl (2S)-4-[[5-chloro-2-methyl-3-[[5-(5-oxopyrrolidin-3-yl)-1,3,4-oxadiazol-2-yl]amino]phenyl]methyl]-2-methyl-piperazine-1-carboxylate,
isopropyl (2S)-4-[[3-[[5-[(1R)-1-aminoethyl]-1,3,4-oxadiazol-2-yl]amino]-2,5-dimethyl-phenyl]methyl]-2-methyl-piperazine-1-carboxylate,
2,2,2-trifluoroethyl (2S)-4-[[5-chloro-3-[[5-(cyanomethyl)-1,3,4-oxadiazol-2-yl]amino]-2-methyl-phenyl]methyl]-2-methyl-piperazine-1-carboxylate,
2,2,2-trifluoroethyl (2S)-4-[[3-[[5-(3-hydroxycyclobutyl)-1,3,4-oxadiazol-2-yl]amino]-2,5-dimethyl-phenyl]methyl]-2-methyl-piperazine-1-carboxylate,
ethyl (2S)-4-[[3-[[5-[(1R)-1-hydroxyethyl]-1,3,4-oxadiazol-2-yl]amino]-2,5-dimethyl-phenyl]methyl]-2-methyl-piperazine-1-carboxylate,
isopropyl (2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate,
isopropyl (2S)-4-[[5-chloro-2-methyl-3-[(5-morpholin-3-yl-1,3,4-oxadiazol-2-yl)amino]phenyl]methyl]-2-methyl-piperazine-1-carboxylate,
tert-butyl (2S)-4-[[5-chloro-3-[[5-(hydroxymethyl)oxazol-2-yl]amino]-2-methyl-phenyl]methyl]-2-methyl-piperazine-1-carboxylate,
[(1R)-2,2,2-trifluoro-1-methyl-ethyl] (2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate,
isopropyl (2S)-4-[[2,5-dimethyl-3-[[5-[(3R)-tetra hydrofuran-3-yl]-1,3,4-oxadiazol-2-yl]amino]phenyl]methyl]-2-methyl-piperazine-1-carboxylate,
isopropyl (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate,
cyclopentyl-[(2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazin-1-yl]methanone,
(3,3-difluorocyclopentyl)-[(2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazin-1-yl]methanone,
[(1R)-2,2,2-trifluoro-1-methyl-ethyl] (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate,
2,2,2-trifluoroethyl (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate,
[(1R)-1-methylpropyl] (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate and
isopropyl (2S)-4-[[2,5-dimethyl-3-[[5-[(3S)-5-oxopyrrolidin-3-yl]-1,3,4-oxadiazol-2-yl]amino]phenyl]methyl]-2-methyl-piperazine-1-carboxylate,
or pharmaceutically acceptable salts, hydrates or solvates thereof.

Embodiment 54. The compound according to any one of the embodiments 1-53 selected from [(1R)-2,2,2-trifluoro-1-methyl-ethyl] (2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate, or pharmaceutically acceptable salts, hydrates or solvates thereof.

Embodiment 55. The compound according to any one of the embodiments 1-54 wherein said compound is [(1R)-2,2,2-trifluoro-1-methyl-ethyl] (2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate.

Embodiment 56. The compound according to any one of the embodiments 1-53 selected from isopropyl (2S)-4-[[2,5-dimethyl-3-[[5-[(3R)-tetrahydrofuran-3-yl]-1,3,4-oxadiazol-2-yl]amino]phenyl]methyl]-2-methyl-piperazine-1-carboxylate, or pharmaceutically acceptable salts, hydrates or solvates thereof.

Embodiment 57. The compound according to any one of the embodiments 1-53 or 56 wherein said compound is isopropyl (2S)-4-[[2,5-dimethyl-3-[[5-[(3R)-tetrahydrofuran-3-yl]-1,3,4-oxadiazol-2-yl]amino]phenyl]methyl]-2-methyl-piperazine-1-carboxylate.

Embodiment 58. The compound according to any one of the embodiments 1-53 selected from isopropyl (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate, or pharmaceutically acceptable salts, hydrates or solvates thereof.

Embodiment 59. The compound according to any one of the embodiments 1-53 or 58 wherein said compound is isopropyl (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate.

Embodiment 60. The compound according to any one of embodiments 1-53 wherein said compound is [(1R)-2,2,2-trifluoro-1-methyl-ethyl] (2S)-4-[[3-[[5-[(1S)-1,2-dihydroxyethyl]-1,3,4-oxadiazol-2-yl]amino]-2,5-dimethyl-phenyl]methyl]-2-methyl-piperazine-1-carboxylate, or pharmaceutically acceptable salts thereof.

Embodiment 61. The compound according to any one of embodiments 1-53 wherein said compound is isopropyl (2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazine-1-carboxylate, or pharmaceutically acceptable salts thereof.

Embodiment 62. The compound according to any one of embodiments 1-53 wherein said compound is isopropyl (2S)-4-[[2,5-dimethyl-3-[[5-[(2S)-1-methylsulfonylpyrrolidin-2-yl]-1,3,4-oxadiazol-2-yl]amino]phenyl]methyl]-2-methyl-piperazine-1-carboxylate, or pharmaceutically acceptable salts thereof.

Embodiment 63. The compound according to any one of embodiments 1-53 wherein said compound is cyclopentyl-[(2S)-4-[[3-[[5-[(2S,3R)-3-hydroxypyrrolidin-2-yl]-1,3,4- oxadiazol-2-yl]amino]-2,5-dimethyl-phenyl]methyl]-2-methyl-piperazin-1-yl]methanone, or pharmaceutically acceptable salts thereof.

Embodiment 64. The compound according to any one of the embodiments 1-63 selected from isopropyl (2S)-4-[[2,5-dimethyl-3-[[5-[(2S)-1-methylsulfonylpyrrolidin-2-yl]-1,3,4-oxadiazol-2-yl]amino]phenyl]methyl]-2-methyl-piperazine-1-carboxylate or pharmaceutically acceptable salts, hydrates or solvates thereof.

Embodiment 65. The compound according to any one of the embodiments 1-63 wherein said compound is isopropyl (2S)-4-[[2,5-dimethyl-3-[[5-[(2S)-1-methylsulfonylpyrrolidin-2-yl]-1,3,4-oxadiazol-2-yl]amino]phenyl]methyl]-2-methyl-piperazine-1-carboxylate.

Embodiment 66. The compound according to any one of the embodiments 1-63 selected from cyclopentyl-[(2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazin-1-yl]methanone or pharmaceutically acceptable salts, hydrates or solvates thereof.

Embodiment 67. The compound according to any one of the embodiments 1-63 wherein said compound is cyclopentyl-[(2S)-4-[[3-[[5-[(2S,3R)-3-hydroxypyrrolidin-2-yl]-1,3,4-oxadiazol-2-yl]amino]-2,5-dimethyl-phenyl]methyl]-2-methyl-piperazin-1-yl]methanone.

Embodiment 68. A compound according to any one of embodiments 1-67 for use as a medicament.

Embodiment 69. A compound according to any one of embodiments 1-67 for use in treatment of autoimmune or inflammatory diseases.

Embodiment 70. The compound for use according to embodiment 69 wherein the autoimmune or inflammatory diseases is selected from psoriasis, psoriatic arthritis, multiple sclerosis, rheumatoid arthritis, Crohns disease, ulcerative colitis, alopecia areata, contact dermatitis, including irritative contact dermatitis and allergic contact dermatitis, spondyloarthritis.

Embodiment 71. A compound according to any one of embodiments 1-67 for use in treatment cancers, including prostate cancer and non-small cell lung cancer.

Embodiment 72. The compound for use according to embodiments 69-70 wherein the autoimmune or inflammatory diseases is psoriasis.

Embodiment 73. A pharmaceutical composition comprising a compound according to any one of embodiments 1-67 together with a pharmaceutically acceptable vehicle or excipient or pharmaceutically acceptable carrier(s).

Embodiment 74. The pharmaceutical composition according to embodiment 1-73 together with one or more other therapeutically active compound(s).

Embodiment 75. A method of preventing, treating or ameliorating psoriasis, the method comprising administering to a person suffering from psoriasis an effective amount of one or more compounds according to according to any one of embodiments 1-67, optionally together with a pharmaceutically acceptable carrier or one or more excipients, optionally in combination with other therapeutically active compounds.

Embodiment 76. A compound according to any one of embodiments 1-67 for use in treatment of a disease, disorder or condition, which disease, disorder or condition is responsive of modulation of RORgamma.

Embodiment 77. A compound according to general formula (II)

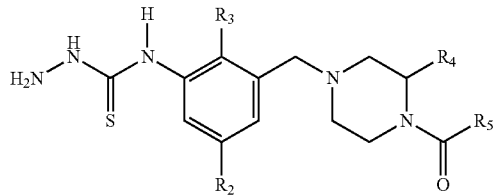

wherein

R$_2$ is selected from the group consisting of halogen, cyano, (C$_1$-C$_4$)alkyl and (C$_3$-C$_7$)cycloalkyl, wherein said (C$_1$-C$_4$)alkyl and (C$_3$-C$_7$)cycloalkyl is optionally substituted with one or more substituents independently selected from —OH and halogen;

R$_3$ is selected from the group consisting of halogen, cyano, (C$_1$-C$_4$)alkyl, (C$_1$-C$_4$)haloalkyl and (C$_3$-C$_7$)cycloalkyl;

R$_4$ is selected from the group consisting of (C$_1$-C$_4$)alkyl and (C$_1$-C$_4$)haloalkyl;

R$_5$ is selected from the group consisting of (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl, (3-7 membered)heterocycloalkyl, phenyl, (5-6 membered)heteroaryl and —OR$_a$; wherein said (C$_1$-C$_6$)alkyl, (C$_3$-C$_7$)cycloalkyl, (C$_1$-C$_6$)alkyl-(C$_3$-C$_7$)cycloalkyl, (C$_3$-C$_7$)cycloalkyl-(C$_1$-C$_6$)alkyl, (3-7 membered) heterocycloalkyl, phenyl, (5-6 membered)heteroaryl and —OR$_a$ is optionally substituted with one or more substituents independently selected from R$_7$;

R$_7$ represents the group consisting of —OH, —CN, halogen, (C$_1$-C$_4$)alkyl, (C$_3$-C$_7$)cycloalkyl and (C$_1$-C$_6$)alkyl-(C$_3$-C$_7$)cycloalkyl-.

Embodiment 78. The compound according to embodiment 77 wherein R$_2$ is selected from the group consisting of halogen and (C$_1$-C$_4$)alkyl, wherein said (C$_1$-C$_4$)alkyl is optionally substituted with one or more substituents independently selected from halogen;

R$_3$ is selected from (C$_1$-C$_4$)alkyl;

R$_4$ is selected from the group (C$_1$-C$_4$)alkyl;

R$_5$ is selected from the group consisting of (C$_1$-C$_6$)alkyl, (C$_3$-C$_7$)cycloalkyl, phenyl and —OR$_a$; wherein said (C$_1$-C$_6$) alkyl, (C$_3$-C$_7$)cycloalkyl, phenyl and —OR$_a$ is optionally substituted with one or more substituents independently selected from halogen Embodiment 79. The compound according to embodiments 77-78, said compound being selected from the list consisting of tert-butyl (2S)-4-[[3-(aminocarbamothioylamino)-5-chloro-2-methyl-phenyl]methyl]-2-methyl-piperazine-1-carboxylate, 1-amino-3-[3-[[(3S)-4-benzoyl-3-methyl-piperazin-1-yl]methyl]-5-chloro-2-methyl-phenyl]thiourea, isopropyl (2S)-4-[[3-(aminocarbamothioylamino)-5-chloro-2-methyl-phenyl]methyl]-2-methyl-piperazine-1-carboxylate, isopropyl (2S)-4-[[3-(aminocarbamothioylamino)-2,5-dimethyl-phenyl]methyl]-2-methyl-piperazine-1-carboxylate, tert-butyl (2S)-4-[[3-(aminocarbamothioylamino)-2,5-dimethyl-phenyl]methyl]-2-methyl-piperazine-1-carboxylate, 1-amino-3-[3-[[(3S)-4-(cyclobutanecarbonyl)-3-methyl-piperazin-1-yl]methyl]-2,5-dimethyl-phenyl]thiourea, isopropyl (2S)-4-[[3-(aminocarbamothioylamino)-5-(difluoromethyl)-2-methyl-phenyl]methyl]-2-methyl-piperazine-1-carboxylate, 1-amino-3-[3-[[(3S)-4-(cyclobutanecarbonyl)-3-methyl-piperazin-1-yl]methyl]-5-(difluoromethyl)-2-methyl-phenyl]thiourea, 1-amino-3-[3-[[(3S)-4-(cyclopentanecarbonyl)-3-methyl-piperazin-1-yl]methyl]-2,5-dimethyl-phenyl]thiourea.

Embodiment 80. A compound according to general formula (IX)

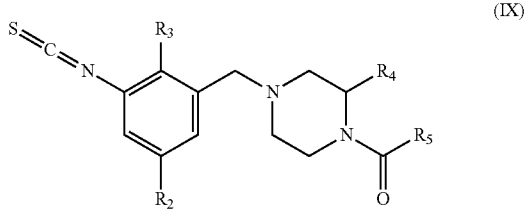

(IX)

wherein $R_2$ is selected from the group consisting of halogen, cyano, $(C_1-C_4)$alkyl and $(C_3-C_7)$cycloalkyl, wherein said $(C_1-C_4)$alkyl and $(C_3-C_7)$cycloalkyl is optionally substituted with one or more substituents independently selected from —OH and halogen;

$R_3$ is selected from the group consisting of halogen, cyano, $(C_1-C_4)$alkyl, $(C_1-C_4)$haloalkyl and $(C_3-C_7)$cycloalkyl;

$R_4$ is selected from the group consisting of $(C_1-C_4)$alkyl and $(C_1-C_4)$haloalkyl;

$R_5$ is selected from the group consisting of $(C_1-C_6)$alkyl, $(C_3-C_7)$cycloalkyl, $(C_1-C_6)$alkyl-$(C_3-C_7)$cycloalkyl, $(C_3-C_7)$cycloalkyl-$(C_1-C_6)$alkyl, (3-7 membered)heterocycloalkyl, phenyl, (5-6 membered)heteroaryl and —$OR_a$; wherein said $(C_1-C_6)$alkyl, $(C_3-C_7)$cycloalkyl, $(C_1-C_6)$alkyl-$(C_3-C_7)$cycloalkyl, $(C_3-C_7)$cycloalkyl-$(C_1-C_6)$alkyl, (3-7 membered) heterocycloalkyl, phenyl, (5-6 membered)heteroaryl and —$OR_a$ is optionally substituted with one or more substituents independently selected from $R_7$;

$R_7$ represents the group consisting of —OH, —CN, halogen, $(C_1-C_4)$alkyl, $(C_3-C_7)$cycloalkyl and $(C_1-C_6)$alkyl-$(C_3-C_7)$cycloalkyl-.

Embodiment 81. The compound according to embodiment 80 wherein $R_2$ is selected from the group consisting of halogen and $(C_1-C_4)$alkyl, wherein said $(C_1-C_4)$alkyl is optionally substituted with one or more substituents independently selected from halogen;

$R_3$ is selected from $(C_1-C_4)$alkyl;

$R_4$ is selected from the group $(C_1-C_4)$alkyl;

$R_5$ is selected from the group consisting of $(C_1-C_6)$alkyl, $(C_3-C_7)$cycloalkyl, phenyl and —$OR_a$; wherein said $(C_1-C_6)$ alkyl, $(C_3-C_7)$cycloalkyl, phenyl and —$OR_a$ is optionally substituted with one or more substituents independently selected from halogen Embodiment 82. The compound according to embodiments 80-81, said compound being selected from the list consisting of tert-butyl (2S)-4-[(5-chloro-3-isothiocyanato-2-methyl-phenyl)methyl]-2-methyl-piperazine-1-carboxylate,

[(2S)-4-[(5-chloro-3-isothiocyanato-2-methyl-phenyl)methyl]-2-methyl-piperazin-1-yl]-phenyl-methanone, isopropyl (2S)-4-[(5-chloro-3-isothiocyanato-2-methyl-phenyl)methyl]-2-methyl-piperazine-1-carboxylate, isopropyl (2S)-4-[(3-isothiocyanato-2,5-dimethyl-phenyl)methyl]-2-methyl-piperazine-1-carboxylate, tert-butyl (2S)-4-[(3-isothiocyanato-2,5-dimethyl-phenyl)methyl]-2-methyl-piperazine-1-carboxylate, cyclobutyl-[(2S)-4-[(3-isothiocyanato-2,5-dimethyl-phenyl)methyl]-2-methyl-piperazin-1-yl]methanone, isopropyl (2S)-4-[[15-(difluoromethyl)-3-isothiocyanato-2-methyl-phenyl]methyl]-2-methyl-piperazine-1-carboxylate, cyclobutyl-[(2S)-4-[[5-(difluoromethyl)-3-isothiocyanato-2-methyl-phenyl]methyl]-2-methyl-piperazin-1-yl]methanone, cyclopentyl-[(2S)-4-[(3-isothiocyanato-2,5-dimethyl-phenyl)methyl]-2-methyl-piperazin-1-yl]methanone.

---

The invention claimed is:
1. A method of treatment comprising administering to a person suffering from an autoimmune or inflammatory disease an effective amount of one or more compounds according to general formula (I)

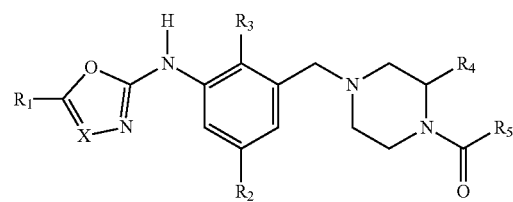

wherein:
X represents N or CH;
$R_1$ is selected from the group consisting of —CN, $(C_1-C_6)$alkyl, $(C_3-C_7)$cycloalkyl, (3-7 membered)heterocycloalkyl, (5-6 membered)heteroaryl, $(C_3-C_7)$cycloalkyl$(C_1-C_4)$alkyl, (3-7 membered)heterocycloalkyl-$(C_1-C_4)$alkyl, and (5-6 membered)heteroaryl-$(C_1-C_4)$alkyl, wherein said $(C_1-C_6)$alkyl, $(C_3-C_7)$cycloalkyl, (3-7 membered)heterocycloalkyl, (5-6-membered)heteroaryl, $(C_3-C_7)$cycloalkyl$(C_1-C_4)$alkyl, (3-7 membered)heterocycloalkyl-$(C_1-C_4)$alkyl, and (5-6 membered)heteroaryl-$(C_1-C_4)$alkyl is optionally substituted with one or more substituents independently selected from $R_6$;
$R_2$ is selected from the group consisting of halogen, cyano, $(C_1-C_4)$alkyl, and $(C_3-C_7)$cycloalkyl, wherein said $(C_1-C_4)$alkyl and $(C_3-C_7)$cycloalkyl is optionally substituted with one or more substituents independently selected from —OH and halogen;
$R_3$ is selected from the group consisting of halogen, cyano, $(C_1-C_4)$alkyl, $(C_1-C_4)$haloalkyl, and $(C_3-C_7)$cycloalkyl;
$R_4$ is selected from the group consisting of $(C_1-C_4)$alkyl and $(C_1-C_4)$haloalkyl; and
$R_5$ is selected from the group consisting of $(C_1-C_6)$alkyl, $(C_3-C_7)$cycloalkyl, $(C_1-C_6)$alkyl-$(C_3-C_7)$cycloalkyl, $(C_3-C_7)$cycloalkyl-$(C_1-C_6)$alkyl, (3-7 membered)heterocycloalkyl, phenyl, (5-6 membered)heteroaryl, and —$OR_a$, wherein said $(C_1-C_6)$alkyl, $(C_3-C_7)$cycloalkyl, $(C_1-C_6)$alkyl-$(C_3-C_7)$cycloalkyl, $(C_3-C_7)$cycloalkyl-$(C_1-C_6)$alkyl, (3-7 membered)heterocycloalkyl, phenyl, (5-6 membered)heteroaryl, and —$OR_a$ is optionally substituted with one or more substituents independently selected from $R_7$;
$R_6$ is selected from the group consisting of —OH, —CN, halogen, =O, —$S(O)_2R_b$, —$NR_cR_d$, —$NR_cC(O)R_d$, —$C(O)NR_cR_d$, —$S(O)_2NR_cR_d$, —$NR_cS(O)_2R_b$, —$OR_b$, —$C(O)R_b$, $(C_1-C_4)$alkyl, hydroxy$(C_1-C_4)$alkyl, halo$(C_1-C_4)$alkyl, $(C_3-C_7)$cycloalkyl, (3-7 membered)heterocycloalkyl, and (5-6 membered)heteroaryl; and
$R_7$ is selected from the group consisting of —OH, —CN, halogen, $(C_1-C_4)$alkyl, $(C_3-C_7)$cycloalkyl, and $(C_1-C_6)$alkyl-$(C_3-C_7)$cycloalkyl-;
$R_a$ is selected from the group consisting of $(C_1-C_6)$alkyl, $(C_3-C_7)$cycloalkyl, $(C_1-C_6)$alkyl-$(C_3-C_7)$cycloalkyl-, and $(C_3-C_7)$-cycloalkyl$(C_1-C_6)$alkyl;

$R_b$ is selected from the group consisting of $(C_1\text{-}C_6)$alkyl and $(C_3\text{-}C_7)$cycloalkyl; and $R_c$ and $R_d$ are each independently selected from the group consisting of H, $(C_1\text{-}C_6)$alkyl and $(C_3\text{-}C_7)$cycloalkyl;

or pharmaceutically acceptable salts, hydrates, or solvates thereof;

wherein the autoimmune or inflammatory disease is selected from psoriasis, psoriatic arthritis, multiple sclerosis, rheumatoid arthritis, Crohns disease, ulcerative colitis, alopecia areata, contact dermatitis, and spondyloarthritis.

2. The method according to claim 1, wherein said autoimmune or inflammatory disease is psoriasis.

3. The method according to claim 1, wherein the one or more compounds according to general formula (I) is contained in a pharmaceutical composition comprising one or more pharmaceutically acceptable vehicles, excipients, and/or carriers.

4. The method according to claim 1, wherein the autoimmune or inflammatory disease is responsive to modulation of retinoic acid-related orphan receptor (ROR) gamma.

5. The method of claim 4, wherein the ROR is $ROR_{\gamma t}$.

* * * * *

UNITED STATES PATENT AND TRADEMARK OFFICE
CERTIFICATE OF CORRECTION

PATENT NO. : 10,934,282 B2
APPLICATION NO. : 16/874961
DATED : March 2, 2021
INVENTOR(S) : Alan Stuart Jessiman et al.

It is certified that error appears in the above-identified patent and that said Letters Patent is hereby corrected as shown below:

On the Title Page

Item (30), under "Foreign Application Priority Data,":
"July 13, 2016 (EP) ............ 16020268"
Should read:
--July 13, 2016 (EP) ............ 16020268.5--.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*